(12) United States Patent
Watkins et al.

(10) Patent No.: US 9,714,419 B2
(45) Date of Patent: Jul. 25, 2017

(54) PEGYLATED TYROSYL-TRNA SYNTHETASE POLYPEPTIDES

(75) Inventors: Jeffrey D. Watkins, Encinitas, CA (US); Ying Ji Buechler, Carlsbad, CA (US); Chi-Fang Wu, San Diego, CA (US); Minh-Ha Do, San Diego, CA (US); Alain P. Vasserot, Carlsbad, CA (US); John D. Mendlein, Encinitas, CA (US)

(73) Assignee: aTyr Pharma, Inc., San Diego, CA (US)

( * ) Notice: Subject to any disclaimer, the term of this patent is extended or adjusted under 35 U.S.C. 154(b) by 420 days.

(21) Appl. No.: 14/237,544

(22) PCT Filed: Aug. 8, 2012

(86) PCT No.: PCT/US2012/050012
§ 371 (c)(1),
(2), (4) Date: May 27, 2014

(87) PCT Pub. No.: WO2013/022982
PCT Pub. Date: Feb. 14, 2013

(65) Prior Publication Data
US 2014/0255378 A1  Sep. 11, 2014

Related U.S. Application Data

(60) Provisional application No. 61/521,696, filed on Aug. 9, 2011.

(51) Int. Cl.
*C12N 9/00* (2006.01)
*A61K 47/48* (2006.01)
*A61K 38/00* (2006.01)

(52) U.S. Cl.
CPC .......... *C12N 9/93* (2013.01); *A61K 47/48215* (2013.01); *C12Y 601/01001* (2013.01); *A61K 38/00* (2013.01)

(58) Field of Classification Search
CPC ............. C12N 9/96; C12Y 601/01001; G01N 2500/00
See application file for complete search history.

(56) References Cited

U.S. PATENT DOCUMENTS

| | | |
|---|---|---|
| 5,370,995 A | 12/1994 | Hennecke et al. |
| 5,484,703 A | 1/1996 | Raben et al. |
| 5,663,066 A | 9/1997 | Raben et al. |
| 5,747,315 A | 5/1998 | Lowlor |
| 5,750,387 A | 5/1998 | Hodgson et al. |
| 5,753,480 A | 5/1998 | Lawlor |
| 5,756,327 A | 5/1998 | Sassanfar et al. |
| 5,759,833 A | 6/1998 | Shiba et al. |
| 5,776,749 A | 7/1998 | Hodgson et al. |
| 5,795,757 A | 8/1998 | Hodgson et al. |
| 5,798,240 A | 8/1998 | Martinis et al. |
| 5,801,013 A | 9/1998 | Tao et al. |
| 5,866,390 A | 2/1999 | Lawlor |
| 5,885,815 A | 3/1999 | Sassanfar et al. |
| 5,928,920 A | 7/1999 | Hodgson et al. |
| 5,939,298 A | 8/1999 | Brown et al. |
| 6,013,483 A | 1/2000 | Coleman et al. |
| 6,225,060 B1 | 5/2001 | Clark et al. |
| 6,255,090 B1 | 7/2001 | Famodu et al. |
| 6,265,188 B1 | 7/2001 | Brown et al. |
| 6,428,960 B1 | 8/2002 | Clark et al. |
| 6,548,060 B1 | 4/2003 | Kim |
| 6,696,619 B1 | 2/2004 | Famodu et al. |
| 6,852,512 B2 | 2/2005 | Choi et al. |
| 6,864,226 B1 | 3/2005 | Coleman et al. |
| 6,903,189 B2 | 6/2005 | Schimmel et al. |
| 7,037,505 B2 | 5/2006 | Kim et al. |
| 7,045,301 B2 | 5/2006 | Coleman et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,282,208 B2 | 10/2007 | Kim |
| 7,413,885 B2 | 8/2008 | Schimmel et al. |
| 7,459,529 B2 | 12/2008 | Kim |
| 7,476,651 B2 | 1/2009 | Schimmel et al. |
| 7,482,326 B2 | 1/2009 | Coleman et al. |
| 7,521,215 B2 | 4/2009 | Schimmel et al. |
| 7,528,106 B2 | 5/2009 | Friedlander et al. |
| 7,572,452 B2 | 8/2009 | Kim |
| 7,745,391 B2 | 6/2010 | Mintz et al. |

(Continued)

FOREIGN PATENT DOCUMENTS

| | | |
|---|---|---|
| CA | 2531146 | 3/2005 |
| CN | 1341725 | 3/2002 |

(Continued)

OTHER PUBLICATIONS

Office Action for European Application No. 09719533, mailed Mar. 28, 2011.
International Preliminary Report on Patentability for International Application No. PCT/US2009/036826, dated Sep. 14, 2010.
International Search Report and Written Opinion for International Application No. PCT/US2009/036826, mailed Oct. 15, 2009.
International Preliminary Report on Patentability for International Application No. PCT/US2009/048915, dated Jan. 5, 2011.
International Search Report and Written Opinion for International Application No. PCT/US2009/048915, mailed Nov. 2, 2009.
Office Action for U.S. Appl. No. 12/482,151, mailed Aug. 13, 2013, 33 pages.

(Continued)

*Primary Examiner* — Kagnew H Gebreyesus
(74) *Attorney, Agent, or Firm* — Cooley LLP

(57) ABSTRACT

The present invention provides PEGylated tyrosyl-tRNA synthetase (YRS) polypeptides, compositions comprising the same, and methods of using such polypeptides and compositions for treating or diagnosing a variety of conditions. The PEGylated YRS polypeptides of the invention have improved controlled release properties, stability, half-life, and other pharmacokinetic properties compared to non-PEGylated YRS polypeptides.

22 Claims, 12 Drawing Sheets

(56) References Cited

U.S. PATENT DOCUMENTS

| | | |
|---|---|---|
| 7,786,085 B2 | 8/2010 | Rodgers et al. |
| 7,842,467 B1 | 11/2010 | Heidbrink et al. |
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,747,840 B2 | 6/2014 | Greene et al. |
| 8,753,638 B2 | 6/2014 | Zhou et al. |
| 8,828,395 B2 | 9/2014 | Watkins et al. |
| 8,835,387 B2 | 9/2014 | Chiang et al. |
| 8,945,541 B2 | 2/2015 | Greene et al. |
| 8,946,157 B2 | 2/2015 | Greene et al. |
| 8,961,960 B2 | 2/2015 | Chiang et al. |
| 8,961,961 B2 | 2/2015 | Greene et al. |
| 8,962,560 B2 | 2/2015 | Greene et al. |
| 8,969,301 B2 | 3/2015 | Greene et al. |
| 8,980,253 B2 | 3/2015 | Greene et al. |
| 8,981,045 B2 | 3/2015 | Greene et al. |
| 8,986,680 B2 | 3/2015 | Greene et al. |
| 8,986,681 B2 | 3/2015 | Greene et al. |
| 8,993,723 B2 | 3/2015 | Greene et al. |
| 8,999,321 B2 | 4/2015 | Greene et al. |
| 9,029,506 B2 | 5/2015 | Greene et al. |
| 9,034,320 B2 | 5/2015 | Greene et al. |
| 9,034,321 B2 | 5/2015 | Greene et al. |
| 9,034,598 B2 | 5/2015 | Greene et al. |
| 9,062,301 B2 | 6/2015 | Greene et al. |
| 9,062,302 B2 | 6/2015 | Greene et al. |
| 9,068,177 B2 | 6/2015 | Greene et al. |
| 9,127,268 B2 | 9/2015 | Watkins et al. |
| 9,273,302 B2 | 3/2016 | Chiang et al. |
| 9,315,794 B2 | 4/2016 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang et al. |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0246509 A1 | 11/2006 | Deiters et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0148887 A1 | 6/2009 | Brustad et al. |
| 2009/0221794 A1 | 9/2009 | Kim et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0255375 A1 | 9/2014 | Belani et al. |
| 2014/0302075 A1 | 10/2014 | Buechler et al. |
| 2014/0335087 A1 | 11/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0064188 A1 | 3/2015 | Greene |
| 2015/0093799 A1 | 4/2015 | Chiang et al. |
| 2015/0140072 A1 | 5/2015 | Watkins et al. |
| 2015/0159148 A1 | 6/2015 | Buechler et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290304 A1 | 10/2015 | Greene et al. |
| 2015/0290305 A1 | 10/2015 | Greene et al. |
| 2015/0344866 A1 | 12/2015 | Greene et al. |

(56) References Cited

U.S. PATENT DOCUMENTS

| | | |
|---|---|---|
| 2015/0353914 A1 | 12/2015 | Greene et al. |
| 2015/0361411 A1 | 12/2015 | Greene et al. |
| 2015/0361412 A1 | 12/2015 | Greene et al. |
| 2015/0361413 A1 | 12/2015 | Greene et al. |
| 2016/0010075 A1 | 1/2016 | Greene et al. |
| 2016/0017311 A1 | 1/2016 | Greene |

FOREIGN PATENT DOCUMENTS

| | | |
|---|---|---|
| CN | 1341727 | 3/2002 |
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| JP | 2003-529354 | 10/2003 |
| JP | 2004-516009 | 6/2004 |
| JP | 2005-523682 | 8/2005 |
| JP | 2008-508349 | 3/2008 |
| WO | WO 96/39506 | 12/1996 |
| WO | WO 97/25426 | 7/1997 |
| WO | WO 97/26351 | 7/1997 |
| WO | WO 97/39017 | 10/1997 |
| WO | WO 98/14591 | 4/1998 |
| WO | WO 98/50554 | 11/1998 |
| WO | WO 99/45130 | 9/1999 |
| WO | WO 01/07628 | 2/2001 |
| WO | WO 01/19999 | 3/2001 |
| WO | WO 01/64892 | 9/2001 |
| WO | WO 01/74841 | 10/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 02/04611 | 1/2002 |
| WO | WO 02/44349 | 6/2002 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/031589 | 4/2003 |
| WO | WO 03/072035 | 9/2003 |
| WO | WO 03/080648 | 10/2003 |
| WO | WO 03/094862 | 11/2003 |
| WO | WO 2004/023973 | 3/2004 |
| WO | WO 2004/030615 | 4/2004 |
| WO | WO 2004/087875 | 10/2004 |
| WO | WO 2005/019258 | 3/2005 |
| WO | WO 2005/019415 | 3/2005 |
| WO | WO 2005/102395 | 11/2005 |
| WO | WO 2005/117954 | 12/2005 |
| WO | WO 2006/016217 | 2/2006 |
| WO | WO 2006/034332 | 3/2006 |
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/127900 | 10/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/158945 | 11/2012 |
| WO | WO 2013/022982 | 2/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |

OTHER PUBLICATIONS

Office Action for U.S. Appl. No. 12/482,151, mailed Oct. 11, 2011, 43 pages.
Office Action for U.S. Appl. No. 12/482,151, mailed Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, mailed Mar. 4, 2010.
Office Action for U.S. Appl. No. 14/180,126, mailed Apr. 20, 2015, 21 pages.
Supplementary European Search Report for European Application No. 06838844.6, mailed Apr. 9, 2009, 10 pages.
Office Action for European Patent Application No. 06838844.6, mailed Apr. 9, 2009.
Office Action for U.S. Appl. No. 12/085,884, mailed Jan. 20, 2011.
Response to Office Action dated Apr. 18, 2011, for U.S. Appl. No. 12/085,884.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
Office Action for U.S. Appl. No. 13/239,796, mailed Nov. 14, 2012.
Supplementary European Search Report for European Application No. 10746935.5, mailed Oct. 26, 2012.
Office Action for U.S. Appl. No. 13/203,831, mailed Oct. 7, 2013, 20 pages.
International Preliminary Report on Patentability for International Application No. PCT/US2010/025642, dated Aug. 30, 2011.
International Search Report and Written Opinion for International Application No. PCT/US2010/025642, mailed Oct. 29, 2010.
Supplementary European Search Report for European Application No. 10764856.0, mailed Sep. 5, 2012.
Office Action for U.S. Appl. No. 12/751,358, mailed Dec. 2, 2014.
Office Action for U.S. Appl. No. 12/751,358, mailed Jun. 11, 2014.
Office Action for U.S. Appl. No. 12/751,358, mailed Oct. 3, 2011.
Office Action for U.S. Appl. No. 12/751,358, mailed Mar. 3, 2011.

(56) References Cited

OTHER PUBLICATIONS

International Preliminary Report on Patentability for International Application No. PCT/US2010/029377, dated Oct. 4, 2011.
International Search Report and Written Opinion for International Application No. PCT/US2010/029377, mailed Jan. 26, 2011.
Office Action for U.S. Appl. No. 12/725,272, mailed Jul. 13, 2012, 9 pages.
Restriction Requirement for U.S. Appl. No. 12/725,272, mailed Apr. 27, 2012.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
Office Action for U.S. Appl. No. 12/965,655, mailed Sep. 6, 2013.
Office Action for U.S. Appl. No. 12/965,655, mailed Mar. 27, 2013.
Office Action for U.S. Appl. No. 12/965,655, mailed Oct. 24, 2014.
International Search Report and Written Opinion for International Application No. PCT/US2010/059964, mailed Aug. 25, 2011.
International Preliminary Report on Patentability for International Application No. PCT/US2010/059964, dated Jun. 12, 2012.
Office Action for U.S. Appl. No. 13/162,559, mailed Aug. 14, 2013.
Communication Pursuant to Article 94(3) EPC for European Application No. 10793402.8, mailed Mar. 27, 2013.
International Preliminary Report on Patentability for International Application No. PCT/US2010/059963, dated Jun. 12, 2012, 18 pages.
International Search Report and Written Opinion for International Application No. PCT/US2010/059963, mailed May 12, 2011.
International Search Report and Written Opinion for International Application No. PCT/US2011/000210, mailed Aug. 12, 2011.
International Preliminary Report on Patentabiltity for International Application No. PCT/US2011/000210, dated Aug. 7, 2012.
Supplementary European Search Report for European Application No. 11778025.4, mailed Nov. 6, 2013.
International Search Report and Written Opinion for International Application No. PCT/US2011/034387, mailed on Mar. 23, 2012.
International Preliminary Report on Patentability for International Application No. PCT/US2011/034387, dated Oct. 30, 2012.
Supplementary European Search Report for European Application No. 11778026.2, mailed Oct. 22, 2013.
International Search Report and Written Opinion for International Application No. PCT/US2011/034388, mailed on Mar. 23, 2012.
International Preliminary Report on Patentability for International Application No. PCT/US2011/034388, dated Oct. 30, 2012.
Supplementary European Search Report for European Application No. 11807357.6, mailed Dec. 22, 2014.
Notice of Allowance for U.S. Appl. No. 13/809,750, mailed Oct. 17, 2014, 10 pages.
International Search Report and Written Opinion for International Application No. PCT/US2011/043596, mailed on Feb. 29, 2012.
International Preliminary Report on Patentability for International Application No. PCT/US2011/043596, dated Jan. 15, 2013.
Supplementary European Search Report for European Application No. 11778118.7, mailed Aug. 19, 2013.
International Search Report and Written Opinion for International Application No. PCT/US2011/034838, mailed Jan. 9, 2012.
International Preliminary Report on Patentability for International Application No. PCT/US2011/034838, dated Nov. 6, 2012.
International Search Report and Written Opinion for International Application No. PCT/US2011/033988, mailed on Feb. 9, 2012.
International Preliminary Report on Patentability for International Application No. PCT/US2011/033988, dated Oct. 30, 2012.
International Search Report and Written Opinion for International Application No. PCT/US2011/038240, mailed on Feb. 9, 2012.
International Preliminary Report on Patentability for International Application No. PCT/US2011/038240, dated Nov. 27, 2012.
Supplementary European Search Report for European Application No. 11778296.1, mailed Nov. 12, 2013.
International Search Report and Written Opinion for International Application No. PCT/US2011/035250, mailed on Jan. 19, 2012.
International Preliminary Report on Patentability for International Application No. PCT/2011/035250, dated Nov. 6, 2012.
International Search Report and Written Opinion for International Application No. PCT/US2011/043756, mailed on Mar. 2, 2012.
International Preliminary Report on Patentability for International Application No. PCT/US2011/043756, dated Jan. 15, 2013.
International Search Report and Written Opinion for International Application No. PCT/US2011/043758, mailed on Mar. 2, 2012.
International Preliminary Report on Patentability for International Application No. PCT/US2011/043758, dated Jan. 15, 2013.
International Search Report and Written Opinion for International Application No. PCT/US2011/034205, mailed on Feb. 8, 2012.
International Preliminary Report on Patentability for International Application No. PCT/US2011/034205, dated Oct. 30, 2012.
International Search Report and Written Opinion for International Application No. PCT/US2011/036684, mailed on Feb. 9, 2012.
International Preliminary Report on Patentability for International Application No. PCT/US2011/036684, dated Nov. 20, 2012.
International Search Report and Written Opinion for International Application No. PCT/US2011/038813, mailed on Mar. 28, 2012.
International Preliminary Report on Patentability for International Application No. PCT/US2011/038813, dated Dec. 4, 2012.
International Search Report and Written Opinion for International Application No. PCT/US2011/035056, mailed on Mar. 23, 2012.
International Preliminary Report on Patentability for International Application No. PCT/US2011/035056, dated Nov. 6, 2012.
International Search Report and Written Opinion for International Application No. PCT/US2011/035053, mailed Mar. 23, 2012.
International Preliminary Report on Patentability for International Application No. PCT/US2011/035053, dated Nov. 6, 2012.
Supplementary European Search Report for European Application No. 11778120.3, mailed Nov. 15, 2013.
International Search Report and Written Opinion for International Application No. PCT/US2011/034840, mailed on Feb. 10, 2012.
International Preliminary Report on Patentability for International Application No. PCT/US2011/034840, dated Nov. 6, 2012.
Supplementary European Search Report for European Application No. 11777984.3, mailed Oct. 18, 2013.
International Search Report and Written Opinion for International Application No. PCT/US2011/034207, mailed Feb. 8, 2012.
International Preliminary Report on Patentability for International Application No. PCT/US2011/034207, dated Oct. 30, 2012.
International Search Report and Written Opinion for International Application No. PCT/US2011/055130, mailed on May 14, 2012.
International Preliminary Report on Patentability for International Application No. PCT/US2011/055130, dated Apr. 9, 2013.
Supplementary European Search Report for European Application No. 11820682.0, mailed Aug. 19, 2014.
International Search Report and Written Opinion for International Application No. PCT/US2011/049223, mailed Mar. 27, 2012.
International Preliminary Report on Patentability for International Application No. PCT/US2011/049223, dated Feb. 26, 2013.
International Search Report and Written Opinion for International Application No. PCT/US2011/034626, mailed on Jan. 19, 2012.
International Preliminary Report on Patentability for International Application No. PCT/US2011/034626, dated Oct. 30, 2012.
Supplementary European Search Report for European Application No. 11781304.8, mailed Oct. 23, 2013.
International Search Report and Written Opinion for International Application No. PCT/US2011/036326, mailed on Feb. 9, 2012.
International Preliminary Report on Patentability for International Application No. PCT/US2011/036326, dated Nov. 20, 2012.
International Search Report and Written Opinion for International Application No. PCT/US2011/035251, mailed on Feb. 8, 2012.
International Preliminary Report on Patentability for International Application No. PCT/US2011/035251, dated Nov. 6, 2012.
International Search Report and Written Opinion for International Application No. PCT/US2012/050012, mailed Feb. 26, 2013, 13 pages.
International Preliminary Report on Patentability for International Application No. PCT/US2012/050012, dated Feb. 11, 2014, 7 pages.

(56) References Cited

OTHER PUBLICATIONS

International Search Report and Written Opinion for International Application No. PCT/US2012/068282, mailed on Apr. 1, 2013.
International Search Report and Written Opinion for International Application No. PCT/US2012/068296, mailed on Apr. 19, 2013.
Supplementary Partial European Search Report for European Application No. 12867497.5, mailed Apr. 29, 2015.
International Preliminary Report on Patentability for International Application No. PCT/US2012/071762, dated Jul. 1, 2014.
International Search Report and Written Opinion for International Application No. PCT/US2012/071762, mailed Aug. 20, 2013, 12 pages.
Adams, M. D. et al., "The genome sequence of Drosophila melanogaster," Science, 287(5961):2185-2195 (2000).
Aderem, A. et al., "Toll-like receptors in the induction of the innate immune response," Nature, 406:782-787 (2000).
Algiman, M. et al., "Natural antibodies to factor VIII (anti-hemophilic factor) in healthy individuals," Proc Natl Acad Sci USA, 1992, 89(9):3795-3799.
Amaar, Y. G. et al., "Cloning and characterization of the C.elegans histidyl-tRNA synthetase gene," Nucleic Acids Research, 21(18):4344-4347 (1993).
Antonellis, A. et al., "Functional Analyses of Glycyl-tRNA Synthetase Mutations Suggest a Key Role for tRNA-Charging Enzymes in Peripheral Axons," The Journal of Neuroscience, 26(41):10397-10406 (2006).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Biosis (Biological Abstracts) Accession No. PREV200300183746, 2003.
Biosis (Biological Abstracts) Accession No. PREV200300256685, 2003.
Biosis (Biological Abstracts) Accession No. PREV200400442099, 2004.
Biosis (Biological Abstracts) Accession No. PREV200700042366, 2007.
Biosis (Biological Abstracts) Accession No. PREV200800526912, 2008.
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Branden et al., "Introduction to Protein Structure," Garland Publishing Inc., New York, p. 247 (1991).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon γ Receptor Deficient Mice Are Resistant to Endotoxic Shock," J. Exp. Med., 179:1437-1444, 1994.
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Chen, M. et al., "Site-specific incorporation of unnatural amino acids into urate oxidase in Escherichia coli," Protein Science, 17(10):1827-1833 (2008).
Cheng, G. et al., "Effect of mini-tyrosyl-tRNA synthetase on ischemic angiogenesis, leukocyte recruitment, and vascular permeability," American Journal Physiol. Regul. Integr. Comp. Physiol., 295:R1138-R1146 (2008).
Cheong et al., "Structure of the N-terminal extension of human aspartyl-tRNA synthetase: implications for its biological function," The International Journal of Biochemistry & Cell Biology, 35:1548-1557, 2003.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Colburn, W. A., "Specific antibodies and fab fragments to alter the pharmacokinetics and reverse the pharmacologic/toxicologic effects of drugs," Drug Metabolism Reviews, 11(2):223-262 (1980).
Copley, "Enzymes with extra talents: moonlighting functions and catalytic promiscuity," Current Opinion in Chemical Biology, 7:265-272 (2003).
Datson, N. A. et al., "Development of the first marmoset-specific DNA microarray (EUMAMA): a new genetic tool for large-scale expression profiling in a non-human primate," BMC Genomics, 8(190):1-9 (2007).
DeBruyn et al., "Ex vivo Expansion of Megakaryocyte Progenitor Cells: Cord Blood Versus Mobilized Peripheral Blood," Stem Cells Development, 14:415-424 (2005).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
De Pouplana, L. R. et al., "Evidence that two present-day components needed for the genetic code appeared after nucleated cells separated from eubacteria," Proc. Natl. Acad. Sci. USA, 93:166-170 (1996).
Dessypris et al., "Thrombopoiesis-stimulating Factor: Its Effects on Megakaryocyte Colony Formation in vitro and Its Relation to Human Granulocyte-Macrophage Colony-stimulating Factor," Exp. Hematol. 18:754-757, 1990.
Devos, D. et al., "Practical limits of function prediction," Proteins: Structure, Function, and Genetics, 41:98-107 (2000).
Dumont, J. A. et al., "Monomeric Fc Fusions: Impact on pharmacokinetic and biological activity of protein therapeutics," Biodrugs: Clinical Immunotherapeutics, Biopharmaceuticals and Gene Therapy, 20(3):151-160 (2006).
Ealey, P. A. et al., "Characterization of monoclonal antibodies raised against solubilized thyrotropin receptors in a cytochemical bioassay for thyroid stimulators," Endocrinology, 116(1):124-131 (1985) (Abstract).
Eriani, G. et al., "Cytoplasmic aspartyl-tRNA synthetase from Saccharomyces cerevisiae. Study of its functional organisation by deletion analysis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).

(56) References Cited

OTHER PUBLICATIONS

Escalante, C. et al., "Expression of Human Aspartyl-tRNA Synthetase in *Escherichia coli*: Functional Analysis of the N-Terminal Putative Amphiphilic Helix," The Journal of Biological Chemistry, 268(8):6014-6023 (1993).
Ewalt, K. L. et al., "Activation of Angiogenic Signaling Pathways by Two Human tRNA Synthetases," Biochemistry, 41(45):13344-13349 (2002).
Fontanesi, L. et al., "Identification and association analysis of several hundred single nucleotide polymorphisms within candidate genes for back fat thickness in Italian large white pigs using a selective genotyping approach," J Anim Sci, 90(8):2450-2464 (2012).
Froelich et al., "Dominant Intermediate Charcot-Marie-Tooth disorder is not due to a catalytic defect in tyrosyl-tRNA synthetase," Biochemistry, 59 pages (2011).
Frommhold, D. et al., "Sialyltransferase ST3Gal-IV controls CXCR2-mediated firm leukocyte arrest during inflammation," Journal of Experimental Medicine, 205(6):1435-1446 (2008).
Fu et al., "tRNA-controlled Nuclear Import of a Human tRNA Synthetase," Journal of Biological Chemistry, 287(12):9330-9334 (2012).
Garcia-Lozano, J. R. et al., "Detection of anti-PL-12 autoantibodies by ELISA using a recombinant antigen; study of the immunoreactive region," Clin. Exp. Immunol., 114:161-165 (1998).
GenBank Accession No. AK074524, Mar. 25, 2002.
GenBank Accession No. AU126197, Oct. 23, 2000.
GenBank Accession No. AW976267, Jun. 2, 2000.
GenBank Accession No. BI258770, Jul. 16, 2001.
GenBank Accession No. BP423196, May 27, 2005.
GenBank Accession No. CA314607, Nov. 4, 2002.
GenBank Accession No. DA018291, Nov. 2, 2005.
GenBank Accession No. DA386636, Nov. 5, 2005.
GenBank Accession No. DA478765, Nov. 6, 2005.
GenBank Accession No. DA552410, Nov. 5, 2005.
GenBank Accession No. DA576766, Nov. 5, 2005.
GenBank Accession No. DB488998, Mar. 31, 2006.
GenBank Accession No. DC366890, Apr. 27, 2007.
GenBank Accession No. DB058369, Dec. 10, 2005.
GenBank Accession No. AA131122, Nov. 27, 1996.
GenBank Accession No. AA174042, Sep. 30, 1997.
GenBank Accession No. AA281081, Apr. 2, 1997.
GenBank Accession No. AA355758, Apr. 21, 1997.
GenBank Accession No. AA984229, published May 27, 1998.
GenBank Accession No. AAP36306.1, published May 13, 2003.
GenBank Accession No. BT007638.1, published May 13, 2003.
GenBank Accession No. AI352487, Dec. 30, 1998.
GenBank Accession No. AI963202, Aug. 20, 1999.
GenBank Accession No. AI821854, Jul. 9, 1999.
GenBank Accession No. AI985978, Aug. 31, 1999.
GenBank Accession No. AJ706186, Jun. 30, 2004.
GenBank Accession No. AK055917, published Jan. 19, 2008.
GenBank Accession No. AK124831, published Jul. 3, 2008.
GenBank Accession No. AK125213, Jul. 3, 2008.
GenBank Accession No. AK126444, Jan. 9, 2008.
GenBank Accession No. AK127182, Jan. 9, 2008.
GenBank Accession No. AK225776, published Jul. 22, 2006.
GenBank Accession No. AK293154, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AL043328, Jul. 8, 1999.
GenBank Accession No. AU129836, published Feb. 18, 2011.
GenBank Accession No. AV685924, Sep. 25, 2000.
GenBank Accession No. AW070887, Oct. 13, 1999.
GenBank Accession No. BC001933, Jul. 15, 2006.
GenBank Accession No. BE561651, Aug. 10, 2000.
GenBank Accession No. BE695954, Sep. 11, 2000.
GenBank Accession No. BE872272, published Jan. 13, 2011.
GenBank Accession No. BF205419, Nov. 3, 2000.
GenBank Accession No. BF308942, Nov. 20, 2000.
GenBank Accession No. BF437672, Nov. 29, 2000.
GenBank Accession No. BF526055, Dec. 4, 2000.
GenBank Accession No. BF791754, published Jan. 13, 2011.
GenBank Accession No. BF876481, Jan. 17, 2001.
GenBank Accession No. BG108830, published Jun. 1, 2001.
GenBank Accession No. BG165437, Feb. 5, 2001.
GenBank Accession No. BG700836, May 7, 2001.
GenBank Accession No. BI559642, Sep. 4, 2001.
GenBank Accession No. BI599431, Sep. 5, 2001.
GenBank Accession No. BM917050, Mar. 11, 2002.
GenBank Accession No. BM827507, Mar. 6, 2002.
GenBank Accession No. BP268250, published Feb. 10, 2011.
GenBank Accession No. BQ002750, Mar. 26, 2002.
GenBank Accession No. BQ231273, May 1, 2002.
GenBank Accession No. BU599828, Sep. 19, 2002.
GenBank Accession No. BX440782, May 15, 2003.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. CX753411, Jan. 22, 2005.
GenBank Accession No. DA083923, published Feb. 17, 2011.
GenBank Accession No. DA119890, Oct. 30, 2005.
GenBank Accession No. DA157534, Oct. 30, 2005.
GenBank Accession No. DA158736, Oct. 30, 2005.
GenBank Accession No. DA269700, Oct. 30, 2005.
GenBank Accession No. DA769799, Nov. 11, 2005.
GenBank Accession No. DA942238, Nov. 13, 2005.
GenBank Accession No. DB146646, published Feb. 16, 2011.
GenBank Accession No. J05032, published Apr. 27, 1993.
GenBank Accession No. Q7QD89, Nov. 28, 2006.
Gen Bank Accession No. Q91WQ3, Jul. 19, 2004.
GenBank Accession No. Q9W60, Nov. 28, 2006.
GenBank Accession No. U09587, Human glycyl-tRNA synthetase mRNA, complete cds, Dec. 9, 1994.
GenBank Accession No. Z11518, published Oct. 7, 2008.
GenBank Accession No. Z28811, Dec. 14, 1993.
Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hanrott, K. et al., "6-Hydroxydopamine-induced Apoptosis Is Mediated via Extracellular Auto-oxidation and Caspase 3-dependent Activation of Protein Kinase Cδ," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).

(56) References Cited

OTHER PUBLICATIONS

Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Hsu, H-C et al., "Circulating levels of thrombopoietic and inflammatory cytokines in patients with clonal and reactive thrombocytosis," J. Lab. Clin. Med., 134(4):392-397 (1999).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jordanova, A. et al., "Disrupted function and axonal distribution of mutant tyrosyl-tRNA synthetase in dominant intermediate Charcot-Marie-Tooth neuropathy," Nature Genetics, 38(2):197-202 (2006).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kleeman, T. A. et al., "Human Tyrosyl-tRNA Synthetase Shares Amino Acid Sequence Homology with a Putative Cytokine," The Journal of Biological Chemistry, 272(22):14420-14425 (1997).
Kobos, R. et al., "Overview of thrombopoietic agents in the treatment of thrombocytopenia," Clinical Lymphoma & Myeloma, 8(1):33-43 (2008).
Kochendoerfer, G. G., "Site-specific polymer modification of therapeutic proteins," Current Opinion in Chemical Biology, 9:555-560 (2005).
Kordysh, M. et al., "Conformational Flexibility of Cytokine-Like C-Module of Tyrosyl-tRNA Synthetase Monitored by Trp 144 Intrinsic Fluorescence," J. Fluoresc., 16:705-711 (2006).
Kovaleski, B. J. et al.,"In vitro characterization of the interaction between HIV-1 Gag and human lysyl-tRNA synthetase," J. Bio. Chem., 281(28):19449-19456 (2006).
Lee, J. W. et al., "Editing-defective tRNA synthetase causes protein misfolding and neurodegeneration," Nature, 443(7107):50-55 (2006).
Lee, P. S. et al., "Uncovering of a short internal peptide activates a tRNA synthetase procytokine," The Journal of Biological Chemistry, 287(24):20504-20508 (2012).
Leitao-Goncalves, R. et al., "*Drosophila* as a platform to predict the pathogenicity of novel aminoacyl-tRNA synthetase mutations in CMT," Amino Acids (2011).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids, " Proc. Nat. Acad. Sci., 103(27):10180-10185 (2006).
Liu, J. et al., "Mutational Switching of a Yeast tRNA Synthetase into a Mammalian-like Synthetase Cytokine," Biochemistry, 41(48):14232-14237 (2002).
Lorber, Bernard, et al., "Properties of N-terminal truncated yeast aspartyl-tRNA synthetase and structural characteristics of the cleaved domain," Eur. J. Biochem. 174, pp. 155-161 (1988).
Ma, P. T. S. et al., "Mevinolin, an inhibitor of cholesterol synthesis, induces mRNA for low density lipoprotein receptor in livers of hamsters and rabbits," Proc. Natl. Acad. Sci. USA, 83:8370-8374 (1986).
Martin, A. et al., "Epitope studies indicate that histidyl-tRNA synthetase is a stimulating antigen in idiopathic myositis," The FASEB Journal, 9:1226-1233 (1995).
Martinis, S. A. et al., "Jekyll & Hyde: Evoluation of a Superfamily," Chemistry & Biology, 14(12):1307-1308 (2007).
Merritt, E. A. et al., "Crystal structure of the aspartyl-tRNA synthetase from Engamoeba histolytica," Mol. Biochem. Parasitol, 169(2):95-100 (2009).
Mihovilovic, M. et al., "Monoclonal antibodies as probes of the alpha-Bungarotoxin and cholinergic binding regions of the acetylcholine receptor," J Biol. Chem., 262(11):4978-4986 (1987).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Mirande, M. et al., "Engineering mammalian aspartyl-tRNA synthetase to probe structural features mediating its association with the multisynthetase complex," Eur. J. Biochem., 203(3):459-466 (1992).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Monteiro, J. P. et al., "Normal hematopoiesis is maintaned by activated bone marrow CD4+ T cells," Blood, 15:1484-1491 (2005).
Motley, W. W. et al., "Gars axonopathy: not every neuron's cup of tRNA," Trends Neurosci., 33(2):59 (2010).
Mukhopadhyay, R. et al., "The Gait System: a gatekeeper of inflammatory gene expression," Trends in Biochemical Sciences, 34(7):324-331 (2009).
Nackley, A. G. et al., "Human Caechol-O-Methytransferase haplotypes modulate protein expression by altering mRNA secondary structure," Science, 314:1930-1933 (2006).
Nangle, L. A. et al., "Charcot-Marie-Tooth disease-associated mutant tRNA synthetases linked to altered dimer interface and neurite distribution defect," PNAS, 104(27):11239-11244 (2007).
NCBI Accession No. NP001340, Feb. 27, 2011.
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).

(56) References Cited

OTHER PUBLICATIONS

O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Otani, A. et al., "A fragment of human TrpRS as a potent antagonist of ocular angiogenesis," PNAS, 99(1):178-183 (2002).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Paukstelis, P. J. et al., "NMR Structure of the C-Terminal Domain of a Tyrosyl-tRNA Synthetase That Functions in Group I Intron Splicing," Biochemistry, 50:3816-3826 (2011).
Paukstelis, P. J. et al., "A Tyrosyl-tRNA Synthetase Adapted to Function in Group I Intron Splicing by Acquiring a New RNA Binding Surface," Molecular Cell, 17:417-428 (2005).
Paukstelis, P. J. et al., "Structure of a tyrosyl-tRNA synthetase splicing factor bound to a group I intron RNA," Nature, 451:94-98 (2008).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Quesniaux, V. F.J. et al., "Hematopoiesis, including lymphocyte developmet and maturation," Principles of Immunopharmacology, pp. 3-17 (2005).
Quinn, C. L. et al., "Species-Specific Microhelix Aminoacylation by a Eukaryotic Pathogen tRNA Synthetase Dependent on a Single Base Pair," Biochemistry, 34(39):12489-12495 (1995).
Raben, N. et al., "A Motif in Human Histidyl-tRNA Synthetase Which Is Shared among Several Aminoacyl-tRNA Synthetases is a Coiled-coil That is Essential for Enzymatic Activity and Contains the Major Autoantigenic Epitope," The Journal of Biological Chemistry, 269(39):24277-24283 (1994).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Genetic dissection of protein-protein interactions in multi-tRNA synthetase complex," Proc. Natl. Acad. Sci. USA, 96:4488-4493 (1999).
Richardson, R. M. et al., "Role of the cytoplasmic tails of CXCR1 and CXCR2 in mediating leukocyte migration, activation, and regulation," Journal of Immunology, 170(6):2904-2911 (2003).
Riley, L. G. et al., "Mutation of the Mitochondrial Tyrosyl-tRNA Synthetase Gene, YARS2, Causes Myopathy, Lactic Acidosis, and Sideroblastic Anemia-MLASA Syndrome," The American Journal of Human Genetics, 87:52-59 (2010).
Rios-Santos, F. et al., "Down-regulation of CXCR2 on Neutrophilis in Severe Sepsis Is Mediated by Inducible Nitric Oxide Synthase-derived Nitric Oxide," Am. J. Respir. Crit. Care. Med., 175:490-497 (2007).
Rozhko, O. T. et al., "Production of polyclonal antibodies to tyrosyl-tRNA synthetase from the bovine liver and characteristics of two forms of the enzyme," Ukr. Biokhim Zh., 69(3):9-16 (1997) (with English Summary).
Rudinger-Thirion et al., "Misfolded human tRNA isodecoder binds and neutralizes a 3' UTR-embedded Alu element," Proc. Natl. Acad. Sci. USA, 108(40):E794-E802 (2011).
Sasarman, F. et al., "A Novel Mutation in YARS2 Causes Myopathy with Lactic Acidosis and Sideroblastic Anemia," Human Mutation, 00(0):1-6 (2012).
Sato et al., "Synergy and Cross-Tolerance Between Toll-Like Receptor (TLR) 2- and TLR4-Mediated Signaling Pathways," The Journal of Immunology, 165:7096-7101 (2000).
Sauna, Z. E. et al., "Silent polymorhisms speak: How they affect pharmacogenomics and the treatment of cancer," Cancer Res., 67(20):9609-9612 (2007).
Schluesener, H., "Tyrosyl-tRNA Synthetase: A Housekeeping Protein and an Attractive Harbinger of Cellular Death," Angew. Chem. Int. Ed., 38(24):3635-3637 (1999).
Seburn, K. L. et al., "An active dominant mutation of glycyl-tRNA synthetase causes neuropathy in a Charcot-Marie-Tooth 2D mouse model," Neuron, 51(6):715-726 (2006).
Seffernick, et al., "Melamine deaminase and Atrazine chlorohydrolase: 98 percent identical but functionally different," J. Bacteriol., 183(8):2405-2410 (2001).
Sen, S. et al., "Developments in directed evolution for improving enzyme functions," Appl. Biochem. Biotechnol., 143:212-223 (2007).
Shi, K-S, "Differential diagnosis for thrombocytopenia," 19(4):447-450 (2008).
Smith, D. F. et al., "Leukocyte phosphoinositide-3 kinase $\gamma$ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Steer, B. A. et al., "Domain-domain communication in a miniature archaebacterial tRNA synthetase," PNAS, 96(24):13644-13649 (1999).
Steer, B. A. et al., "Major Anticodon-binding Region Missing from an Archaebacterial tRNA Synthetase," The Journal of Biological Chemistry, 274(50):35601-35606 (1999).
Storkebaum, E. et al., "Dominant mutations in the tyrosyl-tRNA synthetase gene recapitulate in *Drosophila* features of human Charcot-Marie-Tooth neuropathy," PNAS, 106(28):11782-11787 (2009).
Stum, M. et al., "An assessment of mechanisms underlying peripheral axonal degeneration caused by aminoacyl-tRNA synthetase mutations," Molecular and Cellular Neuroscience, 46:432-443 (2011).
Sultan, S. M. et al., "Re-classifiyng myositis," Rheumatology, 49:831-833 (2010).
Suzuki, K-I. et al., "Efficient assay for evaluating human thrombopoiesis using NOD/SCID mice transplanted with cord blood CD34 cells," Journal Compilation, 78:123-130 (2006).
Tarabishy, A. B. et al., "Retinal Vasculitis Associated with the Anti-Synthetase Syndrome," Ocular Immunology & Inflamation, 18(1):16-18 (2010).
Targoff, I. N. et al., "Antibodies to glycyl-transfer RNA synthetase in patients with myositis and interstitial lung disease," Arthritis Rheum., 35(7):821-830 (1992).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_2$," Journal of Leukocyte Biology, 76(2):441-450 (2004).
Trischitta, V. et al., "Endocytosis, recycling, and degradation of the insulin receptor," The Journal of Biological Chemistry, 264(9):5041-5046 (1989).
Tsui, H. W. et al., "Transcriptional analyses of the gene region that encodes human histidyl-tRNA sysnthetase: identification of a novel bidirectional regulatory element," Gene, 131:201-208 (1993).
Tzima, E. et al., "Inhibition of tumor angiogenesis by a natural fragment of a tRNA synthetase," TRENDS in Biochemical Sciences, 31(1):7-10 (2006).

(56) References Cited

OTHER PUBLICATIONS

Tzima, E. et al., "Biologically Active Fragment of a Human tRNA Synthetase Inhibits Fluid Shear Stress-activated Respones of Endothelial Cells," Proc. Natl. Acad. Sci. USA, 100(25):14903-14907 (2003).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Vo, M-N. et al., "Dissociating Quaternary Structure Regulates Cell-signaling Functions of a Secreted Human tRNA Synthetase," The Journal of Biological Chemistry, 286(13):11563-11568 (2011).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wakasugi et al., "Highly Differentiated Motifs Responsible for Two Cytokine Activities of a Split Human tRNA Synthetase," The Journal of Biological Chemistry, 274(33):23155-23159 (1999).
Wallace, E. A. et al., "Diagnosis and management of inflammatory muscle disease," The Journal of Musculoskeletal Medicine, 27(12):1-7 (2010).
Wan et al., "Epitope Map for a Growth Hormone Receptor Agonist Monoclonal Antibody, MAb 263," Molecular Endocrinology, 17(11):2240-2250 (2003).
Wasenius, V-M et al., "Hepatocyte Growth Factor Receptor, Matrix Metalloproteinase-11, Tissue Inhibitor of Metalloproteinase-1, and Fibronectin Are Up-Regulated in Papillary Thyroid Carcinoma: A cDNA and Tissue Microarray Study," Clin. Cancer Res., 9:68-75 (2003).
Watkins, "Aminoacyl-tRNA Synthetases for Modulating Hematopoieses," U.S. Appl. No. 13/162,559, filed Jun. 16, 2011.
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Xie et al., "Crystallization and preliminary X-ray analysis of a native human tRNA synthetase whose allelic variants are associated with Charcot-Marie-Tooth disease," Acta. Cryst., F62:1243-1246 (2006).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Crystal structures that suggest late development of genetic code components for differentiating aromatic side chains," PNAS, 100(26):15376-15380 (2003).
Yang, X-L et al., "Gain-of-Function Mutational Activation of Human tRNA Synthetase Procytokine," Chemistry & Biology, 14(12):1323-1333 (2007).
Yokoyama, M. et al., "Effects of lipoprotein lipase and statins on cholesterol uptake into heart and skeletal muscle," J. Lipid Res., 48:646-655 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).
Zeng, R. et al., "Different angiogenesis effect of mini-TyrRS/mini-TrpRS by systemic administration of modified siRNAs in rats with acute myocardial infarction," Heart Vessels, 25:324-332 (2010).
Zeng, R. et al., "Effect of mini-tyrosyl-tRNA synthetase/mini-tryptophanyl-tRNA synthetase on ischemic angiogenesis in rats: proliferation and migration of endothelial cells," Heart Vessels, 26:69-80 (2011).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Guo, H. H., "Protein tolerance to random amino acid change," PNAS, 101(25):9205-9210 (Jun. 22, 2004).
Matthews, B. W., "Structural and genetic analysis of protein stability," Annu. Rev. Biochem., 62:139-160 (1993).

SEQUENCE LISTING

<160> NUMBER OF SEQ ID NOS: 115

<210> SEQ ID NO 1
<211> LENGTH: 528
<212> TYPE: PRT
<213> ORGANISM: Homo sapiens

<400> SEQUENCE: 1

Met Gly Asp Ala Pro Ser Pro Glu Glu Lys Leu His Leu Ile Thr Arg
 1               5                  10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365

```
Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Leu Cys Asn Leu Lys Pro Gln Lys Met Arg
                420                 425                 430

Gly Val Glu Ser Gln Gly Met Leu Leu Cys Ala Ser Ile Glu Gly Ile
                435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
                500                 505                 510

Lys Leu Gly Ser Ile Ser Cys Lys Ser Leu Lys Gly Gly Asn Ile Ser
                515                 520                 525

<210> SEQ ID NO 2
<211> LENGTH: 1587
<212> TYPE: DNA
<213> ORGANISM: Homo sapiens

<400> SEQUENCE: 2
atgggggacg ctcccagccc tgaagagaaa ctgcacctta tcacccggaa cctgcaggag    60
gttctggggg aagagaagct gaaggagata ctgaaggagc gggaacttaa atttactgg   120 ggaacggcaa ccacgggcaa accacatgtg gcttactttg tgcccatgtc aaagattgca   180
gacttcttaa aggcagggtg tgaggtaaca attctgtttg cggacctcca cgcatacctg   240
gataacatga agccccatg gaacttcta gaactccgag tcagttacta tgagaatgtg   300
atcaaagcaa tgctggagag cattggtgtg cccttggaga agctcaagtt catcaaaggc   360
actgattacc agctcagcaa agagtacaca ctagatgtgt acagactctc ctccgtggtc   420
acacagcacg attccaagaa ggctggagct gaggtggtaa agcaggtgga gcacccttg   480 ctgagtggcc tcttataccc cggactgcag gctttggatg aagagtattt aaaagtagat   540
gcccaatttg gaggcattga tcagagaaag atttttcacct ttgcagagaa gtacctccct   600
gcacttggct attcaaaacg ggtccatctg atgaatccta tggttccagg attaacaggc   660
agcaaaatga gctcttcaga agaggagtcc aagattgatc tccttgatcg aaggaggat   720 gtgaagaaaa aactgaagaa ggccttctgt gagccaggaa atgtggagaa caatggggtt   780
ctgtccttca tcaagcatgt ccttttttccc cttaagtccg agtttgtgat cctacgagat   840
gagaaatggg gtgaaacaa aacctacaca gcttacgtgg acctggaaaa ggactttgct   900
gctgaggttg tacatcctgg agacctgaag aattctgttg aagtcgcact gaacaagttg   960
ctggatccaa tccgggaaaa gtttaatacc cctgccctga aaaaactggc cagcgctgcc  1020
tacccagatc cctcaaagca gaagccaatg gccaaaggcc ctgccaagaa ttcagaacca  1080
gaggaggtca tcccatcccg gctggatatc cgtgtgggga aaatcatcac tgtggagaag  1140
cacccagatg cagacagcct gtatgtagag aagattgacg tgggggaagc tgaaccacgg  1200
actgtggtga gcggcctggt acagttcgtg cccaaggagg aactgcagga caggctggta  1260
```

-continued

```
gtggtgctgt gcaacctgaa accccagaag atgagaggag tcgagtccca aggcatgctt    1320
ctgtgtgctt ctatagaagg gataaaccgc caggttgaac ctctggaccc tccggcaggc    1380
tctgctcctg gtgagcacgt gtttgtgaag ggctatgaaa agggccaacc agatgaggag    1440
ctcaagccca agaagaaagt cttcgagaag ttgcaggctg acttcaaaat ttctgaggag    1500
tgcatcgcac agtggaagca aaccaacttc atgaccaagc tgggctccat ttcctgtaaa    1560
tcgctgaaag gggggaacat tagctag                                        1587
```

<210> SEQ ID NO 3
<211> LENGTH: 329
<212> TYPE: PRT
<213> ORGANISM: Homo sapiens

<400> SEQUENCE: 3

```
Met Gly Asp Ala Pro Ser Pro Glu Glu Lys Leu His Leu Ile Thr Arg
 1               5                  10                  15

Asn Leu Gln Glu Val Leu Gly Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
        50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
```

```
                305                 310                 315                 320
Leu Asp Pro Ile Arg Glu Lys Phe Asn
                325

<210> SEQ ID NO 4
<211> LENGTH: 343
<212> TYPE: PRT
<213> ORGANISM: Homo sapiens

<400> SEQUENCE: 4

Met Gly Asp Ala Pro Ser Pro Glu Glu Lys Leu His Leu Ile Thr Arg
  1               5                  10                  15

Asn Leu Gln Glu Val Leu Gly Glu Lys Leu Lys Glu Ile Leu Lys
                 20                  25                  30

Glu Arg Glu Leu Lys Ile Tyr Trp Gly Thr Ala Thr Thr Gly Lys Pro
             35                  40                  45

His Val Ala Tyr Phe Val Pro Met Ser Lys Ile Ala Asp Phe Leu Lys
         50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp
            340
```

```
<210> SEQ ID NO 5
<211> LENGTH: 344
<212> TYPE: PRT
<213> ORGANISM: Homo sapiens

<400> SEQUENCE: 5

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro
            340

<210> SEQ ID NO 6
<211> LENGTH: 350
<212> TYPE: PRT
<213> ORGANISM: Homo sapiens
```

<400> SEQUENCE: 6

| | | | | | | | | | | | | | | | |
|---|---|---|---|---|---|---|---|---|---|---|---|---|---|---|---|
| Met | Gly | Asp | Ala | Pro | Ser | Pro | Glu | Glu | Lys | Leu | His | Leu | Ile | Thr | Arg |
| 1 | | | | 5 | | | | | 10 | | | | | 15 | |
| Asn | Leu | Gln | Glu | Val | Leu | Gly | Glu | Lys | Leu | Lys | Glu | Ile | Leu | Lys | |
| | | | 20 | | | | | 25 | | | | | 30 | | |
| Glu | Arg | Glu | Leu | Lys | Ile | Tyr | Trp | Gly | Thr | Ala | Thr | Thr | Gly | Lys | Pro |
| | | 35 | | | | | 40 | | | | | 45 | | | |
| His | Val | Ala | Tyr | Phe | Val | Pro | Met | Ser | Lys | Ile | Ala | Asp | Phe | Leu | Lys |
| | 50 | | | | | 55 | | | | | 60 | | | | |
| Ala | Gly | Cys | Glu | Val | Thr | Ile | Leu | Phe | Ala | Asp | Leu | His | Ala | Tyr | Leu |
| 65 | | | | | 70 | | | | | 75 | | | | | 80 |
| Asp | Asn | Met | Lys | Ala | Pro | Trp | Glu | Leu | Leu | Glu | Leu | Arg | Val | Ser | Tyr |
| | | | | 85 | | | | | 90 | | | | | 95 | |
| Tyr | Glu | Asn | Val | Ile | Lys | Ala | Met | Leu | Glu | Ser | Ile | Gly | Val | Pro | Leu |
| | | | 100 | | | | | 105 | | | | | 110 | | |
| Glu | Lys | Leu | Lys | Phe | Ile | Lys | Gly | Thr | Asp | Tyr | Gln | Leu | Ser | Lys | Glu |
| | | | | 115 | | | | | 120 | | | | | 125 | |
| Tyr | Thr | Leu | Asp | Val | Tyr | Arg | Leu | Ser | Ser | Val | Val | Thr | Gln | His | Asp |
| | 130 | | | | | 135 | | | | | 140 | | | | |
| Ser | Lys | Lys | Ala | Gly | Ala | Glu | Val | Val | Lys | Gln | Val | Glu | His | Pro | Leu |
| 145 | | | | | 150 | | | | | 155 | | | | | 160 |
| Leu | Ser | Gly | Leu | Leu | Tyr | Pro | Gly | Leu | Gln | Ala | Leu | Asp | Glu | Glu | Tyr |
| | | | | 165 | | | | | 170 | | | | | 175 | |
| Leu | Lys | Val | Asp | Ala | Gln | Phe | Gly | Gly | Ile | Asp | Gln | Arg | Lys | Ile | Phe |
| | | | 180 | | | | | 185 | | | | | 190 | | |
| Thr | Phe | Ala | Glu | Lys | Tyr | Leu | Pro | Ala | Leu | Gly | Tyr | Ser | Lys | Arg | Val |
| | | 195 | | | | | 200 | | | | | 205 | | | |
| His | Leu | Met | Asn | Pro | Met | Val | Pro | Gly | Leu | Thr | Gly | Ser | Lys | Met | Ser |
| | 210 | | | | | 215 | | | | | 220 | | | | |
| Ser | Ser | Glu | Glu | Ser | Lys | Ile | Asp | Leu | Leu | Asp | Arg | Lys | Glu | Asp | |
| 225 | | | | | 230 | | | | | 235 | | | | | 240 |
| Val | Lys | Lys | Leu | Lys | Lys | Ala | Phe | Cys | Glu | Pro | Gly | Asn | Val | Glu | |
| | | | | 245 | | | | | 250 | | | | | 255 | |
| Asn | Asn | Gly | Val | Leu | Ser | Phe | Ile | Lys | His | Val | Leu | Phe | Pro | Leu | Lys |
| | | | 260 | | | | | 265 | | | | | 270 | | |
| Ser | Glu | Phe | Val | Ile | Leu | Arg | Asp | Glu | Lys | Trp | Gly | Gly | Asn | Lys | Thr |
| | | 275 | | | | | 280 | | | | | 285 | | | |
| Tyr | Thr | Ala | Tyr | Val | Asp | Leu | Glu | Lys | Asp | Phe | Ala | Ala | Glu | Val | Val |
| | 290 | | | | | 295 | | | | | 300 | | | | |
| His | Pro | Gly | Asp | Leu | Lys | Asn | Ser | Val | Glu | Val | Ala | Leu | Asn | Lys | Leu |
| 305 | | | | | 310 | | | | | 315 | | | | | 320 |
| Leu | Asp | Pro | Ile | Arg | Glu | Lys | Phe | Asn | Thr | Pro | Ala | Leu | Lys | Lys | Leu |
| | | | | 325 | | | | | 330 | | | | | 335 | |
| Ala | Ser | Ala | Ala | Tyr | Pro | Asp | Pro | Ser | Lys | Gln | Lys | Pro | Met | | |
| | | | 340 | | | | | 345 | | | | | 350 | | |

<210> SEQ ID NO 7
<211> LENGTH: 353
<212> TYPE: PRT
<213> ORGANISM: Homo sapiens

<400> SEQUENCE: 7

| | | | | | | | | | | | | | | | |
|---|---|---|---|---|---|---|---|---|---|---|---|---|---|---|---|
| Met | Gly | Asp | Ala | Pro | Ser | Pro | Glu | Glu | Lys | Leu | His | Leu | Ile | Thr | Arg |
| 1 | | | | 5 | | | | | 10 | | | | | 15 | |

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Gly Lys Pro
        35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
 210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly

<210> SEQ ID NO 8
<211> LENGTH: 364
<212> TYPE: PRT
<213> ORGANISM: Homo sapiens

<400> SEQUENCE: 8

Met Gly Asp Ala Pro Ser Pro Glu Glu Lys Leu His Leu Ile Thr Arg
 1               5                  10                  15

Asn Leu Gln Glu Val Leu Gly Glu Glu Lys Leu Lys Glu Ile Leu Lys
            20                  25                  30

```
Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile
        355                 360

<210> SEQ ID NO 9
<211> LENGTH: 368
<212> TYPE: PRT
<213> ORGANISM: Homo sapiens

<400> SEQUENCE: 9

Met Gly Asp Ala Pro Ser Pro Glu Glu Lys Leu His Leu Ile Thr Arg
 1               5                  10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Thr Gly Lys Pro
```

```
            35                  40                  45
His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Gly Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365

<210> SEQ ID NO 10
<211> LENGTH: 382
<212> TYPE: PRT
<213> ORGANISM: Homo sapiens

<400> SEQUENCE: 10

Met Gly Asp Ala Pro Ser Pro Glu Glu Lys Leu His Leu Ile Thr Arg
 1               5                  10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45
```

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
             100                 105                 110

Glu Lys Leu Lys Phe Ile Lys Gly Thr Asp Tyr Gln Leu Ser Lys Glu
         115                 120                 125

Tyr Thr Leu Asp Val Tyr Arg Leu Ser Ser Val Val Thr Gln His Asp
130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                 165                 170                 175

Leu Lys Val Asp Ala Gln Phe Gly Gly Ile Asp Gln Arg Lys Ile Phe
             180                 185                 190

Thr Phe Ala Glu Lys Tyr Leu Pro Ala Leu Gly Tyr Ser Lys Arg Val
         195                 200                 205

His Leu Met Asn Pro Met Val Pro Gly Leu Thr Gly Ser Lys Met Ser
210                 215                 220

Ser Ser Glu Glu Glu Ser Lys Ile Asp Leu Leu Asp Arg Lys Glu Asp
225                 230                 235                 240

Val Lys Lys Lys Leu Lys Ala Phe Cys Glu Pro Gly Asn Val Glu
                 245                 250                 255

Asn Asn Gly Val Leu Ser Phe Ile Lys His Val Leu Phe Pro Leu Lys
             260                 265                 270

Ser Glu Phe Val Ile Leu Arg Asp Glu Lys Trp Gly Gly Asn Lys Thr
         275                 280                 285

Tyr Thr Ala Tyr Val Asp Leu Glu Lys Asp Phe Ala Ala Glu Val Val
         290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                 325                 330                 335

Ala Ser Ala Ala Tyr Pro Asp Pro Ser Lys Gln Lys Pro Met Ala Lys
             340                 345                 350

Gly Pro Ala Lys Asn Ser Glu Pro Glu Glu Val Ile Pro Ser Arg Leu
         355                 360                 365

Asp Ile Arg Val Gly Lys Ile Ile Thr Val Glu Lys His Pro
370                 375                 380

<210> SEQ ID NO 11
<211> LENGTH: 388
<212> TYPE: PRT
<213> ORGANISM: Homo sapiens

<400> SEQUENCE: 11

Met Gly Asp Ala Pro Ser Pro Glu Glu Lys Leu His Leu Ile Thr Arg
  1               5                  10                  15

Asn Leu Gln Glu Val Leu Gly Glu Lys Leu Lys Glu Ile Leu Lys
             20                  25                  30

Glu Arg Glu Leu Lys Ile Tyr Trp Gly Thr Ala Thr Thr Gly Lys Pro
         35                  40                  45

His Val Ala Tyr Phe Val Pro Met Ser Lys Ile Ala Asp Phe Leu Lys
                50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
        130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Tyr
                165                 170                 175

Leu Lys Val Asp Ala Gln Phe Gly Gly Ile Asp Gln Arg Lys Ile Phe
                180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
        210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
        290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Val Ile Pro Ser Arg Leu
            355                 360                 365

Asp Ile Arg Val Gly Lys Ile Ile Thr Val Glu Lys His Pro Asp Ala
370                 375                 380

Asp Ser Leu Tyr
385

<210> SEQ ID NO 12
<211> LENGTH: 395
<212> TYPE: PRT
<213> ORGANISM: Homo sapiens

<400> SEQUENCE: 12

Met Gly Asp Ala Pro Ser Pro Glu Glu Lys Leu His Leu Ile Thr Arg
 1               5                   10                  15

Asn Leu Gln Glu Val Leu Gly Glu Glu Lys Leu Lys Glu Ile Leu Lys

```
                20                  25                  30
Glu Arg Glu Leu Lys Ile Tyr Trp Gly Thr Ala Thr Thr Gly Lys Pro
                35                  40                  45

His Val Ala Tyr Phe Val Pro Met Ser Lys Ile Ala Asp Phe Leu Lys
         50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Glu Leu Arg Val Ser Tyr
                 85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Thr Gln His Asp
            130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
                180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
            290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Val Ile Pro Ser Arg Leu
            355                 360                 365

Asp Ile Arg Val Gly Lys Ile Ile Thr Val Glu Lys His Pro Asp Ala
            370                 375                 380

Asp Ser Leu Tyr Val Glu Lys Ile Asp Val Gly
385                 390                 395

<210> SEQ ID NO 13
<211> LENGTH: 266
<212> TYPE: PRT
<213> ORGANISM: Homo sapiens

<400> SEQUENCE: 13
```

```
Asp Asn Met Lys Ala Pro Trp Glu Leu Leu Glu Leu Arg Val Ser Tyr
1               5                   10                  15

Tyr Glu Asn Val Ile Lys Ala Met Leu Glu Ser Ile Gly Val Pro Leu
            20                  25                  30

Glu Lys Leu Lys Phe Ile Lys Gly Thr Asp Tyr Gln Leu Ser Lys Glu
        35                  40                  45

Tyr Thr Leu Asp Val Tyr Arg Leu Ser Ser Val Val Thr Gln His Asp
    50                  55                  60

Ser Lys Lys Ala Gly Ala Glu Val Val Lys Gln Val Glu His Pro Leu
65                  70                  75                  80

Leu Ser Gly Leu Leu Tyr Pro Gly Leu Gln Ala Leu Asp Glu Glu Tyr
                85                  90                  95

Leu Lys Val Asp Ala Gln Phe Gly Gly Ile Asp Gln Arg Lys Ile Phe
                100                 105                 110

Thr Phe Ala Glu Lys Tyr Leu Pro Ala Leu Gly Tyr Ser Lys Arg Val
            115                 120                 125

His Leu Met Asn Pro Met Val Pro Gly Leu Thr Gly Ser Lys Met Ser
        130                 135                 140

Ser Ser Glu Glu Glu Ser Lys Ile Asp Leu Leu Asp Arg Lys Glu Asp
145                 150                 155                 160

Val Lys Lys Lys Leu Lys Lys Ala Phe Cys Glu Pro Gly Asn Val Glu
                165                 170                 175

Asn Asn Gly Val Leu Ser Phe Ile Lys His Val Leu Phe Pro Leu Lys
                180                 185                 190

Ser Glu Phe Val Ile Leu Arg Asp Glu Lys Trp Gly Gly Asn Lys Thr
            195                 200                 205

Tyr Thr Ala Tyr Val Asp Leu Glu Lys Asp Phe Ala Ala Glu Val Val
    210                 215                 220

His Pro Gly Asp Leu Lys Asn Ser Val Glu Val Ala Leu Asn Lys Leu
225                 230                 235                 240

Leu Asp Pro Ile Arg Glu Lys Phe Asn Thr Pro Ala Leu Lys Lys Leu
                245                 250                 255

Ala Ser Ala Ala Tyr Pro Asp Pro Ser Lys
                260                 265

<210> SEQ ID NO 14
<211> LENGTH: 260
<212> TYPE: PRT
<213> ORGANISM: Homo sapiens

<400> SEQUENCE: 14

Trp Glu Leu Leu Glu Leu Arg Val Ser Tyr Tyr Glu Asn Val Ile Lys
1               5                   10                  15

Ala Met Leu Glu Ser Ile Gly Val Pro Leu Glu Lys Leu Lys Phe Ile
            20                  25                  30

Lys Gly Thr Asp Tyr Gln Leu Ser Lys Glu Tyr Thr Leu Asp Val Tyr
        35                  40                  45

Arg Leu Ser Ser Val Val Thr Gln His Asp Ser Lys Lys Ala Gly Ala
    50                  55                  60

Glu Val Val Lys Gln Val Glu His Pro Leu Leu Ser Gly Leu Leu Tyr
65                  70                  75                  80

Pro Gly Leu Gln Ala Leu Asp Glu Glu Tyr Leu Lys Val Asp Ala Gln
                85                  90                  95

Phe Gly Gly Ile Asp Gln Arg Lys Ile Phe Thr Phe Ala Glu Lys Tyr
                100                 105                 110
```

```
Leu Pro Ala Leu Gly Tyr Ser Lys Arg Val His Leu Met Asn Pro Met
            115                 120                 125

Val Pro Gly Leu Thr Gly Ser Lys Met Ser Ser Glu Glu Glu Ser
        130                 135                 140

Lys Ile Asp Leu Leu Asp Arg Lys Glu Asp Val Lys Lys Leu Lys
145                 150                 155                 160

Lys Ala Phe Cys Glu Pro Gly Asn Val Glu Asn Asn Gly Val Leu Ser
            165                 170                 175

Phe Ile Lys His Val Leu Phe Pro Leu Lys Ser Glu Phe Val Ile Leu
                180                 185                 190

Arg Asp Glu Lys Trp Gly Gly Asn Lys Thr Tyr Thr Ala Tyr Val Asp
            195                 200                 205

Leu Glu Lys Asp Phe Ala Ala Glu Val Val His Pro Gly Asp Leu Lys
        210                 215                 220

Asn Ser Val Glu Val Ala Leu Asn Lys Leu Leu Asp Pro Ile Arg Glu
225                 230                 235                 240

Lys Phe Asn Thr Pro Ala Leu Lys Lys Leu Ala Ser Ala Ala Tyr Pro
                245                 250                 255

Asp Pro Ser Lys
            260

<210> SEQ ID NO 15
<211> LENGTH: 201
<212> TYPE: PRT
<213> ORGANISM: Homo sapiens

<400> SEQUENCE: 15

Phe Asn Thr Pro Ala Leu Lys Lys Leu Ala Ser Ala Ala Tyr Pro Asp
1               5                   10                  15

Pro Ser Lys Gln Lys Pro Met Ala Lys Gly Pro Ala Lys Asn Ser Glu
            20                  25                  30

Pro Glu Glu Val Ile Pro Ser Arg Leu Asp Ile Arg Val Gly Lys Ile
        35                  40                  45

Ile Thr Val Glu Lys His Pro Asp Ala Asp Ser Leu Tyr Val Glu Lys
50                  55                  60

Ile Asp Val Gly Glu Ala Glu Pro Arg Thr Val Val Ser Gly Leu Val
65                  70                  75                  80

Gln Phe Val Pro Lys Glu Glu Leu Gln Asp Arg Leu Val Val Val Leu
                85                  90                  95

Cys Asn Leu Lys Pro Gln Lys Met Arg Gly Val Glu Ser Gln Gly Met
            100                 105                 110

Leu Leu Cys Ala Ser Ile Glu Gly Ile Asn Arg Gln Val Glu Pro Leu
        115                 120                 125

Asp Pro Pro Ala Gly Ser Ala Pro Gly Glu His Val Phe Val Lys Gly
    130                 135                 140

Tyr Glu Lys Gly Gln Pro Asp Glu Glu Leu Lys Pro Lys Lys Val
145                 150                 155                 160

Phe Glu Lys Leu Gln Ala Asp Phe Lys Ile Ser Glu Glu Cys Ile Ala
            165                 170                 175

Gln Trp Lys Gln Thr Asn Phe Met Thr Lys Leu Gly Ser Ile Ser Cys
            180                 185                 190

Lys Ser Leu Lys Gly Gly Asn Ile Ser
                195                 200
```

```
<210> SEQ ID NO 16
<211> LENGTH: 189
<212> TYPE: PRT
<213> ORGANISM: Homo sapiens

<400> SEQUENCE: 16

Ala Tyr Pro Asp Pro Ser Lys Gln Lys Pro Met Ala Lys Gly Pro Ala
 1               5                  10                  15

Lys Asn Ser Glu Pro Glu Glu Val Ile Pro Ser Arg Leu Asp Ile Arg
            20                  25                  30

Val Gly Lys Ile Ile Thr Val Glu Lys His Pro Asp Ala Asp Ser Leu
        35                  40                  45

Tyr Val Glu Lys Ile Asp Val Gly Glu Ala Glu Pro Arg Thr Val Val
 50                  55                  60

Ser Gly Leu Val Gln Phe Val Pro Lys Glu Glu Leu Gln Asp Arg Leu
65                  70                  75                  80

Val Val Val Leu Cys Asn Leu Lys Pro Gln Lys Met Arg Gly Val Glu
                85                  90                  95

Ser Gln Gly Met Leu Leu Cys Ala Ser Ile Glu Gly Ile Asn Arg Gln
            100                 105                 110

Val Glu Pro Leu Asp Pro Pro Ala Gly Ser Ala Pro Gly Glu His Val
        115                 120                 125

Phe Val Lys Gly Tyr Glu Lys Gly Gln Pro Asp Glu Glu Leu Lys Pro
130                 135                 140

Lys Lys Lys Val Phe Glu Lys Leu Gln Ala Asp Phe Lys Ile Ser Glu
145                 150                 155                 160

Glu Cys Ile Ala Gln Trp Lys Gln Thr Asn Phe Met Thr Lys Leu Gly
                165                 170                 175

Ser Ile Ser Cys Lys Ser Leu Lys Gly Gly Asn Ile Ser
            180                 185

<210> SEQ ID NO 17
<211> LENGTH: 168
<212> TYPE: PRT
<213> ORGANISM: Homo sapiens

<400> SEQUENCE: 17

Glu Glu Val Ile Pro Ser Arg Leu Asp Ile Arg Val Gly Lys Ile Ile
 1               5                  10                  15

Thr Val Glu Lys His Pro Asp Ala Asp Ser Leu Tyr Val Glu Lys Ile
            20                  25                  30

Asp Val Gly Glu Ala Glu Pro Arg Thr Val Val Ser Gly Leu Val Gln
        35                  40                  45

Phe Val Pro Lys Glu Glu Leu Gln Asp Arg Leu Val Val Val Leu Cys
 50                  55                  60

Asn Leu Lys Pro Gln Lys Met Arg Gly Val Glu Ser Gln Gly Met Leu
65                  70                  75                  80

Leu Cys Ala Ser Ile Glu Gly Ile Asn Arg Gln Val Glu Pro Leu Asp
                85                  90                  95

Pro Pro Ala Gly Ser Ala Pro Gly Glu His Val Phe Val Lys Gly Tyr
            100                 105                 110

Glu Lys Gly Gln Pro Asp Glu Glu Leu Lys Pro Lys Lys Lys Val Phe
        115                 120                 125

Glu Lys Leu Gln Ala Asp Phe Lys Ile Ser Glu Glu Cys Ile Ala Gln
130                 135                 140

Trp Lys Gln Thr Asn Phe Met Thr Lys Leu Gly Ser Ile Ser Cys Lys
```

```
145                 150                 155                 160
Ser Leu Lys Gly Gly Asn Ile Ser
                165
```

```
<210> SEQ ID NO 18
<211> LENGTH: 139
<212> TYPE: PRT
<213> ORGANISM: Homo sapiens

<400> SEQUENCE: 18

Glu Lys Ile Asp Val Gly Glu Ala Glu Pro Arg Thr Val Val Ser Gly
1               5                   10                  15

Leu Val Gln Phe Val Pro Lys Glu Glu Leu Gln Asp Arg Leu Val Val
            20                  25                  30

Val Leu Cys Asn Leu Lys Pro Gln Lys Met Arg Gly Val Glu Ser Gln
        35                  40                  45

Gly Met Leu Leu Cys Ala Ser Ile Glu Gly Ile Asn Arg Gln Val Glu
    50                  55                  60

Pro Leu Asp Pro Pro Ala Gly Ser Ala Pro Gly Glu His Val Phe Val
65                  70                  75                  80

Lys Gly Tyr Glu Lys Gly Gln Pro Asp Glu Glu Leu Lys Pro Lys Lys
                85                  90                  95

Lys Val Phe Glu Lys Leu Gln Ala Asp Phe Lys Ile Ser Glu Glu Cys
            100                 105                 110

Ile Ala Gln Trp Lys Gln Thr Asn Phe Met Thr Lys Leu Gly Ser Ile
        115                 120                 125

Ser Cys Lys Ser Leu Lys Gly Gly Asn Ile Ser
    130                 135
```

```
<210> SEQ ID NO 19
<211> LENGTH: 60
<212> TYPE: PRT
<213> ORGANISM: Homo sapiens

<400> SEQUENCE: 19

Met Gly Asp Ala Pro Ser Pro Glu Glu Lys Leu His Leu Ile Thr Arg
1               5                   10                  15

Asn Leu Gln Ser Gln Trp Pro Lys Ala Leu Pro Arg Ile Gln Asn Gln
            20                  25                  30

Arg Arg Ser Ser His Pro Gly Trp Ile Ser Val Trp Gly Lys Ser Ser
        35                  40                  45

Leu Trp Arg Ser Thr Gln Met Gln Thr Ala Cys Met
    50                  55                  60
```

```
<210> SEQ ID NO 20
<211> LENGTH: 348
<212> TYPE: PRT
<213> ORGANISM: Homo sapiens

<400> SEQUENCE: 20

Met Pro Asn Leu Glu Ala Leu Ile Arg Glu Ile Phe Thr Phe Ala Glu
1               5                   10                  15

Lys Tyr Leu Pro Ala Leu Gly Tyr Ser Lys Arg Val His Leu Met Asn
            20                  25                  30

Pro Met Val Pro Gly Leu Thr Gly Ser Lys Met Ser Ser Ser Glu Glu
        35                  40                  45

Glu Ser Lys Ile Asp Leu Leu Asp Arg Lys Glu Asp Val Lys Lys Lys
    50                  55                  60
```

Leu Lys Lys Ala Phe Cys Glu Pro Gly Asn Val Glu Asn Asn Gly Val
65                  70                  75                  80

Leu Ser Phe Ile Lys His Val Leu Phe Pro Leu Lys Ser Glu Phe Val
            85                  90                  95

Ile Leu Arg Asp Glu Lys Trp Gly Gly Asn Lys Thr Tyr Thr Ala Tyr
            100                 105                 110

Val Asp Leu Glu Lys Asp Phe Ala Ala Glu Val Val His Pro Gly Asp
            115                 120                 125

Leu Lys Asn Ser Val Glu Val Ala Leu Asn Lys Leu Leu Asp Pro Ile
            130                 135                 140

Arg Glu Lys Phe Asn Thr Pro Ala Leu Lys Lys Leu Ala Ser Ala Ala
145                 150                 155                 160

Tyr Pro Asp Pro Ser Lys Gln Lys Pro Met Ala Lys Gly Pro Ala Lys
                165                 170                 175

Asn Ser Glu Pro Glu Glu Val Ile Pro Ser Arg Leu Asp Ile Arg Val
            180                 185                 190

Gly Lys Ile Ile Thr Val Glu Lys His Pro Asp Ala Asp Ser Leu Tyr
            195                 200                 205

Val Glu Lys Ile Asp Val Gly Glu Ala Glu Pro Arg Thr Val Val Ser
            210                 215                 220

Gly Leu Val Gln Phe Val Pro Lys Glu Leu Gln Asp Arg Leu Val
225                 230                 235                 240

Val Val Leu Cys Asn Leu Lys Pro Gln Lys Met Arg Gly Val Glu Ser
                245                 250                 255

Gln Gly Met Leu Leu Cys Ala Ser Ile Glu Gly Ile Asn Arg Gln Val
            260                 265                 270

Glu Pro Leu Asp Pro Pro Ala Gly Ser Ala Pro Gly Glu His Val Phe
            275                 280                 285

Val Lys Gly Tyr Glu Lys Gly Gln Pro Asp Glu Glu Leu Lys Pro Lys
            290                 295                 300

Lys Lys Val Phe Glu Lys Leu Gln Ala Asp Phe Lys Ile Ser Glu Glu
305                 310                 315                 320

Cys Ile Ala Gln Trp Lys Gln Thr Asn Phe Met Thr Lys Leu Gly Ser
                325                 330                 335

Ile Ser Cys Lys Ser Leu Lys Gly Gly Asn Ile Ser
                340                 345

<210> SEQ ID NO 21
<211> LENGTH: 388
<212> TYPE: PRT
<213> ORGANISM: Homo sapiens

<400> SEQUENCE: 21

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Gly Lys Pro
            35                  40                  45

His Val Ala Tyr Phe Val Pro Met Ser Lys Ile Ala Asp Phe Leu Lys
            50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr

```
                     85                  90                  95
Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Thr Gln His Asp
    130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Leu Pro Arg Ile Gln Asn Gln Arg Arg Ser Ser His Pro Gly Trp
        355                 360                 365

Ile Ser Val Trp Gly Lys Ser Ser Leu Trp Arg Ser Thr Gln Met Gln
    370                 375                 380

Thr Ala Cys Met
385

<210> SEQ ID NO 22
<211> LENGTH: 318
<212> TYPE: PRT
<213> ORGANISM: Homo sapiens

<400> SEQUENCE: 22

Met Asn Pro Met Val Pro Gly Leu Thr Gly Ser Lys Met Ser Ser Ser
1               5                   10                  15

Glu Glu Glu Ser Lys Ile Asp Leu Leu Asp Arg Lys Glu Asp Val Lys
            20                  25                  30

Lys Lys Leu Lys Lys Ala Phe Cys Glu Pro Gly Asn Val Glu Asn Asn
        35                  40                  45

Gly Val Leu Ser Phe Ile Lys His Val Leu Phe Pro Leu Lys Ser Glu
    50                  55                  60
```

```
Phe Val Ile Leu Arg Asp Glu Lys Trp Gly Gly Asn Lys Thr Tyr Thr
 65                  70                  75                  80

Ala Tyr Val Asp Leu Glu Lys Asp Phe Ala Ala Glu Val Val His Pro
                 85                  90                  95

Gly Asp Leu Lys Asn Ser Val Glu Val Ala Leu Asn Lys Leu Leu Asp
            100                 105                 110

Pro Ile Arg Glu Lys Phe Asn Thr Pro Ala Leu Lys Lys Leu Ala Ser
        115                 120                 125

Ala Ala Tyr Pro Asp Pro Ser Lys Gln Lys Pro Met Ala Lys Gly Pro
    130                 135                 140

Ala Lys Asn Ser Glu Pro Glu Val Ile Pro Ser Arg Leu Asp Ile
145                 150                 155                 160

Arg Val Gly Lys Ile Ile Thr Val Glu Lys His Pro Asp Ala Asp Ser
                165                 170                 175

Leu Tyr Val Glu Lys Ile Asp Val Gly Glu Ala Glu Pro Arg Thr Val
            180                 185                 190

Val Ser Gly Leu Val Gln Phe Val Pro Lys Glu Glu Leu Gln Asp Arg
        195                 200                 205

Leu Val Val Val Leu Cys Asn Leu Lys Pro Gln Lys Met Arg Gly Val
    210                 215                 220

Glu Ser Gln Gly Met Leu Leu Cys Ala Ser Ile Glu Gly Ile Asn Arg
225                 230                 235                 240

Gln Val Glu Pro Leu Asp Pro Ala Gly Ser Ala Pro Gly Glu His
                245                 250                 255

Val Phe Val Lys Gly Tyr Glu Lys Gly Gln Pro Asp Glu Glu Leu Lys
            260                 265                 270

Pro Lys Lys Lys Val Phe Glu Lys Leu Gln Ala Asp Phe Lys Ile Ser
        275                 280                 285

Glu Glu Cys Ile Ala Gln Trp Lys Gln Thr Asn Phe Met Thr Lys Leu
    290                 295                 300

Gly Ser Ile Ser Cys Lys Ser Leu Lys Gly Gly Asn Ile Ser
305                 310                 315

<210> SEQ ID NO 23
<211> LENGTH: 179
<212> TYPE: PRT
<213> ORGANISM: Homo sapiens

<400> SEQUENCE: 23

Met Ala Lys Gly Pro Ala Lys Asn Ser Glu Pro Glu Glu Val Ile Pro
  1               5                  10                  15

Ser Arg Leu Asp Ile Arg Val Gly Lys Ile Ile Thr Val Glu Lys His
                 20                  25                  30

Pro Asp Ala Asp Ser Leu Tyr Val Glu Lys Ile Asp Val Gly Glu Ala
             35                  40                  45

Glu Pro Arg Thr Val Val Ser Gly Leu Val Gln Phe Val Pro Lys Glu
         50                  55                  60

Glu Leu Gln Asp Arg Leu Val Val Val Leu Cys Asn Leu Lys Pro Gln
 65                  70                  75                  80

Lys Met Arg Gly Val Glu Ser Gln Gly Met Leu Leu Cys Ala Ser Ile
                 85                  90                  95

Glu Gly Ile Asn Arg Gln Val Glu Pro Leu Asp Pro Ala Gly Ser
            100                 105                 110

Ala Pro Gly Glu His Val Phe Val Lys Gly Tyr Glu Lys Gly Gln Pro
        115                 120                 125
```

```
Asp Glu Glu Leu Lys Pro Lys Lys Val Phe Glu Lys Leu Gln Ala
            130                 135                 140

Asp Phe Lys Ile Ser Glu Glu Cys Ile Ala Gln Trp Lys Gln Thr Asn
145                 150                 155                 160

Phe Met Thr Lys Leu Gly Ser Ile Ser Cys Lys Ser Leu Lys Gly Gly
                165                 170                 175

Asn Ile Ser

<210> SEQ ID NO 24
<211> LENGTH: 188
<212> TYPE: PRT
<213> ORGANISM: Homo sapiens

<400> SEQUENCE: 24

Met Gly Phe Phe Ser Phe Pro Glu Pro Met Ala Lys Gly Pro Ala Lys
1               5                   10                  15

Asn Ser Glu Pro Glu Glu Val Ile Pro Ser Arg Leu Asp Ile Arg Val
            20                  25                  30

Gly Lys Ile Ile Thr Val Glu Lys His Pro Asp Ala Asp Ser Leu Tyr
        35                  40                  45

Val Glu Lys Ile Asp Val Gly Glu Ala Glu Pro Arg Thr Val Val Ser
    50                  55                  60

Gly Leu Val Gln Phe Val Pro Lys Glu Glu Leu Gln Asp Arg Leu Val
65                  70                  75                  80

Val Val Leu Cys Asn Leu Lys Pro Gln Lys Met Arg Gly Val Glu Ser
                85                  90                  95

Gln Gly Met Leu Leu Cys Ala Ser Ile Glu Gly Ile Asn Arg Gln Val
            100                 105                 110

Glu Pro Leu Asp Pro Pro Ala Gly Ser Ala Pro Gly Glu His Val Phe
        115                 120                 125

Val Lys Gly Tyr Glu Lys Gly Gln Pro Asp Glu Glu Leu Lys Pro Lys
    130                 135                 140

Lys Lys Val Phe Glu Lys Leu Gln Ala Asp Phe Lys Ile Ser Glu Glu
145                 150                 155                 160

Cys Ile Ala Gln Trp Lys Gln Thr Asn Phe Met Thr Lys Leu Gly Ser
                165                 170                 175

Ile Ser Cys Lys Ser Leu Lys Gly Gly Asn Ile Ser
            180                 185

<210> SEQ ID NO 25
<211> LENGTH: 377
<212> TYPE: PRT
<213> ORGANISM: Homo sapiens

<400> SEQUENCE: 25

Met Gly Asp Ala Pro Ser Pro Glu Glu Lys Leu His Leu Ile Thr Arg
1               5                   10                  15

Asn Leu Gln Ala Leu Asp Glu Glu Tyr Leu Lys Val Asp Ala Gln Phe
            20                  25                  30

Gly Gly Ile Asp Gln Arg Lys Ile Phe Thr Phe Ala Glu Lys Tyr Leu
        35                  40                  45

Pro Ala Leu Gly Tyr Ser Lys Arg Val His Leu Met Asn Pro Met Val
    50                  55                  60

Pro Gly Leu Thr Gly Ser Lys Met Ser Ser Ser Glu Glu Glu Ser Lys
65                  70                  75                  80
```

```
Ile Asp Leu Leu Asp Arg Lys Glu Asp Val Lys Lys Leu Lys Lys
            85                  90                  95
Ala Phe Cys Glu Pro Gly Asn Val Glu Asn Asn Gly Val Leu Ser Phe
        100                 105                 110
Ile Lys His Val Leu Phe Pro Leu Lys Ser Glu Phe Val Ile Leu Arg
        115                 120                 125
Asp Glu Lys Trp Gly Gly Asn Lys Thr Tyr Thr Ala Tyr Val Asp Leu
    130                 135                 140
Glu Lys Asp Phe Ala Ala Glu Val Val His Pro Gly Asp Leu Lys Asn
145                 150                 155                 160
Ser Val Glu Val Ala Leu Asn Lys Leu Leu Asp Pro Ile Arg Glu Lys
                165                 170                 175
Phe Asn Thr Pro Ala Leu Lys Lys Leu Ala Ser Ala Ala Tyr Pro Asp
            180                 185                 190
Pro Ser Lys Gln Lys Pro Met Ala Lys Gly Pro Ala Lys Asn Ser Glu
        195                 200                 205
Pro Glu Glu Val Ile Pro Ser Arg Leu Asp Ile Arg Val Gly Lys Ile
    210                 215                 220
Ile Thr Val Glu Lys His Pro Asp Ala Asp Ser Leu Tyr Val Glu Lys
225                 230                 235                 240
Ile Asp Val Gly Glu Ala Glu Pro Arg Thr Val Val Ser Gly Leu Val
                245                 250                 255
Gln Phe Val Pro Lys Glu Glu Leu Gln Asp Arg Leu Val Val Val Leu
            260                 265                 270
Cys Asn Leu Lys Pro Gln Lys Met Arg Gly Val Glu Ser Gln Gly Met
        275                 280                 285
Leu Leu Cys Ala Ser Ile Glu Gly Ile Asn Arg Gln Val Glu Pro Leu
    290                 295                 300
Asp Pro Pro Ala Gly Ser Ala Pro Gly Glu His Val Phe Val Lys Gly
305                 310                 315                 320
Tyr Glu Lys Gly Gln Pro Asp Glu Glu Leu Lys Pro Lys Lys Lys Val
                325                 330                 335
Phe Glu Lys Leu Gln Ala Asp Phe Lys Ile Ser Glu Glu Cys Ile Ala
            340                 345                 350
Gln Trp Lys Gln Thr Asn Phe Met Thr Lys Leu Gly Ser Ile Ser Cys
        355                 360                 365
Lys Ser Leu Lys Gly Gly Asn Ile Ser
    370                 375

<210> SEQ ID NO 26
<211> LENGTH: 454
<212> TYPE: PRT
<213> ORGANISM: Homo sapiens

<400> SEQUENCE: 26

Met Gly Asp Ala Pro Ser Pro Glu Glu Lys Leu His Leu Ile Thr Arg
1               5                   10                  15
Asn Leu Gln Glu Val Leu Gly Glu Glu Lys Leu Lys Glu Ile Leu Lys
            20                  25                  30
Glu Arg Glu Leu Lys Ile Tyr Trp Gly Thr Ala Thr Thr Gly Lys Pro
        35                  40                  45
His Val Ala Tyr Phe Val Pro Met Ser Lys Ile Ala Asp Phe Leu Lys
    50                  55                  60
Ala Gly Cys Glu Val Thr Ile Leu Phe Ala Asp Leu His Ala Tyr Leu
65                  70                  75                  80
```

-continued

Asp Asn Met Lys Ala Pro Trp Glu Leu Leu Glu Leu Arg Val Ser Tyr
            85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
                180                 185                 190

Thr Phe Ala Glu Lys Tyr Leu Pro Ala Leu Gly Tyr Ser Lys Arg Val
                195                 200                 205

His Leu Met Asn Pro Met Val Pro Gly Leu Thr Gly Ser Lys Met Ser
            210                 215                 220

Ser Ser Glu Glu Val Val His Pro Gly Asp Leu Lys Asn Ser Val Glu
225                 230                 235                 240

Val Ala Leu Asn Lys Leu Leu Asp Pro Ile Arg Glu Lys Phe Asn Thr
                245                 250                 255

Pro Ala Leu Lys Lys Leu Ala Ser Ala Ala Tyr Pro Asp Pro Ser Lys
                260                 265                 270

Gln Lys Pro Met Ala Lys Gly Pro Ala Lys Asn Ser Glu Pro Glu Glu
                275                 280                 285

Val Ile Pro Ser Arg Leu Asp Ile Arg Val Gly Lys Ile Ile Thr Val
            290                 295                 300

Glu Lys His Pro Asp Ala Asp Ser Leu Tyr Val Glu Lys Ile Asp Val
305                 310                 315                 320

Gly Glu Ala Glu Pro Arg Thr Val Val Ser Gly Leu Val Gln Phe Val
                325                 330                 335

Pro Lys Glu Glu Leu Gln Asp Arg Leu Val Val Val Leu Cys Asn Leu
                340                 345                 350

Lys Pro Gln Lys Met Arg Gly Val Glu Ser Gln Gly Met Leu Leu Cys
                355                 360                 365

Ala Ser Ile Glu Gly Ile Asn Arg Gln Val Pro Leu Asp Pro Pro
370                 375                 380

Ala Gly Ser Ala Pro Gly Glu His Val Phe Val Lys Gly Tyr Glu Lys
385                 390                 395                 400

Gly Gln Pro Asp Glu Glu Leu Lys Pro Lys Lys Val Phe Glu Lys
                405                 410                 415

Leu Gln Ala Asp Phe Lys Ile Ser Glu Glu Cys Ile Ala Gln Trp Lys
                420                 425                 430

Gln Thr Asn Phe Met Thr Lys Leu Gly Ser Ile Ser Cys Lys Ser Leu
                435                 440                 445

Lys Gly Gly Asn Ile Ser
    450

<210> SEQ ID NO 27
<211> LENGTH: 245
<212> TYPE: PRT
<213> ORGANISM: Homo sapiens

<400> SEQUENCE: 27

```
Met Gly Asp Ala Pro Ser Pro Glu Glu Lys Leu His Leu Ile Thr Arg
  1               5                  10                  15

Asn Leu Gln Val Val His Pro Gly Asp Leu Lys Asn Ser Val Glu Val
             20                  25                  30

Ala Leu Asn Lys Leu Leu Asp Pro Ile Arg Glu Lys Phe Asn Thr Pro
         35                  40                  45

Ala Leu Lys Lys Leu Ala Ser Ala Ala Tyr Pro Asp Pro Ser Lys Gln
     50                  55                  60

Lys Pro Met Ala Lys Gly Pro Ala Lys Asn Ser Glu Pro Glu Glu Val
 65                  70                  75                  80

Ile Pro Ser Arg Leu Asp Ile Arg Val Gly Lys Ile Ile Thr Val Glu
                 85                  90                  95

Lys His Pro Asp Ala Asp Ser Leu Tyr Val Glu Lys Ile Asp Val Gly
            100                 105                 110

Glu Ala Glu Pro Arg Thr Val Val Ser Gly Leu Val Gln Phe Val Pro
        115                 120                 125

Lys Glu Glu Leu Gln Asp Arg Leu Val Val Val Leu Cys Asn Leu Lys
    130                 135                 140

Pro Gln Lys Met Arg Gly Val Glu Ser Gln Gly Met Leu Leu Cys Ala
145                 150                 155                 160

Ser Ile Glu Gly Ile Asn Arg Gln Val Glu Pro Leu Asp Pro Pro Ala
                165                 170                 175

Gly Ser Ala Pro Gly Glu His Val Phe Val Lys Gly Tyr Glu Lys Gly
            180                 185                 190

Gln Pro Asp Glu Glu Leu Lys Pro Lys Lys Val Phe Glu Lys Leu
        195                 200                 205

Gln Ala Asp Phe Lys Ile Ser Glu Glu Cys Ile Ala Gln Trp Lys Gln
    210                 215                 220

Thr Asn Phe Met Thr Lys Leu Gly Ser Ile Ser Cys Lys Ser Leu Lys
225                 230                 235                 240

Gly Gly Asn Ile Ser
                245
```

<210> SEQ ID NO 28
<211> LENGTH: 377
<212> TYPE: PRT
<213> ORGANISM: Homo sapiens

<400> SEQUENCE: 28

```
Met Gly Asp Ala Pro Ser Pro Glu Glu Lys Leu His Leu Ile Thr Arg
  1               5                  10                  15

Asn Leu Gln Ala Leu Asp Glu Glu Tyr Leu Lys Val Asp Ala Gln Phe
             20                  25                  30

Gly Gly Ile Asp Gln Arg Lys Ile Phe Thr Phe Ala Glu Lys Tyr Leu
         35                  40                  45

Pro Ala Leu Gly Tyr Ser Lys Arg Val His Leu Met Asn Pro Met Val
     50                  55                  60

Pro Gly Leu Thr Gly Ser Lys Met Ser Ser Glu Glu Ser Lys
 65                  70                  75                  80

Ile Asp Leu Leu Asp Arg Lys Glu Asp Val Lys Lys Leu Lys Lys
                 85                  90                  95

Ala Phe Cys Glu Pro Gly Asn Val Glu Asn Asn Gly Val Leu Ser Phe
            100                 105                 110
```

```
Ile Lys His Val Leu Phe Pro Leu Lys Ser Glu Phe Val Ile Leu Arg
        115                 120                 125

Asp Glu Lys Trp Gly Gly Asn Lys Thr Tyr Thr Ala Tyr Val Asp Leu
    130                 135                 140

Glu Lys Asp Phe Ala Ala Glu Val Val His Pro Gly Asp Leu Lys Asn
145                 150                 155                 160

Ser Val Glu Val Ala Leu Asn Lys Leu Leu Asp Pro Ile Arg Glu Lys
                165                 170                 175

Phe Asn Thr Pro Ala Leu Lys Lys Leu Ala Ser Ala Ala Tyr Pro Asp
            180                 185                 190

Pro Ser Lys Gln Lys Pro Met Ala Lys Gly Pro Ala Lys Asn Ser Glu
        195                 200                 205

Pro Glu Glu Val Ile Pro Ser Arg Leu Asp Ile Arg Val Gly Lys Ile
    210                 215                 220

Ile Thr Val Glu Lys His Pro Asp Ala Asp Ser Leu Tyr Val Glu Lys
225                 230                 235                 240

Ile Asp Val Gly Glu Ala Glu Pro Arg Thr Val Val Ser Gly Leu Val
                245                 250                 255

Gln Phe Val Pro Lys Glu Glu Leu Gln Asp Arg Leu Val Val Val Leu
            260                 265                 270

Cys Asn Leu Lys Pro Gln Lys Met Arg Gly Val Glu Ser Gln Gly Met
        275                 280                 285

Leu Leu Cys Ala Ser Ile Glu Gly Ile Asn Arg Gln Val Glu Pro Leu
    290                 295                 300

Asp Pro Pro Ala Gly Ser Ala Pro Gly Glu His Val Phe Val Lys Gly
305                 310                 315                 320

Tyr Glu Lys Gly Gln Pro Asp Glu Glu Leu Lys Pro Lys Lys Lys Val
                325                 330                 335

Phe Glu Lys Leu Gln Ala Asp Phe Lys Ile Ser Glu Glu Cys Ile Ala
            340                 345                 350

Gln Trp Lys Gln Thr Asn Phe Met Thr Lys Leu Gly Ser Ile Ser Cys
        355                 360                 365

Lys Ser Leu Lys Gly Gly Asn Ile Ser
    370                 375

<210> SEQ ID NO 29
<211> LENGTH: 497
<212> TYPE: PRT
<213> ORGANISM: Homo sapiens

<400> SEQUENCE: 29

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110
```

-continued

Glu Lys Leu Lys Phe Ile Lys Gly Thr Asp Tyr Gln Leu Ser Lys Glu
    115                 120                 125

Tyr Thr Leu Asp Val Tyr Arg Leu Ser Ser Val Thr Gln His Asp
    130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Glu Ser Lys Ile Asp Leu Leu Asp Arg Lys Glu
                195                 200                 205

Asp Val Lys Lys Lys Leu Lys Lys Ala Phe Cys Glu Pro Gly Asn Val
    210                 215                 220

Glu Asn Asn Gly Val Leu Ser Phe Ile Lys His Val Leu Phe Pro Leu
225                 230                 235                 240

Lys Ser Glu Phe Val Ile Leu Arg Asp Glu Lys Trp Gly Gly Asn Lys
                245                 250                 255

Thr Tyr Thr Ala Tyr Val Asp Leu Glu Lys Asp Phe Ala Ala Glu Val
            260                 265                 270

Val His Pro Gly Asp Leu Lys Asn Ser Val Glu Val Ala Leu Asn Lys
        275                 280                 285

Leu Leu Asp Pro Ile Arg Glu Lys Phe Asn Thr Pro Ala Leu Lys Lys
    290                 295                 300

Leu Ala Ser Ala Ala Tyr Pro Asp Pro Ser Lys Gln Lys Pro Met Ala
305                 310                 315                 320

Lys Gly Pro Ala Lys Asn Ser Glu Pro Glu Glu Val Ile Pro Ser Arg
                325                 330                 335

Leu Asp Ile Arg Val Gly Lys Ile Ile Thr Val Glu Lys His Pro Asp
            340                 345                 350

Ala Asp Ser Leu Tyr Val Glu Lys Ile Asp Val Gly Glu Ala Glu Pro
        355                 360                 365

Arg Thr Val Val Ser Gly Leu Val Gln Phe Val Pro Lys Glu Glu Leu
    370                 375                 380

Gln Asp Arg Leu Val Val Leu Cys Asn Leu Lys Pro Gln Lys Met
385                 390                 395                 400

Arg Gly Val Glu Ser Gln Gly Met Leu Leu Cys Ala Ser Ile Glu Gly
                405                 410                 415

Ile Asn Arg Gln Val Glu Pro Leu Asp Pro Pro Ala Gly Ser Ala Pro
            420                 425                 430

Gly Glu His Val Phe Val Lys Gly Tyr Glu Lys Gly Gln Pro Asp Glu
        435                 440                 445

Glu Leu Lys Pro Lys Lys Val Phe Glu Lys Leu Gln Ala Asp Phe
    450                 455                 460

Lys Ile Ser Glu Glu Cys Ile Ala Gln Trp Lys Gln Thr Asn Phe Met
465                 470                 475                 480

Thr Lys Leu Gly Ser Ile Ser Cys Lys Ser Leu Lys Gly Gly Asn Ile
                485                 490                 495

Ser

<210> SEQ ID NO 30
<211> LENGTH: 230
<212> TYPE: PRT

<213> ORGANISM: Homo sapiens

<400> SEQUENCE: 30

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Ser Leu
225                 230

<210> SEQ ID NO 31
<211> LENGTH: 343
<212> TYPE: PRT
<213> ORGANISM: Homo sapiens

<400> SEQUENCE: 31

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu

```
            115                 120                 125
Tyr Thr Leu Asp Val Tyr Arg Leu Ser Ser Val Val Thr Gln His Asp
        130                 135                 140
Ser Lys Lys Ala Gly Ala Glu Val Val Lys Gln Val Glu His Pro Leu
145                 150                 155                 160
Leu Ser Gly Leu Leu Tyr Pro Gly Leu Gln Ala Leu Asp Glu Glu Tyr
                165                 170                 175
Leu Lys Val Asp Ala Gln Phe Gly Gly Ile Asp Gln Arg Lys Ile Phe
            180                 185                 190
Thr Phe Ala Glu Lys Tyr Leu Pro Ala Leu Gly Tyr Ser Lys Arg Val
        195                 200                 205
His Leu Met Asn Pro Met Val Pro Gly Leu Thr Gly Ser Lys Met Ser
    210                 215                 220
Ser Ser Glu Glu Glu Ser Lys Ile Asp Leu Leu Asp Arg Lys Glu Asp
225                 230                 235                 240
Val Lys Lys Lys Leu Lys Lys Ala Phe Cys Glu Pro Gly Asn Val Glu
                245                 250                 255
Asn Asn Gly Val Leu Ser Phe Ile Lys His Val Leu Phe Pro Leu Lys
            260                 265                 270
Ser Glu Phe Val Ile Leu Arg Asp Glu Lys Trp Gly Gly Asn Lys Thr
        275                 280                 285
Tyr Thr Ala Tyr Val Asp Leu Glu Lys Asp Phe Ala Ala Glu Ser Gln
    290                 295                 300
Trp Pro Lys Ala Leu Pro Arg Ile Gln Asn Gln Arg Arg Ser Ser His
305                 310                 315                 320
Pro Gly Trp Ile Ser Val Trp Gly Lys Ser Ser Leu Trp Arg Ser Thr
                325                 330                 335
Gln Met Gln Thr Ala Cys Met
            340

<210> SEQ ID NO 32
<211> LENGTH: 387
<212> TYPE: PRT
<213> ORGANISM: Homo sapiens

<400> SEQUENCE: 32

Met Gly Asp Ala Pro Ser Pro Glu Glu Lys Leu His Leu Ile Thr Arg
1               5                   10                  15
Asn Leu Gln Glu Val Leu Gly Glu Glu Lys Leu Lys Glu Ile Leu Lys
            20                  25                  30
Glu Arg Glu Leu Lys Ile Tyr Trp Gly Thr Ala Thr Thr Gly Lys Pro
        35                  40                  45
His Val Ala Tyr Phe Val Pro Met Ser Lys Ile Ala Asp Phe Leu Lys
    50                  55                  60
Ala Gly Cys Glu Val Thr Ile Leu Phe Ala Asp Leu His Ala Tyr Leu
65                  70                  75                  80
Asp Asn Met Lys Ala Pro Trp Glu Leu Leu Glu Leu Arg Val Ser Tyr
                85                  90                  95
Tyr Glu Asn Val Ile Lys Ala Met Leu Glu Ser Ile Gly Val Pro Leu
            100                 105                 110
Glu Lys Leu Lys Phe Ile Lys Gly Thr Asp Tyr Gln Leu Ser Lys Glu
        115                 120                 125
Tyr Thr Leu Asp Val Tyr Arg Leu Ser Ser Val Val Thr Gln His Asp
    130                 135                 140
```

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
            165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
            245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
            290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
            325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
            355                 360                 365

Asp Ile Arg Val Gly Lys Ile Ile Thr Val Glu Lys Arg Arg Asp Lys
            370                 375                 380

Pro Pro Gly
385

<210> SEQ ID NO 33
<211> LENGTH: 470
<212> TYPE: PRT
<213> ORGANISM: Homo sapiens

<400> SEQUENCE: 33

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
            50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
            85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
            130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Glu Ser Lys Ile Asp Leu
                165                 170                 175

Leu Asp Arg Lys Glu Asp Val Lys Lys Leu Lys Lys Ala Phe Cys
            180                 185                 190

Glu Pro Gly Asn Val Glu Asn Asn Gly Val Leu Ser Phe Ile Lys His
                195                 200                 205

Val Leu Phe Pro Leu Lys Ser Glu Phe Val Ile Leu Arg Asp Glu Lys
            210                 215                 220

Trp Gly Gly Asn Lys Thr Tyr Thr Ala Tyr Val Asp Leu Glu Lys Asp
225                 230                 235                 240

Phe Ala Ala Glu Val Val His Pro Gly Asp Leu Lys Asn Ser Val Glu
                245                 250                 255

Val Ala Leu Asn Lys Leu Leu Asp Pro Ile Arg Glu Lys Phe Asn Thr
            260                 265                 270

Pro Ala Leu Lys Lys Leu Ala Ser Ala Ala Tyr Pro Asp Pro Ser Lys
                275                 280                 285

Gln Lys Pro Met Ala Lys Gly Pro Ala Lys Asn Ser Glu Pro Glu Glu
        290                 295                 300

Val Ile Pro Ser Arg Leu Asp Ile Arg Val Gly Lys Ile Ile Thr Val
305                 310                 315                 320

Glu Lys His Pro Asp Ala Asp Ser Leu Tyr Val Glu Lys Ile Asp Val
                325                 330                 335

Gly Glu Ala Glu Pro Arg Thr Val Val Ser Gly Leu Val Gln Phe Val
            340                 345                 350

Pro Lys Glu Glu Leu Gln Asp Arg Leu Val Val Val Leu Cys Asn Leu
                355                 360                 365

Lys Pro Gln Lys Met Arg Gly Val Glu Ser Gln Gly Met Leu Leu Cys
        370                 375                 380

Ala Ser Ile Glu Gly Ile Asn Arg Gln Val Glu Pro Leu Asp Pro Pro
385                 390                 395                 400

Ala Gly Ser Ala Pro Gly Glu His Val Phe Val Lys Gly Tyr Glu Lys
                405                 410                 415

Gly Gln Pro Asp Glu Glu Leu Lys Pro Lys Lys Val Phe Glu Lys
            420                 425                 430

Leu Gln Ala Asp Phe Lys Ile Ser Glu Glu Cys Ile Ala Gln Trp Lys
                435                 440                 445

Gln Thr Asn Phe Met Thr Lys Leu Gly Ser Ile Ser Cys Lys Ser Leu
        450                 455                 460

Lys Gly Gly Asn Ile Ser
465                 470

<210> SEQ ID NO 34
<211> LENGTH: 454
<212> TYPE: PRT
<213> ORGANISM: Homo sapiens

<400> SEQUENCE: 34

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys

```
            20                  25                  30
Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
        50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
            130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Pro Met Ala Lys Gly Pro Ala Lys Asn Ser Glu Pro Glu Glu
            275                 280                 285

Val Ile Pro Ser Arg Leu Asp Ile Arg Val Gly Lys Ile Ile Thr Val
            290                 295                 300

Glu Lys His Pro Asp Ala Asp Ser Leu Tyr Val Glu Lys Ile Asp Val
305                 310                 315                 320

Gly Glu Ala Glu Pro Arg Thr Val Val Ser Gly Leu Val Gln Phe Val
                325                 330                 335

Pro Lys Glu Glu Leu Gln Asp Arg Leu Val Val Val Leu Cys Asn Leu
            340                 345                 350

Lys Pro Gln Lys Met Arg Gly Val Glu Ser Gln Gly Met Leu Leu Cys
            355                 360                 365

Ala Ser Ile Glu Gly Ile Asn Arg Gln Val Glu Pro Leu Asp Pro Pro
            370                 375                 380

Ala Gly Ser Ala Pro Gly Glu His Val Phe Val Lys Gly Tyr Glu Lys
385                 390                 395                 400

Gly Gln Pro Asp Glu Glu Leu Lys Pro Lys Lys Val Phe Glu Lys
                405                 410                 415

Leu Gln Ala Asp Phe Lys Ile Ser Glu Glu Cys Ile Ala Gln Trp Lys
            420                 425                 430

Gln Thr Asn Phe Met Thr Lys Leu Gly Ser Ile Ser Cys Lys Ser Leu
            435                 440                 445
```

```
Lys Gly Gly Asn Ile Ser
    450
```

<210> SEQ ID NO 35
<211> LENGTH: 18
<212> TYPE: PRT
<213> ORGANISM: Homo sapiens

<400> SEQUENCE: 35

```
Met Thr Lys Leu Gly Ser Ile Ser Cys Lys Ser Leu Lys Gly Gly Asn
 1               5                  10                  15

Ile Ser
```

<210> SEQ ID NO 36
<211> LENGTH: 1587
<212> TYPE: DNA
<213> ORGANISM: Artificial Sequence
<220> FEATURE:
<223> OTHER INFORMATION: Codon optimized DNA encoding the full length
      TyrRS synthetase containing the Y341A mutation

<400> SEQUENCE: 36

| | |
|---|---|
| atgggtgatg caccgtcacc ggaagaaaaa ctgcatctga ttacccgtaa tctgcaggaa | 60 |
| gttctgggcg aagaaaaact gaaagaaatt ctgaaagaac gcgaactgaa atctattgg | 120 |
| ggcaccgcaa ccaccggtaa ccgcatgtt gcatatttg tgccgatgag caaaattgcc | 180 |
| gattttctga agccggttg tgaagttacc attctgttg ctgatctgca tgcctatctg | 240 |
| gataatatga agcaccgtg ggaactgctg gaactgcgtg ttagctatta tgaaaatgtg | 300 |
| attaaagcca tgctggaaag cattggtgtt ccgctggaaa aactgaaatt tattaaaggc | 360 |
| accgattatc agctgtccaa agaatatacc ctggatgttt atcgtctgag cagcgttgtt | 420 |
| acccagcatg atagcaaaaa agccggtgcc gaagttgtta acaggttga catccgctg | 480 |
| ctgtctggtc tgctgtatcc gggtctgcag gcactggatg aagaatatct gaaagtggat | 540 |
| gcacagtttg gtggtattga tcagcgcaaa atttttacct tgccgaaaaa atatctgcct | 600 |
| gcactgggct atagcaaacg tgttcatctg atgaatccga tggttccggg tctgaccggt | 660 |
| agcaaaatga gcagcagcga agaagaaagc aaaattgatc tgctggatcg caagaagat | 720 |
| gtgaaaaaa actgaaaaa agccttttgc gaaccgggta atgtggaaaa taatggcgtt | 780 |
| ctgagctta ttaaacatgt gctgttccg ctgaaaagcg aatttgtgat tctgcgtgat | 840 |
| gaaaaatggg gtggcaataa aacctatacc gcctatgtgg atctgaaaaa agattttgca | 900 |
| gccgaagttg tgcatccggg tgatctgaaa atagcgtgg aagtggccct gaataaactg | 960 |
| ctggatccga ttcgcgaaaa atttaataca ccggcactga aaaaactggc aagcgcagca | 1020 |
| gcaccggatc cgagcaaaca gaaaccgatg gcaaaaggtc cggcaaaaaa cagcgaaccg | 1080 |
| gaagaagtta ttccgagccg tctggatatt cgtgtgggca aaattattac cgtgaaaaaa | 1140 |
| catccggatg cagatagcct gtatgtggaa aaaattgatg tgggtgaagc agaaccgcgt | 1200 |
| accgttgtta gcggtctggt tcagtttgtt ccgaaagaag aactgcagga tcgtctggtt | 1260 |
| gttgttctgt gtaatctgaa accgcagaaa atgcgtggtt tgaaagcca gggtatgctg | 1320 |
| ctgtgtgcaa gcattgaagg tattaatcgt caggttgaac cgctggatcc tccggctggt | 1380 |
| tctgcaccgg gtaacatgt ttttgtgaaa ggctatgaaa aggtcagcc ggatgaagaa | 1440 |
| ctgaaaccga aaaaaaagt gtttgaaaaa ctgcaggccg attttaaaat tagcgaagaa | 1500 |
| tgcattgcac agtggaaaca gaccaatttt atgaccaaac tgggtagcat tagctgtaaa | 1560 | agcctgaaag gtggcaatat tagctaa                                        1587

<210> SEQ ID NO 37
<211> LENGTH: 42
<212> TYPE: DNA
<213> ORGANISM: Artificial Sequence
<220> FEATURE:
<223> OTHER INFORMATION: PCR primer used to amplify coY341A gene

<400> SEQUENCE: 37
ctttaagaag gagatataca tatgggtgat gcaccgtcac cg                         42

<210> SEQ ID NO 38
<211> LENGTH: 45
<212> TYPE: DNA
<213> ORGANISM: Artificial Sequence
<220> FEATURE:
<223> OTHER INFORMATION: PCR primer used to amplify coY341A gene

<400> SEQUENCE: 38
gtggtggtgg tggtgctcga gttagctaat attgccacct ttcag                     45

<210> SEQ ID NO 39
<211> LENGTH: 45
<212> TYPE: DNA
<213> ORGANISM: Artificial Sequence
<220> FEATURE:
<223> OTHER INFORMATION: primer

<400> SEQUENCE: 39
gaaaggtggc aatattagct aatgagatcc ggctgctaac aaagc                     45

<210> SEQ ID NO 40
<211> LENGTH: 45
<212> TYPE: DNA
<213> ORGANISM: Artificial Sequence
<220> FEATURE:
<223> OTHER INFORMATION: primer

<400> SEQUENCE: 40
gctttgttag cagccggatc tcattagcta atattgccac ctttc                     45

<210> SEQ ID NO 41
<211> LENGTH: 86
<212> TYPE: DNA
<213> ORGANISM: Artificial Sequence
<220> FEATURE:
<223> OTHER INFORMATION: primer

<400> SEQUENCE: 41
atcgagatct cgatcccgcg aaatgagctg ttgacaatta atcatcggct cgtataatgt     60
gtggaattgt gagcggataa caattc                                          86

<210> SEQ ID NO 42
<211> LENGTH: 86
<212> TYPE: DNA
<213> ORGANISM: Artificial Sequence
<220> FEATURE:
<223> OTHER INFORMATION: primer

<400> SEQUENCE: 42
gaattgttat ccgctcacaa ttccacacat tatacgagcc gatgattaat tgtcaacagc     60
tcatttcgcg ggatcgagat ctcgat                                          86

<210> SEQ ID NO 43
<211> LENGTH: 53
<212> TYPE: DNA
<213> ORGANISM: Artificial Sequence
<220> FEATURE:
<223> OTHER INFORMATION: primer

<400> SEQUENCE: 43
cactgaaaaa actggcaagc gcagcatatc cggatccgag caaacagaaa ccg        53

<210> SEQ ID NO 44
<211> LENGTH: 53
<212> TYPE: DNA
<213> ORGANISM: Artificial Sequence
<220> FEATURE:
<223> OTHER INFORMATION: primer

<400> SEQUENCE: 44
cggtttctgt tgctcggat ccggatatgc tgcgcttgcc agttttttca gtg         53

<210> SEQ ID NO 45
<211> LENGTH: 49
<212> TYPE: DNA
<213> ORGANISM: Artificial Sequence
<220> FEATURE:
<223> OTHER INFORMATION: primer

<400> SEQUENCE: 45
gggctttgtt agcagccgga tctcattaac cttttgccat cggtttctg             49

<210> SEQ ID NO 46
<211> LENGTH: 60
<212> TYPE: DNA
<213> ORGANISM: Artificial Sequence
<220> FEATURE:
<223> OTHER INFORMATION: primer

<400> SEQUENCE: 46
gcagatcagc aaacagaatg gtaacttcgc taccggcttt cagaaaatcg gcaattttgc    60

<210> SEQ ID NO 47
<211> LENGTH: 60
<212> TYPE: DNA
<213> ORGANISM: Artificial Sequence
<220> FEATURE:
<223> OTHER INFORMATION: primer

<400> SEQUENCE: 47
attattttcc acattacccg gttcgctaaa ggcttttttc agtttttttt tcacatcttc    60

<210> SEQ ID NO 48
<211> LENGTH: 45
<212> TYPE: DNA
<213> ORGANISM: Artificial Sequence
<220> FEATURE:
<223> OTHER INFORMATION: primer

<400> SEQUENCE: 48
ggagatatac atatgggtga ttgcccgtca ccggaagaaa aactg                  45

<210> SEQ ID NO 49
<211> LENGTH: 45
<212> TYPE: DNA
<213> ORGANISM: Artificial Sequence
<220> FEATURE:
<223> OTHER INFORMATION: primer

```
<400> SEQUENCE: 49 cagttttct tccggtgacg ggcaatcacc catatgtata tctcc          45

<210> SEQ ID NO 50
<211> LENGTH: 45
<212> TYPE: DNA
<213> ORGANISM: Artificial Sequence
<220> FEATURE:
<223> OTHER INFORMATION: primer

<400> SEQUENCE: 50
ccgagcaaac agaaaccgat gtgcaaaggt taatgagatc cggct          45

<210> SEQ ID NO 51
<211> LENGTH: 45
<212> TYPE: DNA
<213> ORGANISM: Artificial Sequence
<220> FEATURE:
<223> OTHER INFORMATION: primer

<400> SEQUENCE: 51
agccggatct cattaacctt tgcacatcgg tttctgtttg ctcgg          45

<210> SEQ ID NO 52
<211> LENGTH: 78
<212> TYPE: DNA
<213> ORGANISM: Artificial Sequence
<220> FEATURE:
<223> OTHER INFORMATION: primer

<400> SEQUENCE: 52
ccgagcaaac agaaaccgat ggcaaaaggt catcatcatc atcatcatta atgagatccg     60
gctgctaaca aagcccga                                                  78

<210> SEQ ID NO 53
<211> LENGTH: 78
<212> TYPE: DNA
<213> ORGANISM: Artificial Sequence
<220> FEATURE:
<223> OTHER INFORMATION: primer

<400> SEQUENCE: 53
tcgggctttg ttagcagccg gatctcatta atgatgatga tgatgatgac cttttgccat     60
cggtttctgt tgctcgg                                                   78

<210> SEQ ID NO 54
<211> LENGTH: 78
<212> TYPE: DNA
<213> ORGANISM: Artificial Sequence
<220> FEATURE:
<223> OTHER INFORMATION: primer

<400> SEQUENCE: 54
ccgagcaaac agaaaccgat gtgcaaaggt catcatcatc atcatcatta atgagatccg     60
gctgctaaca aagcccga                                                  78

<210> SEQ ID NO 55
<211> LENGTH: 78
<212> TYPE: DNA
<213> ORGANISM: Artificial Sequence
<220> FEATURE:
<223> OTHER INFORMATION: primer
```

<400> SEQUENCE: 55

```
tcgggctttg ttagcagccg gatctcatta atgatgatga tgatgatgac ctttgcacat    60
cggtttctgt ttgctcgg                                                  78
```

<210> SEQ ID NO 56
<211> LENGTH: 1059
<212> TYPE: DNA
<213> ORGANISM: Artificial Sequence
<220> FEATURE:
<223> OTHER INFORMATION: polynucleotide encoding non-tagged YRS A4C
      point mutation polypeptide
<220> FEATURE:
<221> NAME/KEY: misc_feature
<222> LOCATION: 12
<223> OTHER INFORMATION: n = T or C
<220> FEATURE:
<221> NAME/KEY: misc_feature
<222> LOCATION: 201
<223> OTHER INFORMATION: n = A, T, C or G
<220> FEATURE:
<221> NAME/KEY: misc_feature
<222> LOCATION: 750
<223> OTHER INFORMATION: n = A, T, C or G

<400> SEQUENCE: 56

```
atgggggact gncccagccc tgaagagaaa ctgcaccttat tcacccggaa cctgcaggag    60
gttctggggg aagagaagct gaaggagata ctgaaggagc gggaacttaa aatttactgg   120
ggaacggcaa ccacgggcaa accacatgtg gcttactttg tgcccatgtc aaagattgca   180
gacttcttaa aggcagggtc ngaggtaaca attctgtttg cggacctcca cgcatacctg   240
gataacatga agcccccatg ggaacttcta gaactccgag tcagttacta tgagaatgtg   300
atcaaagcaa tgctggagag cattggtgtg cccttggaga agctcaagtt catcaaaggc   360
actgattacc agctcagcaa agagtacaca ctagatgtgt acagactctc ctccgtggtc   420
acacagcacg attccaagaa ggctggagct gaggtggtaa agcaggtgga gcacccttttg   480
ctgagtggcc tcttataccc cggactgcag gctttggatg aagagtattt aaaagtagat   540
gcccaattg gaggcattga tcagagaaag attttcacct ttgcagagaa gtacctccct   600
gcacttggct attcaaaacg ggtccatctg atgaatccta tggttccagg attaacaggc   660
agcaaaatga gctcttcaga agaggagtcc aagattgatc tccttgatcg gaaggaggat   720
gtgaagaaaa aactgaagaa ggccttctcn gagccaggaa atgtggagaa caatgggggtt   780
ctgtccttca tcaagcatgt ccttttttccc cttaagtccg agtttgtgat cctacgagat   840
gagaaatggg gtgaaacaa aacctacaca gcttacgtgg acctggaaaa ggactttgct   900
gctgaggttg tacatcctgg agacctgaag aattctgttg aagtcgcact gaacaagttg   960
ctggatccaa tccgggaaaa gtttaatacc cctgccctga aaaaactggc cagcgctgcc  1020
tacccagatc cctcaaagca gaagccaatg gccaaaggc                         1059
```

<210> SEQ ID NO 57
<211> LENGTH: 1059
<212> TYPE: DNA
<213> ORGANISM: Artificial Sequence
<220> FEATURE:
<223> OTHER INFORMATION: polynucleotide encoding non-tagged YRS A351C
      point mutation polypeptide
<220> FEATURE:
<221> NAME/KEY: misc_feature
<222> LOCATION: 201
<223> OTHER INFORMATION: n = A, T, C or G
<220> FEATURE:
<221> NAME/KEY: misc_feature

| <222> LOCATION: 750
| <223> OTHER INFORMATION: n = A, T, C or G
| <220> FEATURE:
| <221> NAME/KEY: misc_feature
| <222> LOCATION: 1053
| <223> OTHER INFORMATION: n = T or C

<400> SEQUENCE: 57

```
atggggacg ctcccagccc tgaagagaaa ctgcacctta tcacccggaa cctgcaggag     60
gttctggggg aagagaagct gaaggagata ctgaaggagc gggaacttaa aatttactgg    120
ggaacggcaa ccacgggcaa accacatgtg gcttactttg tgcccatgtc aaagattgca    180
gacttcttaa aggcagggtc ngaggtaaca attctgtttg cggacctcca cgcatacctg    240
gataacatga aagcccatg ggaacttcta gaactccgag tcagttacta tgagaatgtg    300
atcaaagcaa tgctggagag cattggtgtg cccttggaga agctcaagtt catcaaaggc    360
actgattacc agctcagcaa agagtacaca ctagatgtgt acagactctc ctccgtggtc    420
acacagcacg attccaagaa ggctggagct gaggtggtaa agcaggtgga gcacccttg     480
ctgagtggcc tcttataccc cggactgcag gctttggatg aagagtattt aaaagtagat    540
gcccaatttg gaggcattga tcagagaaag atttttcacct ttgcagagaa gtacctccct    600
gcacttggct attcaaaacg ggtccatctg atgaatccta tggttccagg attaacaggc    660
agcaaaatga gctcttcaga agaggagtcc aagattgatc tccttgatcg aaggaggat     720
gtgaagaaaa aactgaagaa ggccttctcn gagccaggaa atgtggagaa caatgggtt     780
ctgtccttca tcaagcatgt cctttttccc cttaagtccg agtttgtgat cctacgagat    840
gagaaatggg gtgaaacaa aacctacaca gcttacgtgg acctggaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg tgnaaaggc                          1059
```

<210> SEQ ID NO 58
<211> LENGTH: 353
<212> TYPE: PRT
<213> ORGANISM: Artificial Sequence
<220> FEATURE:
<223> OTHER INFORMATION: Non-tagged YRS A4C point mutation polypeptide

<400> SEQUENCE: 58

```
Met Gly Asp Cys Pro Ser Pro Glu Glu Lys Leu His Leu Ile Thr Arg

Tyr Thr Leu Asp Val Tyr Arg Leu Ser Ser Val Val Thr Gln His Asp
            130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Ser Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
            290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly

<210> SEQ ID NO 59
<211> LENGTH: 353
<212> TYPE: PRT
<213> ORGANISM: Artificial Sequence
<220> FEATURE:
<223> OTHER INFORMATION: Non-tagged YRS A351C point mutation polypeptide

<400> SEQUENCE: 59

Met Gly Asp Ala Pro Ser Pro Glu Glu Lys Leu His Leu Ile Thr Arg
1               5                  10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Ser Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
            165                 170                 175

Leu Lys Val Asp Ala Gln Phe Gly Gly Ile Asp Gln Arg Lys Ile Phe
        180                 185                 190

Thr Phe Ala Glu Lys Tyr Leu Pro Ala Leu Gly Tyr Ser Lys Arg Val
    195                 200                 205

His Leu Met Asn Pro Met Val Pro Gly Leu Thr Gly Ser Lys Met Ser
210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Ser Pro Gly Asn Val Glu
            245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Cys Lys
                340                 345                 350

Gly

<210> SEQ ID NO 60
<211> LENGTH: 1077
<212> TYPE: DNA
<213> ORGANISM: Artificial Sequence
<220> FEATURE:
<223> OTHER INFORMATION: Polynucleotide encoding tagged YRS A4C point
      mutation polypeptide
<220> FEATURE:
<221> NAME/KEY: misc_feature
<222> LOCATION: 12
<223> OTHER INFORMATION: n = T or C
<220> FEATURE:
<221> NAME/KEY: misc_feature
<222> LOCATION: 201
<223> OTHER INFORMATION: n = A, T, C or G
<220> FEATURE:
<221> NAME/KEY: misc_feature
<222> LOCATION: 750
<223> OTHER INFORMATION: n = A, T, C or G
<220> FEATURE:
<221> NAME/KEY: misc_feature
<222> LOCATION: 1062, 1065, 1068, 1071, 1074, 1077
<223> OTHER INFORMATION: n = T or C

<400> SEQUENCE: 60
atgggggact gncccagccc tgaagagaaa ctgcacctta tcacccggaa cctgcaggag    60
gttctggggg aagagaagct gaaggagata ctgaaggagc gggaacttaa aatttactgg   120
ggaacggcaa ccacgggcaa accacatgtg gcttactttg tgcccatgtc aaagattgca   180
gacttcttaa aggcagggtc ngaggtaaca attctgtttg cggacctcca cgcatacctg   240
gataacatga agcccccatg ggaacttcta gaactccgag tcagttacta tgagaatgtg   300

```
atcaaagcaa tgctggagag cattggtgtg cccttggaga agctcaagtt catcaaaggc        360
actgattacc agctcagcaa agagtacaca ctagatgtgt acagactctc ctccgtggtc        420
acacagcacg attccaagaa ggctggagct gaggtggtaa agcaggtgga gcacccttg         480 ctgagtggcc tcttataccc cggactgcag gctttggatg aagagtattt aaaagtagat        540
gcccaatttg gaggcattga tcagagaaag attttcacct ttgcagagaa gtacctccct        600
gcacttggct attcaaaacg ggtccatctg atgaatccta tggttccagg attaacaggc        660
agcaaaatga gctcttcaga agaggagtcc aagattgatc tccttgatcg gaaggaggat        720
gtgaagaaaa aactgaagaa ggccttctcn gagccaggaa atgtggagaa caatggggtt        780
ctgtccttca tcaagcatgt ccttttccc  cttaagtccg agtttgtgat cctacgagat        840
gagaaatggg gtgaaacaa aacctacaca gcttacgtgg acctgaaaa  ggactttgct         900 gctgaggttg tacatcctgg agacctgaag aattctgttg aagtcgcact gaacaagttg        960
ctggatccaa tccgggaaaa gtttaatacc cctgccctga aaaaactggc cagcgctgcc       1020
tacccagatc cctcaaagca gaagccaatg gccaaaggcc ancancanca ncancan         1077

<210> SEQ ID NO 61
<211> LENGTH: 1077
<212> TYPE: DNA
<213> ORGANISM: Artificial Sequence
<220> FEATURE:
<223> OTHER INFORMATION: Polynucleotide encoding tagged YRS A351C point
      mutation polypeptide
<220> FEATURE:
<221> NAME/KEY: misc_feature
<222> LOCATION: 201
<223> OTHER INFORMATION: n = A, T, C or G
<220> FEATURE:
<221> NAME/KEY: misc_feature
<222> LOCATION: 750
<223> OTHER INFORMATION: n = A, T, C or G
<220> FEATURE:
<221> NAME/KEY: misc_feature
<222> LOCATION: 1053
<223> OTHER INFORMATION: n = T or C
<220> FEATURE:
<221> NAME/KEY: misc_feature
<222> LOCATION: 1062, 1065, 1068, 1071, 1074, 1077
<223> OTHER INFORMATION: n = T or C

<400> SEQUENCE: 61
atgggggacg ctcccagccc tgaagagaaa ctgcaccttw tcacccggaa cctgcaggag         60
gttctggggg aagagaagct gaaggagata ctgaaggagc gggaacttaa aatttactgg        120
ggaacggcaa ccacgggcaa accacatgtg gcttactttg tgcccatgtc aaagattgca        180
gacttcttaa aggcagggtc ngaggtaaca attctgtttg cggacctcca cgcataccctg       240 gataacatga agcccatg  ggaacttcta gaactccgag tcagttacta tgagaatgtg        300
atcaaagcaa tgctggagag cattggtgtg cccttggaga agctcaagtt catcaaaggc        360
actgattacc agctcagcaa agagtacaca ctagatgtgt acagactctc ctccgtggtc        420
acacagcacg attccaagaa ggctggagct gaggtggtaa agcaggtgga gcacccttg         480 ctgagtggcc tcttataccc cggactgcag gctttggatg aagagtattt aaaagtagat        540
gcccaatttg gaggcattga tcagagaaag attttcacct ttgcagagaa gtacctccct        600
gcacttggct attcaaaacg ggtccatctg atgaatccta tggttccagg attaacaggc        660
agcaaaatga gctcttcaga agaggagtcc aagattgatc tccttgatcg gaaggaggat        720
gtgaagaaaa aactgaagaa ggccttctcn gagccaggaa atgtggagaa caatggggtt        780
```

```
ctgtccttca tcaagcatgt ccttttccc cttaagtccg agtttgtgat cctacgagat    840
gagaaatggg gtggaaacaa aacctacaca gcttacgtgg acctggaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg tgnaaaggcc ancancanca ncancan      1077
```

<210> SEQ ID NO 62
<211> LENGTH: 359
<212> TYPE: PRT
<213> ORGANISM: Artificial Sequence
<220> FEATURE:
<223> OTHER INFORMATION: Tagged YRS A4C point mutation polypeptide

<400> SEQUENCE: 62

```
Met Gly Asp Cys Pro Ser Pro Glu Glu Lys Leu His Leu Ile Thr Arg
 1               5

```
305                 310                 315                 320
Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly His His His His His
            355

<210> SEQ ID NO 63
<211> LENGTH: 359
<212> TYPE: PRT
<213> ORGANISM: Artificial Sequence
<220> FEATURE:
<223> OTHER INFORMATION: Tagged YRS A351C point mutation polypeptide

<400> SEQUENCE: 63

Met Gly Asp Ala Pro Ser Pro Glu Glu Lys Leu His Leu Ile Thr Arg
 1               5                  10                  15

Asn Leu Gln Glu Val Leu Gly Glu Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
        50                  55                  60

Ala Gly Ser Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
        130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
                180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
        210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Ser Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
        290                 295                 300

His Pro Gly Asp Leu Lys Asn Ser Val Glu Val Ala Leu Asn Lys Leu
```

```
            305                 310                 315                 320
Leu Asp Pro Ile Arg Glu Lys Phe Asn Thr Pro Ala Leu Lys Lys Leu
                    325                 330                 335

Ala Ser Ala Ala Tyr Pro Asp Pro Ser Lys Gln Lys Pro Met Cys Lys
                340                 345                 350

Gly His His His His His
            355

<210> SEQ ID NO 64
<211> LENGTH: 26
<212> TYPE: DNA
<213> ORGANISM: Homo sapiens

<400> SEQUENCE: 64
tgccccactc caagtcctca ctcaca                                              26

<210> SEQ ID NO 65
<211> LENGTH: 25
<212> TYPE: DNA
<213> ORGANISM: Homo sapiens

<400> SEQUENCE: 65
agaagcacac agaagcatgc cttgg                                               25

<210> SEQ ID NO 66
<211> LENGTH: 26
<212> TYPE: DNA
<213> ORGANISM: Homo sapiens

<400> SEQUENCE: 66
gcacagcacc actaccagcc tgtcct                                              26

<210> SEQ ID NO 67
<211> LENGTH: 25
<212> TYPE: DNA
<213> ORGANISM: Homo sapiens

<400> SEQUENCE: 67
cagttcctcc ttgggcacga actgt                                               25

<210> SEQ ID NO 68
<211> LENGTH: 26
<212> TYPE: DNA
<213> ORGANISM: Homo sapiens

<400> SEQUENCE: 68
tatccagccg ggatgggatg acctcc                                              26

<210> SEQ ID NO 69
<211> LENGTH: 25
<212> TYPE: DNA
<213> ORGANISM: Homo sapiens

<400> SEQUENCE: 69
ctggttctga attcttggca gggcc                                               25

<210> SEQ ID NO 70
<211> LENGTH: 26
<212> TYPE: DNA
<213> ORGANISM: Homo sapiens

<400> SEQUENCE: 70
```

```
ggccagcgct gcctacccag atccct                                          26

<210> SEQ ID NO 71
<211> LENGTH: 25
<212> TYPE: DNA
<213> ORGANISM: Homo sapiens

<400> SEQUENCE: 71
aaagcagagt aaggccagct ggaga                                           25

<210> SEQ ID NO 72
<211> LENGTH: 26
<212> TYPE: DNA
<213> ORGANISM: Homo sapiens

<400> SEQUENCE: 72
ggttctgaat tcttggcagg gccttt                                          26

<210> SEQ ID NO 73
<211> LENGTH: 25
<212> TYPE: DNA
<213> ORGANISM: Homo sapiens

<400> SEQUENCE: 73
ggccattggc tctgggaatg agaag                                           25

<210> SEQ ID NO 74
<211> LENGTH: 26
<212> TYPE: DNA
<213> ORGANISM: Homo sapiens

<400> SEQUENCE: 74
ggagagcatt ggtgtgccct tggaga                                          26

<210> SEQ ID NO 75
<211> LENGTH: 25
<212> TYPE: DNA
<213> ORGANISM: Homo sapiens

<400> SEQUENCE: 75
gctcaagttc atcaaaggca ctgat                                           25

<210> SEQ ID NO 76
<211> LENGTH: 26
<212> TYPE: DNA
<213> ORGANISM: Homo sapiens

<400> SEQUENCE: 76
ccacatgtgg cttactttgt gcccat                                          26

<210> SEQ ID NO 77
<211> LENGTH: 25
<212> TYPE: DNA
<213> ORGANISM: Homo sapiens

<400> SEQUENCE: 77
tcaaagattg cagacttctt aaagg                                           25

<210> SEQ ID NO 78
<211> LENGTH: 26
<212> TYPE: DNA
<213> ORGANISM: Homo sapiens

<400> SEQUENCE: 78
```
agactctcct ccgtggtcac acagca 26

<210> SEQ ID NO 79
<211> LENGTH: 25
<212> TYPE: DNA
<213> ORGANISM: Homo sapiens

<400> SEQUENCE: 79
gattccaaga aggctggagc tgagg 25

<210> SEQ ID NO 80
<211> LENGTH: 26
<212> TYPE: DNA
<213> ORGANISM: Homo sapiens

<400> SEQUENCE: 80
gtgatcctac gagatgagaa atgggg 26

<210> SEQ ID NO 81
<211> LENGTH: 25
<212> TYPE: DNA
<213> ORGANISM: Homo sapiens

<400> SEQUENCE: 81
ggaaacaaaa cctacacagc ttacg 25

<210> SEQ ID NO 82
<211> LENGTH: 26
<212> TYPE: DNA
<213> ORGANISM: Homo sapiens

<400> SEQUENCE: 82
aaaccacatg tggcttactt tgtgcc 26

<210> SEQ ID NO 83
<211> LENGTH: 25
<212> TYPE: DNA
<213> ORGANISM: Homo sapiens

<400> SEQUENCE: 83
atgtcaaaga ttgcagactt cttaa 25

<210> SEQ ID NO 84
<211> LENGTH: 26
<212> TYPE: DNA
<213> ORGANISM: Homo sapiens

<400> SEQUENCE: 84
ccatgggaac ttctagaact ccgagt 26

<210> SEQ ID NO 85
<211> LENGTH: 25
<212> TYPE: DNA
<213> ORGANISM: Homo sapiens

<400> SEQUENCE: 85
agttactatg agaatgtgat caaag 25

<210> SEQ ID NO 86
<211> LENGTH: 26
<212> TYPE: DNA
<213> ORGANISM: Homo sapiens

```
<400> SEQUENCE: 86
agtggcctct tatacccgg actgca                                           26

<210> SEQ ID NO 87
<211> LENGTH: 25
<212> TYPE: DNA
<213> ORGANISM: Homo sapiens

<400> SEQUENCE: 87
gtacttaagg gggatggagt ggccc                                           25

<210> SEQ ID NO 88
<211> LENGTH: 26
<212> TYPE: DNA
<213> ORGANISM: Homo sapiens

<400> SEQUENCE: 88
agttcctcct tgggcacgaa ctgtac                                          26

<210> SEQ ID NO 89
<211> LENGTH: 25
<212> TYPE: DNA
<213> ORGANISM: Homo sapiens

<400> SEQUENCE: 89
aggccgctca ccacagtccg tggtt                                           25

<210> SEQ ID NO 90
<211> LENGTH: 4
<212> TYPE: PRT
<213> ORGANISM: Artificial Sequence
<220> FEATURE:
<223> OTHER INFORMATION: Thrombin cleavable linkage

<400> SEQUENCE: 90

Gly Arg Gly Asp
 1

<210> SEQ ID NO 91
<211> LENGTH: 6
<212> TYPE: PRT
<213> ORGANISM: Artificial Sequence
<220> FEATURE:
<223> OTHER INFORMATION: Thrombin cleavable linkage

<400> SEQUENCE: 91

Gly Arg Gly Asp Asn Pro
 1               5

<210> SEQ ID NO 92
<211> LENGTH: 5
<212> TYPE: PRT
<213> ORGANISM: Artificial Sequence
<220> FEATURE:
<223> OTHER INFORMATION: Thrombin cleavable linkage

<400> SEQUENCE: 92

Gly Arg Gly Asp Ser
 1               5

<210> SEQ ID NO 93
<211> LENGTH: 7
<212> TYPE: PRT
<213> ORGANISM: Artificial Sequence
<220> FEATURE:
```

<223> OTHER INFORMATION: Thrombin cleavable linkage

<400> SEQUENCE: 93

Gly Arg Gly Asp Ser Pro Lys
1               5

<210> SEQ ID NO 94
<211> LENGTH: 4
<212> TYPE: PRT
<213> ORGANISM: Artificial Sequence
<220> FEATURE:
<223> OTHER INFORMATION: Elastase cleavable linkage

<400> SEQUENCE: 94

Ala Ala Pro Val
1

<210> SEQ ID NO 95
<211> LENGTH: 4
<212> TYPE: PRT
<213> ORGANISM: Artificial Sequence
<220> FEATURE:
<223> OTHER INFORMATION: Elastase cleavable linkage

<400> SEQUENCE: 95

Ala Ala Pro Leu
1

<210> SEQ ID NO 96
<211> LENGTH: 4
<212> TYPE: PRT
<213> ORGANISM: Artificial Sequence
<220> FEATURE:
<223> OTHER INFORMATION: Elastase cleavable linkage

<400> SEQUENCE: 96

Ala Ala Pro Phe
1

<210> SEQ ID NO 97
<211> LENGTH: 4
<212> TYPE: PRT
<213> ORGANISM: Artificial Sequence
<220> FEATURE:
<223> OTHER INFORMATION: Elastase cleavable linkage

<400> SEQUENCE: 97

Ala Ala Pro Ala
1

<210> SEQ ID NO 98
<211> LENGTH: 4
<212> TYPE: PRT
<213> ORGANISM: Artificial Sequence
<220> FEATURE:
<223> OTHER INFORMATION: Elastase cleavable linkage

<400> SEQUENCE: 98

Ala Tyr Leu Val
1

<210> SEQ ID NO 99
<211> LENGTH: 6
<212> TYPE: PRT
<213> ORGANISM: Artificial Sequence
<220> FEATURE:
<223> OTHER INFORMATION: Matrix metalloproteinase cleavable linkage

```
<220> FEATURE:
<221> NAME/KEY: VARIANT
<222> LOCATION: 3, 6
<223> OTHER INFORMATION: Xaa = Any amino acid

<400> SEQUENCE: 99

Gly Pro Xaa Gly Pro Xaa
1               5

<210> SEQ ID NO 100
<211> LENGTH: 4
<212> TYPE: PRT
<213> ORGANISM: Artificial Sequence
<220> FEATURE:
<223> OTHER INFORMATION: Matrix metalloproteinase cleavable linkage
<220> FEATURE:
<221> NAME/KEY: VARIANT
<222> LOCATION: 4
<223> OTHER INFORMATION: Xaa = Any amino acid

<400> SEQUENCE: 100

Leu Gly Pro Xaa
1

<210> SEQ ID NO 101
<211> LENGTH: 6
<212> TYPE: PRT
<213> ORGANISM: Artificial Sequence
<220> FEATURE:
<223> OTHER INFORMATION: Matrix metalloproteinase cleavable linkage
<220> FEATURE:
<221> NAME/KEY: VARIANT
<222> LOCATION: 6
<223> OTHER INFORMATION: Xaa = Any amino acid

<400> SEQUENCE: 101

Gly Pro Ile Gly Pro Xaa
1               5

<210> SEQ ID NO 102
<211> LENGTH: 5
<212> TYPE: PRT
<213> ORGANISM: Artificial Sequence
<220> FEATURE:
<223> OTHER INFORMATION: Matrix metalloproteinase cleavable linkage
<220> FEATURE:
<221> NAME/KEY: VARIANT
<222> LOCATION: 5
<223> OTHER INFORMATION: Xaa = Any Amino Acid

<400> SEQUENCE: 102

Ala Pro Gly Leu Xaa
1               5

<210> SEQ ID NO 103
<211> LENGTH: 6
<212> TYPE: PRT
<213> ORGANISM: Artificial Sequence
<220> FEATURE:
<223> OTHER INFORMATION: Collagenase cleavable linkage
<220> FEATURE:
<221> NAME/KEY: VARIANT
<222> LOCATION: 6
<223> OTHER INFORMATION: Xaa = Any amino acid

<400> SEQUENCE: 103

Pro Leu Gly Pro Arg Xaa
1               5
```

```
<210> SEQ ID NO 104
<211> LENGTH: 7
<212> TYPE: PRT
<213> ORGANISM: Artificial Sequence
<220> FEATURE:
<223> OTHER INFORMATION: Collagenase cleavable linkage
<220> FEATURE:
<221> NAME/KEY: VARIANT
<222> LOCATION: 7
<223> OTHER INFORMATION: Xaa = Any amino acid

<400> SEQUENCE: 104

Pro Leu Gly Leu Leu Gly Xaa
 1               5

<210> SEQ ID NO 105
<211> LENGTH: 7
<212> TYPE: PRT
<213> ORGANISM: Artificial Sequence
<220> FEATURE:
<223> OTHER INFORMATION: Collagenase cleavable linkage

<400> SEQUENCE: 105

Pro Gln Gly Ile Ala Gly Trp
 1               5

<210> SEQ ID NO 106
<211> LENGTH: 5
<212> TYPE: PRT
<213> ORGANISM: Artificial Sequence
<220> FEATURE:
<223> OTHER INFORMATION: Collagenase cleavable linkage

<400> SEQUENCE: 106

Pro Leu Gly Cys His
 1               5

<210> SEQ ID NO 107
<211> LENGTH: 6
<212> TYPE: PRT
<213> ORGANISM: Artificial Sequence
<220> FEATURE:
<223> OTHER INFORMATION: Collagenase cleavable linkage

<400> SEQUENCE: 107

Pro Leu Gly Leu Tyr Ala
 1               5

<210> SEQ ID NO 108
<211> LENGTH: 7
<212> TYPE: PRT
<213> ORGANISM: Artificial Sequence
<220> FEATURE:
<223> OTHER INFORMATION: Collagenase cleavable linkage

<400> SEQUENCE: 108

Pro Leu Ala Leu Trp Ala Arg
 1               5

<210> SEQ ID NO 109
<211> LENGTH: 7
<212> TYPE: PRT
<213> ORGANISM: Artificial Sequence
<220> FEATURE:
<223> OTHER INFORMATION: Collagenase cleavable linkage

<400> SEQUENCE: 109

Pro Leu Ala Tyr Trp Ala Arg
```

```
1               5

<210> SEQ ID NO 110
<211> LENGTH: 7
<212> TYPE: PRT
<213> ORGANISM: Artificial Sequence
<220> FEATURE:
<223> OTHER INFORMATION: Stromelysin cleavable linkage

<400> SEQUENCE: 110

Pro Tyr Ala Tyr Tyr Met Arg
1               5

<210> SEQ ID NO 111
<211> LENGTH: 7
<212> TYPE: PRT
<213> ORGANISM: Artificial Sequence
<220> FEATURE:
<223> OTHER INFORMATION: Gelatinase cleavable linkage

<400> SEQUENCE: 111

Pro Leu Gly Met Tyr Ser Arg
1               5

<210> SEQ ID NO 112
<211> LENGTH: 4
<212> TYPE: PRT
<213> ORGANISM: Artificial Sequence
<220> FEATURE:
<223> OTHER INFORMATION: Angiotensin converting enzyme cleavable linkage

<400> SEQUENCE: 112

Gly Asp Lys Pro
 1

<210> SEQ ID NO 113
<211> LENGTH: 5
<212> TYPE: PRT
<213> ORGANISM: Artificial Sequence
<220> FEATURE:
<223> OTHER INFORMATION: Angiotensin converting enzyme cleavable linkage

<400> SEQUENCE: 113

Gly Ser Asp Lys Pro
1               5

<210> SEQ ID NO 114
<211> LENGTH: 4
<212> TYPE: PRT
<213> ORGANISM: Artificial Sequence
<220> FEATURE:
<223> OTHER INFORMATION: Cathepsin B cleavable linkage

<400> SEQUENCE: 114

Ala Leu Ala Leu
 1
```

```
<210> SEQ ID NO 115
<211> LENGTH: 4
<212> TYPE: PRT
<213> ORGANISM: Artificial Sequence
<220> FEATURE:
<223> OTHER INFORMATION: Cathepsin B cleavable linkage

<400> SEQUENCE: 115

Gly Phe Leu Gly
 1
```

PEGYLATED TYROSYL-TRNA SYNTHETASE POLYPEPTIDES

CROSS-REFERENCE TO RELATED APPLICATIONS

This application claims benefit under 35 U.S.C. §119(e) of U.S. Provisional Application No. 61/521,696, filed Aug. 9, 2011, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_104_01WO_ST25.txt. The text file is about 123 KB, was created on Aug. 8, 2012, and is being submitted electronically via EFS-Web.

BACKGROUND

Technical Field

The present invention relates generally to PEGylated tyrosyl-tRNA synthetase (YRS) polypeptides, compositions comprising the same, and methods of using such polypeptides and compositions for treating or diagnosing a variety of conditions.

Description of the Related Art

The term "PEGylation" refers to the modification of biological molecules by covalent conjugation with polyethylene glycol (PEG), a non-toxic, non-immunogenic polymer. PEGylation is typically used as a strategy to overcome particular disadvantages associated with some biopharmaceuticals. PEGylation can change the physical and chemical properties of a biological molecule, such as its conformation, electrostatic binding, hydrophobicity, and pharmacokinetic profile. In general, PEGylation improves drug solubility and decreases immunogenicity. PEGylation also increases drug stability and the retention time of the conjugates in blood, and reduces proteolysis and renal excretion, thereby allowing a reduced dosing frequency. In order to benefit from these favorable pharmacokinetic consequences, a variety of therapeutic proteins, peptides, and antibody fragments, as well as small molecule drugs, have been PEGylated.

A number of properties of the PEG polymer—e.g. mass, number of linking chains, the molecular site of PEG attachment—have been shown to affect the biological activity and bioavailability of the PEGylated product. Releasable PEGs have been designed to slowly release the native protein from the conjugates into the blood, aiming at avoiding any loss of efficacy that may occur with stable covalent PEGylation. Since the first PEGylated drug was developed in the 1970s, PEGylation of therapeutic proteins has significantly improved the treatment of several chronic diseases, including hepatitis C, leukemia, severe combined immunodeficiency disease, rheumatoid arthritis, and Crohn's disease.

Tyrosyl-tRNA synthetases (YRS), and fragments and variants thereof, have been shown to possess a variety of non-canonical activities of therapeutic and diagnostic relevance. Examples of such activities include modulation of hematopoietic pathways such as thrombopoiesis, modulation of angiogenesis, and modulation of inflammatory pathways, among others. To best exploit these and other activities in therapeutic or diagnostic settings, there is a need in the art for YRS polypeptides having improved pharmacokinetic properties.

The present invention is focused on the development of PEGylated versions of YRS polypeptides that retain the biological activity of the native YRS polypeptides and exhibit superior pharmacokinetic properties. These improved therapeutic forms of the YRS polypeptides enable the development of more effective therapeutic regimens for the treatment of various diseases and disorders, and require significantly less frequent administration than the unmodified proteins.

These improved methods are based, at least in part, on animal studies and in vitro studies that surprisingly demonstrate that PEGylated versions of the YRS polypeptides actually exhibit enhanced biological activity compared to the native molecules, while also exhibiting vastly superior pharmacokinetic characteristics.

BRIEF SUMMARY OF THE INVENTION

Embodiments of the present invention relate generally to PEGylated tyrosyl-tRNA synthetase (YRS) polypeptides, pharmaceutical compositions comprising such molecules, and methods for their therapeutic use. Certain embodiments of the invention include a PEGylated tyrosyl-tRNA synthetase (YRS) polypeptide, comprising an amino acid sequence at least 80% identical as that set forth in any of SEQ ID NOS:1-29, and comprising at least one PEG moiety covalently attached to (a) an amino acid residue within about 10 amino acid residues of the C-terminus or the N-terminus, (b) a solvent accessible surface amino acid of the YRS polypeptide, or any combination thereof.

In some embodiments, the PEGylated YRS polypeptide comprises a PEG moiety which has a molecular weight of between about 10 KDa and about 80 KDa. In some embodiments, the PEG moiety has a molecular weight of between about 20 KDa and about 60 KDa. In some embodiments, the PEG moiety has a molecular weight of between about 30 KDa and about 50 KDa. In some embodiments, the PEG moiety has a molecular weight has a molecular weight of about 40 KDa. In some embodiments, the PEG moiety has a molecular weight has a molecular weight of about 20 KDa.

In some embodiments, the PEG moiety is attached to an amino acid residue within about 10 amino acid residues of the N-terminus of the YRS polypeptide. In some embodiments the PEG moiety is attached to the N-terminal amino acid of the YRS polypeptide. In some embodiments the PEG moiety is attached to an amino acid residue within about 10 amino acid residues of the C-terminus. In some embodiments the PEG moiety is attached to the C-terminal amino acid of the YRS polypeptide.

In some embodiments, the PEG moiety is attached to a cysteine (C) residue. In some embodiments the cysteine residue is naturally occurring. In specific aspects, the naturally-occurring cysteine residue is C67 or C250.

In some embodiments, the cysteine residue is introduced into the YRS polypeptide. In some embodiments of the PEGylated YRS polypeptide, the PEGylated YRS polypeptide comprises an inserted cysteine residue within about 10 amino acids of the N terminus, the C-terminus, a solvent accessible surface amino acid of the YRS polypeptide or any combination thereof. In some embodiments, the solvent accessible surface amino acids of the YRS polypeptide used for the insertion of the cysteine residue are selected from the group consisting of: A4, S6, G23, S95, A150, A201, G203, S205, G220, S221, G253, A300, A301, S338, A339, A351, and 353. In some embodiments, the PEGylated YRS polypeptide comprises a substituted cysteine residue wherein the substituted amino acid is introduced at position A4 or A351.

In some embodiments of the PEGylated YRS polypeptide, at least one endogenous cysteine residue has been substituted with another amino acid to block PEGylation at that position. In some embodiments the endogenous cysteine residue has been substituted with a conservative amino acid. In some embodiments the endogenous cysteine residue is selected from C67 and C250.

In some embodiments, the PEG moiety is attached to a non-naturally occurring amino acid. In some embodiments the non-naturally occurring amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxyl amide, and organosilane group. In some embodiments the non-naturally occurring amino acid is selected from the group consisting of: p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

In some embodiments, the YRS polypeptide is selected from the group consisting of YRS(1-329), YRS(1-343), YRS(1-350), YRS(1-353), YRS(1-364), YRS(1-368), YRS(1-382) and YRS(1-388). In one aspect, the YRS polypeptide is YRS(1-353).

In some embodiments, the PEGylated product exhibits a higher specific activity in a charging assay compared to the non PEGylated protein.

In some embodiments, the PEGylated YRS polypeptide has the following structure (I):

X-L-Y-YRS wherein:
X is the PEG moiety;
L is an optional linker;
Y is a covalent linkage; and
YRS is the YRS polypeptide.

In some embodiments, X, in formula (I) is $R_1$—$(CH_2CH_2O)_n$ or $R_1$—$(OCH_2CH_2)_n$, wherein $R_1$=alkyl, alkoxy, aryl, glucose, or galactose; and n is 20 to 800.

In some embodiments, $R_1$ is an alkoxy selected from the group consisting of: methoxy, ethoxy, and benzyloxy.

In some embodiments, L in formula (I) comprises a chain of 1 to 20 atoms selected from the group consisting of: C, S, N, P, and O.

In some embodiments, L in formula (I) comprises one or more of the following linkages: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$— CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —C(O)—NH—CH$_2$—CH$_2$—, —CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)— CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$— CH$_2$—, —NH—CH$_2$—, —NH—CH$_2$—CH$_2$—, —CH$_2$—NH—CH$_2$—, —CH$_2$—CH$_2$—NH—CH$_2$—, —C(O)— CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)— CH$_2$—CH$_2$—, —CH$_2$—CH$_2$—C(O)—, —CH$_2$—CH$_2$— CH$_2$—C(O)—NH—CH$_2$—CH$_2$—NH—, —CH$_2$—CH$_2$— CH$_2$—C(O)—NH—CH$_2$—CH$_2$—NH—C(O)—, —CH$_2$— CH$_2$—CH$_2$—C(O)—NH—CH$_2$—CH$_2$—NH—C(O)— CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

In some embodiments, L in formula (I) comprises a releasable linkage. In some embodiments, the releasable linkage is selected from the group consisting of: carboxylate ester, phosphate ester, anhydride, acetal, ketal, acyloxyalkyl ether, imine, orthoester, thio ester, thiol ester, carbonate, and hydrazone.

In some embodiments, L in formula (I) comprises a stable linkage. In some embodiments, the stable linkage is selected from the group consisting of: succinimide, propionic acid, carboxymethylate linkages, ethers, carbamates, amides, amines, carbamides, imides, aliphatic C—C bonds, and thio ethers.

In some embodiments, Y in formula (I) is selected from the group consisting of: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulfhydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, and alkylthio.

In some embodiments, the PEGylated YRS polypeptides of formula (I) comprise a structure selected from the group consisting of:

wherein n=20-800.
In one aspect, the PEGylated YRS polypeptides of formula (I) have the structure:

$$H_3CO-(CH_2CH_2)_n-O-CH_2CH_2-\overset{O}{\overset{\|}{C}}-NH-CH_2CH_2-NH-\overset{O}{\overset{\|}{C}}-CH_2CH_2-N\overset{\displaystyle\diagup\!\!\!\diagdown}{\underset{\diagdown\!\!\!\diagup}{\bigcirc}}-S-YRS$$

In some embodiments, the PEGylated YRS polypeptide comprises a branched PEG polymer. In some embodiments of the PEGylated YRS polypeptide, the PEGylated YRS polypeptide has the following structure (II):

(X-L$_1$)$_m$-B-L$_2$-Y-YRS wherein:
X is an independently selected PEG moiety for each m;
L$_1$ and L$_2$ are independently selected optional linkers, wherein L$_1$ is also independently selected for each m;
m is 2, 3, 4, or 5;
B is a branching moiety;
Y is a covalent linkage; and
YRS is the YRS polypeptide.

In some embodiments, the PEGylated YRS polypeptide has the following structure (IIA):

```
X—L₁—CH₂
        |
X—L₂—CH
        |
        CH₂—L₃—Y—YRS
``` wherein:
X is an independently selected water soluble polymer moiety;
L$_1$, L$_2$ and L$_3$ are independently selected optional linkers;
Y is a covalent linkage between the YRS polypeptide and the remainder of the conjugate; and
YRS refers to a YRS polypeptide as disclosed herein.

In some embodiments, the PEGylated YRS polypeptide has the following structure (IIB):

```
X—L₁—CH₂
        |
        HC—L₃—Y—YRS
        |
X—L₂—CH₂
``` wherein:
X is an independently selected water soluble polymer moiety;
L$_1$, L$_2$ and L$_3$ are independently selected optional linkers;
Y is a covalent linkage between the YRS polypeptide and the remainder of the conjugate; and
YRS refers to a YRS polypeptide as disclosed herein.

In some embodiments, the PEGylated YRS polypeptide has the following structure (IIC):

```
X—L₁
     \
      Lysine—L₃—Y—YRS
     /
X—L₂
``` wherein:
X is an independently selected water soluble polymer moiety;
L$_1$, L$_2$ and L$_3$ are independently selected optional linkers, and wherein the linkers connecting the lysine residue to the water soluble polymer moiety are connected via the amino groups of the lysine molecule, and the linker connecting the lysine molecule to the YRS polypeptide is attached via the C-terminal carboxylate group of the lysine molecule;
Y is a covalent linkage between the YRS polypeptide and the remainder of the conjugate; and YRS refers to a YRS polypeptide as disclosed herein.

In some embodiments, the PEGylated YRS polypeptide has the following structure (IID):

```
X—L₁
     \
      N—L₃—Y—YRS
     /
X—L₂
``` wherein:
X is an independently selected water soluble polymer moiety;
L$_1$, L$_2$ and L$_3$ are independently selected optional linkers;
Y is a covalent linkage between the YRS polypeptide and the remainder of the conjugate; and YRS refers to a YRS polypeptide as disclosed herein.

In some embodiments, in any of formulae (II), (IIA), (IIB), (IIC), or (IID), each X is independently $R_1$—(CH$_2$CH$_2$O) or $R_1$—(OCH$_2$CH$_2$)$_n$, wherein $R_1$=alkyl, alkoxy, aryl, glucose, or galactose; and n is 20 to 800. In some embodiments, $R_1$ is an alkoxy selected from the group consisting of: methoxy, ethoxy, and benzyloxy.

In some embodiments, in any of formulae (II), (IIA), (IIB), (IIC), or (IID), L$_2$ and each of L$_1$ independently comprise a chain of 1 to 20 atoms selected from the group consisting of: C, S, N, P, and O.

In some embodiments, in any of formulae (II), (IIA), (IIB), (IIC), or (IID), L$_2$ and each of L$_1$ independently comprise one or more of the following linkages: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

In some embodiments of the PEGylated YRS polypeptide of formulae (II), (IIA), (IIB), (IIC), or (IID), $L_2$ and each of $L_1$ independently comprise a releasable linkage or a stable linkage.

In some embodiments of the PEGylated YRS polypeptide of formulae (II), (IIA), (IIB), (IIC), or (IID) $L_2$ and each of $L_1$ independently comprise a releasable linkage.

In some embodiments of the PEGylated YRS polypeptide of formulae (II), (IIA), (IIB), (IIC), or (IID) $L_2$ and each of $L_1$ independently comprise a stable linkage.

In some embodiments of the PEGylated YRS polypeptide of formulae (II), (IIA), (IIB), (IIC), or (IID), the stable linkage is selected from the group consisting of: succinimide, propionic acid, carboxymethylate linkages, ethers, carbamates, amides, amines, carbamides, imides, aliphatic C—C bonds, and thio ethers.

In some embodiments of the PEGylated YRS polypeptide of formulae (II), (IIA), (IIB), (IIC), or (IID), Y is selected from the group consisting of: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulfhydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, and alkylthio.

In some embodiments of the PEGylated YRS polypeptide of formulae (II), (IIA), (IIB), (IIC), or (IID), B is selected from the group consisting of: an amino acid linkage or an aliphatic hydrocarbon chain of 3 to 6 carbons.

In some embodiments of the PEGylated YRS polypeptide of formula (II), B is selected from arginine, histidine, lysine, glutamine, serine, threonine, asparagine, aspartic acid, glutamic acid, cysteine, and seleno cysteine. In one aspect, B is lysine. In some embodiments of the PEGylated YRS polypeptide of formula (II), B is an aliphatic hydrocarbon chain is derived from propane, butane, pentane, or hexane. In some embodiments of the PEGylated YRS polypeptide of formula (II), B is an aliphatic hydrocarbon chain derived from a polyol selected from the groups consisting of: glycerol, erythritol, xylitol, and sorbitol. In some embodiments of the PEGylated YRS polypeptide of formula (II), B is an aliphatic hydrocarbon chain is derived from glycerol or propane.

In some embodiments, the PEGylated YRS polypeptide of formulae (II), (IIA), (IIB), (IIC), or (IID) comprises a structure selected from the group consisting of:

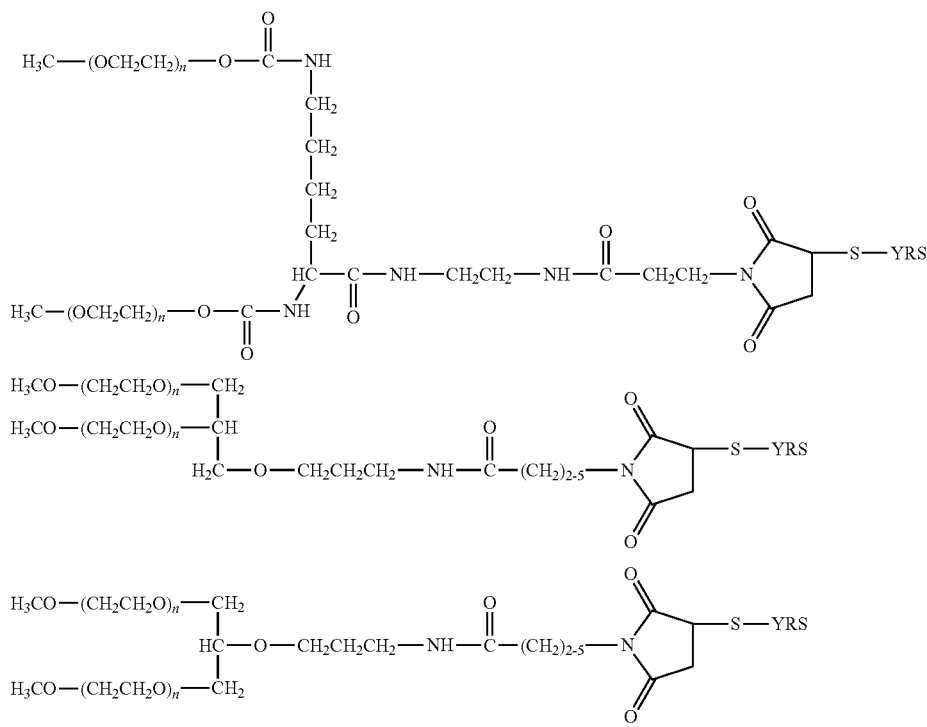

-continued

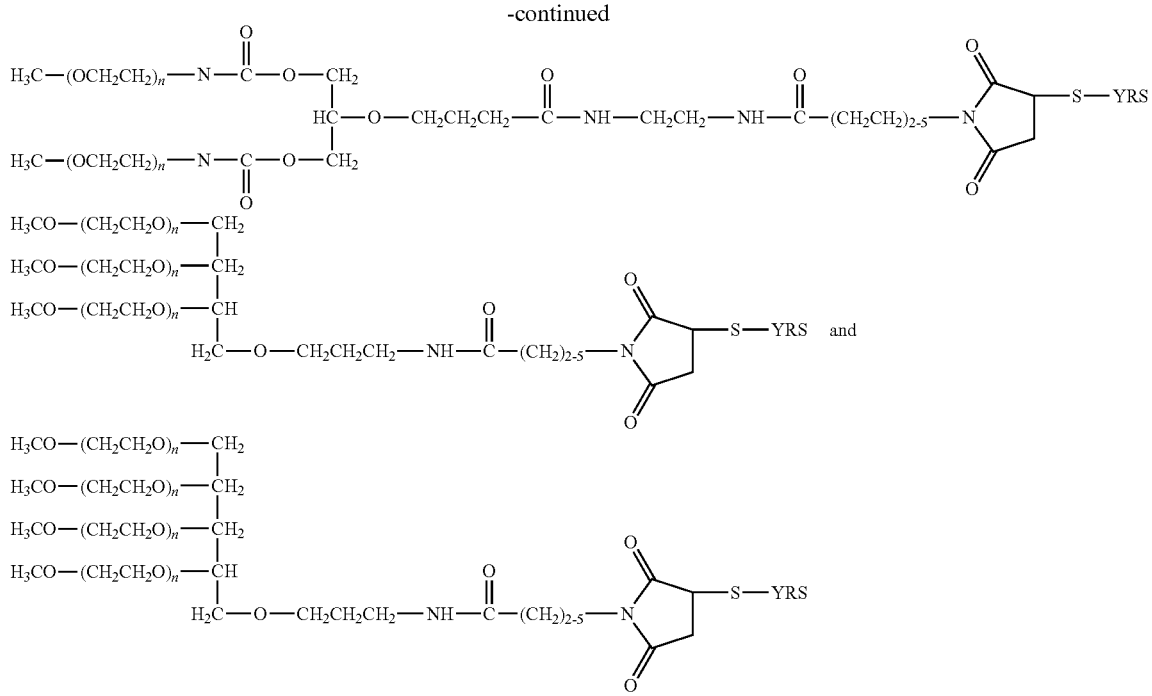

wherein n is independently any integer from 20 to 800.

In some embodiments, the PEGylated YRS polypeptide, comprises the sequence set forth in SEQ ID NO:7 YRS(1-353), which is modified by A4C, C67S, and C250S substitutions, where a maleimide monomethoxy polyethylene glycol (mPEG) derivative of about 40,000 Daltons is covalently attached via a thio ether linkage to A4C.

In some embodiments, the PEGylated YRS polypeptide consists essentially of the sequence set forth in SEQ ID NO:7 (YRS1-353), which is modified by A4C, C67S, and C250S substitutions, where a maleimide monomethoxy polyethylene glycol (mPEG) derivative of about 40,000 Daltons is covalently attached via a thio ether linkage to A4C.

In some embodiments, the PEGylated YRS polypeptide consists of the sequence set forth in SEQ ID NO:7 (YRS1-353), which is modified by A4C, C67S, and C250S substitutions, where a maleimide monomethoxy polyethylene glycol (mPEG) derivative of about 40,000 Daltons is covalently attached via a thio ether linkage to A4C.

In some embodiments, the PEGylated YRS polypeptide comprises the sequence set forth in SEQ ID NO:7 (YRS1-353), which is modified by C67S, C250S, and A351C substitutions, where a maleimide monomethoxy polyethylene glycol (mPEG) derivative of about 40,000 Daltons is covalently attached via a thio ether linkage to A351C.

In some embodiments, the PEGylated YRS polypeptide consists essentially of the sequence set forth in SEQ ID NO:7 (YRS1-353), which is modified by C67S, C250S, and A351C substitutions, where a maleimide monomethoxy polyethylene glycol (mPEG) derivative of about 40,000 Daltons is covalently attached via a thio ether linkage to A351C.

In some embodiments, the PEGylated YRS polypeptide consists of the sequence set forth in SEQ ID NO:7 (YRS1-353), which is modified by C67S, C250S, and A351C substitutions, where a maleimide monomethoxy polyethylene glycol (mPEG) derivative of about 40,000 Daltons is covalently attached via a thio ether linkage to A351C.

In certain aspects, the PEGylated product exhibits a higher specific activity in a charging assay compared to the non PEGylated protein. In specific aspects, the PEGylated YRS polypeptide comprises the structure:

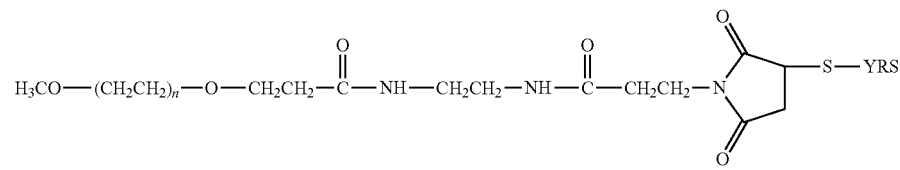

In one aspect, the PEGylated YRS polypeptide comprises the structure:

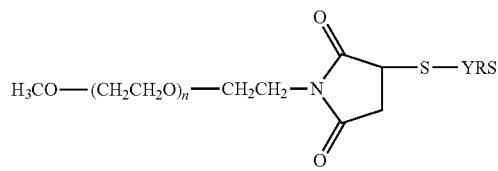

In one aspect, the PEGylated YRS polypeptide comprises the structure:

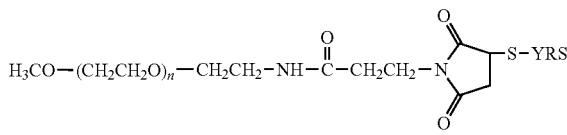

In one aspect, the PEGylated YRS polypeptide comprises the structure:

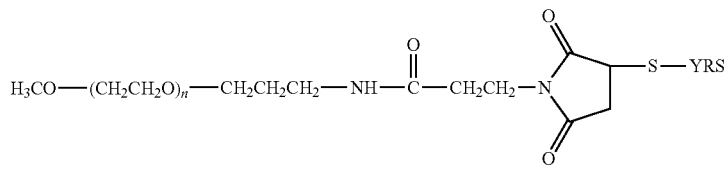

In one aspect of any of these PEGylated YRS polypeptides, the PEGylated YRS polypeptide has substantially the same secondary structure as unmodified YRS polypeptide, as determined via UV circular dichroism analysis.

In one aspect of any of these PEGylated YRS polypeptides, the PEGylated YRS polypeptide has a plasma or sera pharmacokinetic AUC profile at least 5-fold greater than unmodified YRS polypeptide when administered to rats.

In one aspect of any of these PEGylated YRS polypeptides, the PEGylated YRS polypeptide has greater than 2 fold the activity of the unPEGylated protein in a charging assay.

In one aspect of any of these PEGylated YRS polypeptides, the PEGylated YRS polypeptide has greater than 4 fold the activity of the unPEGylated protein in a charging assay.

Certain embodiments include a dosing regimen which maintains an average steady-state concentration of YRS polypeptide in the subjects' plasma of between about 0.3 μg/ml and about 3 μg/ml when using a dosing interval of 3 days or longer, comprising administering to the patient a therapeutic dose of any of the PEGylated YRS polypeptides listed above.

Particular embodiments include a method for maintaining YRS polypeptide levels above the minimum effective therapeutic level in a subject in need thereof, comprising administering to the subject a therapeutic dose of any of the PEGylated YRS polypeptides listed above.

Some embodiments include a method for treating a hematopoiesis related disease in a subject in need thereof, comprising administering to the subject a therapeutic dose of any of the PEGylated YRS polypeptides listed above. In some embodiments, the hematopoiesis related disease is selected from thrombocytopenia, lymphocytopenia, neutropenia, basopenia, eosinopenia, anemias, polycythemia, neutrophilia, eosinophilia, or basophilia.

Also included are methods for treating a subject with a myelodysplastic syndrome comprising administering to the subject a therapeutic dose of PEGylated YRS polypeptide of any of the PEGylated YRS polypeptides listed above and a pharmaceutically acceptable carrier. In some embodiments, the myelodysplastic syndrome is selected from Refractory Anemia (RA) (ICD-O code M9980/3), Refactory cytopenia with unilineage dysplasia (Refactory anemia, Refactory neutropenia, and Refractory thrombocytopenia), Refractory Anemia with Ring Sideroblasts (RARS) (ICD-O code M9982/3), Refractory Anemia with Ring Sideroblasts—thromocytosis, Refractory cytopenia with multilineage dysplasia (RCMD), Refractory Anemia with Excess Blasts (RAEB) (ICD-O code M9983/3), Refractory Anemia with Excess Blasts I or II, Refractory Anemia with Excess Blasts in Transformation (RAEB-T) (ICD-O code M9984/3), Chronic Myelomoncytic Leukemia (CMML) (ICD-O code M9945/3), 5q-syndrome, myelodyplastic-myeloproliferative overlap syndromes, Myelodyplasia unclassificable, and refractory cytopenia of childhood.

Certain embodiments relate to a pharmaceutical composition comprising any of the PEGylated YRS polypeptides listed above and a pharmaceutically acceptable carrier or excipient. In some embodiments, the composition is buffered to a pH of about 5.5 to about 6.5. In some embodiments, the composition is buffered to a pH of about 6.0. In some embodiments, the composition is buffered with a phosphate buffer at a concentration of about 10 to 20 mM. In some embodiments, the composition is characterized by decreased aggregation of the PEGylated YRS polypeptides of any of claims 1 to 71 compared to a composition incubated under identical conditions but at pH 7.0 or higher.

Also included are improved methods for preparing a purified poly-His tagged YRS polypeptide comprising the steps of binding the poly His tagged YRS polypeptide to a nickel chelate resin, and the washing the resin to remove non-specifically bound proteins, wherein the improvement involves eluting the poly His tagged YRS polypeptide from the resin with an elution buffer at a pH within the range of about pH 6.0 to about pH 6.5. In some embodiments, the purified poly-His tagged YRS is characterized by significantly less aggregation compared to a YRS polypeptide eluted at pH 7.0.

SEQUENCE IDENTIFIERS

SEQ ID NO:1 is the full-length amino acid sequence of human tyrosyl-tRNA synthetase (YRS).

SEQ ID NO:2 is the full-length DNA sequence of human tyrosyl-tRNA synthetase (YRS).

SEQ ID NO:3 is the amino acid sequence of TyrRS1$^{N5}$/YRS(1-329).

SEQ ID NO:4 is the amino acid sequence of MiniY/TyrRS1$^{N2}$/YRS (1-343)

SEQ ID NO:5 is the amino acid sequence of YRS(1-344)

SEQ ID NO:6 is the amino acid sequence of YRS(1-350)

SEQ ID NO:7 is the amino acid sequence of TyrRS1$^{N9}$/YRS(1-353)

SEQ ID NO:8 is the amino acid sequence of TyrRS1$^{N10}$/YRS(1-364)

SEQ ID NO:9 is the amino acid sequence of TyrRS1$^{N4}$/YRS(1-368).

SEQ ID NO:10 is the amino acid sequence of YRS(1-382).

SEQ ID NO:10 is the amino acid sequence of YRS(1-388)

SEQ ID NO:12 is the amino acid sequence of TyrRS1$^{N3}$/YRS(1-395)

SEQ ID NO:13 is the amino acid sequence of TyrRS1$^{J1}$/YRS(81-346).

SEQ ID NO:14 is the amino acid sequence of TyrRS1$^{J2}$/YRS(87-346).

SEQ ID NO:15 is the amino acid sequence of YRS(328-528).

SEQ ID NO:16 is the amino acid sequence of TyrRS1$^{C2}$/YRS(340-528).

SEQ ID NO:17 is the amino acid sequence of EMAPIII/YRS(361-528).

SEQ ID NO:18 is the amino acid sequence of TyrRS1$^{C1}$/YRS(390-528).

SEQ ID NO:19 is the amino acid sequence of TyrRS1$^{N7}$/YRS(1-19+41).

SEQ ID NO:20 is the amino acid sequence of SP1/YRS(1-9+190-528).

SEQ ID NO:21 is the amino acid sequence of SP2/YRS(1-353+5).

SEQ ID NO:22 is the amino acid sequence of SP3/SV8/YRS(211-528)

SEQ ID NO:23 is the amino acid sequence of SP4/TyrRS1$^{C3}$/YRS(350-528).

SEQ ID NO:24 is the amino acid sequence of SP5/YRS(8+349-528).

SEQ ID NO:25 is the amino acid sequence of SV7/YRS(1-17+169-524).

SEQ ID NO:26 is the amino acid sequence of TyrRS1$^{N8}$/YRS(1-228+303-528).

SEQ ID NO:27 is the amino acid sequence of TyrRS1$^{C4}$/YRS(1-19+303-528).

SEQ ID NO:28 is the amino acid sequence of TyrRS1$^{C5}$/YRS(1-19+171-528).

SEQ ID NO:29 is the amino acid sequence of TyrRS1$^{C6}$/YRS(1-197+229-528).

SEQ ID NO:30 is the amino acid sequence of TyrRS1$^{N11}$/YRS (1-228+2 amino acids).

SEQ ID NO:31 is the amino acid sequence of TyrRS1$^{N12}$/YRS(1-302+41 amino acids).

SEQ ID NO:32 is the amino acid sequence of TyrRS1$^{N13}$/YRS(1-380+7 amino acids).

SEQ ID NO:33 is the amino acid sequence of TyrRS1$^{C7}$/YRS(1-170+229-528).

SEQ ID NO:34 is the amino acid sequence of TyrRS1$^{C8}$/YRS(1-274+349-528).

SEQ ID NO:35 is the amino acid sequence of TyrRS1$^{C9}$/YRS(511-528).

SEQ ID NO:36 is a polynucleotide sequence of codon optimized full length YRS containing the mutation Y341A (coY341A).

SEQ ID NOS:37-38 are primers used to PCR amplify the coY341A gene.

SEQ ID NOS:39-55 are primers used to engineer various YRS polypeptide expression vectors.

SEQ ID NO:56 set forth a polynucleotide sequence encoding a non-tagged YRS (1-353) A4C polypeptide.

SEQ ID NO:57 set forth a polynucleotide sequence encoding a non-tagged YRS (1-353) A351C polypeptide.

SEQ ID NO:58 set forth a non-tagged YRS (1-353) A4C polypeptide sequence.

SEQ ID NO:59 set forth a non-tagged YRS (1-353) A351C polypeptide sequence.

SEQ ID NO:60 set forth a polynucleotide sequence encoding a HIS-tagged YRS (1-353) A4C polypeptide.

SEQ ID NO:61 set forth a polynucleotide sequence encoding a HIS-tagged YRS (1-353) A351C polypeptide.

SEQ ID NO:62 set forth a HIS-tagged YRS (1-353) A4C polypeptide sequence.

SEQ ID NO:63 set forth a HIS-tagged YRS (1-353) A35C polypeptide sequence.

BRIEF DESCRIPTION OF THE DRAWINGS

FIGS. 5A and C shows the result of size exclusion chromatography of unPEGylated and PEGylated versions of YRS(1-353)A4C, respectively. FIGS. 5B and D shows the result of size exclusion chromatography of unPEGylated and PEGylated versions of YRS (1-353) A351C polypeptides, respectively.

FIG. 7 shows the results UV circular dichroism scanning analysis of the unPEGylated and PEGylated versions of YRS(1-353)A4C and YRS(1-353)A351C.

DETAILED DESCRIPTION OF THE INVENTION

Figure 1:
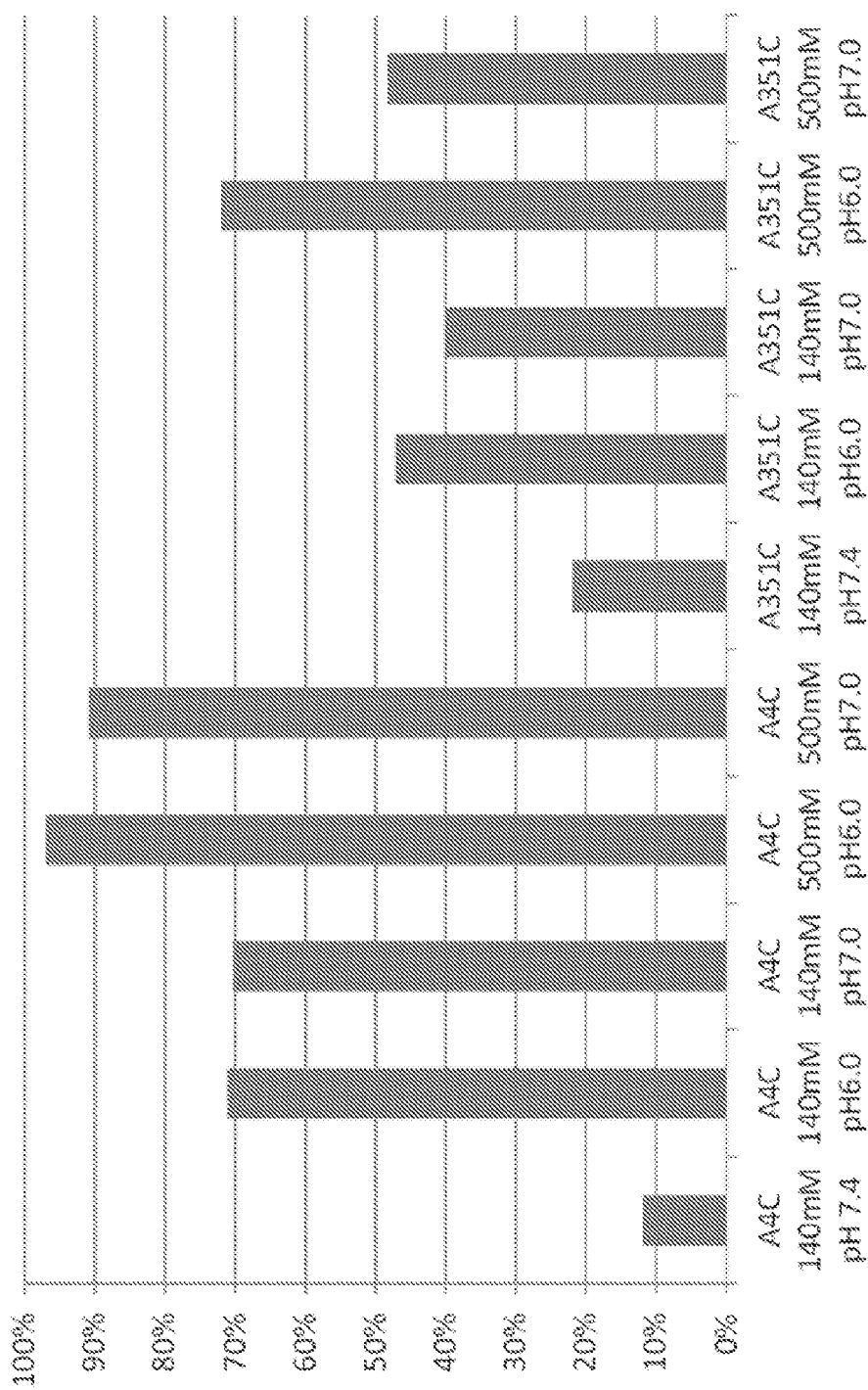
FIG. 1 shows the percentage of YRS(1-353)A4C and YRS(1-353)A351C protein recovery dialyzed against different buffers.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken N.J., John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., *"Use of functionalized Poly(Ethylene Glycols) for modification of polypeptides"* in Polyethylene Glycol Chemistry: Biotechnical and Biomedical Applications.

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "alkyl" or "alkylene" group, depending upon its position in a molecule and the number of points of attachment of the group to atoms other than hydrogen, refers to a hydrocarbon chain or moiety, typically ranging from about 1 to 50 atoms in length. Such hydrocarbon chains are preferably but not necessarily saturated unless so indicated and may be branched or straight chain, although typically straight chain is preferred in particular embodiments. Exemplary alkyl groups include methyl, ethyl, propyl, butyl, pentyl, 1-methylbutyl, 1-ethylpropyl, 3-methylpentyl, and the like.

"Alicyclic" refers to any aliphatic compound that contains a ring of carbon atoms. An alicyclic group is one that contains a "cycloalkyl" or "cycloalkylene" group as defined above that is substituted with one or more alkyl or alkylenes.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), and in some embodiments, preferably $C_1$-$C_5$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Atom length" or "chain length" refers to the number of atoms making up a particular fragment, spacer, linker or the like. By chain length is meant the number of atoms in a single chain, not counting substituents. For instance, —$CH_2$— counts as one atom with respect to chain length, —$CH_2CH_2CH_2$— counts as 3 atoms with respect to chain length, and so on.

"Bifunctional" in the context of a polymer of the invention refers to a PEG polymer possessing two reactive functional groups which may be the same or different.

"Branched" in reference to the geometry or overall structure of a PEG polymer refers to polymer having 2 or more PEG polymer "arms." A branched polymer may possess 2, 3, 4, 5, 6, 7, 8, 9, 10 or more PEG polymer arms.

"Branch moiety" refers to a moiety comprising one or more atoms at which a PEG polymer splits or branches from a linear structure into one or more additional PEG polymer arms.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent attachment of a molecule, e.g., a biologically active molecule, to a reactive polymer molecule, preferably a branched reactive polymer of the invention.

"Cycloalkyl" or "cycloalkylene", depending upon its position in a molecule and the number of points of attachment to atoms other than hydrogen, refers to a saturated or unsaturated cyclic hydrocarbon chain, including polycyclics such as bridged, fused, or spiro cyclic compounds, preferably made up of 3 to about 12 carbon atoms, more preferably 3 to about 8.

The recitation "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing YRS polypeptides in and isolating them from eukaryotic cells such as mammalian cells to reduce, if not eliminate, the risk of endotoxins being present in a composition of the invention. Preferred are methods of producing YRS polypeptides in and isolating them from serum free cells.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml. Typically, 1 ng lipopolysaccharide (LPS) corresponds to about 1-10 EU.

"Electrophile" refers to an ion, atom, or collection of atoms that may be ionic, having an electrophilic center, i.e., a center that is electron seeking, capable of reacting with a nucleophile.

The terms "end-capped" and "terminally capped" are interchangeably used herein to refer to a terminal or endpoint of a polymer having an end-capping moiety. Typically, although not necessarily, the end-capping moiety comprises a hydroxy or an alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cycloalkyl, heterocyclo, and the like. In particular embodiments, the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane or acrylate. In certain embodiments, the end-capping group can also comprise a phospholipid. When the polymer has an end-capping group comprising a phospholipid, unique properties can be imparted to the polymer and the resulting conjugate, e.g., YRS polypeptide. Exemplary phospholipids include, without limitation, phosphatidylcholines, such as, for example, dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

A "hydrolytically stable" linkage or bond refers to a linker, or chemical bond, that is substantially stable in water, that is to say, does not undergo hydrolysis under physiological conditions to any appreciable extent over an extended period of time. Examples of hydrolytically stable linkages include, but are not limited to, the following: succinimide, propionic acid, carboxymethylate linkages, ethers, carbamates, amides, amines, carbamides, imides, aliphatic C—C bonds, thio ethers, thiocarbamates, thiocarbamides, and the like. Generally, a hydrolytically stable linkage is one that exhibits a rate of hydrolysis of less than about 0.5%, about 1%, about 2%, about 3%, about 4%, or about 5% per day under physiological conditions.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "half maximal effective concentration" or "$EC_{50}$" refers to the concentration of a PEGylated YRS polypeptide agent described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of a PEGylated YRS protein is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, biotherapeutic composition will have an $EC_{50}$ value of about 1 nM or less.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

The terms "functional group," "active moiety," "reactive site," "chemically reactive group," and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with a functional group, is intended to include those functional groups that react readily with electrophilic or nucleophilic groups on other molecules, in contrast to those groups that require strong catalysts or highly impractical reaction conditions in order to react (i.e., "non-reactive" or "inert" groups).

The term "linkage," "linker," "linker moiety," or "L" is used herein to refer to an atom or a collection of atoms used to link, preferably by one or more covalent bonds, interconnecting moieties such as two polymer segments or a terminus of a polymer and a reactive functional group present on a polypeptide, e.g., a YRS polypeptide. The linker may be hydrolytically stable or may include a releasable linkage such as a physiologically hydrolyzable or enzymatically degradable linkage.

"Lower alkyl" or "lower alkylene" refers to an alkyl or alkylene group as defined above containing from 1 to 6 carbon atoms, and may be straight chain or branched, as exemplified by methyl, ethyl, n-butyl, i-butyl, t-butyl.

"Lower cycloalkyl" or "lower cycloalkylene" refers to a cycloalkyl group or cycloalkylene group containing from 1 to 6 carbon atoms.

The term "modulating" includes "increasing," "enhancing" or "stimulating," as well as "decreasing" or "reducing," typically in a statistically significant or a physiologically significant amount as compared to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., in the absence of any of the PEGylated YRS polypeptides of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the PEGylated YRS polypeptide of interest compared to a corresponding un-PEGylated YRS polypeptide. Other examples of "statistically significant" amounts will be apparent from the description provided herein.

"Monofunctional" in the context of a polymer of the invention refers to a PEG polymer possessing a single reactive functional group.

"Multifunctional" in the context of a polymer of the invention means a PEG polymer having 3 or more functional groups attached thereto, where the functional groups may be the same or different. Multifunctional polymers of the invention will typically comprise from about 3 to 100 functional groups, or from 3 to 50 functional groups, or from 3 to 25 functional groups, or from 3 to 15 functional groups, or from 3 to 10 functional groups, or will contain 3, 4, 5, 6, 7, 8, 9 or 10 functional groups attached to the polymer backbone.

"Non-canonical" activity as used herein, refers generally to either i) a new activity possessed by YRS polypeptide of the invention that is not possessed to any significant degree by the intact native full length parental protein, or ii) a non-aminoacylation activity that was possessed by the by the intact native full length parental protein, where the YRS polypeptide either exhibits a significantly higher (e.g., at least 20% greater) specific activity with respect to the non-canonical activity compared to the intact native full length parental protein, or exhibits the activity in a new context; for example by isolating the activity from other activities possessed by the intact native full length parental protein. In the case of YRS polypeptides, non-limiting examples of non-canonical activities include extracellular signaling, RNA-binding, amino acid-binding, modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, and the like.

"Non-interfering substituents" are those groups that, when present in a molecule, are typically non-reactive with other functional groups contained within the molecule.

"Nucleophile" refers to an ion or atom or collection of atoms that may be ionic, having a nucleophilic center, i.e., a center that is seeking an electrophilic center, and capable of reacting with an electrophile.

As used herein, the term "polyalkylene glycol" or "poly(alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

As used herein, the terms "PEG," "polyethylene glycol" and "poly(ethylene glycol)" as used herein, are interchangeable and meant to encompass any water-soluble poly(ethylene oxide) derivative. PEG is a well-known polymer with good solubility in many aqueous and organic solvents, which exhibits low toxicity, lack of immunogenicity, and is clear, colorless, odorless, and stable. For these reasons and others, PEG has been selected as the preferred polymer for attachment, but it has been employed solely for purposes of illustration and not limitation. Similar products may be obtained with other water-soluble polymers, as described herein, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Typically, PEGs for use in accordance with the invention comprise the following structure "—$(OCH_2CH_2)_n$—" where (n) is about 2 to 4000, alternatively from about 20 to 1400, or about 20-800. In particular embodiments, PEG also includes "—O—$(CH_2CH_2O)_n$—$CH_2CH_2$—" and "—$(OCH_2CH_2)_n$—O—" depending upon whether or not the terminal oxygens have been displaced. Throughout the specification and claims, it should be understood that in certain embodiments, the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

Representative polymeric reagents and methods for conjugating such polymers to an active moiety are described in Harris, J. M. and Zalipsky, S., Eds, Poly(ethylene glycol), *Chemistry and Biological Applications*, ACS, Washington, 1997; Veronese, F., and J. M. Harris, Eds., *Peptide and Protein PEGylation, Advanced Drug Delivery Reviews*, 54(4); 453-609 (2002); Zalipsky, S., et al., "Use of Functionalized Poly Ethylene Glycols) for Modification of Polypeptides" in *Polyethylene Glycol Chemistry: Biotechnical and Biomedical Applications*, J. M. Harris, ed., Plenus Press, New York (1992); Zalipsky (1995) *Advanced Drug Reviews* 16:157-182; and in Roberts et al., *Adv. Drug Delivery Reviews*, 54, 459-476 (2002).

A wide variety of PEG derivatives are both commercially available and suitable for use in the preparation of the PEG-conjugates of the invention. For example, NOF Corp.'s SUNBRIGHT® Series provides numerous PEG derivatives, including methoxypolyethylene glycols and activated PEG derivatives such as succinimidyl ester, methoxy-PEG amines, maleimides, and carboxylic acids, for coupling by various methods to YRS polypeptides and Nektar Therapeutics' Advanced PEGylation also offers diverse PEG-coupling technologies to improve the safety and efficacy of therapeutics. Additional PEGs for use in forming a YRS polypeptide conjugate of the invention include those available from Polypure (Norway), from QuantaBioDesign LTD (Ohio) JenKem Technology, Nanocs Corporation, and Sunbio, Inc (South Korea). Further PEG reagents suitable for use in forming a conjugate of the invention, and methods of conjugation are described in the Pasut. G., et al., *Expert Opin. Ther. Patents* (2004), 14(6) 859-893.

A number of investigators have disclosed the preparation of linear or branched PEG polymers and derivatives or conjugates thereof (see, e.g., U.S. Pat. Nos. 4,904,584; 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087; 6,180,095; 6,448,369; 6,495,659; 6,602,498; 6,858,736; 6,828,401; 7,026,440; 7,608,678; 7,655,747; 7,786,221; 7,872,072; and 7,910,661, each of which is incorporated herein by reference in its entirety.

In certain embodiments, the "purity" of any given agent (e.g., PEGylated YRS polypeptide) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides. Without wishing to be bound to any particular theory, an "enzymatically degradable linkage" means a linkage, e.g., amino acid sequence, that is subject to degradation by one or more enzymes, e.g., peptidases or proteases.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

A "releasable linkage" includes, but is not limited to, a physiologically cleavable bond, a hydrolyzable bond, and an enzymatically degradable linkage. Thus, a "releasable linkage" is a linkage that may undergo either spontaneous hydrolysis, or cleavage by some other mechanism (e.g., enzyme-catalyzed, acid-catalyzed, base-catalyzed, and so forth) under physiological conditions. For example, a "releasable linkage" can involve an elimination reaction that has a base abstraction of a proton, (e.g., an ionizable hydrogen atom, Ha), as the driving force. For purposes herein, a "releasable linkage" is synonymous with a "degradable linkage." In particular embodiments, a releasable linkage has a half life at pH 7.4, 25° C., e.g., a physiological pH, human body temperature, of about 30 min., about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or par "Substituted heteroaryl" is heteroaryl having one or more non-interfering groups as substituents.

"Substituted heterocycle" is a heterocycle having one or more side chains formed from non-interfering substituents.

The term "solubility" refers to the property of a PEGylated YRS polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a PEGylated YRS polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "subject," as used herein, includes any animal that exhibits a symptom, or is at risk for exhibiting a symptom, which can be treated or diagnosed with a PEGylated YRS polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

As used herein, the term "water soluble polymer" refers to any polymer that is soluble in aqueous solvents. Linkage of water soluble polymers to YRS polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered receptor dimerization or multimerization, modulated toxicity, and modulation of one or more the biological activities of YRS polypeptides including side effects found with current YRS therapeutics. The water soluble polymer may or may not have its own biological activity, and may be utilized as a linker for attaching YRS polypeptides to other substances, including but not limited to one or more YRS polypeptides, and/or one or more biologically active molecules. Suitable polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof.

Specific examples of such water soluble polymers include, but are not limited to, polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

Tyrosyl-tRNA Synthetase Derived Polypeptides

Embodiments of the present invention relate to PEGylated tyrosyl-tRNA synthetase derived polypeptides ("YRS polypeptides"). Tyrosyl-tRNA synthetases belong to the class I tRNA synthetase family, which has two highly conserved sequence motifs at the active site, HIGH and KMSKS. Class I tRNA synthetases aminoacylate at the 2'-OH of an adenosine nucleotide, and are usually monomeric or dimeric (one or two subunits, respectively).

The human tyrosyl-tRNA synthetase is composed of three broadly recognized canonical domains: 1) an amino-terminal Rossmann fold domain that is responsible for formation of the activated E. Tyr-AMP intermediate and is conserved among bacteria, archeae, and eukaryotes; 2) a tRNA anticodon recognition domain that has not been conserved between bacteria and eukaryotes; and 3) a carboxyl-terminal domain that is unique to the human tyrosyl-tRNA synthetase, and whose primary structure is 49% identical to the putative human cytokine endothelial monocyte-activating protein II, 50% identical to the carboxyl-terminal domain of methionyl-tRNA synthetase from *Caenorhabditis elegans*, and 43% identical to the carboxyl-terminal domain of Arc1p from *Saccharomyces cerevisiae*.

The first two domains of the human tyrosyl-tRNA synthetase are 52%, 36%, and 16% identical to tyrosyl-tRNA synthetases from *S. cerevisiae, Methanococcus jannaschii*, and *Bacillus stearothermophilus*, respectively. Nine of fifteen amino acids known to be involved in the formation of the tyrosyl-adenylate complex in *B. stearothermophilus* are conserved across all of the organisms, whereas amino acids involved in the recognition of tRNA$^{Tyr}$ are not conserved. Kinetic analyses of recombinant human and *B. stearothermophilus* tyrosyl-tRNA synthetases expressed in *Escherichia coli* indicate that human tyrosyl-tRNA synthetase aminoacylates human but not *B. stearothermophilus* tRNA$^{Tyr}$, and vice versa. It is believed that the carboxyl-terminal domain of human tyrosyl-tRNA synthetase evolved from gene duplication of the carboxyl-terminal domain of methionyl-tRNA synthetase and may direct tRNA to the active site of the enzyme.

More recently it has been established that some biological fragments, or alternatively spliced isoforms of eukaryotic tyrosyl-tRNA synthetases, or in some contexts the intact synthetase, can activate certain cell-signaling pathways, or act within the nucleus to modulate transcription, e.g., to regulate hematopoietic pathways, such as megakaryopoiesis or thrombopoiesis. These fragments may be produced naturally by either alternative splicing or proteolysis, and can act in a cell autonomous (i.e., within the host cell), or non-cell automonous fashion (i.e., outside the host cell) to regulate a variety of homeostatic mechanisms. For example, as provided in the present invention, the N-terminal fragment YRS (1-353) is capable of modulating hematopoiesis in vivo. In addition, certain mutations or deletions relative to the full-length YRS polypeptide sequence confer increased hematopoietic-modulating or other non-canonical activities (e.g., Y341A, mini-YRS). The sequences of various exemplary YRS polypeptides are provided in Table 1.

TABLE 1

Exemplary YRS Polypeptides

| Amino Acid Residue Range of SEQ. ID. No. 1 | Name(s) | | Ref | SEQ. ID. No. |
|---|---|---|---|---|
| 1-528 | Full length (protein) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKKL KKAFCEPGNVENNGVLSFIKHVLFPLKSEFVILRDE KWGGNKTYTAYVDLEKDFAAEVVHPGDLKNSVE VALNKLLDPIREKFNTPALKKLASAAYPDPSKQKP MAKGPAKNSEPEEVIPSRLDIRVGKIITVEKHPDAD SLYVEKIDVGEAEPRTVVSGLVQFVPKEELQDRLV VVLCNLKPQKMRGVESQGMLLCASIEGINRQVEPL DPPAGSAPGEHVFVKGYEKGQPDEELKPKKKVFE KLQADFKISEECIAQWKQTNFMTKLGSISCKSLKG GNIS | Kleeman et al, (1997) J. Biol. Chem. 272 (22) 14420-14425 | SEQ ID NO: 1 |
| 1-528 | Full length DNA | ATGGGGACGCTCCCAGCCCTGAAGAGAAACTG CACCTTATCACCCGGAACCTGCAGGAGGTTCTG GGGGAAGAGAAGCTGAAGGAGATACTGAAGG AGCGGGAACTTAAAATTTACTGGGGAACGGC AACCACGGGCAAACCACATGTGGCTTACTTTG TGCCCATGTCAAAGATTGCAGACTTCTTAAAG GCAGGGTGTGAGGTAACAATTCTGTTTGCGGAC CTCCACGCATACCTGGATAACATGAAAGCCCCA TGGGAACTTCTAGAACTCCGAGTCAGTTACTATG AGAATGTGATCAAAGCAATGCTGGAGAGCATTG GTGTGCCCTTGGAGAAGCTCAAGTTCATCAAAG GCACTGATTACCAGCTCAGCAAAGAGTACACAC TAGATGTGTACAGACTCTCCTCCGTGGTCACACA GCACGATTCCAAGAAGGCTGGAGCTGAGGTGGT AAAGCAGGTGGAGCACCCTTTGCTGAGTGGCCT | Kleeman et al, (1997) J. Biol. Chem. 272 (22) 14420-14425 | SEQ ID NO: 2 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| | | CTTATACCCCGGACTGCAGGCTTTGGATGAAGA | | |
| | | GTATTTAAAAGTAGATGCCCAATTTGGAGGCATT | | |
| | | GATCAGAGAAAGATTTTCACCTTTGCAGAGAAG | | |
| | | TACCTCCCTGCACTTGGCTATTCAAAACGGGT | | |
| | | CCATCTGATGAATCCTATGGTTCCAGGATTAA | | |
| | | CAGGCAGCAAAATGAGCTCTTCAGAAGAGGA | | |
| | | GTCCAAGATTGATCTCCTTGATCGGAAGGAGGA | | |
| | | TGTGAAGAAAAAACTGAAGAAGGCCTTCTGTGA | | |
| | | GCCAGGAAATGTGGAGAACAATGGGGTTCTGTC | | |
| | | CTTCATCAAGCATGTCCTTTTTCCCCTTAAGTCCG | | |
| | | AGTTTGTGATCCTACGAGATGAGAAATGGGGTG | | |
| | | GAAACAAAACCTACACAGCTTACGTGGACCTGG | | |
| | | AAAAGGACTTTGCTGCTGAGGTTGTACATCCTGG | | |
| | | AGACCTGAAGAATTCTGTTGAAGTCGCACTGAA | | |
| | | CAAGTTGCTGGATCCAATCCGGGAAAAGTTTAA | | |
| | | TACCCCTGCCCTGAAAAAACTGGCCAGCGCTGC | | |
| | | CTACCCACGATCCCTCAAAGCAGAAGCCAATGGC | | |
| | | CAAAGGCCCTGCCAAGAATTCAGAACCAGAGGA | | |
| | | GGTCATCCCATCCCGGCTGGATATCCGTGTGGGG | | |
| | | AAAATCATCACTGTGGAGAAGCACCCAGATGCA | | |
| | | GACAGCCTGTATGTAGAGAAGATTGACGTGGGG | | |
| | | GAAGCTGAACCACGGACTGTGGTGAGCGGCCTG | | |
| | | GTACAGTTCGTGCCCAAGGAGGAACTGCAGGAC | | |
| | | AGGCTGGTAGTGGTGCTGTGCAACCTGAAACCC | | |
| | | CAGAAGATGAGAGGAGTCGAGTCCCAAGGCATG | | |
| | | CTTCTGTGTGCTTCTATAGAAGGGATAAACCGCC | | |
| | | AGGTTGAACCTCTGGACCCTCCGGCAGGCTCTGC | | |
| | | TCCTGGTGAGCACGTGTTTGTGAAGGGCTATGAA | | |
| | | AAGGGCCAACCAGATGAGGAGCTCAAGCCCAAG | | |
| | | AAGAAAGTCTTCGAGAAGTTCAGGCTGACTTC | | |
| | | AAAATTTCTGAGGAGTGCATCGCACAGTGGAAG | | |
| | | CAAACCAACTTCATGACCAAGCTGGGCTCCATTT | | |
| | | CCTGTAAATCGCTGAAAGGGGGGAACATTAGCT | | |
| | | AG | | |

N-terminal Fragments

| 1-329 | TyrRS1<sup>N5</sup>/YRS (1-329) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFN | U.S. 61/377,006 U.S. 61/377,015 U.S. 61/377,019 all filed Aug. 25, 2010 | SEQ ID NO: 3 |
| 1-343 | MiniY/ TyrRS1<sup>N2</sup>/YRS (1-343) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPD | U.S. Pat. No. 7,144,985 | SEQ ID NO: 4 |
| 1-344 | YRS (1-344) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDP | WO 2011/072266. | SEQ ID NO: 5 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| 1-350 | YRS (1-350) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PM | WO 2011/072266. | SEQ ID NO: 6 |
| 1-353 | TyrRS1[N9]/YRS (1-353) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKG | U.S. 61/377,006 U.S. 61/377,015 U.S. 61/377,019 all filed Aug. 25, 2010 | SEQ ID NO: 7 |
| 1-364 | TyrRS1[N10]/ YRS (1-364) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVI | U.S. Pat. No. 7,144,985 | SEQ ID NO: 8 |
| 1-368 | TyrRS1[N4]/YRS (1-368) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVIPSRL | U.S. 61/377,006 U.S. 61/377,015 U.S. 61/377,019 all filed Aug. 25, 2010 | SEQ ID NO: 9 |
| 1-382 | YRS (1-382) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVIPSRLDIRVGKIITVEKHP | U.S. 61/377,006 U.S. 61/377,015 U.S. 61/377,019 all filed Aug. 25, 2010 | SEQ ID NO: 10 |
| 1-388 | YRS (1-388) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVIPSRLDIRVGKIITVEKHPDA DSLY | Biochem 34 12489 | SEQ ID NO: 11 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| 1-395 | TyrRS1$^{N3}$/YRS (1-395) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVIPSRLDIRVGKIITVEKHPDA DSLYVEKIDVG | U.S. 61/377,006 U.S. 61/377,015 U.S. 61/377,019 all filed Aug. 25, 2010 | SEQ ID NO: 12 |
| | | Internal Fragments | | |
| 81-346 | TyrRS1$^{I1}$/YRS (81-346) | DNMKAPWELLELRVSYYENVIKAMLESIGVPLEKL KFIKGTDYQLSKEYTLDVYRLSSVVTQHDSKKAG AEVVKQVEHPLLSGLLYPGLQALDEEYLKVDAQF GGIDQRKIFTFAEKYLPALGYSKRVHLMNPMVPGL TGSKMSSSEEESKIDLLDRKEDVKKKLKKAFCEPG NVENNGVLSFIKHVLFPLKSEFVILRDEKWGGNKT YTAYVDLEKDFAAEVVHPGDLKNSVEVALNKLLD PIREKFNTPALKKLASAAYPDPSK | U.S. 61/377,006 U.S. 61/377,015 U.S. 61/377,019 all filed Aug. 25, 2010 | SEQ ID NO: 13 |
| 87-346 | TyrRS1$^{I2}$/YRS (87-346) | WELLELRVSYYENVIKAMLESIGVPLEKLKFIKGT DYQLSKEYTLDVYRLSSVVTQHDSKKAGAEVVKQ VEHPLLSGLLYPGLQALDEEYLKVDAQFGGIDQRK IFTFAEKYLPALGYSKRVHLMNPMVPGLTGSKMSS SEEESKIDLLDRKEDVKKKLKKAFCEPGNVENNG VLSFIKHVLFPLKSEFVILRDEKWGGNKTYTAYVD LEKDFAAEVVHPGDLKNSVEVALNKLLDPIREKFN TPALKKLASAAYPDPSK | U.S. 61/377,006 U.S. 61/377,015 U.S. 61/377,019 all filed Aug. 25, 2010 | SEQ ID NO: 14 |
| | | C-terminal fragments | | |
| 328-528 | YRS (328-528) | FNTPALKKLASAAYPDPSKQKPMAKGPAKNSEPE EVIPSRLDIRVGKIITVEKHPDADSLYVEKIDVGE AEPRTVVSGLVQFVPKEELQDRLVVVLCNLKPQKM RGVESQGMLLCASIEGINRQVEPLDPPAGSAPGEH VFVKGYEKGQPDEELKPKKKVFEKLQADFKISEEC IAQWKQTNFMTKLGSISCKSLKGGNIS | U.S. 61/377,006 U.S. 61/377,015 U.S. 61/377,019 all filed Aug. 25, 2010 | SEQ ID NO: 15 |
| 340-528 | TyrRS1$^{C2}$/YRS (340-528) | AYPDPSKQKPMAKGPAKNSEPEEVIPSRLDIRVGKI ITVEKHPDADSLYVEKIDVGEAEPRTVVSGLVQFV PKEELQDRLVVVLCNLKPQKMRGVESQGMLLCAS IEGINRQVEPLDPPAGSAPGEHVFVKGYEKGQPDE ELKPKKKVFEKLQADFKISEECIAQWKQTNFMTKL GSISCKSLKGGNIS | U.S. 61/377,006 U.S. 61/377,015 U.S. 61/377,019 all filed Aug. 25, 2010 | SEQ ID NO: 16 |
| 361-528 | EMAPIII/YRS (361-528) | EEVIPSRLDIRVGKIITVEKHPDADSLYVEKIDVG EAEPRTVVSGLVQFVPKEELQDRLVVVLCNLKPQK MRGVESQGMLLCASIEGINRQVEPLDPPAGSAPGE HVFVKGYEKGQPDEELKPKKKVFEKLQADFKISEE CIAQWKQTNFMTKLGSISCKSLKGGNIS | U.S. Pat. No. 6,864,226; U.S. Pat. No. 6,013,483; U.S. Pat. No. 7,045,301 U.S. Pat. No. 7,482,326 | SEQ ID NO: 17 |
| 390-528 | TyrRS1$^{C1}$/YRS (390-528) | EKIDVGEAEPRTVVSGLVQFVPKEELQDRLVVVLC NLKPQKMRGYESQGMLLCASIEGINRQVEPLDPPA GSAPGEHVFVKGYEKGQPDEELKPKKKVFEKLQA DFKISEECIAQWKQTNFMTKLGSISCKSLKGGNIS | U.S. 61/377,006 U.S. 61/377,015 U.S. 61/377,019 all filed Aug. 25, 2010 | SEQ ID NO: 18 |
| | | Alternatively Spliced Variants | | |
| 1-19 + 41 aa | TyrRS1$^{N7}$/YRS (1-19 + 41) | MGDAPSPEEKLHLITRNLQSQWPKALPRIQNQRRS SHPGWISVWGKSSLWRSTQMQTACM | U.S. 61/377,006 U.S. 61/377,015 U.S. 61/377,019 all filed Aug. 25, 2010 | SEQ ID NO: 19 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| 10 + 190-528 | SP1/YRS (1-10 + 190-528) | MPNLEALIREIFTFAEKYLPALGYSKRVHLMNPMV PGLTGSKMSSSEEESKIDLLDRKEDVKKKLKKAFC EPGNVENNGVLSFIKHVLFPLKSEFVILRDEKWGG NKTYTAYVDLEKDFAAEVVHPGDLKNSVEVALN KLLDPIREKFNTPALKKLASAAYPDSKQKPMAKG PAKNSEPEEVIPSRLDIRVGKIITVEKHPDADSLY VEKIDVGEAEPRTVVSGLVQFVPKEELQDRLVVVL CNLKPQKMRGYESQGMLLCASIEGINRQVEPLDPP AGSAPGEHVFVKGYEKGQPDEELKPKKKVFEKLQA DFKISEECIAQWKQTNFMTKLGSISCKSLKGGNIS | WO2009/152247 | SEQ ID NO: 20 |
| 1-353 + 35 aa | SP2/YRS (1-353 + 35 aa) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDSKQK PMAKGLPRIQNQRRSSHPGWISVWGKSSLWRSTQ MQTACM | WO2009/152247 | SEQ ID NO: 21 |
| 211-528 | SP3/SV8/YRS (211-528) | MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDSKQK PMAKGPAKNSEPEEVIPSRLDIRVGKIITVEKHPDA DSLYVEKIDVGEAEPRTVVSGLVQFVPKEELQDRL VVVLCNLKPQKMRGVESQGMLLCASIEGINRQVE PLDPPAGSAPGEHVFVKGYEKGQPDEELKPKKKV FEKLQADFKISEECIAQWKQTNFMTKLGSISCKSL KGGNIS | WO2009/152247 | SEQ ID NO: 22 |
| 350-528 | SP4/TyrRS1[C3]/ YRS (350-528) | MAKGPAKNSEPEEVIPSRLDIRVGKIITVEKHPDAD SLYVEKIDVGEAEPRTVVSGLVQFVPKEELQDRLV VVLCNLKPQKMRGVESQGMLLCASIEGINRQVEPL DPPAGSAPGEHVFVKGYEKGQPDEELKPKKKVFE KLQADFKISEECIAQWKQTNFMTKLGSISCKSLKG GNIS | WO2009/152247 | SEQ ID NO: 23 |
| 8 + 349-528 | SP5/YRS (8 + 349-528) | MGFFSFPEPMAKGPAKNSEPEEVIPSRLDIRVGKI ITVEKHPDADSLYVEKIDVGEAEPRTVVSGLVQFV PKEELQDRLVVVLCNLKPQKMRGVESQGMLLCASI EGINRQVEPLDPPAGSAPGEHVFVKGYEKGQPDEE LKPKKKVFEKLQADFKISEECIAQWKQTNFMTKLG SISCKSLKGGNIS | WO2009/152247 | SEQ ID NO: 24 |
| 1-19 + 171-524 | SV7/YRS (1-19 + 171-528) | MGDAPSPEEKLHLITRNLQALDEEYLKVDAQFGGI DQRKIFTFAEKYLPALGYSKRVHLMNPMVPGLTG SKMSSSEEESKIDLLDRKEDVKKKLKKAFCEPGNV ENNGVLSFIKHVLFPLKSEFVILRDEKWGGNKTYT AYVDLEKDFAAEVVHPGDLKNSVEVALNKLLDPI REKFNTPALKKLASAAYPDSKQKPMAKGPAKNS EPEEVIPSRLDIRVGKIITVEKHPDADSLYVEKID VGEAEPRTVVSGLVQFVPKEELQDRLVVVLCNLKP QKMRGVESQGMLLCASIEGINRQVEPLDPPAGSAP GEHVFVKGYEKGQPDEELKPKKKVFEKLQADFKIS EECIAQWKQTNFMTKLGSISCKSLKGGNIS | U.S. 61/377,006 U.S. 61/377,015 U.S. 61/377,019 all filed Aug. 25, 2010 | SEQ ID NO: 25 |
| 1-228 + 303-528 | TyrRS1[N8]/YRS (1-228 + 303-528) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEVVHPGDLKNSVEVALN KLLDPIREKFNTPALKKLASAAYPDSKQKPMAKG PAKNSEPEEVIPSRLDIRVGKIITVEKHPDADSLY VEKIDVGEAEPRTVVSGLVQFVPKEELQDRLVVVL | U.S. 61/377,006 U.S. 61/377,015 U.S. 61/377,019 all filed Aug. 25, 2010 | SEQ ID NO: 26 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| | | CNLKPQKMRGVESQGMLLCASIEGINRQVEPLDPP AGSAPGEHVFVKGYEKGQPDEELKPKKKVFEKLQA DFKISEECIAQWKQTNFMTKLGSISCKSLKGGNIS | | |
| 1-19 + 303-528 | TyrRS1$^{C4}$/YRS (1-19 + 303-528) | MGDAPSPEEKLHLITRNLQVVHPGDLKNSVEVAL NKLLDPIREKFNTPALKKLASAAYPDPSKQKPMAK GPAKNSEPEEVIPSRLDIRVGKIITVEKHPDADSLY VEKIDVGEAEPRTVVSGLVQFVPKEELQDRLVVVL CNLKPQKMRGVESQGMLLCASIEGINRQVEPLDPP AGSAPGEHVFVKGYEKGQPDEELKPKKKVFEKLQ ADFKISEECIAQWKQTNFMTKLGSISCKSLKGGNIS | U.S. 61/377,006 U.S. 61/377,015 U.S. 61/377,019 all filed Aug. 25, 2010 | SEQ ID NO: 27 |
| 1-19 + 171-528 | TyrRS1$^{C5}$/YRS (1-19 + 171-528) | MGDAPSPEEKLHLITRNLQALDEEYLKVDAQFGGI DQRKIFTFAEKYLPALGYSKRVHLMNPMVPGLTG SKMSSSEEESKIDLLDRKEDVKKKLKKAFCEPGNV ENNGVLSFIKHVLFPLKSEFVILRDEKWGGNKTYT AYVDLEKDFAAEVVHPGDLKNSVEVALNKLLDPI REKFNTPALKKLASAAYPDPSKQKPMAKGPAKNS EPEEVIPSRLDIRVGKIITVEKHPDADSLYVEKID VGEAEPRTVVSGLVQFVPKEELQDRLVVVLCNLK PQKMRGVESQGMLLCASIEGINRQVEPLDPPAGSA PGEHVFVKGYEKGQPDEELKPKKKVFEKLQADFK ISEECIAQWKQTNFMTKLGSISCKSLKGGNIS | U.S. 61/377,006 U.S. 61/377,015 U.S. 61/377,019 all filed Aug. 25, 2010 | SEQ ID NO: 28 |
| 1-197 + 229-528 | TyrRS1$^{C6}$/YRS (1-197 + 229-528) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKESKIDLLDRKEDV KKKLKKAFCEPGNVENNGVLSFIKHVLFPLKSEFVI LRDEKWGGNKTYTAYVDLEKDFAAEVVHPGDLK NSVEVALNKLLDPIREKFNTPALKKLASAAYPDPS KQKPMAKGPAKNSEPEEVIPSRLDIRVGKIITVEKH PDADSLYVEKIDVGEAEPRTVVSGLVQFVPKEELQ DRLVVVLCNLKPQKMRGVESQGMLLCASIEGINR QVEPLDPPAGSAPGEHVFVKGYEKGQPDEELKPK KKVFEKLQADFKISEECIAQWKQTNFMTKLGSISC KSLKGGNIS | U.S. 61/377,006 U.S. 61/377,015 U.S. 61/377,019 all filed Aug. 25, 2010 | SEQ ID NO: 29 |
| 1-228 + 2aa | TyrRS1$^{N11}$ YRS (1-228 + 2aa) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEESL | Not previously reported | SEQ ID NO: 30 |
| 1-302 + 41aa | TyrRS1$^{N12}$ YRS (1-302 + 41aa) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAESQWPKALPRIQN QRRSSHPGWISVWGKSSLWRSTQMQTACM | Not previously reported | SEQ ID NO: 31 |
| 1-380 + 7aa | TyrRS1N$^{13}$ YRS (1-380 + 7aa) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEFVILRD EKWGGNKTYTAYVDLEKDFAAEVVHPGDLKNSV EVALNKLLDPIREKFNTPALKKLASAAYPDPSKQK PMAKGPAKNSEPEEVIPSRLDIRVGKIITVEKRRDK PPG | Not previously reported | SEQ ID NO: 32 |

TABLE 1-continued

Exemplary YRS Polypeptides

| Amino Acid Residue Range of SEQ. ID. No. 1 | Name(s) | | Ref | SEQ. ID. No. |
|---|---|---|---|---|
| 1-170 + 229-528 | TyrRS1^C7 YRS (1-170 + 229-528) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQESKIDL LDRKEDVKKKLKKAFCEPGNVENNGVLSFIKHVL FPLKSEFVILRDEKWGGNKTYTAYVDLEKDFAAE VVHPGDLKNSVEVALNKLLDPIREKFNTPALKKLA SAAYPDPSKQKPMAKGPAKNSEPEEVIPSRLDIRV GKIITVEKHPDADSLYVEKIDVGEAEPRTVVSGLV QFVPKEELQDRLVVVLCNLKPQKMRGVESQGMLL CASIEGINRQVEPLDPPAGSAPGEHVFVKGYEKGQ PDEELKPKKKVFEKLQADFKISEECIAQWKQTNFM TKLGSISCKSLKGGNIS | Not previously reported | SEQ ID NO: 33 |
| 1-274 + 349-528 | TyrRS1^C8 YRS (1-274 + 349-528) | MGDAPSPEEKLHLITRNLQEVLGEEKLKEILKEREL KIYWGTATTGKPHVAYFVPMSKIADFLKAGCEVTI LFADLHAYLDNMKAPWELLELRVSYYENVIKAML ESIGVPLEKLKFIKGTDYQLSKEYTLDVYRLSSVVT QHDSKKAGAEVVKQVEHPLLSGLLYPGLQALDEE YLKVDAQFGGIDQRKIFTFAEKYLPALGYSKRVHL MNPMVPGLTGSKMSSSEEESKIDLLDRKEDVKKK LKKAFCEPGNVENNGVLSFIKHVLFPLKSEPMAKG PAKNSEPEEVIPSRLDIRVGKIITVEKHPDADSLY VEKIDVGEAEPRTVVSGLVQFVPKEELQDRLVVVL CNLKPQKMRGVESQGMLLCASIEGINRQVEPLDPP AGSAPGEHVFVKGYEKGQPDEELKPKKKVFEKLQA DFKISEECIAQWKQTNFMTKLGSISCKSLKGGNIS | Not previously reported | SEQ ID NO: 34 |
| 511-528 | TyrRS1^C9 YRS (511-528) | MTKLGSISCKSLKGGNIS | Not previously reported | SEQ ID NO: 35 |

Accordingly, the terms "YRS polypeptide" "YRS protein" or "YRS protein fragment" as used herein includes all naturally-occurring and synthetic forms of the tyrosyl-tRNA synthetase that retain non canonical activity. Such YRS polypeptides include the full length human protein, as well as the YRS peptides derived from the full length protein listed in Table 1, as well as YRS polypeptides derived other animal species and genera, preferably mammals. Preferably, the term YRS polypeptide refers to a polypeptide sequence derived from human tyrosyl-tRNA synthetase (SEQ ID NO:1 in Table 1).

A number of naturally occurring tyrosyl-tRNA synthetase single nucleotide polymorphisms (SNPs) and naturally occurring variants have been sequenced, and are known in the art to be at least partially functionally interchangeable. It would thus be a routine matter to select a naturally occurring variant such as a YRS polypeptide encoded by a SNP, or other naturally occurring variant in place of any of the YRS polypeptide sequences listed in Table 1. Several such variants of tyrosyl-tRNA synthetase (i.e., representative tyrosyl-tRNA synthetase SNPs) are shown in Table 2.

TABLE 2

| GenBank Accession No. | 5' flanking sequence | Nucleotide change | 3' flanking sequence. |
|---|---|---|---|
| rs76862302 | TGCCCCACTCCAAGTCCTCACTCACA (SEQ ID NO: 64) | C/T | AGAAGCACACAGAAGCATGCCT TGG (SEQ ID NO: 65) |
| rs76611863 | GCACAGCACCACTACCAGCCTGTCCT (SEQ ID NO: 66) | G/T | CAGTTCCTCCTTGGGCACGAAC TGT (SEQ ID NO: 67) |
| rs61737106 | TATCCAGCCGGGATGGGATGACCTCC (SEQ ID NO: 68) | A/T | CTGGTTCTGAATTCTTGGCAGG GCC (SEQ ID NO: 69) |
| rs35746182 | GGCCAGCGCTGCCTACCCAGATCCCT (SEQ ID NO: 70) | C/T | AAAGCAGAGTAAGGCCAGCTGG AGA (SEQ ID NO: 71) |
| rs34213904 | GGTTCTGAATTCTTGGCAGGGCCTTT (SEQ ID NO: 72) | -/T | GGCCATTGGCTCTGGGAATGAG AAG (SEQ ID NO: 73) |
| rs11544327 | GGAGAGCATTGGTGTGCCCTTGGAGA (SEQ ID NO: 74) | A/C | GCTCAAGTTCATCAAAGGCACT GAT (SEQ ID NO: 75) |

TABLE 2-continued

| GenBank Accession No. | 5' flanking sequence | Nucleotide change | 3' flanking sequence. |
|---|---|---|---|
| rs11544326 | CCACATGTGGCTTACTTTGTGCCCAT (SEQ ID NO: 76) | G/T | TCAAAGATTGCAGACTTCTTAA AGG (SEQ ID NO: 77) |
| rs11544325 | AGACTCTCCTCCGTGGTCACACAGCA (SEQ ID NO: 78) | C/T | GATTCCAAGAAGGCTGGAGCTG AGG (SEQ ID NO: 79) |
| rs11544324 | GTGATCCTACGAGATGAGAAATGGGG (SEQ ID NO: 80) | C/T | GGAAACAAAACCTACACAGCTT ACG (SEQ ID NO: 81) |
| rs11544323 | AAACCACATGTGGCTTACTTTGTGCC (SEQ ID NO: 82) | C/T | ATGTCAAAGATTGCAGACTTCT TAA (SEQ ID NO: 83) |
| rs11544322 | CCATGGGAACTTCTAGAACTCCGAGT (SEQ ID NO: 84) | C/T | AGTTACTATGAGAATGTGATCA AAG (SEQ ID NO: 85) |
| rs2128600 | AGTGGCCTCTTATACCCCGGACTGCA (SEQ ID NO: 86) | G/T | GTACTTAAGGGGATGGAGTGG CCC (SEQ ID NO: 87) |
| rs699005 | AGTTCCTCCTTGGGCACGAACTGTAC (SEQ ID NO: 88) | C/G | AGGCCGCTCACCACAGTCCGTG GTT (SEQ ID NO: 89) |

Thus all such homologues, orthologs, and naturally-occurring isoforms of tyrosyl-tRNA synthetase from human (SEQ. ID Nos. 1-35) as well as other species are included in any of the methods and pharmaceutical compositions of the invention, as long as they retain detectable non canonical activity.

The YRS polypeptides may be in their native form, i.e., as different variants as they appear in nature in different species which may be viewed as functionally equivalent variants of human tyrosyl-tRNA synthetase, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of any YRS polypeptide, are also specifically included in any of the methods and pharmaceutical compositions of the invention including, e.g., pyroglutamyl, isoaspartyl, proteolytic, phosphorylated, glycosylated, oxidatized, isomerized, and deaminated variants of a YRS polypeptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using a YRS polypeptide or variant thereof, e.g., by the use of automated computer recognition programs to identify potential T cell epitopes, and directed evolution approaches to identify less immunogenic forms.

Certain embodiments relate to polynucleotides that encode a YRS polypeptide. Among other uses, these embodiments may be utilized to recombinantly produce a desired YRS polypeptide or variant thereof, or to express the YRS polypeptide in a selected cell or subject. It will be appreciated by those of ordinary skill in the art that, as a result of the degeneracy of the genetic code, there are many nucleotide sequences that encode a YRS polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

Therefore, multiple polynucleotides can encode the YRS polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., *Nuc. Acid. Res.* (2000) 28 (1): 292). In addition, silent mutations can be incorporated in order to introduce, or eliminate restriction sites, decrease the density of CpG dinucleotide motifs (see for example, Kameda et al., *Biochem. Biophys. Res. Commun.* (2006) 349(4): 1269-1277) or reduce the ability of single stranded sequences to form stem-loop structures: (see, e.g., Zuker M., *Nucl. Acid Res.* (2003); 31(13): 3406-3415). In addition, mammalian expression can be further optimized by including a Kozak consensus sequence [i.e., (a/g)cc(a/g) ccATGg] at the start codon. Kozak consensus sequences useful for this purpose are known in the art (Mantyh et al. *PNAS.* 92: 2662-2666 (1995); Mantyh et al., *Prot. Exp. & Purif.* 6, 124 (1995)).

As noted above, embodiments of the present invention include the YRS polypeptides of SEQ ID NOS:1-35. Also included are "variants" of these YRS reference polypeptides. The recitation polypeptide "variant" refers to polypeptides that are distinguished from a reference YRS polypeptide by the addition, deletion, and/or substitution of at least one amino acid residue, and which typically retain (e.g., mimic) or modulate (e.g., antagonize) one or more non-canonical activities of a reference YRS polypeptide. In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide. In certain embodiments, the polypeptide variant comprises substitutions that introduce a functional group suitable for the attachment of a PEG group.

Specific examples of YRS polypeptide variants useful in any of the methods and compositions of the invention include full-length YRS polypeptides, or truncations or splice variants thereof (e.g., SEQ ID NOS: 1-35), having one or more amino acid substitutions selected from positions A4, (including A4C), I14 (including I14L, I14A I14V, and I14T), N17 (including N17G, N17A, N17L, and N17K), L27 (including L27I, L27A, L27V), C67 (including C67A, C67S, C67G, and C67L), A85 (including A85G, A85S, and A85L), R93 (including R93Q, R93K, and R93N), V156 (including V156L, V156A, and V156I), C250 (including C250A, C250S, C250G, and C250L), Y343, (including Y343G, Y343A, Y343L, Y343S, and Y343T), and A351 (including A351C) and any combinations thereof.

In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a YRS reference polypeptide, as described herein, and substantially retains the non-canonical activity of that reference polypeptide. Also included are sequences differing from the reference YRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference YRS polypeptide. In certain embodiments, the amino acid additions or deletions occur at the C-terminal end and/or the N-terminal end of the YRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length YRS polypeptide) that are proximal to the C-terminal end and/or the N-terminal end of the YRS reference polypeptide.

In some embodiments, the YRS polypeptides comprise, or consist essentially of the amino acids 1-329, 1-330, 1-331, 1-332, 1-333, 1-334, 1-335, 1-336, 1-337, 1-338, 1-339, 1-340, 1-341, or 1-342 of the YRS polypeptide sequence set forth in SEQ ID NO:1, and variants thereof.

Other YRS polypeptides of the invention comprise, or consist essentially of amino acids 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364 or 1-365 amino acids of the YRS polypeptide sequence set forth in SEQ ID NO:1, and variants thereof. In certain embodiments, a YRS polypeptide of the invention comprises the minimal active fragment of a full-length YRS polypeptide capable of modulating hematopoiesis, e.g., megakaryopoiesis, thrombopoiesis, etc., in vivo or having other desirable non-canonical tyrosyl tRNA synthetase activities. In one aspect, such a minimal active fragment consists essentially of the aminoacylation domain, (i.e. amino acids 1-237 of SEQ. ID. NO:1.

The structure of human mini-YRS (i.e., YRS (1-343)), which contains both the catalytic and the anticodon recognition domain, has been reported to a resolution of 1.18 Å. Whereas the catalytic domains of the human and bacterial enzymes superimpose, the spatial disposition of the anticodon recognition domain relative to the catalytic domain is unique in mini-YRS relative to the bacterial orthologs. Without wishing to be bound by any one theory, the unique orientation, or conformation, of the anticodon-recognition domain and aminoacylation domains in certain YRS polypeptides may contribute to the enhanced non canonical activities observed in these proteins. In certain embodiments, non canonical activity may be modulated by the selective deletion, in whole or part of the EMAP II domain, the anticodon domain, or the aminoacylation domain. Specific examples of splice variants that accomplish such embodiments include for example SP4/TyrRS1$^{C3}$/YRS (350-528) (deletion of the aminoacylation and anticodon domains), TyrRS1$^{C4}$/YRS (1-19+303-528) and TyrRS1$^{C5}$/YRS (1-19+171-528) (partial deletion of the aminoacylation domain), TyrRS1 N7 (1-19+41 aa) (partial deletion of the anticodon binding domain and EMAP II domain, TyrRS1$^{N8}$/YRS (1-228+303-528) (partial deletion of the anticodon domain).

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Tip, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

In certain embodiments, variant polypeptides differ from the corresponding YRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.). The differences are, suitably, differences or changes at a non-essential residue or a conservative substitution. In certain embodiments, the molecular weight of a variant YRS polypeptide differs from that of the YRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

Also included are biologically active "fragments" of the YRS reference polypeptides, i.e., biologically active fragments of the YRS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between a YRS polypeptide and a cellular binding partner, such as a cellular receptor or other host molecule that participates in the non-canonical activity of the YRS polypeptide.

A biologically active fragment of an YRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 450, 500 or more contiguous or non-contiguous amino acids, including all integers (e.g., 101, 102, 103) and ranges (e.g., 50-100, 50-150, 50-200) in between, of the amino acid sequences set forth in any one of the YRS reference polypeptides described herein. In certain embodiments, a biologically active fragment comprises a non-canonical activity-related sequence, domain, or motif. In certain embodiments, the C-terminal or N-terminal region of any YRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated YRS polypeptide retains the non-canonical activity of the reference polypeptide. Typically, the biologically-active fragment has no less than about 1%, 10%, 25%, or 50% of an activity of the biologically-active (i.e., non-canonical activity) YRS reference polypeptide from which it is derived. Exemplary methods for measuring such non-canonical activities are described in the Examples.

In some embodiments, PEGylated YRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In some embodiments, the binding affinity of a pegylated YRS protein fragment for a selected cellular binding partner, particularly a binding partner that participates in a non-canonical activity, can be stronger than that of the YRS protein's corresponding un-pegylated YRS polypeptide, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a YRS polypeptide may be altered in various ways including amino acid substitutions, deletions, truncations, and insertions. Methods for such manipulations are generally known in the art. For example, amino acid sequence variants of a YRS reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found, Washington, D.C.).

Biologically active truncated and/or variant YRS polypeptides may contain conservative amino acid substitutions at various locations along their sequence, as compared to a reference YRS amino acid residue. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science*, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

| Amino acid sub-classification | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant YRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a truncated and/or variant YRS polypeptide is typically replaced with another amino acid residue from the same side chain family. Alternatively, mutations can be introduced randomly along all or part of a YRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference YRS sequence. An "essential" amino acid residue is a residue that, when altered from the reference sequence of a YRS polypeptide, results in abolition of an activity of the parent molecule such that less than 20% of the reference activity is present. For example, such essential amino acid residues include those that are conserved in YRS polypeptides across different species, including those sequences that are conserved in the active binding site(s) or motif(s) of YRS polypeptides from various sources.

For certain types of site-specific PEGylation, described below, YRS polypeptides may have one or more cysteine substitutions, where one or more naturally-occurring (non-cysteine) residues are substituted with cysteine, for example, to facilitate thiol-based attachment of PEG molecules. In some embodiments, cysteine substitutions are near the N-terminus and/or C-terminus of the YRS polypeptide (e.g., SEQ ID NOS: 1-35). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of any one of SEQ ID NOS: 1-35 are substituted with a cysteine residue.

Specific embodiments of such YRS polypeptides with an N-terminal cysteine substitution, include for example, those with an A4C substitution, including the YRS polypeptides of any of SEQ ID NOs: 1-12, 19-21, and 25-34. Specific embodiments of such YRS polypeptides with a C-terminal cysteine substitution, include for example, those with an A351C substitution, including the YRS polypeptides of any of SEQ ID NOs: 3-9.

These and related YRS polypeptides may also have additional substitutions at C67 and/or C250, to remove naturally-occurring cysteine residues, and to facilitate site-specific pegylation at the selectively introduced cysteine residue(s). Specific embodiments include any one of SEQ ID NOS: 1-35, or variants thereof, having at mutation at C67 and/or C250. Exemplary mutations at these positions include for example the mutation of cysteine to serine, alanine, leucine, or glycine.

For some types of site-specific pegylation, YRS polypeptides may have one or more glutamine substitutions, where one or more naturally-occurring (non-glutamine) residues are substituted with glutamine, for example, to facilitate transglutaminase-catalyzed attachment of PEG molecules to the glutamine's amide group. In some embodiments, glutamine substitutions are introduced near the N-terminus and/or C-terminus of the YRS polypeptide (e.g., SEQ ID NOS: 1-35). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS: 1-35 are substituted with a glutamine residue. These and related YRS polypeptides can also include substitutions (e.g., conservative substitutions) to remove any naturally-occurring glutamine residues, if desired, and thereby regulate the degree of site-specific pegylation.

For other types of site-specific pegylation, YRS polypeptides may have one or more lysine substitutions, where one or more naturally-occurring (non-lysine) residues are substituted with lysine, for example, to facilitate acylation or alkylation-based attachment of PEG molecules to the lysine's amino group. These methods also typically result in attachment of PEG to the N-terminal residue. In some embodiments, lysine substations are near the N-terminus and/or C-terminus of the YRS polypeptide (e.g., SEQ ID NOS: 1-35). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids to the N-terminus and/or C-terminus of any one of SEQ ID NOS:1-35 are substituted with a lysine residue. These and related YRS polypeptides can also include substitutions (e.g., conservative substitutions) to remove any naturally-occurring lysine residues, if desired, and thereby regulate the degree of site-specific pegylation.

Site-specific PEGylation of YRS polypeptides may also be performed by substituting one or more solvent accessible surface amino acids of a YRS polypeptide. For example, suitable solvent accessible amino acids may be determined based on the predicted solvent accessibility using the SPIDER server (http://sppider.cchmc.org/) using the published crystal structure of an exemplary YRS polypeptide (PDB ID: 1N3L; Yang et al., *Proc. Natl. Acad. Sci.* USA 99: 15369-15374, 2002). Based on this analysis several amino acids on the surface may potentially be used as mutation sites to introduce functional groups suitable for PEGylation. The following Table 3 lists the surface accessibility score of amino acids based on the crystal structure above. In this table, the higher scores represent better accessibility. Accordingly, higher scores (for example, >40) are preferred for better PEG-coupling efficiency.

TABLE 3

Surface Exposed amino acids

| ID | Position | Amino Acid | Score |
|---|---|---|---|
| 22 | 33 | E | 64 |
| 23 | 32 | K | 63 |
| 24 | 301 | A | 60 |
| 25 | 66 | G | 60 |
| 26 | 25 | E | 60 |
| 27 | 203 | G | 59 |
| 28 | 338 | S | 58 |
| 29 | 221 | S | 58 |
| 30 | 84 | K | 58 |
| 31 | 64 | K | 58 |
| 32 | 220 | G | 57 |
| 33 | 219 | T | 57 |
| 34 | 331 | P | 56 |
| 35 | 113 | E | 56 |
| 36 | 29 | E | 56 |
| 37 | 297 | K | 55 |
| 38 | 154 | K | 55 |
| 39 | 329 | N | 54 |
| 40 | 147 | K | 54 |
| 41 | 34 | R | 54 |
| 42 | 16 | R | 54 |
| 43 | 158 | H | 53 |
| 44 | 339 | A | 52 |
| 45 | 326 | E | 52 |
| 46 | 256 | E | 52 |
| 47 | 247 | K | 52 |
| 48 | 201 | A | 52 |
| 49 | 330 | T | 51 |
| 50 | 257 | N | 51 |
| 51 | 239 | E | 51 |
| 52 | 157 | E | 51 |
| 53 | 91 | E | 51 |
| 54 | 12 | H | 51 |
| 55 | 335 | K | 50 |
| 56 | 290 | T | 50 |
| 57 | 284 | G | 50 |
| 58 | 282 | K | 50 |
| 59 | 229 | E | 50 |
| 60 | 205 | S | 50 |
| 61 | 253 | G | 49 |
| 62 | 95 | S | 48 |
| 63 | 23 | G | 48 |
| 64 | 300 | A | 47 |

TABLE 3-continued

Surface Exposed amino acids

| ID | Position | Amino Acid | Score |
|---|---|---|---|
| 65 | 237 | R | 47 |
| 66 | 200 | P | 47 |
| 67 | 315 | V | 46 |
| 68 | 293 | V | 46 |
| 69 | 254 | N | 46 |
| 70 | 155 | Q | 46 |
| 71 | 319 | K | 45 |
| 72 | 286 | N | 45 |
| 73 | 102 | K | 45 |
| 74 | 35 | E | 45 |
| 75 | 19 | Q | 45 |
| 76 | 311 | N | 44 |
| 77 | 294 | D | 44 |
| 78 | 287 | K | 44 |
| 79 | 281 | E | 44 |
| 80 | 280 | D | 44 |
| 81 | 243 | K | 44 |
| 82 | 197 | K | 44 |
| 83 | 127 | K | 44 |
| 84 | 265 | K | 43 |
| 85 | 238 | K | 43 |
| 86 | 178 | K | 43 |
| 87 | 143 | H | 43 |
| 88 | 88 | E | 43 |
| 89 | 28 | K | 43 |
| 90 | 252 | P | 42 |
| 91 | 24 | E | 42 |
| 92 | 251 | E | 41 |
| 93 | 146 | K | 41 |
| 94 | 106 | E | 41 |
| 95 | 322 | D | 40 |
| 96 | 283 | W | 40 |
| 97 | 150 | A | 40 |
| 98 | 87 | W | 40 |
| 99 | 86 | P | 40 |
| 100 | 61 | D | 40 |

In particular embodiments, a solvent accessible surface amino acid from Table 3 is selected from the group consisting of: alanine, glycine, and serine, and can be substituted with naturally occurring amino acids including, but not limited to, cysteine, glutamine, or lysine, or a non-naturally occurring amino acid that is optimized for site specific PEGylation. In certain embodiments, one or more solvent accessible surface amino acids of the YRS polypeptide are selected from the group consisting of: A4, S6, G23, G66, S95, A150, A201, G203, S205, G220, S221, G253, G284, A300, A301, S338, A339, and A351 are substituted with cysteine, glutamine, lysine, or a non-naturally occurring amino acid.

In various embodiments, the present invention contemplates site-specific pegylation at any amino acid position in a YRS polypeptide by virtue of substituting a non-naturally occurring amino acid comprising a functional group that will form a covalent bond with the functional group attached to a PEG moiety. Non-natural amino acids can be inserted or substituted at, for example, one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS: 1-35; at the N-terminus and/or C-terminus of any one of SEQ ID NOS: 1-35; or a solvent accessible surface amino acid residue as described in Table 3.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

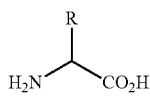

A non-natural amino acid is typically any structure having the foregoing formula wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Accordingly, one may select a non-naturally occurring amino acid comprising a functional group that forms a covalent bond with any preferred functional group of a PEG moiety. Non-natural amino acids, once selected, can either be purchased from vendors, or chemically synthesized. Any number of non-natural amino acids may be incorporated into the target molecule and may vary according to the number of desired water soluble polymers, e.g., PEG moieties, that are to be attached. The PEG moieties may be attached to all or only some of the non-natural amino acids. Further, the same or different non-natural amino acids may be incorporated into a YRS polypeptide, depending on the desired outcome. In certain embodiments, about 1, 2, 3, 4, 5, 6, 7, 8, 9, 10 or more non-natural amino acids are incorporated into a YRS polypeptide any or all of which may be conjugated to a PEG comprising a desired functional group.

In certain aspects, the use of non-natural amino acids can be utilized to modify (e.g., increase) a selected non-canonical activity of a YRS polypeptide, or to alter the in vivo or in vitro half-life of the protein. Non-natural amino acids can also be used to facilitate (selective) chemical modifications (e.g., pegylation) of a YRS protein, as described elsewhere herein. For instance, certain non-natural amino acids allow selective attachment of polymers such as PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the YRS polypeptides of the present invention may be composed of naturally occurring and non-naturally occurring amino acids as well as amino acid analogs and mimetics.

Production of YRS Polypeptides and PEGylated YRS Polypeptides

YRS polypeptide may be produced synthetically using standard solid-phase peptide synthesis, or by recombinant technology using a genetically modified host. In an alternative approach to direct coupling via a cysteine residue, the PEG reagent, or a suitable activated functional group, may be incorporated at a desired position of the YRS polypeptide during peptide synthesis. In this way, site-selective introduction of one or more PEGs can be achieved. See, e.g., International Patent Publication No. WO 95/00162, which describes the site selective synthesis of conjugated peptides.

YRS polypeptides can also be produced by expressing a DNA sequence encoding the YRS polypeptide in question in a suitable host cell by well known techniques.

The polynucleotide sequence coding for the YRS polypeptide may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3:801-805. According to the phosphoramidite method, oligonucleotides are synthesized, e.g., in an automatic DNA synthesizer, purified, duplexed and ligated to form the synthetic DNA construct. Alternatively the DNA construct can be constructed using standard recombinant molecular biological techniques including restriction enzyme mediated cloning and PCR based gene amplification.

The polynucleotide sequences may also be of mixed genomic, cDNA, and synthetic origin. For example, a genomic or cDNA sequence encoding a leader peptide may be joined to a genomic or cDNA sequence encoding the YRS polypeptide, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems.

The "control elements" or "regulatory sequences" present in an expression vector are non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ *E. coli*-based expression systems (see, e.g., Structural Genomics Consortium et al., *Nature Methods.* 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. Cell lysis and sample handling may also be improved using reagents sold under the trademarks BENZONASE® nuclease and BUG-BUSTER® Protein Extraction Reagent.

For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG. Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987). Also included are *Pichia pandoris* expression systems (see, e.g., Li et al., *Nature Biotechnology.* 24, 210-215, 2006; and Hamilton et al., *Science,* 301:1244, 2003). Certain embodiments include yeast systems that are engineered to selectively glycosylate proteins, including yeast that have humanized N-glycosylation pathways, among others (see, e.g., Hamilton et al., *Science.* 313:1441-1443, 2006; Wildt et al., *Nature Reviews Microbiol.* 3:119-28, 2005; and Gerngross et al., *Nature-Biotechnology.* 22:1409-1414, 2004; U.S. Pat. Nos. 7,629, 163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *Proc. Natl. Acad. Sci. U.S.A.* 91:3224-3227 (1994)). Also included are baculovirus expression systems, including those that utilize SF9, SF21, and *T. ni* cells (see, e.g., Murphy and Piwnica-Worms, *Curr Protoc Protein Sci.* Chapter 5:Unit 5.4, 2001). Insect systems can provide post-translation modifications that are similar to mammalian systems.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. No. 7,939,496; U.S. Pat. No. 7,816,320; U.S. Pat. No. 7,947,473; U.S. Pat. No. 7,883,866; U.S. Pat. No. 7,838,265; U.S. Pat. No. 7,829,310; U.S. Pat. No. 7,820,766; U.S. Pat. No. 7,820,766; U.S. Pat. No. 77,737,226, U.S. Pat. No. 7,736,872; U.S. Pat. No. 7,638,299; U.S. Pat. No. 7,632,924; and U.S. Pat. No. 7,230,068). Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

PEGylated YRS Polypeptides

A wide variety of PEG polymers can be linked to YRS polypeptides of the present invention to modulate biological properties of the YRS polypeptide, and/or provide new biological properties to the YRS polypeptide. PEG polymers can be linked to the YRS polypeptide via a naturally encoded amino acid, via a non-naturally encoded amino acid, or any functional substituent of a natural or non-natural amino acid, or any substituent or functional group added to a natural or non-natural amino acid.

PEGylated polypeptides can also be designed so as to control the rate of release of the bioactive polypeptide into a patient's bloodstream, and thus, PEGylation of therapeutic polypeptides is a useful and attractive strategy for designing next generation polypeptide-based drugs. Moreover, site specific PEGylation also minimizes undesirable collateral effects on the therapeutic activities of the PEGylated polypeptide. PEGylation of polypeptide-based drugs can change their physical and chemical properties, such as conformation, electrostatic binding, hydrophobicity, and pharmacokinetic profile. PEGylation also improves drug solubility, stability, and the retention time of the conjugates in blood and decreases immunogenicity, proteolysis and renal excretion, thereby allowing a reduced dosing frequency.

In various embodiments, the present invention contemplates, in part, pegylated YRS polypeptides, compositions comprising such pegylated polypeptides, and methods of use thereof. In certain embodiments, the pegylated YRS polypeptides described herein have improved pharmacokinetic properties compared to non-PEGylated YRS polypeptides.

PEG polymers suitable for conjugation to YRS polypeptides of the invention are not limited to a particular structure and can be linear (e.g., monofunctional PEG or bifunctional PEG), branched or multi-armed (e.g., PEG attached to a polyol core or forked PEG), dendritic. In one embodiment, the internal structure of a polyalkylene glycol polymer can be organized in any number of different patterns and can be selected from the group consisting of homopolymer, alternating copolymer, random copolymer, block copolymer, alternating tripolymer, random tripolymer, and block tripolymer.

In particular embodiments, the total average molecular weight of the PEG polymers polymer in the conjugate is from about 1000 Daltons to about 150,000 Daltons. Exemplary ranges of total average molecular weights of PEG polymers conjugated to a YRS polypeptide of the invention include, but are not limited to: about 5,000 Daltons to about 120,000 Daltons, about 10,000 Daltons to about 100,000 Daltons, about 10,000 Daltons to about 80,000 Daltons, about 10,000 Daltons to about 60,000 Daltons, about 10,000 Daltons to about 40,000 Daltons, about 20,000 Daltons to about 100,000 Daltons, about 20,000 Daltons to about 80,000 Daltons, about 20,000 Daltons to about 60,000 Daltons, about 20,000 Daltons to about 40,000 Daltons, about 40,000 Daltons to about 120,000 Daltons, about 40,000 Daltons to about 100,000 Daltons, about 40,000 Daltons to about 80,000 Daltons, or about 40,000 Daltons to about 60,000 Daltons, or any intervening range.

Exemplary ranges of total average molecular weights of PEG polymers conjugated to a YRS polypeptide of the invention include, but are not limited to: about 1,000 Daltons, about 5000 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 100,000 Daltons, about 110,000 Daltons, about 120,000 Daltons, about 130,000 Daltons, about 140,000 Daltons, or about 150,000 Daltons any intervening molecular weight.

In particular embodiments comprising 1, 2, 3, 4, 5, 6, 7, 8, 9, or 10 or more PEG polymers conjugated to a YRS polypeptide of the present invention, the average molecular weight of each PEG polymer conjugated to the YRS polypeptide includes, but is not limited to: about 1000 Daltons, about 5000 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, or about 100,000 Daltons, or any intervening molecular weight.

It will be appreciated that because virtually all PEG polymers exist as mixtures of diverse high molecular mass, the PEG polymer molecular weights (MW) above represent the average MWs of different sized chains within the polymer.

The PEG polymers of the invention will for a given molecular weight typically consist of a range of ethylene glycol (or ethyleneoxide; $OCH_2CH_2$) monomers. For example, a PEG polymer of molecular weight 2000 Da will typically consist of 43±10 monomers, the average being around 43-44 monomers.

The PEG polymers of the present invention will typically comprise a number of subunits, e.g., each "n", "$n_1$" or "$n_2$" in any of the claimed compounds may each independently be from about 1 to about 1000, from about 1 to about 800, from about 1 to about 600, from about 1 to about 400, from about 1 to about 300, from about 1 to about 200. Well-suited PEG groups are such wherein the number of subunits (e.g., n, $n_1$ or $n_2$) are independently selected from the group consisting of from about 800 to about 1000; from about 800 to about 950; from about 600 to about 850; from about 400 to about 650; from about 200 to about 450, from about 180 to about 350; from about 100 to about 150; from about 35 to about 55; from about 42 to about 62; from about 12 to about 25 subunits, from about 1 to 10 subunits. In certain embodiments the PEGylated YRS polypeptide will have a molecular weight of about 40 kDa, and thus n for each PEG chain in the branch chain PEGs will be within the range of about 440 to about 550, or about 450 to about 520.

Branched versions of the PEG polymer (e.g., a branched 40,000 Da PEG polymer comprised of two or more 10,000 Da to 20,000 Da PEG polymers or the like) having a total molecular weight of any of the foregoing can also be used.

Typically, PEG polymers are activated with a suitable activating group appropriate for coupling to a desired site on a YRS polypeptide. Thus, a polymeric reagent will possess a functional group for reaction with a corresponding functional group on a YRS polypeptide, e.g., lysine, cysteine, histidine, arginine, aspartic acid, glutamic acid, serine, threonine, tyrosine, and the N-terminal amino and C-terminal carboxylic acid group of amino acids. Representative polymeric reagents and methods for conjugating these polymers to an active moiety are known in the art and further described in Zalipsky, S., et al., "Use of Functionalized Poly (Ethylene Glycols) for Modification of Polypeptides" in *Polyethylene Glycol Chemistry: Biotechnical and Biomedical Applications*, J. M. Harris, Plenus Press, New York (1992), Zalipsky (1995) *Advanced Drug Reviews* 16:157-182; and Roberts et al., *Advanced Drug Delivery Reviews* 54 (2002): 459-476.

In general, PEG functional groups suitable for conjugating PEG to a polypeptide of the invention include, but are not limited to a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal.

In one embodiment, the active functional group of a PEG moiety selected from the group consisting of: a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal forms a covalent linkage with a non-natural amino acid having the formula:

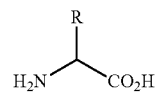

wherein the sidechain, R, of the non-naturally occurring amino acid comprises a functional group selected from the group consisting of: alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxyl amide, or organosilane group, and the like and any combination thereof.

In another embodiment, the active functional group of a PEG moiety selected from the group consisting of: a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal forms a covalent linkage with a non-natural amino acid selected from the group consisting of: p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

In particular embodiments, the active functional group of a PEG polymer is conjugated to an amino group of a YRS polypeptide. In this approach, the PEG bearing the active functional group is reacted with the YRS polypeptide in aqueous media under appropriate pH conditions, at room temperature or 4° C., for a few hours to overnight. Typically the polymeric reagent is coupled to the activated functional group via a linker as described herein.

Suitable active functional groups to conjugate PEG to an amino group of the polypeptide, such as those found in lysine, arginine, or histidine residues or an N-terminal residue of a YRS polypeptide, include, but are not limited to: succinimidyl esters (NHS), e.g., succinimidyl carbonate, succinimidyl carboxylmethyl, succinimidyl glutarate, succinimidyl valerate, succinimidyl succinate, and the like; p-nitrophenyl esters, e.g., p-nitrophenyl carbonate, p-nitrophenyl carboxymethyl, p-nitrophenyl glutarate, p-nitrophenyl valerate, p-nitrophenyl succinate, and the like; succinimidyl carbamate (NSC); dichlorotriazines; tresylates; benzotriazole carbonates; trichlorophenyl carbonates; isocyanates; isothiocyanates; acyl azides; sulfonyl chloride; aldehydes, e.g., proprionaldehyde, acetalaldehyde, butyraldehyde, and the like; carboxylic acid derivatives, e.g., propionic acid, butanoic acid, and the like; imidioesters, e.g., carbonylimidazole, oxycarbonylimidazoles, and the like; cyclic imide thiones; epoxides; acrylates; and anhydrides. Exemplary activated PEGs capable of reacting with amino groups of the YRS polypeptide include, e.g., those listed in Table 4.

PEGylation of a YRS polypeptide via amino group, with a PEG reagent bearing an N-hydroxysuccinimide ester (NHS group), is typically carried out at room temperature, or 4° C., in a polar aprotic solvent such as dimethylformamide (DMF) or acetonitrile, or a combination thereof (with small amounts of water to solubilize the peptide) under slightly basic pH conditions, e.g., from pHs ranging from about 7.5 to about 9. Reaction times are typically in the range of 1 to 24 hours, depending upon the pH and temperature of the reaction.

PEGylation of a YRS polypeptide via amino group, with a PEG reagent bearing an aldehyde group, is typically conducted under mild conditions, in the presence of sodium cyanoborohydride (10 equiv.), 4° C., at pHs from about 5 to 10, for about 20 to 36 hours. PEGylation may be conducted, for example, in 100 mM sodium acetate or 100 mM sodium biphosphate buffer at pH 5.0~6.0. The buffer may additionally contain 20 mM sodium cyanoborahydride. The molar ratio of compound to mPEG-aldehyde may be 1:5~1:10. The PEGylation reaction is then stirred overnight at ambient or refrigeration temperature.

PEGylation of a YRS polypeptide via amino group, with a PEG reagent bearing p-Nitrophenyloxycarbonyl group, is typically conducted with borate or phosphate buffer at pHs from about pH 8 to 8.3 pH, at room temperature overnight.

For all the coupling reactions, varying ratios of polymeric reagent to the YRS polypeptide may be employed, e.g., from an equimolar ratio up to a 10-fold molar excess of polymer reagent. Typically, up to a 2-fold molar excess of polymer reagent will suffice. In the following Table 4, selected PEGylation reagents are listed. Obviously other active groups and linkers may be employed, and are known to those skilled in the art.

TABLE 4

| Structure/Functionality | Abbreviation & Molecular Weight Range (in Da) |
|---|---|
| Exemplary Activated Linear PEGs Capable of Reacting With Amino Groups | |
| 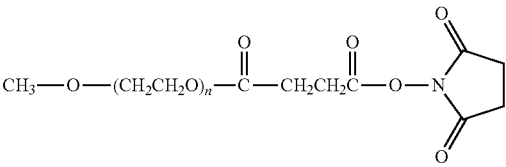<br>N-hydroxysuccinimide ester | SUNBRIGHT ME-020CS MW = 2,000<br>SUNBRIGHT ME-050CS MW = 5,000<br>SUNBRIGHT ME-100CS MW = 10,000<br>SUNBRIGHT ME-200CS MW = 20,000<br>SUNBRIGHT ME-300CS MW = 30,000<br>SUNBRIGHT ME-400CS MW = 40,000 |
| 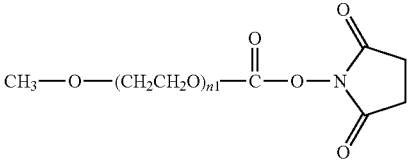<br>N-hydroxysuccinimide ester | SUNBRIGHT ME-050GS MW = 5,000<br>SUNBRIGHT ME-200GS MW = 20,000<br>SUNBRIGHT ME-300GS MW = 30,000<br>SUNBRIGHT ME-400GS MW = 40,000 |

TABLE 4-continued

| Structure/Functionality | Abbreviation & Molecular Weight Range (in Da) |
|---|---|
| $CH_3-O-(CH_2CH_2O)_{n1}-\overset{O}{\underset{\|}{C}}-O-N\begin{pmatrix}O\\O\end{pmatrix}$<br><br>N-hydroxysuccinimide ester | SUNBRIGHT ME-050TS MW = 5,000<br>SUNBRIGHT ME-200TS MW = 20,000<br>SUNBRIGHT ME-300TS MW = 30,000<br>SUNBRIGHT ME-400TS MW = 40,000 |
| $CH_3-O-(CH_2CH_2O)_{n1}-CH_2-\overset{O}{\underset{\|}{C}}-O-N\begin{pmatrix}O\\O\end{pmatrix}$<br><br>N-hydroxysuccinimide ester | SUNBRIGHT ME-020AS MW = 2,000<br>SUNBRIGHT ME-050AS MW = 5,000 |
| $CH_3-O-(CH_2CH_2O)_{n1}-(CH_2)_5\overset{O}{\underset{\|}{C}}-O-N\begin{pmatrix}O\\O\end{pmatrix}$<br><br>N-hydroxysuccinimide ester | SUNBRIGHT ME-050HS MW = 5,000<br>SUNBRIGHT ME-200HS MW = 20,000<br>SUNBRIGHT ME-300HS MW = 30,000<br>SUNBRIGHT ME-400HS MW = 40,000 |
| $CH_3-O-(CH_2CH_2O)_{n1}-\overset{O}{\underset{\|}{C}}-O-\text{C}_6H_4-NO_2$<br><br>p-Nitrophenyl | SUNBRIGHT MENP-020H MW = 2,000<br>SUNBRIGHT MENP-050H MW = 5,000<br>SUNBRIGHT MENP-10T MW = 10,000<br>SUNBRIGHT MENP-20T MW = 20,000<br>SUNBRIGHT MENP-30T MW = 30,000<br>SUNBRIGHT MENP-40T MW = 40,000 |
| $CH_3-O-(CH_2CH_2O)_n-N=C=O$<br><br>Isocyanate | |
| $CH_3-O-(CH_2CH_2O)_n-CH_2-\overset{O}{\underset{\|}{C}}-O-CH_2CH_2\overset{O}{\underset{\|}{C}}H$<br><br>Aldehyde | SUNBRIGHT ME-050AL MW = 5,000<br>SUNBRIGHT ME-100AL MW = 10,000<br>SUNBRIGHT ME-200AL MW = 20,000<br>SUNBRIGHT ME-300AL MW = 30,000<br>SUNBRIGHT ME-400AL MW = 40,000 |
| $CH_3-O-(CH_2CH_2O)_n-CH_2CH_2\overset{O}{\underset{\|}{C}}H$<br><br>Aldehyde | SUNBIO P1PAL-5 MW = 5,000<br>SUNBIO P1PAL-10 MW = 10,000<br>SUNBIO P1PAL-20 MW = 20,000<br>SUNBIO P1PAL-30 MW = 30,000 |
| $CH_3-O-(CH_2CH_2O)_n-CH_2\overset{O}{\underset{\|}{C}}NHCH_2CH_2\overset{O}{\underset{\|}{C}}H$<br><br>Amide Aldehyde | SUNBIO P1APAL-5 MW = 5,000<br>SUNBIO P1APAL-10 MW = 10,000<br>SUNBIO P1APAL-20 MW = 20,000<br>SUNBIO P1APAL-30 MW = 30,000 |
| $CH_3-O-(CH_2CH_2O)_n-\overset{O}{\underset{\|}{C}}NHCH_2CH_2\overset{O}{\underset{\|}{C}}H$<br><br>Urethane Aldehyde | SUNBIO P1TPAL-5 MW = 5,000 |
| $CH_3-O-(CH_2CH_2O)_n-CH_2CH_2CH_2\overset{O}{\underset{\|}{C}}H$<br><br>Aldehyde | SUNBIO P1BAL-5 MW = 5,000<br>SUNBIO P1BAL-10 MW = 10,000<br>SUNBIO P1BAL-20 MW = 20,000<br>SUNBIO P1BAL-30 MW = 30,000 |

TABLE 4-continued

| Structure/Functionality | Abbreviation & Molecular Weight Range (in Da) |
|---|---|
| $CH_3-O-(CH_2CH_2O)_n-CH_2\overset{O}{\underset{\|}{C}}NHCH_2CH_2CH_2\overset{O}{\underset{\|}{C}}H$<br><br>Amide Aldehyde | SUNBIO P1ABAL-5 MW = 5,000<br>SUNBIO P1ABAL-10 MW = 10,000<br>SUNBIO P1ABAL-20 MW = 20,000<br>SUNBIO P1ABAL-30 MW = 30,000 |
| $CH_3-O-(CH_2CH_2O)_n-\overset{O}{\underset{\|}{C}}NHCH_2CH_2CH_2\overset{O}{\underset{\|}{C}}H$<br><br>Urethane Aldehyde | SUNBIO P1TBAL-5 MW = 5,000 |
| $R_1O(CH_2CH_2O)_n-C(O)_x-(CH_2)_y-C(O)-O-N$ (succinimide)<br><br>N-hydroxysuccinimide ester | X = 0, y = 1 SUNBRIGHT-AS<br>X = 0, y = 5 SUNBRIGHT-HS<br>X = 1, y = 2 SUNBRIGHT-CS<br>X = 1, y = 3 SUNBRIGHT-GS |
| $R_1O(CH_2CH_2O)_n-(CH_2)_3NH-(CH_2)_z-N$ (maleimide)<br><br>Maleimide | z = 2 SUNBRIGHT-MA<br>z = 5 SUNBRIGHT-MA3 |

Exemplary Activated Branched PEGs Capable of Reacting With Amino Groups

| Structure/Functionality | Abbreviation & Molecular Weight Range (in Da) |
|---|---|
| $CH_3-O-(CH_2CH_2O)_{n1}-CH_2CH_2$<br>$CH_3-O-(CH_2CH_2O)_{n2}-CH_2CH_2$ N—$CH_2$—$\overset{O}{\underset{\|}{C}}$—O—N(succinimide)<br><br>N-hydroxysuccinimide ester | JENKEM A0001-1 Y-NHS-40K |
| $R_1-O-(CH_2CH_2O)_{n1}-CH_2$<br>$R_1-O-(CH_2CH_2O)_{n2}-CH$<br>$H_2C-OCH_2CH_2CH_2NHC(CH_2)_3CO-N$(succinimide)<br><br>N-hydroxysuccinimide ester | SUNBRIGHT GL2-200GS2 MW = 20,000<br>SUNBRIGHT GL2-400GS2 MW = 40,000<br>SUNBRIGHT GL2-400GS2 MW = 60,000<br>SUNBRIGHT GL2-800GS2 MW = 80,000 |
| $R_1-O-(CH_2CH_2O)_{n1}-CH_2$<br>$R_1-O-(CH_2CH_2O)_{n2}-CH$<br>$H_2C-OCO-C_6H_4-NO_2$<br><br>p-Nitrophenyl | SUNBRIGHT GL2-100NP MW = 10,000<br>SUNBRIGHT GL2-200NP MW = 20,000<br>SUNBRIGHT GL2-400NP MW = 40,000<br>SUNBRIGHT GL2-600NP MW = 60,000<br>SUNBRIGHT GL2-800NP MW = 80,000 |
| $R_1-O-(CH_2CH_2O)_{n1}-CH_2$<br>$R_1-O-(CH_2CH_2O)_{n2}-CH$<br>$H_2C-OCO-N$(succinimide)<br><br>N-hydroxysuccinimide ester | SUNBRIGHT GL2-200TS MW = 20,000<br>SUNBRIGHT GL2-400TS MW = 40,000<br>SUNBRIGHT GL2-600TS MW = 60,000<br>SUNBRIGHT GL2-800TS MW = 80,000 |

TABLE 4-continued

| Structure/Functionality | Abbreviation & Molecular Weight Range (in Da) |
|---|---|
| 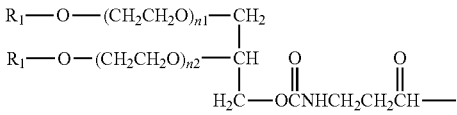 Aldehyde | SUNBRIGHT GL2-200AL3 MW = 20,000<br>SUNBRIGHT GL2-400AL3 MW = 40,000<br>SUNBRIGHT GL2-600AL3 MW = 60,000<br>SUNBRIGHT GL2-800AL3 MW = 80,000 |
| 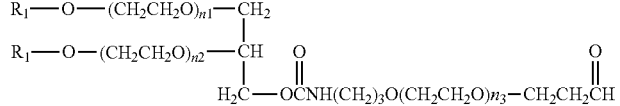 Aldehyde | SUNBRIGHT GL3-400AL100U MW = 50,000 |
| 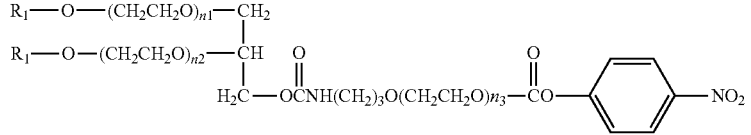 p-Nitrophenyl | SUNBRIGHT GL3-400NP100U MW = 50,000 |
| 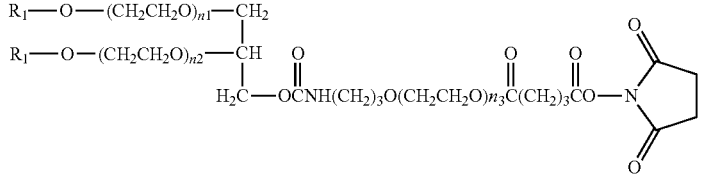 N-hydroxysuccinimide ester | SUNBRIGHT GL3-400GS100U MW = 50,000 |
| 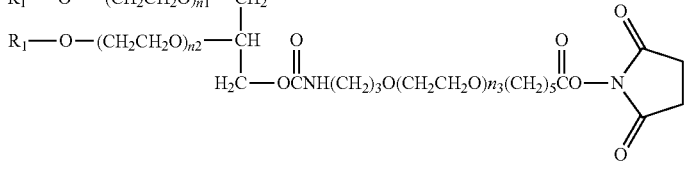 N-hydroxysuccinimide ester | SUNBRIGHT GL3-400HS100U MW = 50,000 |
| 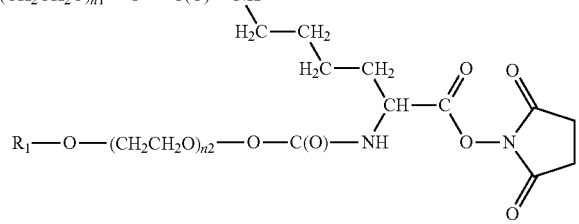 N-hydroxysuccinimide ester | SUNBRIGHT LY-400NS MW = 40,000 |
| 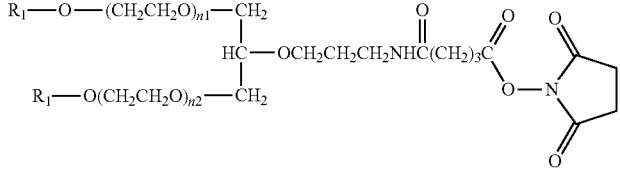 | MW = 40,000 |

In certain embodiments, the active functional group of a PEG polymer is conjugated to a thiol group of a YRS polypeptide. Suitable active functional groups to conjugate PEG to a thiol group of the polypeptide, such as those found in a cysteine residue of a YRS polypeptide, include, but are not limited to: thiols, maleimides, vinylsulfones, iodoacetamides, orthopyridyl disulfides, haloacetyls, alkyl halide derivatives, aziridines, acrylol derivatives arylating agents, and the like.

Exemplary activated PEGs capable of reacting with amino groups of the YRS polypeptide include, e.g., those listed in Table 5.

TABLE 5

| Structure/Functionality | Abbreviation & Molecular Weight Range (in Da) |
|---|---|
| Exemplary Activated Linear PEGs Capable of Reacting With Thiol Groups | |
| 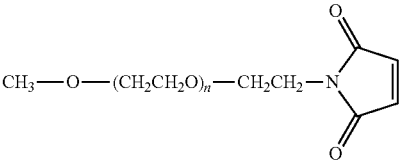 Maleimide | NANOCS PEG2-0001 MW = 5000<br>NANOCS PEG2-0002 MW = 2000<br>NANOCS PEG2-0003 MW = 1000<br>NANOCS PEG2-0004 MW = 10000<br>NANOCS PEG2-0005 MW = 20000<br>NANOCS PEG2-0006 MW = 30000<br>NANOCS PEG2-0006 MW = 40000 |
| 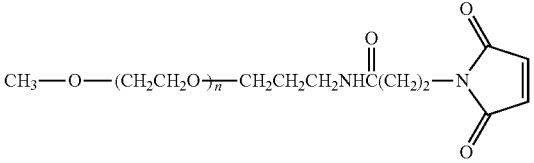 Maleimide | SUNBRIGHT ME-020MA MW = 2,000<br>SUNBRIGHT ME-050MA MW = 5,000<br>SUNBRIGHT ME-120MA MW = 12,000<br>SUNBRIGHT ME-200MA MW = 20,000<br>SUNBRIGHT ME-300MA MW = 30,000<br>SUNBRIGHT ME-400MA MW = 40,000 |
| 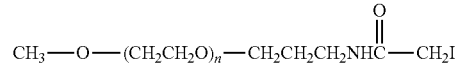 Iodoacetamide | SUNBRIGHT ME-200IA MW = 20,000<br>SUNBRIGHT ME-300IA MW = 30,000<br>SUNBRIGHT ME-400IA MW = 40,000 |
| 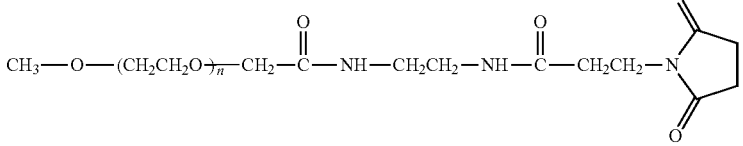 Maleimide | JENKEM A3073 M-MAL-2000<br>JENKEM A3014 M-MAL-5000<br>JENKEM A3045 M-MAL-10K<br>JENKEM A3002 M-MAL-20K<br>JENKEM A3046 M-MAL-30K<br>JENKEM A3042 M-MAL-40K |
| 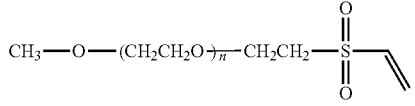 Vinyl sulfone | JENKEM A3034 M-VS-5000<br>JENKEM A3006 M-VS-20K |
| 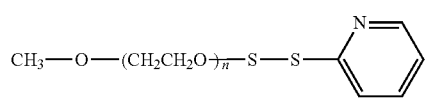 Orthopyridyl disufide | NANOCS PEG2-0011 MW = 5000<br>NANOCS PEG2-0012 MW = 2000<br>NANOCS PEG2-0014 MW = 10000 |
| Exemplary Activated Branched PEGs Capable of Reacting With Thiol Groups | |
| 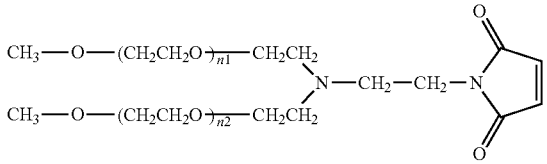 Maleimide | JENKEM A0002-1 Y-MAL-40K |

TABLE 5-continued

| Structure/Functionality | Abbreviation & Molecular Weight Range (in Da) |
|---|---|
| $CH_3-O-(CH_2CH_2O)_{n1}-CH_2$<br>$CH_3-O-(CH_2CH_2O)_{n2}-CH$<br>$H_2C-OCH_2CH_2CH_2NHC(CH_2)_2-$ [succinimide] | SUNBRIGHT GL2-200GS MW = 20,000<br>SUNBRIGHT GL2-400GS MW = 40,000<br>SUNBRIGHT GL2-600GS MW = 60,000<br>SUNBRIGHT GL2-800GS MW = 80,000 |
| Maleimide | |
| $CH_3-O-(CH_2CH_2O)_{n1}-O-\overset{O}{\overset{\|}{C}}-NH-CH_2-CH_2-CH_2-CH_2-CH_2-$<br>$CH_3-O-(CH_2CH_2O)_{n1}-O-\overset{O}{\overset{\|}{C}}-HN-HC-\overset{H_2}{C}-N$ [maleimide] | SUNBRIGHT LY-400MA MW = 40,000 |

PEGylation of a YRS polypeptide via amino group, with a PEG reagent bearing a maleimide group, iodoacetamide or vinyl sulfone is typically carried out in phosphate buffer 50-100 mM under mild conditions around pH 6.5-7.5 and at 4° C. for 4 to 24 hours.

In particular embodiments, PEG polymers may be attached to wild-type cysteine residues (i.e., cysteine residues present in the wild-type YRS sequence), or to "substituted" or "inserted" cysteine residues (e.g., cysteine residues introduced into the wild-type sequence by replacing a naturally-occurring residue with a cysteine, (such as via the A4C or A351C substitutions) or by inserting a cysteine into the sequence without necessarily altering or removing the nearby residues, e.g. by appending an N- or C-terminal fusion protein), so as to target the PEG to a desired location.

In certain embodiments, certain of the wild-type YRS cysteines residues may be first substituted with another amino acid to prevent attachment of the PEG polymer to these wild-type cysteines (e.g., C67, C250), for example, to prevent the PEG molecule(s) from disrupting an otherwise desirable biological activity.

In other embodiments, the active functional group of a PEG polymer is conjugated to a carboxylic acid group of a YRS polypeptide, e.g., at the C-terminus. Suitable active functional groups to conjugate the PEG to the carboxylic acid group of the YRS polypeptide include, but are not limited to: primary amines, hydrazines, and hydrazides, e.g., carbazates, semicarbazates, thiocarbazates, and the like.

Exemplary activated PEGs capable of reacting with carboxylic acid groups of the YRS polypeptide include, e.g., those listed in Table 6.

TABLE 6

Exemplary Activated Linear PEGs Capable of Reacting With Carboxylate Groups

| Structure/Functionality | Abbreviation & Molecular Weight Range (in Da) |
|---|---|
| $CH_3-O-(CH_2CH_2O)_n-CH_2CH_2CH_2NH_2$<br>Primary Amine | SUNBRIGHT MEPA-20H MW = 2,000<br>SUNBRIGHT MEPA-50H MW = 5,000<br>SUNBRIGHT MEPA-12T MW = 12,000<br>SUNBRIGHT MEPA-20T MW = 20,000<br>SUNBRIGHT MEPA-30T MW = 30,000<br>SUNBRIGHT MEPA-40T MW = 40,000 |
| $CH_3-O-(CH_2CH_2O)_n-CH_2CH_2NH_2$<br>Primary Amine | SUNBRIGHT MEPA-20H MW = 2,000<br>SUNBRIGHT ME-050EA MW = 5,000<br>SUNBRIGHT ME-100EA MW = 12,000<br>SUNBRIGHT ME-200EA MW = 20,000<br>SUNBRIGHT ME-300EA MW = 30,000<br>SUNBRIGHT ME-400EA MW = 40,000 |
| $CH_3-O-(CH_2CH_2O)_n-CH_2\overset{O}{\overset{\|}{C}}-NH-NH_2$ | JENKEM A3060 M-HZ MW = 5,000<br>JENKEM A3096 M-HZ MW = 10,000<br>JENKEM A3059 M-HZ MW = 20,000<br>JENKEM A3065 M-HZ MW = 30,000 |

PEGylation of a YRS polypeptide via carboxyl group, with a PEG reagent bearing a primary amine can be carried out in 50 mM Phosphate buffer (pH 7.2), in the presence of WSC (2 eq), 4C, for 10 to 24 hours. PEGylation of a YRS polypeptide via carboxyl group, with a PEG reagent bearing a hydrazide group can be carried out in the presence of N,N'-dicyclohexylcarbodiimide (DCC), or in presence of a water soluble coupling agent such as N—(-3-dimethylaminopropyl)-N'-ethylcarbodiimide hydrochloride (EDC) under mildly acid conditions (pH 6.0-6.5).

In further embodiments, the active functional group of a PEG polymer is conjugated to a hydroxyl group of a YRS polypeptide. Suitable active functional groups to conjugate the PEG to the hydroxyl group of the polypeptide, such as those found in a serine, threonine, or tyrosine residue of a polypeptide, include, but are not limited to: amines, hydrazides, epoxides, p-nitrophenylcarbonates, and isocyanates.

In various embodiments, the present invention provides PEGylated tyrosyl-tRNA synthetase (YRS) polypeptides, comprising at least one PEG moiety covalently attached to an amino acid residue within about 5, about 10, about 15, about 20, or about 25 amino acid residues of the C-terminus, the N-terminus, or a solvent accessible surface amino acid of the YRS polypeptide or any combination thereof. In certain preferred embodiments, the PEG moieties comprise linear or branched PEG polymers.

In one embodiment, the present invention, contemplates, in part, YRS polypeptides conjugated to a linear water soluble polymer, e.g., a PEG moiety. A wide variety of linear water soluble polymers, comprising functional groups suitable for conjugation to amino, thiol, hydroxyl, and carboxylic acid groups of a YRS polypeptide are commercially available in the art, e.g., from Nanocs Corporation, NOF Corporation, SunBio, Nektar, and Jenkem Technology. In particular embodiments, any commercially available water soluble polymer is suitable for conjugation to a YRS polypeptide. In various embodiments, a linear, water soluble polymer conjugated to a YRS polypeptide of the invention comprises a water soluble polymer moiety, optionally bound to a linker, and a covalent linkage that binds the YRS polypeptide to the remainder of the conjugate. A generalized structure (I) of a water soluble polymer conjugated to a YRS polypeptide of the invention has the following structure:

$$X-L-Y-YRS \quad (I)$$

wherein:
X is a water soluble polymer moiety;
L is an optional linker;
Y is a covalent linkage; and
YRS is a YRS polypeptide.

In another embodiment, the present invention, contemplates, in part, YRS polypeptides conjugated to branched chain water soluble polymers comprising two or more, e.g., two, three, four, five, six, seven, eight, nine, ten, or more water soluble moieties Illustrative multi-armed water soluble polymers having 2 arms, 3 arms, 4 arms, and 8 arms are known in the art, and are available commercially e.g., from Nanocs, NOF, Nektar, SunBio and Jenkem. In particular embodiments, any commercially available branched water soluble polymer, such as any branched chain PEG is suitable for PEGylation of a YRS polypeptide. Additional branched-water soluble polymers for use in forming a YRS polypeptide conjugate of the present invention can be prepared following techniques known to those skilled in the art. (See generally Pasut et al., (2004) Protein, peptide and non-peptide drug PEGylation for therapeutic application. *Expert Opinin. Ther. Patents* 14(6) 859-894) and are also described in U.S. Patent Application Publication Nos. 20050009988, 20060194940, 20090234070, 20070031371, U.S. Pat. Nos. 6,664,331; 6,362,254; 6,437,025; 6,541,543; 6,664,331; 6,730,334; 6,774,180; 6,838,528; 7,030,278; 7,026,440; 7,053,150; 7,157,546; 7,223,803; 7,265,186; 7,419,600; 7,432,330; 7,432,331; 7,511,094; 7,528,202; 7,589,157; and PCT publication numbers WO2005000360, WO2005108463, WO2005107815, WO2005028539 and WO200605108463.

The branching moiety (i.e., central core molecule) can be an aliphatic hydrocarbon having a carbon chain length of at least three carbon atoms (i.e., propane, butane, pentane, hexane, heptane, octane, nonane, decane, and the like) or an appropriate amino acid backbone, e.g., lysine, arginine, histidine, glutamine, serine, threonine, asparagine, aspartic acid, glutamic acid, cysteine, and seleno cysteine.

Other suitable core molecules include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane. Other suitable cores include polyamines, and PEG moieties comprising multiple functional terminal end groups. In one embodiment, the branching moiety comprises a lysine residue.

Since the branched polymers of the invention combine at least two polymer arms in a single molecule, a polymer with sufficient molecular weight to impart beneficial properties to a YRS polypeptide can be formed using shorter, easier to prepare polymer chains. The branched polymers of the invention are preferably monofunctional, meaning the polymer molecule contains only a single reactive site for conjugation to a YRS polypeptide.

Although the carbon atoms of the branching moiety can have PEG polymers extending from any of the aforementioned carbons, in particular embodiments, the overall branched conjugate is symmetrical. For example, for a three carbon branching moiety, the PEG polymers extend from positions 1 and 3, with a site suitable for covalent attachment to a YRS polypeptide extending from the central carbon or the carbon at position 2. Similarly, for a five carbon branching moiety, the PEG polymers can extend from positions 1 and 5, with a site suitable for covalent attachment to a YRS polypeptide extending from position 3, or PEG polymers extending from positions 2 and 4, or, if a highly branched structure is desired, with PEG polymers extending from each of positions 1, 2, 4, and 5. In certain embodiments, the overall branched conjugate is asymmetrical, for example, in an embodiment comprising a four carbon branching moiety. For example, for a four carbon branching moiety, the PEG polymers extend from positions 1, 2, and 3, with a site suitable for covalent attachment to a YRS polypeptide extending from the central carbon or the carbon at position 4.

A YRS polypeptide comprising branched chain water soluble polymer conjugate of the invention will typically comprise at least two water soluble moieties, each optionally bound to a linker, covalently attached to a branching moiety, also optionally bound to a linker, covalently attached to a covalent linkage that binds the YRS polypeptide to the remainder of the conjugate. A generalized structure (II) of the branched YRS polypeptide polymer conjugates of the invention is shown below:

$$(X-L_1)_m-B-L_2-Y-YRS \qquad (II)$$

wherein:
X is an independently selected water soluble polymer moiety, for each m;
$L_1$ and $L_2$ are independently selected optional linkers, wherein $L_1$ is also independently selected for each m;
m is 2, 3, 4, 5, 6, 7, 8, 9, or 10, preferably 2 to about 5 (e.g., 2, 3, 4, or 5);
Y is a covalent linkage between the YRS polypeptide and the remainder of the conjugate; and
YRS is a YRS polypeptide as disclosed elsewhere herein.

In certain embodiments the branched YRS polypeptide polymer conjugates of the invention may have a generalized formula (IIA)

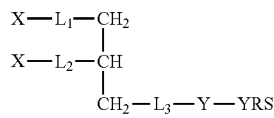

wherein:
X is an independently selected water soluble polymer moiety;
$L_1$, $L_2$ and $L_3$ are independently selected optional linkers;
Y is a covalent linkage between the YRS polypeptide and the remainder of the conjugate; and
YRS refers to a YRS polypeptide as disclosed herein.

In certain embodiments the branched YRS polypeptide polymer conjugates of the invention may have a generalized formula (IIB):

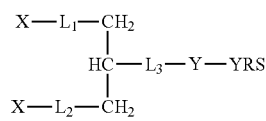

wherein:
X is an independently selected water soluble polymer moiety;
$L_1$, $L_2$ and $L_3$ are independently selected optional linkers;
Y is a covalent linkage between the YRS polypeptide and the remainder of the conjugate; and YRS refers to a YRS polypeptide as disclosed herein.

In certain embodiments the branched YRS polypeptide polymer conjugates of the invention may have a generalized formula (IIC):

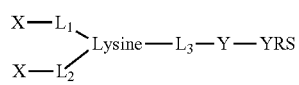

wherein:
X is an independently selected water soluble polymer moiety;
$L_1$, $L_2$ and $L_3$ are independently selected optional linkers, and wherein the linkers connecting the lysine residue to the water soluble polymer moiety are connected via the amino groups of the lysine molecule, and the linker connecting the lysine molecule to the YRS polypeptide is attached via the C-terminal carboxylate group of the lysine molecule;
Y is a covalent linkage between the YRS polypeptide and the remainder of the conjugate; and YRS refers to a YRS polypeptide as disclosed herein.

In certain embodiments the branched YRS polypeptide polymer conjugates of the invention may have a generalized formula (IID):

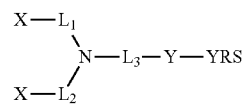

wherein:
X is an independently selected water soluble polymer moiety;
$L_1$, $L_2$ and $L_3$ are independently selected optional linkers;
Y is a covalent linkage between the YRS polypeptide and the remainder of the conjugate; and YRS refers to a YRS polypeptide as disclosed herein.

In certain embodiments of any of the generalized structures (I), (II), (IIA), (IIB), (IIC) or (IID) each water soluble polymer moiety, X, is independently selected and is represented by the formula $R_1-(CH_2CH_2O)_n$ or $R_1-(OCH_2CH_2)_n$; wherein $R_1$ is selected from alkyl, alkoxy, and aryl groups.

In certain embodiments n is from about 5 to about 1,200, from about 10 to about 1,000, from about 20 to about 800, from about 50 to about 600, or from about 100 to about 500. In one embodiment, n is about 5, about 10, about 20, about 50, about 100, about 200, about 300, about 400, about 500, about 600, about 700, about 800, about 900, about 1,000, about 1,100, about 1,200, about 1,300, about 1,400, or about 1,500 or any intervening integer. In some embodiments, n is from about 200 to about 800.

Typically, branched PEGylated YRS polypeptides of general formula (II) comprise two or more, three or more, four or more, or five or more of the same PEG polymer. That is to say, the polymer arms are each PEG polymers composed of the same type of subunits, which have similar geometries and similar molecular weights. Typically in the PEGylated YRS polypeptides of general formula (I), (II), (IIA), (IIB), (IIC) or (IID), each PEG moiety, X, may be end-capped, having at least one terminus capped with a relatively inert group, $R_1$. Suitable inert groups for $R_1$ include, but are not limited to alkyl groups, alkoxy groups, aryl groups, and sugars, such as, for example glucose, galactose, fructose, or sucrose. In particular embodiments, $R_1$ is an alkoxy group including, but not limited to methoxy, ethoxy, propoxy, butoxy, pentoxy, hexoxy, or benzyloxy. In some embodiments, $R_1$ is methoxy, and the PEG moiety is a methoxy-PEG or mPEG.

Those of ordinary skill in the art will recognize that the foregoing discussion describing linear and branched chain PEGs for use in forming a YRS polypeptide conjugate is by no means exhaustive and is merely illustrative, and that all water soluble polymers, and PEG structures having the qualities described herein are contemplated. Moreover, based on the instant invention, one of ordinary skill in the art can readily determine the appropriate size and optimal structure of alternative PEGylated YRS polypeptides using routine experimentation, for example, by obtaining the clearance profile for each conjugate by administering the conjugate to a patient and taking periodic blood and/or urine samples, as described herein. Once a series of clearance profiles has been obtained for each tested conjugate, a conjugate or mixture of conjugates, having the desired clearance profile(s) can be determined.

Linkers

In particular embodiments, the conjugates of the invention comprise one or more linkers, e.g., L, $L_1$, $L_2$. In a linear PEGylated YRS conjugate, linkers separate the PEG polymers from the covalent linkage to a YRS polypeptide. In a branched PEGylated YRS conjugate, linkers separate the PEG polymers from the branch moiety and/or the branch moiety from the covalent bond that links the conjugate to a YRS polypeptide of the invention. Each linker can be independently selected. Each linker in a branched conjugate can be the same linker or each linker can be different from each other linker. In certain embodiments any one or more of the linkers are optional.

The particular linkage between the YRS polypeptide and the water-soluble polymer or branch moiety depends on a number of factors, including the desired stability of the linkage, its hydrophobicity, the particular linkage chemistry employed, and impact on the aqueous solubility, and aggregation state of the PEGylated YRS polypeptide. Exemplary linkages are hydrolytically stable, and water soluble, representative suitable linker can comprise any combination of amide, a urethane (also known as carbamate), amine, thioether (also known as sulfide), or urea (also known as carbamide) groups.

There are many commercially available examples of suitable water-soluble linker moieties and/or these can be prepared following techniques known to those skilled in the art. Certain illustrative exemplary linker moieties are described below. The corresponding activated intermediates are provided in Tables 4-6.

Suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, wherein the atoms in the chain comprise C, S, N, P, and O. In certain embodiments, a linker is optional, e.g., a PEG conjugated polypeptide does not comprises a linker. In further embodiments a PEG comprising a functional group is directly conjugated to a polypeptide.

Illustrative examples of linkers or linkages useful in particular embodiments of the present invention include, but are not limited to one or more of the following: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N($R^6$)—, $R^6$ is H or an organic radical selected from the group consisting of alkyl, substituted alkyl, alkenyl, substituted alkenyl, alkynyl, substituted alkynyl, aryl and substituted aryl. Additionally, any of the above linker moieties may further include an ethylene oxide oligomer chain comprising 1 to 20 ethylene oxide monomer units [i.e., —(CH$_2$CH$_2$O)$_{1-20}$]— That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

Each linker moiety may be hydrolytically stable or may include a releasable linkage such as a physiologically hydrolyzable or enzymatically degradable linkage.

Releasable Linkers

In particular embodiments, the PEG and related polymer derivatives of the invention are capable of imparting improved water solubility, increased size, a slower rate of kidney clearance, and reduced immunogenicity to a conjugate formed by covalent attachment thereto, while also providing for controllable hydrolytic release of a YRS polypeptide into an aqueous environment—by virtue of the design of the linkages provided herein. The invention can be used to enhance the solubility and blood circulation lifetime of YRS polypeptides in the bloodstream, while also delivering a YRS polypeptide into the bloodstream that, subsequent to hydrolysis, is substantially free of PEG. The invention is especially useful in those cases where YRS polypeptides, when permanently conjugated to PEG, demonstrate reduced activity. By using the linkages as provided herein, such YRS polypeptides can maintain their therapeutic activity when in conjugated form.

Representative, but non-limiting, examples of releasable linkages include physiologically cleavable bonds, hydrolyzable bonds, and enzymatically degradable linkages. In particular embodiments, a releasable linkage has a half life at pH 7.4, 25° C., e.g., a physiological pH, human body temperature, of about 30 min., about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a PEGylated YRS polypeptide can be finely tailored by using a particular releasable linkage.

Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

Additional illustrative embodiments of hydrolytically unstable or weak linkages include, but are not limited to: —$O_2C$—$(CH_2)_b$—O—, where b is from 1 to 5, —O—$(CH_2)_b$—$CO_2$—$(CH_2)_c$—, where b is from 1 to 5 and c is from 2-5, —O—$(CH_2)_b$—$CO_2$—$(CH_2)_c$—O—, where b is from 1 to 5 and c is from 2-5, —$(CH_2)_b$—$OPO_3$—$(CH_2)_{b'}$—, where b is 1-5 and b' is 1-5, —C(O)—(NH—CHR—CO)$_a$—NH—CHR—, where a is 2 to 20 and R is a substituent found on an α-amino acid, —O—$(CH_2)_b$—$CO_2$—$CHCH_2$—$CH_2$—, where b is from 1-5, —O—$C_6H_4$—CH=N—$(CH_2)_b$—O—, where b is from 1-5, and —O—$(CH_2)_b$—$CH_2$—CH=N—$(CH_2)_b$—O—, where each b is independently from 1-5.

Other illustrative examples of releasable linkers can be benzyl elimination-based linkers, trialkyl lock-based linkers (or trialkyl lock lactonization based), bicine-based linkers, and acid labile linkers. Among the acid labile linkers can be disulfide bond, hydrazone-containing linkers and thiopropionate-containing linkers.

Enzymatically degradable linkages suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp- (SEQ ID NO:90), -Gly-Gly-Arg-, -Gly-Arg-Gly-Asp-Asn-Pro- (SEQ ID NO:91), -Gly-Arg-Gly-Asp-Ser- (SEQ ID NO:92), -Gly-Arg-Gly-Asp-Ser-Pro-Lys- (SEQ ID NO:93), -Gly-Pro-Arg-, -Val-Pro-Arg-, and -Phe-Val-Arg-. Illustrative examples of elastase-cleavable amino acid sequences include, but are not limited to: -Ala-Ala-, -Ala-Ala-Pro-Val- (SEQ ID NO:94), -Ala-Ala-Pro-Leu- (SEQ ID NO:95), -Ala-Ala-Pro-Phe- (SEQ ID NO:96), -Ala-Ala-Pro-Ala- (SEQ ID NO:97), and -Ala-Tyr-Leu-Val- (SEQ ID NO:98).

Enzymatically degradable linkages suitable for use in particular embodiments of the present invention also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z- (SEQ ID NO:99), -Gly-Pro-, Leu-Gly-Pro-Z- (SEQ ID NO:100), -Gly-Pro-Ile-Gly-Pro-Z- (SEQ ID NO:101), and -Ala-Pro-Gly-Leu-Z- (SEQ ID NO:102), where Y and Z are amino acids. Illustrative examples of collagenase-cleavable amino acid sequences include, but are not limited to: -Pro-Leu-Gly-Pro-D-Arg-Z- (SEQ ID NO:103), -Pro-Leu-Gly-Leu-Leu-Gly-Z- (SEQ ID NO:104), -Pro-Gln-Gly-Ile-Ala-Gly-Trp- (SEQ ID NO:105), -Pro-Leu-Gly-Cys(Me)-His- (SEQ ID NO:106), -Pro-Leu-Gly-Leu-Tyr-Ala- (SEQ ID NO:107), -Pro-Leu-Ala-Leu-Trp-Ala-Arg- (SEQ ID NO:108), and -Pro-Leu-Ala-Tyr-Trp-Ala-Arg- (SEQ ID NO:109), where Z is an amino acid. An illustrative example of a stromelysin-cleavable amino acid sequence is -Pro-Tyr-Ala-Tyr-Tyr-Met-Arg- (SEQ ID NO:110); and an example of a gelatinase-cleavable amino acid sequence is -Pro-Leu-Gly-Met-Tyr-Ser-Arg- (SEQ ID NO:111).

Enzymatically degradable linkages suitable for use in particular embodiments of the present invention also include amino acid sequences that can be cleaved by an angiotensin converting enzyme, such as, for example, -Asp-Lys-Pro-, -Gly-Asp-Lys-Pro- (SEQ ID NO:112), and -Gly-Ser-Asp-Lys-Pro- (SEQ ID NO:113).

Enzymatically degradable linkages suitable for use in particular embodiments of the present invention also include amino acid sequences that can be degraded by cathepsin B, such as, for example, Val-Cit, Ala-Leu-Ala-Leu (SEQ ID NO:114), Gly-Phe-Leu-Gly (SEQ ID NO:115) and Phe-Lys.

Examples of hydrolytically stable linkages include, but are not limited to, the following: succinimide, propionic acid, carboxymethylate linkages, ethers, carbamates, amides, amines, carbamides, imides, aliphatic C—C bonds, thio ethers, thiocarbamates, thiocarbamides, and the like. Generally, a hydrolytically stable linkage is one that exhibits a rate of hydrolysis of less than about 1-2% per day under physiological conditions.

In certain embodiments, the half-life of the PEGylated YRS polypeptide conjugate is regulated by incorporating one or more linkers of various stability into the conjugate. For example, if a relatively stable PEGylated YRS conjugate is desired, the conjugate can comprise one or more linkers that are hydrolytically stable or resistant to degradation. Hydrolytically stable linkers are known in the art and are described elsewhere herein, and generally result in a rate of hydrolysis of about 0.5%, about 1%, about 2%, about 3%, about 4%, or about 5% per day. Illustrative examples of hydrolytically stable linkers that can be used in PEGylated YRS conjugates of the invention include, but are not limited to: succinimide, propionic acid, carboxymethylate linkages, ethers, carbamates, amides, amines, carbamides, imides, aliphatic C—C bonds, thio ethers, thiocarbamates, thiocarbamides, and the like.

In other embodiments, a PEGylated YRS conjugate comprises one or more releasable linkages that result in a shorter half-life and more rapid clearance of the conjugate. For example, PEG can be prepared with ester linkages in the polymer backbone that are subject to hydrolysis. This hydrolysis results in cleavage of the polymer into fragments of lower molecular weight. Other hydrolytically degradable linkages are known in the art and described elsewhere herein, and include carbonate linkages; imine linkages resulting, for example, from reaction of an amine and an aldehyde; phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; and ortho ester linkages that are, for example, formed by reaction between a formate and an alcohol. Other suitable releasable linkers for use in branched conjugates of the invention include enzymatically degradable linkages and discussed elsewhere herein.

Such optional features of the conjugate, i.e., the introduction of one or more degradable linkages into the polymer chain, may provide for additional control over the final desired pharmacological properties of the conjugate upon administration. For example, a large and relatively inert PEGylated YRS polypeptide conjugate (i.e., having one or more high molecular weight PEG chains attached thereto, for example, one or more PEG chains having a molecular weight greater than about 10,000) may be administered, which is then hydrolyzed in vivo to generate a bioactive YRS polypeptide conjugate possessing a portion of the original PEG chain or lacking PEG entirely. In this way, the properties of the PEGylated YRS polypeptide conjugate can be more effectively tailored to balance the bioactivity and circulating half-life of the conjugate over time.

Covalent Linkages ("Y")

In forming the PEGylated YRS polypeptide conjugates of the invention, the branching moiety or a linker comprises a functional group that forms a covalent bond or linkage, Y, with a functional group on a YRS polypeptide, thereby forming a conjugate. Exemplary functional groups of linkers and YRS polypeptides are disclosed elsewhere herein, supra. Illustrative examples of covalent linkages, Y, in any of the PEGylated YRS polypeptide conjugates of the invention include, but are not limited to: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulfhydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, or alkylthio.

For example, a reaction between a PEG comprising a succinimidyl ester functional group and a YRS polypeptide comprising an amino group results in an amide linkage; a reaction between a PEG comprising a oxycarbonylimidizaole functional group and a YRS polypeptide comprising an amino group results in an carbamate linkage; a reaction between a PEG comprising a p-nitrophenyl carbonate functional group and a YRS polypeptide comprising an amino group results in an carbamate linkage; a reaction between a PEG comprising a trichlorophenyl carbonate functional group and a YRS polypeptide comprising an amino group results in an carbamate linkage; a reaction between a PEG comprising a thio ester functional group and a YRS polypeptide comprising an n-terminal amino group results in an amide linkage; a reaction between a PEG comprising a proprionaldehyde functional group and a YRS polypeptide comprising an amino group results in a secondary amine linkage; a reaction between a PEG comprising a butyraldehyde functional group and a YRS polypeptide comprising an amino group results in a secondary amine linkage; a reaction between a PEG comprising a acetal functional group and a YRS polypeptide comprising an amino group results in a secondary amine linkage; a reaction between a PEG comprising a piperidone functional group and a YRS polypeptide comprising an amino group results in a secondary amine linkage; a reaction between a PEG comprising a methylketone functional group and a YRS polypeptide comprising an amino group results in a secondary amine linkage; a reaction between a PEG comprising a tresylate functional group and a YRS polypeptide comprising an amino group results in a secondary amine linkage; a reaction between a PEG comprising a maleimide functional group and a YRS polypeptide comprising an amino group results in a secondary amine linkage; a reaction between a PEG comprising a aldehyde functional group and a YRS polypeptide comprising an amino group results in a secondary amine linkage; and a reaction between a PEG comprising a hydrazine functional group and a YRS polypeptide comprising an carboxylic acid group results in a secondary amine linkage.

In another non-limiting example, a reaction between a PEG comprising a maleimide functional group and a YRS polypeptide comprising a thiol group results in a thio ether linkage; a reaction between a PEG comprising a vinyl sulfone functional group and a YRS polypeptide comprising a thiol group results in a thio ether linkage; a reaction between a PEG comprising a thiol functional group and a YRS polypeptide comprising a thiol group results in a di-sulfide linkage; a reaction between a PEG comprising a orthopyridyl disulfide functional group and a YRS polypeptide comprising a thiol group results in a di-sulfide linkage; and a reaction between a PEG comprising an iodoacetamide functional group and a YRS polypeptide comprising a thiol group results in a thio ether linkage.

The particular coupling chemistry employed will depend upon the structure of the biologically active agent, the potential presence of multiple functional groups within the biologically active molecule, the need for protection/deprotection steps, chemical stability of the molecule, and the like, and will be readily determined by one skilled in the art. Illustrative linking chemistry useful for preparing the branched polymer conjugates of the invention can be found, for example, in Wong, S. H., (1991), "Chemistry of Protein Conjugation and Crosslinking", CRC Press, Boca Raton, Fla. and in Brinkley, M. (1992) "A Brief Survey of Methods for Preparing Protein Conjugates with Dyes, Haptens, and Crosslinking Reagents", in Bioconjug. Chem., 3, 2013.

More specific structural embodiments of the conjugates of the invention will now be described, all of which are intended to be encompassed by the structure above. The specific structures shown below are presented as exemplary structures only, and are not intended to limit the scope of the invention.

In one embodiment, a PEGylated YRS polypeptide comprises any of the structures 1-5:

(1)

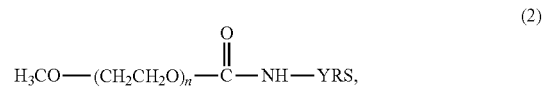

(2)

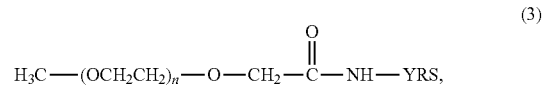

(3)

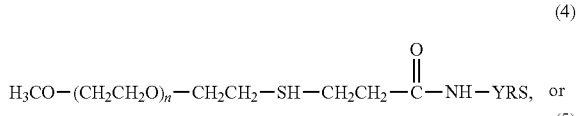

(4)

or

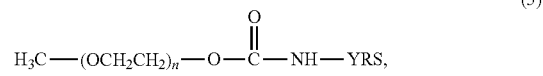

(5)

wherein "NH" of NH-YRS refers to an amino group of a YRS polypeptide and n is any integer from 20 to 800.

In another embodiment, a PEGylated YRS polypeptide comprises the structure:

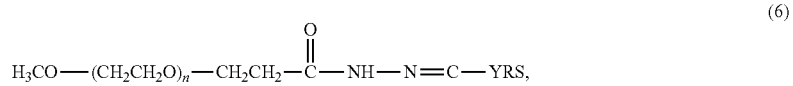

(6)

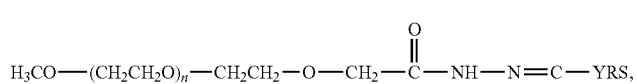
(7)
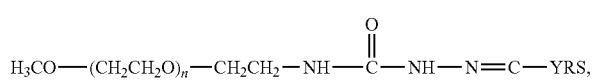
(8)
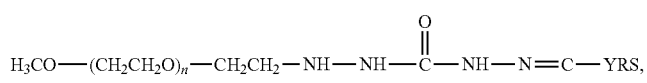
(9)
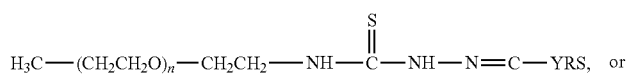
(10)
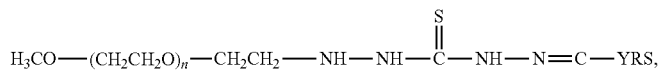
(11)
wherein "C" of C-YRS refers to carboxyl group of a YRS polypeptide and n is any integer from 20 to 800.
In another embodiment, a PEGylated YRS polypeptide comprises the structure:
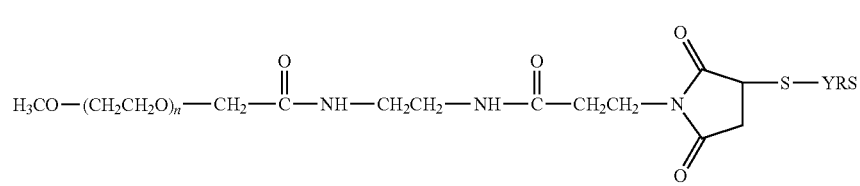
(12)
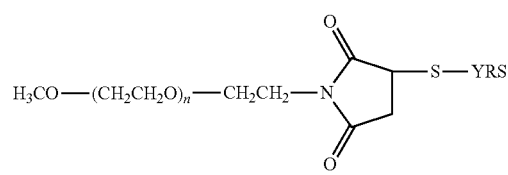
(13)
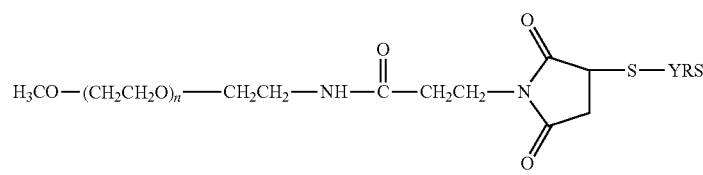
(14)
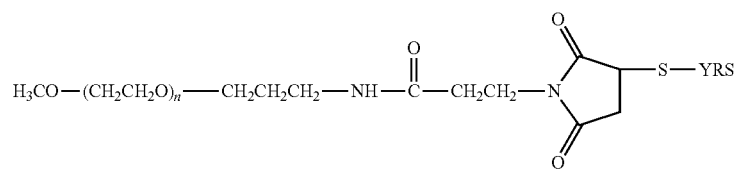
(15)
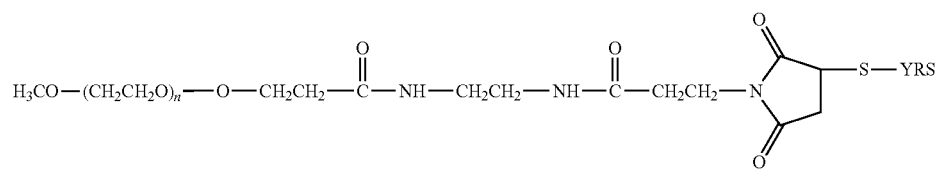
(16)
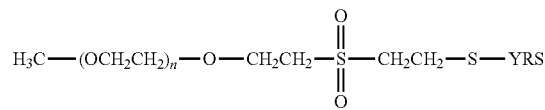
(17)

(18)
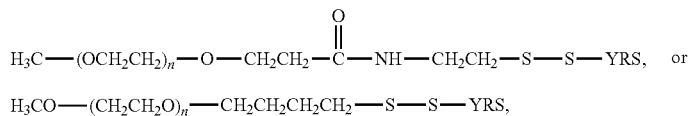
or
(19)
H₃CO—(CH₂CH₂O)$_n$—CH₂CH₂CH₂CH₂—S—S—YRS,
wherein "S" of S-YRS refers to thiol group of a YRS polypeptide and n is any integer from 20 to 800.
In one embodiment, a branched PEGylated YRS polypeptide of the invention comprises the structure:
(20)
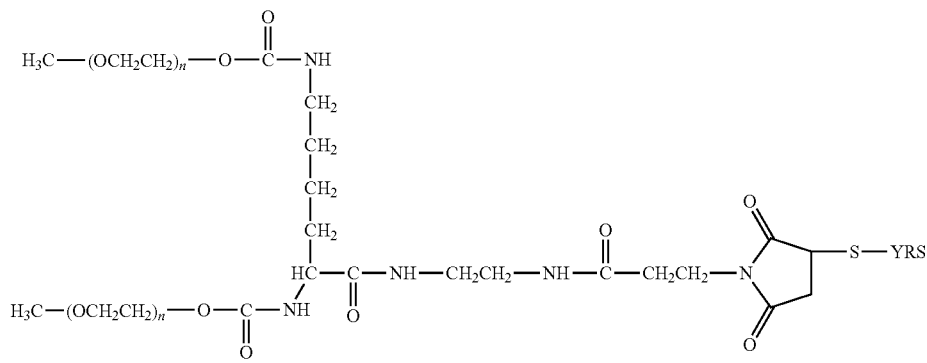
(21)
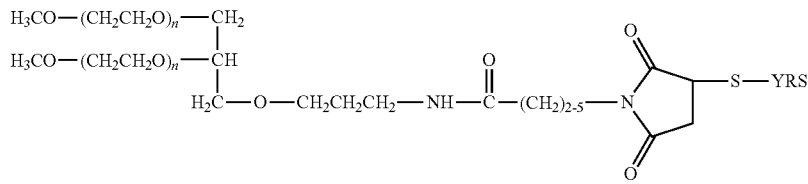
(22)
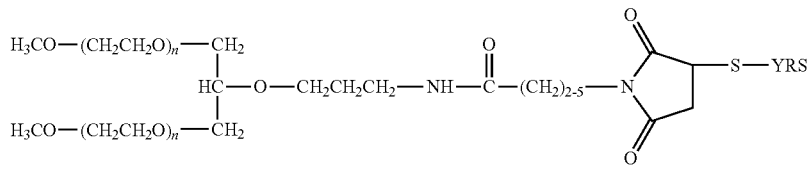
(23)
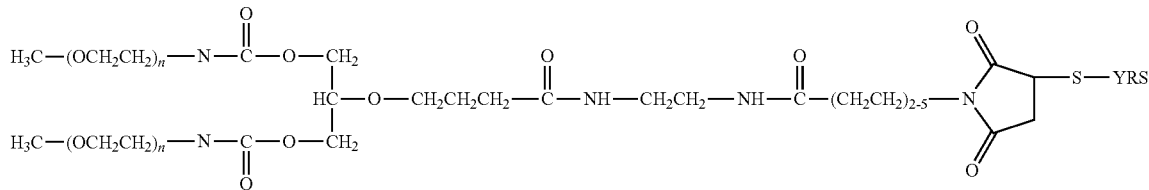
(24)
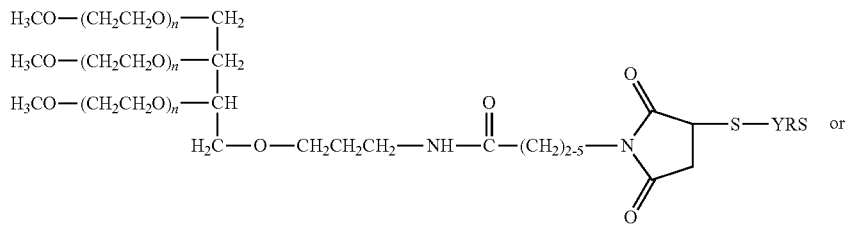

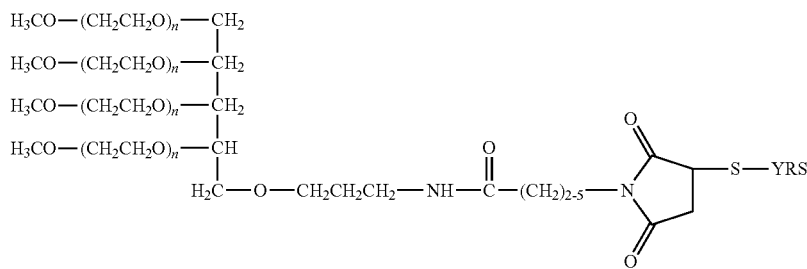

(25)

wherein "S" of S-YRS refers to thiol group of a YRS polypeptide and n is independently selected any integer from 20 to 800.

In different embodiments of any of the disclosed YRS conjugates, the YRS polypeptide is a full-length YRS polypeptide, or a truncated, or splice variant thereof, (e.g., one of SEQ ID NOS:1-35) which comprises a linear or branched chain polyethylene glycol (mPEG) derivative of general formula (I), (II), (IIA), (IIB), (IIC) or (IID) of about 20,000 to 60,000 Daltons. In one aspect of any of these YRS conjugates, the conjugated polymer has a structure selected from any of compounds (1) to (25).

In some embodiments, the YRS polypeptide differs from any SEQ ID NOS:1-35, by at least one amino acid selected from A4C, C67A, C250A, or A351C. In some embodiments the conjugate comprises a linear or branched chain polyethylene glycol (mPEG) derivative of general formula (I), (II), (IIA), (IIB), (IIC) or (IID) of about 20,000 to 60,000 Daltons that is covalently attached to the YRS polypeptide via a thio ether linkage. In one aspect of any of these YRS conjugates, the conjugated polymer has a structure selected from any of compounds (12) to (25). In one aspect the conjugated YRS polypeptide is coupled via amino acids A4C and/or A351C.

In some embodiments, the present invention provides PEGylated tyrosyl-tRNA synthetase (YRS) polypeptides, comprising the sequence set forth in SEQ ID NO:2 (1-329), and which differs from SEQ ID NO:2 by at least the mutations A4C, C67S, and C250S, and further comprises a maleimide monomethoxy polyethylene glycol (mPEG) derivative of general formula (I) having a molecular weight of about 40,000 to 60,000 Daltons that is covalently attached via a thio ether linkage to A4C and/or A351C.

In further embodiments, the present invention provides PEGylated tyrosyl-tRNA synthetase (YRS) polypeptides, comprising the sequence set forth in SEQ ID NO:7 YRS (1-353), which is modified by A4C and/or A351C, comprises C67S, and C250S substitutions, and further comprises a maleimide monomethoxy polyethylene glycol (mPEG) derivative of general formula (I) having a molecular weight of about 40,000 to 60,000 Daltons that is covalently attached via a thio ether linkage to A4C and/or A351C.

In further embodiments, the present invention provides PEGylated tyrosyl-tRNA synthetase (YRS) polypeptides, consisting essentially of the sequence set forth in SEQ ID NO:7 (1-353), which is modified by A4C and/or A351C, and C67S, and C250S substitutions, and having a maleimide monomethoxy polyethylene glycol (mPEG) derivative general formula (I) having a molecular weight of about 40,000 to 60,000 Daltons is covalently attached via a thio ether linkage to A4C and/or A351C.

In further embodiments, the present invention provides PEGylated tyrosyl-tRNA synthetase (YRS) polypeptides, consisting of the sequence set forth in SEQ ID NO:7 (1-353), which is modified by A4C and/or A351C, and C67S, and C250S substitutions, and having a maleimide monomethoxy polyethylene glycol (mPEG) derivative of about 40,000 Daltons is covalently attached via a thio ether linkage to A4C and/or A351C.

Modulation of Hematopoiesis and Methods of Use

Embodiments of the present invention relate to the discovery that PEGylated tyrosyl-tRNA synthetase (YRS) polypeptides, and fragments and variants thereof, offer improved method of modulating hematopoiesis in a variety of useful ways, both in vitro and in vivo. For instance, in certain embodiments, the PEGylated YRS polypeptides of the present invention modulate or reduce erythropoiesis, such as by leading to a reduction in the formation of erythroid progenitor cells or modulate or stimulate megakaryopoiesis and/or thrombopoiesis better than or comparable to non-PEGylated YRS polypeptides. More generally, PEGylated YRS polypeptides are capable of modulating cells from the myeloid, megakaryocyte, erythrocyte, granulocyte, lymphoid, thrombocytes, and/or endothelial progenitor (EPC) lineages, among others described herein.

The PEGylated YRS polypeptides of the present invention may therefore be used to treat various diseases or conditions that benefit from the modulation of hematopoietic processes. Likewise, related agents such as antibodies and other binding agents that interact with these hematopoiesis-regulating PEGylated YRS polypeptides may also be used to modulate hematopoietic process, and thereby treat or manage diseases and conditions associated with the same, as described herein and known in the art.

"Hematopoiesis" refers generally to the process of cellular differentiation or formation of particular, specialized blood cells from a stem cell or hematopoietic stem cell (HSC). Examples of hematopoietic processes that may be modulated by the PEGylated YRS polypeptides of the invention include, without limitation, the formation of myeloid cells (e.g., erythroid cells, mast cells monocytes/macrophages, myeloid dendritic cells, granulocytes such as basophils, neutrophils, and eosinophils, megakaryocytes, platelets) and lymphoid cells (e.g., natural killer cells, lymphoid dendritic cells, B-cells, and T-cells).

The methods of modulating hematopoiesis may be practiced in vivo, in vitro, ex vivo, or in any combination thereof. These methods can be practiced on any biological sample, cell culture, or tissue that contains hematopoietic stem cells, hematopoietic progenitor cells, or other stem or progenitor cells that are capable of differentiating along the hematopoietic lineage (e.g., adipose tissue derived stem cells). For in vitro and ex vivo methods, stem cells and progenitor cells, whether of hematopoietic origin or otherwise, can be isolated and/or identified according to the techniques and characteristics described herein and known in the art.

PEGylated YRS polypeptides may modulate hematopoiesis in a variety of ways. For instance, PEGylated YRS polypeptides may modulate hematopoiesis by directly interacting with a hematopoietic cell or a cell that has the potential to enter the hematopoietic lineage, such as a stem cell PEGylated YRS polypeptides may also modulate hematopoiesis by indirectly altering the tissue microenvironment surrounding a hematopoietic cell or stem cell. In certain embodiments, these relatively indirect mechanisms may involve modulating the activity of any combination of osteoblast cells, vascular cells, and immune cells. For instance, certain embodiments include methods of increasing the hematopoiesis-stimulatory activity of at least one of an osteoblast cell or a vascular cell, reducing the hematopoiesis-stimulatory activity of at least one of an osteoblast cell or a vascular cell, increasing the hematopoiesis-inhibitory activity of at least one of an osteoblast cell or a vascular cell, and reducing the hematopoiesis-inhibitory activity of at least one of an osteoblast cell or a vascular cell. Without wishing to be bound by any one theory, it is believed that the vascular niche, including vascular cells such as endothelial cells, smooth muscle cells, and fibroblasts may play a role in modulating hematopoiesis, and that the osteoblast niche, including osteoblast cells, may also play a role in hematopoietic cell differentiation.

In certain embodiments, PEGylated YRS polypeptides remodel the vasculature and/or regulate the necessary interactions between blood vessels and hematopoietic progenitor cells. In these and related embodiments, PEGylated YRS polypeptides may be used to treat or manage bone marrow abnormalities, such as those associated with the stroma, the vasculature, bone, blood cells, or bone-marrow microenvironment. As one non-illustrative example, certain bone marrow conditions such as myelodysplastic syndrome involve the abnormal development of hematopoietic progenitors, and antagonistic PEGylated YRS polypeptides may reduce or manage this abnormal development. Additional illustrative bone marrow abnormalities are discussed below.

Also included are methods of increasing the hematopoiesis-stimulatory activity of immune cells such as neutrophils. In these and related embodiments, PEGylated YRS polypeptides increase the neutrophil-mediated effect on the release of hematopoietic stem cells and other progenitor cells from the stem cell niche in the bone marrow. Without wishing to be bound by any one theory, it is believed that PEGylated YRS polypeptides and variants (e.g., Y431 mutants, mini-YRS) may stimulate the release of neutrophil proteases which degrade the molecules responsible for anchoring hematopoietic stem cells in the stem cell niche, and thereby facilitate their mobilization into the periphery. Also included are methods of decreasing the hematopoiesis-stimulatory activity of neutrophils. In these and related embodiments, PEGylated YRS polypeptides and variants may decrease the neutrophil-mediated effect on the release of hematopoietic stem cells and other progenitor cells from the stem cell niche in the bone marrow, and thereby reduce their mobilization into the periphery.

Also included are methods of modulating the trafficking or mobilization of hematopoietic cells, including hematopoietic stem cells, progenitor cells, erythrocytes, granulocytes, lymphocytes, megakaryocytes, and thrombocytes. In certain embodiments, these methods increase the trafficking of one or more selected hematopoietic cells between the bone marrow and periphery, and thereby increase the concentration of the one or more selected hematopoietic cells in the periphery. These methods can be practiced in vivo, in vitro, and ex vivo. For instance, in certain embodiments, PEGylated YRS polypeptides may be used to increase the concentration of selected peripheral hematopoietic cells in a bone marrow, stem cell, or blood donor prior to removal of those cells from the donor. In certain embodiments, PEGylated YRS polypeptides may be used to increase the number of (stem) cells that can be collected for transplantation before a subject undergoes myeloablative radiation treatment.

Certain specific hematopoietic processes include erythropoiesis, granulopoiesis, lymphopoiesis, megakaryopoiesis, thrombopoiesis, and others. "Erythropoiesis" refers generally to the process by which red blood cells (erythrocytes) are produced from HSCs, and includes the formation of erythroid progenitor cells. "Granulopoiesis" refers to generally to the development of the granulocytic white blood cells, neutrophils, eosinophils, and basophils, and includes the formation of granulocyte progenitor cells, such as myelocytes and promelyocytes. "Lymphopoiesis" refers to process by which lymphocytes, such as T-cells and B-cells are produced from HSCs, and includes the formation lymphocyte progenitor cells, such as lymphoblasts. "Megakaryopoiesis" refers generally to the process by which HSCs in the bone marrow differentiate into mature megakaryocytes, and includes the formation of megakaryocyte progenitor cells. "Thrombopoiesis" refers generally to the formation of blood platelets.

"Erythropoiesis" is a carefully ordered sequence of events. Initially occurring in fetal hepatocytes, the process is taken over by the bone marrow in the child and adult. Although multiple cytokines and growth factors are dedicated to the proliferation of the red blood cell, the primary regulator is erythropoietin (EPO). Red blood cell development is initially regulated by stem cell factor (SCF), which commits hematopoietic stem cells to develop into erythroid progenitors. Subsequently, EPO continues to stimulate the development and terminal differentiation of these progenitors. In the fetus, EPO is produced by monocytes and macrophages found in the liver. After birth, EPO is produced in the kidneys; however, Epo messenger RNA (mRNA) and EPO protein are also found in the brain and in red blood cells (RBCs), suggesting the presence of paracrine and autocrine functions.

Erythropoiesis escalates as increased expression of the EPO gene produces higher levels of circulating EPO. EPO gene expression is known to be affected by multiple factors, including hypoxemia, transition metals ($Co^{2+}$, $Ni^{2+}$, $Mn^{2+}$), and iron chelators. However, the major influence is hypoxia, including factors of decreased oxygen tension, red blood cell loss, and increased oxygen affinity of hemoglobin. For instance, EPO production may increase as much as 1000-fold in severe hypoxia.

In certain embodiments, the PEGylated YRS polypeptides of the present invention reduce erythropoiesis, and may be used to treat a condition associated with increased red blood cells. In certain embodiments, the PEGylated YRS polypeptides of the present invention increase erythropoiesis, and may be used to treat a condition associated with reduced red blood cells, such as anemia.

In certain embodiments, the PEGylated YRS polypeptides of the present invention may modulate erythropoiesis by reducing formation of erythroid progenitors or by reducing the formation of red blood cells. In certain embodiments, the PEGylated YRS polypeptides may modulate erythropoiesis by increasing or stimulating the formation (i.e., production) of erythroid progenitors or by increasing the formation of red blood cells.

In certain embodiments, these methods may utilize particular PEGylated YRS polypeptides or selected dosages or forms (e.g., monomers, dimers, oligomers) of PEGylated YRS polypeptides that both reduce erythropoiesis and increase megakaryopoiesis, including thrombopoiesis (i.e., the formation of platelets). In certain embodiments, depending on the condition to be treated, these methods may utilize particular PEGylated YRS polypeptides or selected dosages of PEGylated YRS polypeptides that reduce erythropoiesis without significantly enhancing megakaryopoiesis.

The methods of modulating erythropoiesis may be practiced in vivo, in vitro, ex vivo, or in any combination thereof. In vitro and ex vivo methods can be practiced on any biological sample or cell culture that contains hematopoietic stem cells, or other stem or progenitor cells that are capable of differentiating along the hematopoietic lineage (e.g., adipose tissue derived stem cells). Examples of biological samples include bone marrow, cord blood, and enriched stem cells, in addition to others described herein and known in the art. In certain instances, it may be advantageous to reduce the formation of erythroid progenitor cells in such biological samples or cell cultures.

In certain erythropoiesis-reducing embodiments, merely by way of non-limiting example, PEGylated YRS polypeptides may be administered directly to a subject to reduce red blood count, if desired. In this regard, a normal red blood cell count typically ranges from about 4.7 to about 6.1 million red blood cells per µl in men, and about 4.2 to about 5.4 million red blood cells per µl in women. A high red blood cell count is generally defined as more than about 5.72 million red blood cells per µl of blood for men and about 5.03 million red blood cells per µl of blood for women. In children, the threshold for high red blood cell count varies with age and sex. Red blood count may also be reflected by a person's hematocrit (i.e., packed cell volume (PCV) or erythrocyte volume fraction (EVF)), which is the proportion or percentage of blood volume that is occupied by red blood cells. A normal hematocrit is normally about 46% for men and about 38% for women. A higher hematocrit value indicates a greater number of red blood cells. In severe cases, a high red blood cell count can impair circulation and lead to abnormal clotting, among other problems.

Hence, certain embodiments of the present invention relate to methods of administering a PEGylated YRS polypeptide to a subject in need thereof, wherein the subject has an increased red blood count (e.g., greater than about 5.72 million red blood cells per µl of blood for men and about 5.03 million red blood cells per µl of blood for women, often by a clinically or statistically significant amount), or an increased hematocrit (e.g., greater than about 46% for men or about 38% for women, often by a clinically or statistically significant amount). In certain embodiments, administration of a PEGylated YRS polypeptide to such a subject reduces their red blood cell count or hematocrit. Also included are methods of reducing red blood cells in a subject, and methods of reducing hematocrit in a subject, including a subject that has a higher than normal red blood cell count or hematocrit, or is at risk for developing such a condition, comprising administering to the subject a PEGylated YRS polypeptide of the present invention, and thereby reducing red blood cell count or hematocrit in the subject.

There are many general diseases or conditions that increase the red blood cell count or hematocrit of a subject, and which may be improved or treated by the PEGylated YRS polypeptides of the present invention. As one general, illustrative example, high red blood cell count may result from increases in red blood cell production, mainly to compensate for low oxygen levels, which may be caused by poor heart or lung function. Also, high red blood cell count may result from increased release of erythropoietin (EPO) from the kidneys (EPO enhances red blood cell production), production of too many red blood cells by the bone marrow, impairment of the oxygen-carrying capacity of red blood cells (leading to over-production), compensation for a limited oxygen supply in higher altitudes, and the loss of blood plasma (i.e., the liquid component of blood), which may create relatively high levels of red blood cells, volume-wise.

Further examples of conditions that are associated with high red blood cell count include, without limitation, living at a high altitude, smoking, congenital heart disease, failure of the right side of the heart (i.e., cor pulmonale), scarring and thickening of the lung tissue (i.e., pulmonary fibrosis), bone marrow disorders (e.g., polycythemia vera), dehydration, such as from severe diarrhea or excessive sweating, kidney disease/cancer, exposure to carbon monoxide, anabolic steroid use, COPD or other lung diseases, such as pulmonary fibrosis, and EPO doping, mainly to enhance athletic performance. Hence, the PEGylated YRS polypeptides can be used to treat or reduce the risk of developing high red blood cell count or volume as it is associated with these or any other conditions known in the art.

Polycythemia refers to an increase in the red blood cell count, hemoglobin, and total red blood cell volume, typically accompanied by an increase in total blood volume. Polycythemia can be distinguished from relative erythrocytosis secondary to fluid loss or decreased intake, because polycythemia results in increased total blood volume, and relative erythrocytosis does not. Two basic categories of polycythemia are typically recognized: primary polycythemias, which are due to factors intrinsic to red cell precursors and include the diagnoses of primary familial and congenital polycythemia (PFCP) and polycythemia vera (PV), and secondary polycythemias, which are caused by factors extrinsic to red cell precursors.

Primary polycythemia refers to a variety of myeloproliferative syndromes that include, for example, polycythemia vera, essential thrombocythemia, agnogenic myeloid metaplasia, and myelofibrosis.

Polycythemia vera has a significant genetic component. For instance, an activating mutation in the tyrosine kinase JAK2 (JAK2$^{V617F}$) now appears to cause most primary cases in adults. Several other mutations of JAK2 have also been described (e.g., exon 12, JAK2$^{H538-K539delinsL}$). These and possibly other JAK2 mutations are thought to cause hypersensitivity to EPO via the EPO receptor. Familial clustering suggests a genetic predisposition. Also, the clonality of polycythemia vera is well established. Studies also suggest hypersensitivity of the myeloid progenitor cells to growth factors, including EPO, IL-3, SCF, GM-CSF, and insulin-like growth factor (IGF)-1, whereas other studies show defects in programmed cell death.

PFCP is caused by a hypersensitivity of erythroid precursors to EPO. Several mutations (approximately 14) have been identified in the Epo receptor (EPOR) gene. Most of the identified EPOR mutations (11) cause truncation of the c-terminal cytoplasmic receptor domain of the receptor. These truncated receptors have heightened sensitivity to circulating Epo due to a lack of negative feedback regulation.

Secondary polycythemia may result from functional hypoxia induced by lung disease, heart disease, increased altitude (hemoglobin increase of 4% for each 1000-m increase in altitude), congenital methemoglobinemia, and other high-oxygen affinity hemoglobinopathies stimulating increased EPO production. Secondary polycythemia may also result from increased EPO production secondary to benign and malignant EPO-secreting lesions. Secondary polycythemia may also be a benign familial polycythemia. Chuvash polycythemia, a congenital polycythemia first recognized in an endemic Russian population, has mutations in the von Hippel-Lindau (VHL) gene, which is associated with a perturbed oxygen dependent regulation of EPO synthesis. Secondary polycythemia of the newborn is fairly common and may result from either chronic or acute fetal hypoxia or delayed cord clamping and stripping of the umbilical cord. Accordingly, PEGylated YRS polypeptides may be used in treating or reducing the risk of primary polycythemia, such as polycythemia vera, or secondary polycythemia.

Also, certain primary treatment regimes may lead to an undesirably increase in red blood cells. For instance, the drugs gentamicin and methyldopa have been associated with increasing the number of red blood cells in a subject. Hence, PEGylated YRS polypeptides may be used in conjunction or combination with one or more of gentamicin, methyldopa, or other drug that leads to increased production of red blood cells, mainly to off-set the undesired effects of producing too many red blood cells. In certain embodiments, by reducing their undesirable side effects, combination therapy with PEGylated YRS polypeptides may allow the use of higher concentrations of gentamicin, methyldopa, or related drugs.

Accordingly, in certain embodiments, PEGylated YRS polypeptides may be used to reduce erythropoiesis, and also to reduce the formation of erythroid progenitors, red blood cells, or both. In certain embodiments, methods of reducing erythropoiesis or red blood cell formation may be used to treat a subject that has or is at risk for having increased red blood cell count, increased hemoglobin levels, or increased total red blood cell volume, as described herein and known in the art.

In certain erythropoiesis-stimulating embodiments, merely by way of non-limiting example, PEGylated YRS polypeptides may be administered directly to a subject to increase or maintain red blood count, if desired, such as to treat a condition associated with reduced blood count or risk of reduced blood count. Typically, conditions associated with reduced blood count are referred to as anemias. Hence, certain embodiments may include the use or administration of PEGylated YRS polypeptides to treat or reduce the risk of anemia, or to treat a condition associated with anemia. Certain embodiments may include the use of PEGylated YRS polypeptides to increase erythropoiesis in vitro or ex vivo, such as to increase the number of erythrocyte progenitor cells or red blood cells in a population of hematopoietic cells, which may then be optionally administered to a subject in need thereof.

Anemia may be associated with any one or more of excessive bleeding, reduced production of red blood cells, or increased destruction of red blood cells. For example, aplastic anemia is typically caused by the inability of the bone marrow to produce blood cells, and pure red cell aplasia is typically caused by the inability of the bone marrow to produce only red blood cells. Aplastic anemia can be inherited, can occur without apparent cause, or can occur when the bone marrow is injured by medications, radiation, chemotherapy, or infection. Also included is thalassemia, a condition that occurs when the red cells fail to mature and grow properly. Thalassemia is an inherited condition that typically affects people of Mediterranean, African, Middle Eastern, and Southeast Asian descent. This condition can range in severity from mild to life-threatening; the most severe form is called Cooley's anemia. As a further example, anemia may be caused by lead exposure, which is toxic to the bone marrow, and reduces red blood cell production. Also included are iatrogenic bone marrow disorders.

Hemolytic anemia is typically caused by excessive breakdown of red blood cells. Causes of hemolytic anemia may include any one or more of inherited conditions, such as sickle cell anemia and thalassemia, stressors such as infections, drugs, snake or spider venom, or certain foods, toxins from advanced liver or kidney disease, inappropriate attack by the immune system (called hemolytic disease of the newborn when it occurs in the fetus of a pregnant woman), vascular grafts, prosthetic heart valves, tumors, severe burns, chemical exposure, severe hypertension, and clotting disorders. In certain cases, an enlarged spleen can trap red blood cells and destroy them before they enter the circulation.

Anemia also associates with excessive bleeding, whether acute or chronic. Red blood cells can be lost through bleeding, which can occur slowly over a long period of time, and can often go undetected. Chronic bleeding associated with anemia may result from any one or more of gastrointestinal conditions such as ulcers, hemorrhoids, gastritis (inflammation of the stomach) and cancer, use of nonsteroidal anti-inflammatory drugs (NSAIDS) such as aspirin or Motrin®, as well as menstruation and childbirth in women, especially if menstrual bleeding is excessive and if there are multiple pregnancies.

Certain types of anemia associate with vitamin deficiencies or iron deficiencies. For instance, vitamin deficiency anemia may occur when vitamin B-12 and folate are deficient. These two vitamins are needed to make red blood cells. Conditions leading to anemia caused by vitamin deficiency include any one or more of megaloblastic anemia, in which vitamin B-12 or folate or both are deficient, pernicious anemia, in which poor vitamin B-12 absorption is caused by conditions such as Crohn's disease, an intestinal parasite infection, surgical removal of part of the stomach or intestine, or infection with HIV, dietary deficiency, in which eating little or no meat may cause a lack vitamin B12, or overcooking or eating too few vegetables may cause a folate deficiency, and other causes, such as pregnancy, certain medications, alcohol abuse, and intestinal diseases such as tropical sprue and gluten-sensitive enteropathy (celiac disease). During early pregnancy, sufficient folic acid can prevent the fetus from developing neural tube defects such as spina bifida.

Anemia also associates with other conditions, and usually occurs when there are too few of the hormones required for red blood cell production. Conditions causing this type of anemia include, for example, advanced kidney disease, hypothyroidism, cancer, infection (e.g., bacterial, viral, parasitic), and autoimmune disorders such as lupus and rheumatoid arthritis.

Certain embodiments may include combination therapies for treating anemias, including the administration of one or more PEGylated YRS polypeptides, in combination with other anemia-based therapeutic agents or treatment modalities. Examples of combination therapies included, without limitation, any one or more of iron supplementation with ferrous sulfate, ferrous gluconate, or vitamin C, the latter of which may aid in the body's ability to absorb iron, vitamin supplements given orally (e.g., folic acid) or subcutaneously (e.g., vitamin B-12), administration of recombinant erythropoietin or epoetin alfa, blood transfusion, or hyperbaric oxygenation.

In certain embodiments, PEGylated YRS polypeptides may be used to modulate granulopoiesis. These embodiments may be practiced in vitro, ex vivo, and in vivo. In certain embodiments, the PEGylated YRS polypeptides of the present invention may stimulate granulopoiesis, and may be used to treat a condition associated with any one or more of neutropenia, eosinopenia, or basopenia. In certain embodiments, the PEGylated YRS polypeptides of the present invention may reduce granulopoiesis, and may be used to treat a condition associated with any one or more of neutrophilia, eosinophilia, or basophilia. In certain in vitro or ex vivo embodiments, PEGylated YRS polypeptides may increase or reduce the number of granulocytes (e.g., neutrophils, eosinophils, basophils) in a population of hematopoietic cells, which may then be optionally administered to a subject in need thereof.

Neutropenia can develop if neutrophils are used up or destroyed in the bloodstream faster than the bone marrow can make new neutrophils. Neutrophils are destroyed faster than they are produced in certain bacterial infections, allergic disorders, and drug treatments. Certain autoimmune diseases may lead to the production of antibodies that destroy neutrophils, and thereby associate with neutropenia. Low neutrophil count may also result from an enlarged spleen, because the enlarged spleen traps and destroys neutrophils.

Neutropenia can also develop if the production of neutrophils in the bone marrow is reduced. Examples of conditions associated with reduced neutrophil production include cancer, viral infections such as influenza, bacterial infections such as tuberculosis, myelofibrosis, and deficiencies of vitamin $B_{12}$ or folate (folic acid). Radiation therapy may also associate with neutropenia, especially if targeted to the bone marrow. Certain drugs, including phenyloin, chloramphenicol, sulfa drugs, chemotherapeutic agents, as well as certain toxins (benzene and insecticides) can also impair the bone marrow's ability to produce neutrophils, and thereby associate with neutropenia. Neutropenia can also result from the colonization of intracellular neutrophilic parasites. Aplastic anemia and various leukemias may also associate with neutropenia. Also included are congenital neutropenia, autosomal recessive Kostmann's syndrome, cyclic neutropenia, and myelokathexis.

Neutrophilia may associate with bacterial infections, any form of acute inflammation, including after a heart attack or other infarct, and the administration of certain drugs, such as prednisone and cortisol, which cause marginated neutrophils to enter the blood stream. Nervousness or emotional stress may also slightly raise the neutrophil count because of this same effect. Neutrophilia also associates with malignancies. For instance, chronic myelogenous leukemia (CML or chronic myeloid leukemia) is characterized by excessive blood cell proliferation, including excessive neutrophil proliferation. Neutrophilia may also associate with eclampsia, gout, thyroiditis, rheumatic fever, appendicitis, vasculitis, trauma, surgery, burns, blood loss, steroids, fungal infection, pregnancy, connective tissue disease, arthritis, dermatitis, hemolytic anemia, and essential thrombocythemia, among other conditions known in the art.

Eosinopenia may associate with steroid use (e.g., Cushing's syndrome), infections (e.g., bacterial infections and sepsis, for which eosinophil count can be a valuable predictor), and psychological stress, among other conditions known in the art. Eosinophilia may be characterized as primary or secondary, or it may be characterized as reactive (i.e., in response to other stimuli such as allergy or infection) or non reactive. Generally, eosinophilia may associate with neoplasia (e.g., lymphoma such as Hodgkin lymphoma and non-Hodgkin lymphoma, human T-cell lymphotropic virus I (HTLV-I) infection, adult T-cell leukemia/lymphoma (ATLL), eosinophilic leukemia, gastric or lung carcinoma), Addison Disease, allergy/asthma, collagen vascular diseases, cholesterol emboli, and parasites. Particular examples of conditions that associate with eosinophilia include, without limitation, coccidioidomycosis fungal infection, hypereosinophilic syndrome, parasitic infections (intestinal helminthiasis), allergic disorders (including eosinophilic esophagitis), certain drug reactions (e.g., DRESS syndrome), cholesterol embolization, Churg-Strauss syndrome, certain forms of chronic myeloid leukemia, Hodgkin's lymphoma, Gleich's syndrome, Addison's disease, *Clonorchis sinensis* (a flatworm infection), eosinophilia-myalgia syndrome, often caused by contaminated tryptophan supplements, Job's Syndrome, typically caused by increased levels of Immunoglobulin E, and certain forms of colitis, such as eosinophilic colitis.

Basopenia may associate with autoimmune urticaria, a chronic itching condition, and may be an indicator of ovulation. Basophilia may associate with myeloproliferative disorders, such as certain forms of leukemia and lymphoma, including chronic granulocytic leukemia and acute basophilic leukemia, a form of acute myeloid leukemia in which blasts are accompanied by abnormal basophils in all stages of differentiation. Increased basophil counts advanced may be found in advanced anemia, malaria, and chronic lead poisoning. Basophilia may also cause or associate with leukocytosis, or the destruction of white blood cells.

Certain embodiments may include combination therapies for treating any one or more of neutropenia, neutrophilia, eosinopenia, eosinophilia, basopenia, or basophilia, including the administration of one or more PEGylated YRS polypeptides in combination with other granulocyte-based therapeutic agents or treatment modalities. Examples include the administration of recombinant G-CSF (granulocyte-colony stimulating factor), typically used in treating neutropenia, corticosteroids and interferon (IFN)-alpha, hydroxyurea, chlorambucil, vincristine, cytarabine, 2-chlorodeoxyadenosine (2-CdA), and etoposide, typically used in treating primary eosinophilia.

In certain embodiments, PEGylated YRS polypeptides may be used to modulate lymphopoiesis. These embodiments may be practiced in vitro, ex vivo, and in vivo. In certain embodiments, the PEGylated YRS polypeptides of the present invention may stimulate lymphopoiesis, and may be used to treat a condition associated with lymphocytopenia. Certain embodiments may be used to treat any one or more of T-lymphocytopenia, B lymphocytopenia, and NK lymphocytopenia. In certain embodiments, the PEGylated YRS polypeptides of the present invention may reduce lymphopoiesis, and may be used to treat a condition associated with lymphocytosis. In certain in vitro or ex vivo embodiments, PEGylated YRS polypeptides may increase or reduce the number of lymphocytes (e.g., B-cells, T-cells, NK cells) in a population of hematopoietic cells, which may then be optionally administered to a subject in need thereof.

Various disorders and conditions, including infection with human immunodeficiency virus (HIV), the virus that causes AIDS, associate with decreased numbers of lymphocytes in the blood. Other viral, bacterial, and fungal agents may associate with lymphocytopenia, such as viral hepatitis, tuberculosis, and typhoid fever. Sepsis may also associate with reduced lymphocytes. Lymphocytopenia may associate with starvation, malnutrition, severe stress, intense or prolonged physical exercise, often due to increased cortisol release, autoimmune disorders such as lupus and rheumatoid arthritis, bone marrow or blood malignancies (e.g., leukemia, Hodgkin's disease, aplastic anemia), use of corticosteroids (such as prednisone), use of chemotherapeutics (e.g., cytotoxic agents, immunosuppressive drugs), and radiation therapy or exposure. Severe reduction in lymphocytes can also occur in certain hereditary or congenital disorders, which are often X-linked disorders, such as DiGeorge anomaly, Wiskott-Aldrich syndrome, severe combined immunodeficiency syndrome, and ataxia-telangiectasia.

Lymphocytosis may associate with any one or more of chronic bacterial infections such as pertussis, chronic lymphocytic leukemia, acute lymphoblastic leukemia, multiple myeloma, mumps, ulcerative colitis, vasculitis, Crohn's disease, and whooping cough. Also included are viral infections, such as infectious mononucleosis (glandular fever), Epstein-Barr virus infection, cytomegalovirus (CMV), and hepatitis, protozoal infections, such as toxoplasmosis and American trypanosomiasis (Chagas disease), and chronic intracellular bacterial infections such as tuberculosis and brucellosis. Certain medications, including corticosteroids, lithium and beta agonists, may also cause lymphocytosis.

In certain embodiments, PEGylated YRS polypeptides may be used to modulate megakaryopoiesis, thrombopoiesis, or both. These embodiments may be practiced in vitro, ex vivo, and in vivo. In certain embodiments, the PEGylated YRS polypeptides of the present invention may stimulate megakaryopoiesis, stimulate thrombopoiesis, or both, and may be used to treat a condition associated with megakaryocytopenia, thrombocytopenia, or both. In certain embodiments, the PEGylated YRS polypeptides of the present invention may reduce megakaryopoiesis, reduce thrombopoiesis, or both, and may be used to treat a condition associated with excess megakaryocytes, excess thrombocytes (e.g., thrombocythemia, thrombocytosis), or both. In certain in vitro or ex vivo embodiments, PEGylated YRS polypeptides may increase or reduce the number of megakaryocytes, megakaryocyte progenitors, or platelets in a population of hematopoietic cells, which may then be optionally administered to a subject in need thereof. In certain embodiments, PEGylated YRS polypeptides increase thrombopoiesis by a thrombopoietin (TPO)-independent mechanism. In certain embodiments, antagonists to YRS polypeptides may be used to reduce thrombopoiesis, or to reduce platelet levels, and thereby treat conditions such as thrombocythemia or thrombocytosis.

In certain embodiments, these methods may be utilized to either enhance or reduce the growth, differentiation, migration, or accumulation of megakaryocyte progenitor cells, including early progenitor cells, i.e., the most primitive lineage-restricted progenitors of the megakaryocyte lineage, late progenitor cells, or both. In certain embodiments, the methods provided herein may impact (i.e., enhance or reduce) the proliferation, cell cycle changes, mobilization, migration, attachment, cell-cell contacts, endomitosis, or polyploidy of megakaryocyte precursors, megakaryoblasts, or megakaryocytes. In certain embodiments, depending on the particular PEGylated YRS polypeptides, or dosages thereof, these methods may selectively enhance the formation of early megakaryocyte progenitor cells. In certain embodiments, these methods may selectively enhance the formation of late megakaryocyte progenitor cells. In certain embodiments, depending on the particular PEGylated YRS polypeptides or dosages thereof, these methods may selectively reduce the formation of early megakaryocyte progenitor cells. In certain embodiments, these methods may selectively modulate (e.g., reduce) the formation of late megakaryocyte progenitor cells. The methods may be practiced in vivo, in vitro, ex vivo, or in any combination thereof.

The methods provided herein may also enhance or reduce platelet formation or cell division. For instance, certain methods relate to modulating the transition from pro-platelets (i.e., compartmentalization of mature megakaryocytes) to platelets, and their release into the circulation. Certain PEGylated YRS polypeptides may increase the transition from pro-platelets to platelets, and thereby increase the release of platelets into the circulation. In certain embodiments, PEGylated YRS polypeptides increase the transition from pro-platelets to platelets. Certain PEGylated YRS polypeptides may reduce the transition from pro-platelets to platelets, and thereby reduce the release of platelets into the circulation.

Also, certain methods relate to modulating the cell division of platelets, which are believed to undergo cell division even in the absence of a nucleus. Certain embodiments therefore relate to the use of PEGylated YRS polypeptides to increase the cell division of platelets. In certain embodiments, PEGylated YRS polypeptides also increase platelet cell division. These methods can be used, for example, to increase the number of platelets in a platelet transfusion prior to administration to a donor, and/or to treat or manage a condition associated with reduced platelet levels. Certain embodiments relate to the use of PEGylated YRS polypeptides to reduce the cell division of platelets. The methods may be practiced in vivo, in vitro, ex vivo, or in any combination thereof.

Included are in vitro or ex vivo methods of modulating megakaryopoiesis. In certain embodiments, these methods relate to stimulating the proliferation or accumulation of megakaryocyte progenitor cells, comprising incubating a culture of hematopoietic stem cells or other blood cells with one or more PEGylated YRS polypeptide, typically for a time sufficient to allow proliferation or accumulation of megakaryocyte progenitor cells, thereby stimulating megakaryopoiesis. In certain embodiments, the progenitor cells include early megakaryocyte progenitor cells, and in certain embodiments they include late megakaryocyte progenitor cells. In these and related embodiments, the PEGylated YRS polypeptides of the invention may be incubated with purified HSCs, partially purified HSCs, whole bone marrow cultures (e.g., for bone marrow transplants), cord blood, or other types of blood or marrow-based cultures, such as those used in hematopoietic graft therapies. Such methods may result in a culture that is enriched for early megakaryocyte progenitor cells, late progenitor cells, or both, and which may be administered to a subject in need thereof (e.g., transplant subject), if desired.

Growth or proliferation (or lack thereof) of megakaryocyte progenitor cells (e.g., early, intermediate, late, etc.) can be measured according to routine techniques known in the art. For instance, among other characteristics, early megakaryocyte progenitors may be identified by immuno-staining as $Lin^-c-Kit^+CD41^+$, and later stage megakaryocyte progenitors may be identified as $Lin^-c-Kit^-CD41^+$ (see, e.g., Perez et al., *PLoS ONE*. 3:e3565, 2008; and Lefebvre et al., *Journal of Hematotherapy & Stem Cell Research*. 9:913-921, 2000, each of which is incorporated by reference in its entirety).

Megakaryocyte progenitor cells are positive for CD34 expression. CD34 is a monomeric cell surface antigen with a molecular mass of approximately 110 kD that is selectively expressed on human hematopoietic progenitor cells. The gene is expressed by small vessel endothelial cells in addition to hematopoietic progenitor cells and is a single-chain 105-120 kDa heavily O-glycosylated transmembrane glycoprotein.

Megakaryocyte progenitor cells also typically express the tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. CD9 interacts with the integrin family and other membrane proteins, and is postulated to participate in cell migration and adhesion.

Megakaryocyte progenitor cells may also express CD41, also referred to as the glycoprotein IIb/IIIa integrin, which is the platelet receptor for fibrinogen and several other extracellular matrix molecules. GP IIIa is a protein of 788 amino acids, including a 26-residue amino terminal signal peptide, a 29-residue transmembrane domain near the carboxy terminus, and 4 tandemly repeated cysteine-rich domains of 33-38 residues.

Megakaryocyte progenitor cells are typically positive for expression of CD117. CD117 is also known as the receptor tyrosine kinase c-Kit. This receptor has been particularly implicated with stem cells, including hematopoietic stem cells. Multiple isoforms of c-Kit also exist as a result of alternate mRNA splicing, proteolytic cleavage and the use of cryptic internal promoters in certain cell types. Structurally, c-Kit contains five immunoglobulin-like domains extracellularly and a catalytic domain divided into two regions by a 77 amino acid insert intracellularly.

Megakaryocyte progenitor cells are typically positive for expression of CD38. CD38 is a 300-amino acid type II transmembrane protein with a short N-terminal cytoplasmic tail and 4 C-terminal extracellular N-glycosylation sites. This marker is also generally associated with lymphocytes, myeloblasts, and erythroblasts.

Megakaryocyte progenitor cells may also have the phenotype of lacking expression of certain lineage specific markers. For staining purposes a cocktail of binding reagents, herein designated "lin" may be used. A "lin" panel may comprise binding reagents (e.g., antibodies and functional binding fragments thereof, ligands, peptidomimetics) that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells. Lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. Megakaryocyte progenitor cells are also typically negative for expression of Thy-1 (CD90), which is a 25-35 kD molecule expressed on 1-4% of human fetal liver cells, cord blood cells, and bone marrow cells.

"Hematopoietic stem cells (HSCs)" relate generally to multipotent "stem cells" that give rise to the blood cell types, including myeloid (e.g., monocytes/macrophages, neutrophils, basophils, eosinophils, erythrocytes, megakaryocytes/platelets, dendritic cells), and lymphoid lineages (e.g., T-cells, B-cells, NK-cells), and others known in the art. "Stem cells" are typically defined by their ability to form all cell types (e.g., pluripotency) or multiple cell types (i.e., multipotency), and their ability to self-renew. In certain embodiments, however, oligopotent and unipotent stem or progenitor cells may be included.

HSCs may be obtained according to known techniques in the art. For instance, HSCs may be found in the bone marrow of adults, which includes femurs, hip, ribs, sternum, and other bones. HSCs may be obtained directly by removal from the hip using a needle and syringe, or from the blood, often following pre-treatment with cytokines, such as G-CSF (granulocyte colony-stimulating factors), that induce cells to be released from the bone marrow compartment. Other sources for clinical and scientific use include umbilical cord blood, placenta, and mobilized peripheral blood. For experimental purposes, fetal liver, fetal spleen, and AGM (Aorta-gonad-mesonephros) of animals are also useful sources of HSCs.

HSCs may be identified according to certain phenotypic or genotypic markers. For example, HSCs may be identified by their small size, lack of lineage (lin) markers, low staining (side population) with vital dyes such as rhodamine 123 (rhodamine$^{DULL}$, also called) rho$^{lo}$) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSCs are mainly negative for the markers that are typically used to detect lineage commitment, and, thus, are often referred to as lin(−) cells. Most human HSCs may be characterized as CD34$^+$, CD59$^+$, Thy1/CD90$^+$, CD38$^{lo/−}$, C-kit/CD117$^+$, and lin(−). However, not all stem cells are covered by these combinations, as certain HSCs are CD34$^−$/CD38$^−$. Also some studies suggest that earliest stem cells may lack c-kit on the cell surface. For human HSCs, CD133 may represent an early marker, as both CD34$^+$ and CD34$^−$ HSCs have been shown to be CD133$^+$.

For purification of lin(−) HSCs by flow cytometry, or FACS, an array of mature blood-lineage marker antibodies may be used to deplete the lin(+) cells or late multipotent progenitors (MPP), including, for example, antibodies to CD13 and CD33 for human myeloid cells, CD71 for human erythroid cells, CD19 for human B cells, CD61 for human megakaryocytic cells, Mac-1 (CD11b/CD18) for monocytes, Gr-1 for Granulocytes, Il7Ra, CD3, CD4, CD5, and CD8 for T cells, among others known in the art. Other purification methods are known in the art, such as those methods that use the particular signature of the 'signaling lymphocyte activation molecules' (SLAM) family of cell surface molecules.

HSCs, whether obtained from, or present in, cord blood, bone marrow, peripheral blood, or other source, may be grown or expanded in any suitable, commercially available or custom defined medium, with or without serum, as desired (see, e.g., Hartshorn et al., *Cell Technology for Cell Products*, pages 221-224, R. Smith, Editor; Springer Netherlands, 2007, herein incorporated by reference in its entirety). For instance, in certain embodiments, serum free medium may utilize albumin and/or transferrin, which have been shown to be useful for the growth and expansion of CD34+ cells in serum free medium. Also, cytokines may be included, such as Flt-3 ligand, stem cell factor (SCF), and thrombopoietin (TPO), among others. HSCs may also be grown in vessels such as bioreactors (see, e.g., Liu et al., *Journal of Biotechnology* 124:592-601, 2006, herein incorporated by reference in its entirety). A suitable medium for ex vivo expansion of HSCs may also comprise HSC supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of HSCs, as well as their progeny.

HSC growth or expansion can be measured in vitro or in vivo according to routine techniques known in the art. For example, WO 2008/073748, herein incorporated by references for these methods, describes methods for measuring in vivo and in vitro expansion of HSCs, and for distinguishing between the growth/expansion of HSCs and the growth/expansion of other cells in a potentially heterogeneous population (e.g., bone marrow), such as intermediate progenitor cells. The administering or incubation step that results in the growth or expansion can occur in vivo, ex vivo, or in vitro, though in certain embodiments, the administration or incubation occurs during ex vivo treatment of HSCs.

"Cord blood" or "umbilical cord blood" relates generally to the relatively small amount of blood (up to about 180 mL) from a newborn baby that returns to the neonatal circulation if the umbilical cord is not prematurely clamped. Cord blood is rich in HSCs, and may be harvested and stored for later use according to techniques known in the art (see, e.g., U.S. Pat. Nos. 7,147,626 and 7,131,958, herein incorporated by reference for such methodologies). Also, if the umbilical cord is ultimately not clamped, a physiological clamping occurs upon interaction with cold air, wherein the internal gelatinous substance, called Wharton's jelly, swells around the umbilical artery and veins. Nonetheless, Wharton's jelly can still serve as a source of HSCs.

However, delayed platelet recovery is an inherent problem with cord blood cell transplantation. In this regard, rapid platelet recovery after transplant reduces the cost of supportive therapy and reduces the risk of fatal bleeding due to severe thrombocytopenia. Delayed platelet recovery in cord blood transplantation is associated with low numbers of megakaryocyte progenitor cells in cord blood grafts (see, e.g., Kanamaru et al., Stem Cells. 18:190-195, 2000). Hence, methods of ex vivo pre-treatment of cord blood grafts with PEGylated YRS polypeptides, methods of in vivo administration of PEGylated YRS polypeptides prior to, during, or after cord blood transplantation, or both methods in combination, may increase the number of megakaryocyte progenitor cells, increase platelet recovery in cord blood transplantation, and thereby reduce secondary costs and improve the therapeutic outcome of such transplant procedures.

As noted above, "ex vivo" refers generally to activities that take place outside an organism, such as experimentation or measurements done in or on living tissue in an artificial environment outside the organism, preferably with minimum alteration of the natural conditions. Most commonly, "ex vivo" procedures involve living cells or tissues taken from an organism and cultured in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The terms "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure to expand the stem cells (e.g., an ex vivo administration step that involves incubating the cells with a composition of the present invention to enhance expansion of desirable cells, such as HSCs or megakaryocyte progenitors), and then administered to the same or different living subject after that optional treatment or procedure. As one example, thrombocytopenia may be alleviated by infusion of megakaryocyte progenitor cells (see, e.g., De Bruyn et al., Stem Cells Dev. 14:415-24, 2005, herein incorporated by reference).

Such ex vivo therapeutic applications may also include an optional in vivo treatment or procedural step, such as by administering a PEGylated YRS polypeptide, one or more times to the living subject prior to, during, or after administration of the organ, cells, or tissue. Both local and systemic administration are contemplated for these embodiments, according to well-known techniques in the art. The amount of PEGylated YRS polypeptide administered to a subject will depend on the characteristics of that subject, such as general health, age, sex, body weight, and tolerance to drugs, as well as the degree, severity, and type of reaction to the polypeptide and/or cell transplant.

Megakaryocytic progenitors can be generated ex vivo, as described herein, and administered to any subject in need thereof, including, for example, subjects having or at risk for developing reduced platelet or thrombocytopenia. Thrombocytopenia is generally characterized by reduced platelet counts, as compared to a normal range of platelet counts for a typical subject. For example, thrombocytopenia refers generally to a decrease in the platelet count to about 150,000/mm$^3$ or lower compared to a normal platelet count. A normal platelet count generally ranges from about 150,000/mm$^3$ to about 450,000/mm$^3$ in a subject.

Thrombocytopenia often causes no signs or symptoms, but may be identified by routine blood tests. If present, possible signs and symptoms of thrombocytopenia include easy bruising and/or excessive bleeding. For example, bleeding in the skin may be the first sign of a low platelet count. Many tiny red dots (petechiae) often appear in the skin on the lower legs, and minor injuries may cause small scattered bruises. In addition, the gums may bleed, and blood may appear in the stool or urine. Menstrual periods may be unusually heavy. Bleeding may be hard to stop.

Bleeding typically worsens as the number of platelets decreases. People who have very few platelets may lose large amounts of blood into the digestive tract or may develop life-threatening bleeding in the brain even though they have not been injured. The rate at which symptoms develop can vary depending on the cause of thrombocytopenia.

Thrombocytopenia may be congenital, acquired, and/or iatrogenic, and may stem from a variety of underlying physiological causes or conditions. For example, thrombocytopenia may result generally from decreased production of platelets, increased destruction of platelets, consumption of platelets, entrapment/sequestration of platelets due to hypersplenism (i.e., enlarged spleen) or hypothermia, and/or from the side-effects of certain medications (i.e., medication induced thrombocytopenia). In addition, idiopathic forms of thrombocytopenia occur, especially in children, transient forms may follow viral infections (e.g., Epstein-Barr or infectious mononucleosis), and pregnant women may develop mild thrombocytopenia, often when close to delivery.

Examples of congenital conditions associated with the decreased production (i.e., diminished or defective production) of platelets include Wiskott-Aldrich syndrome, maternal ingestion of thiazides, congenital amegakaryocytic thrombocytopenia, thrombocytopenia absent radius syndrome, Fanconi anemia, Bernard-Soulier syndrome, May- Hegglin anomaly, Grey platelet syndrome, Alport syndrome, and neonatal rubella. Examples of acquired conditions associated with the decreased production of platelets include aplastic anemia, myelodysplastic syndrome, marrow infiltration (e.g., acute and chronic leukemias, tumors, cancer of the bone marrow), lymphomas, nutritional deficiencies (e.g., $B_{12}$, folic acid), the use of myelosuppressive agents, the use of drugs that directly influence platelet production (e.g., thiazides, alcohol, hormones), radiation exposure (e.g., radiation therapy), exposure to toxic chemicals (e.g., pesticides, arsenic, benzene), decreased production of thrombopoietin by the liver in liver failure, bacterial sepsis, and certain viral infections (e.g., chickenpox, mumps, parvovirus, measles, dengue, HIV, HCV). PEGylated YRS polypeptides and ex vivo expanded megakaryocyte progenitors generated therefrom, as described herein, may be used to treat or manage any of these conditions.

Examples of congenital conditions associated with increased peripheral platelet destruction include nonimmune conditions, such as prematurity, erythroblastosis fetalis, infection; and immune conditions, such as drug sensitivity, idiopathic thrombocytopenic purpura (ITP), and maternal ITP. Examples of acquired conditions associated with increased peripheral platelet destruction include nonimmune conditions, such as hemolytic-uremic syndrome, disseminated intravascular coagulation, thrombotic thrombocytopenic purpura (TTP); immune conditions, such as drug-induced thrombocytopenia (e.g., especially with quinine and quinidine), post-transfusion purpura, systemic lupus erythematosus, rheumatoid arthritis, neonatal alloimmune thrombocytopenia, paroxysmal nocturnal hemoglobinuria, acute and chronic ITP, sepsis, and alcohol; in addition to the use of invasive lines and devices (e.g., arterial or central venous catheters), intra-aortic ballon pumps, prosthetic heart valves, as well as the use of heparin-related therapies. PEGylated YRS polypeptides and ex vivo expanded megakaryocyte progenitors generated therefrom, as described herein, may be used to treat or manage any of these conditions.

Medication-induced thrombocytopenia may result in particular from certain drugs, such as chemotherapeutic agents, nonsteroidal anti-inflammatory agents, sulfonamides, vancomycin, clopidogrel, glycoprotein IIb/IIIa inhibitors, interferons, valproic acid, abciximab, linezolid, famotidine, mebeverine, histamine blockers, alkylating agents, heparin, alcohol, antibiotic chemotherapeutic agents, carbapenems, ureido-penicillins, cefazolin, among others known in the art. Particular examples of chemotherapeutic agents include, but are not limited to, cisplatin (CDDP), carboplatine, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, temazolomide (an aqueous form of DTIC), or any analog or derivative variant of the foregoing. PEGylated YRS polypeptides and ex vivo expanded megakaryocyte progenitors generated therefrom, as described herein, may be used to treat or manage any of these medication-induced conditions.

The present invention includes methods of treating, or reducing the risks of developing, thrombocytopenia (i.e., decreased platelet count) in a subject, such as in a subject having one or more of the exemplary diseases or conditions provided herein, among others known in the art, by administering to the subject a composition comprising a therapeutically effective concentration of a PEGylated YRS polypeptide, or by expanding megakaryocyte progenitor cells ex vivo in the presence of PEGylated YRS polypeptides, and administering those cells to the subject. In one aspect, the subject has been diagnosed with a myelodysplastic syndrome (MDS) (formerly known as "preleukemia"). In some embodiments, the myelodysplastic syndrome is selected from Refractory Anemia (RA) (ICD-O code M9980/3), Eefactory cytopenia with unilineage dysplasia (Refactory anemia, Refactory neutropenia, and Refractory thrombocytopenia), Refractory Anemia with Ring Sideroblasts (RARS) (ICD-O code M9982/3), Refractory Anemia with Ring Sideroblasts—thromocytosis, Refractory cytopenia with multilineage dysplasia (RCMD), Refractory Anemia with Excess Blasts (RAEB) (ICD-O code M9983/3), Refractory Anemia with Excess Blasts I or II, Refractory Anemia with Excess Blasts in Transformation (RAEB-T) (ICD-O code M9984/3), Chronic Myelomoncytic Leukemia (CMML) (ICD-O code M9945/3), 5q-syndrome, myelodysplastic-myeloproliferative overlap syndromes, Myelodyplasia unclassificable, and refractory cytopenia of childhood.

Embodiments of the present invention encompass methods of treatment intended not only to increase or improving the platelet count in a subject having a reduced, decreased, abnormal, or low platelet count, but to maintain a normal platelet count in a subject at risk for developing a low platelet count. Certain embodiments also contemplate the use of PEGylated YRS polypeptides to increase the platelet count in a platelet donor, including an otherwise healthy donor (i.e., a donor with a normal platelet count), such as administering a PEGylated YRS polypeptide to the donor prior to, during, and/or after the platelet donation or apheresis process, or by administering ex vivo expanded megakaryocyte progenitor cells, or both.

Accordingly, certain embodiments include methods for increasing the platelet count in a subject, comprising administering to the subject a composition comprising a PEGylated YRS polypeptide, or by administering ex vivo or in vitro expanded megakaryocyte progenitor cells (e.g., early or late progenitor cells), thereby increasing the platelet count in the subject. Other embodiments include methods of maintaining a normal platelet count in subject, comprising administering to the subject a composition comprising a PEGylated YRS polypeptide, or by administering ex vivo or in vitro expanded megakaryocyte progenitor cells, such as wherein the subject is at risk for developing a low platelet count. Certain embodiments may include methods of stimulating thrombopoiesis in a subject, such as by administering to the subject a composition comprising a PEGylated YRS polypeptide, or by administering ex vivo or in vitro expanded megakaryocyte progenitor cells, or both. In certain aspects, the subject has a reduced, lowered, or abnormal platelet count, such as a platelet count of about 100,000/$mm^3$ or less. In certain aspects, the PEGylated YRS polypeptides provided herein may be utilized to stimulate the proliferation and/or differentiation of megakaryocytes and/or neutrophils in the subject.

A subject having a reduced platelet count may also be at risk for developing other problems associated with thrombocytopenia, such as bleeding or bruising, hemorrhage, gastrointestinal bleeding, eptistaxis (i.e., nose bleeds), or intracranial hemorrhage (i.e., bleeding in the brain). As one particular example, septic patients with thrombocytopenia have increased bleeding. Accordingly, certain aspects of the invention may utilize the thrombopoietic compositions provided herein to reduce the risk of developing these types of thrombocytopenia associated problems, among others. In other aspects, the subject may be at risk for developing a reduced, lowered, or otherwise abnormal platelet count, such as from an acquired condition associated with lowered platelet levels (e.g., certain medical therapies, leukemias, among others). Also included are surgical patients. For instance, PEGylated YRS polypeptides may be administered prophylactically, for instance before surgery, to reduce blood loss.

In certain aspects, the methods of treatments described herein may be employed independently of other therapeutic modalities, and may be the only or primary therapeutic modality relied upon to manage a thrombocytopenic condition and/or otherwise reduce the risk not only of developing thrombocytopenia, but of developing other medical problems associated therewith, such as bleeding. For example, a subject having thrombocytopenia for which there is no known, underlying cause (e.g., idiopathic thrombocytopenic purpura), may benefit from the methods of treatment provided herein to increase and/or manage platelet levels.

In certain aspects, the methods and compositions of the present invention may be employed as part of a combination therapy, such as by administration with other agents that may impact thrombopoietic and/or hematopoietic pathways in a subject. Examples of other agents that may be used as part of a combination therapy include thrombopoietin (TPO) and TPO agonists/mimetics, mpl-signaling agonists, cytokines (e.g., IL-11, SDF-1, CXCL-12), chemokines, chemokine receptor ligands (e.g., CXCR-1, CXCR-2, CXCR-4 ligands), adhesion molecules (e.g., NCAM, ICAM-1, VCAM-1, PECAM-1, L1, CHL1, MAG, Nectins), and/or growth factors (e.g., vascular endothelial growth factor (VEGF), fibroblast growth factors (FGF) such as FGF-1, FGF-2, FGF-4, and other FGFR ligands) or other signaling molecules involved in thrombopoiesis or hematopoiesis, including biologically active fragments or variants thereof. In certain embodiments, these combination therapies achieve additive or synergistic effects. Without wishing to be bound by any one theory, certain particular embodiments, such as the combination of a PEGylated YRS polypeptide and TPO or other TPO peptide agonist or mimetic, achieve synergistic effects in increasing thrombopoiesis because certain PEGylated YRS polypeptides are believed to increase thrombopoiesis by a TPO-independent mechanism; hence, the two independent thrombopoietic-stimulatory mechanisms may cooperate synergistically to increase thrombopoiesis.

In certain aspects, the methods of the present invention may be employed in conjunction with other therapeutic modalities, such as those involved in treating the underlying condition that causes the condition associated with thrombocytopenia. For example, a subject having congenital amegakaryocytic thrombocytopenia (CAMT) may ultimately undergo a bone marrow transplantation procedure, but may also benefit from a separate treatment, as provided herein, to either enhance platelet levels and/or to maintain platelet levels within a normal range. The thrombopoietic polypeptides of the present invention may be employed in this and similar regards.

In certain aspects, the methods provided herein may be employed in combination with a subject undergoing other medical treatments, such as treatments that either cause thrombocytopenia or increase the risk of developing thrombocytopenia. For example, the methods provided herein may be employed with a subject undergoing, a subject about to undergo, and/or a subject who has undergone, radiation therapy, chemotherapy, or other type of treatment, including various types of pharmaceutical treatments, as described herein and known in the art, since such treatments are known to reduce the platelet count in a subject. Accordingly, the methods provided herein may be utilized before, during, and/or after other medical treatments to reduce the risk of developing thrombocytopenia resulting from such treatments, and/or to manage or improve thrombocytopenia resulting from such treatments. For instance, in certain embodiments, megakaryocytic progenitors can be generated ex vivo and administered to autologous peripheral blood progenitor cell transplant subjects, bone marrow transplant subjects, stem cell transplant subjects, or any other transplant subjects. Examples of such subjects include cancer patients (e.g., breast cancer, non-Hodgkin's lymphoma) undergoing autologous peripheral blood progenitor cell transplant. In these and other embodiments, administration of enriched megakaryocyte progenitors may abrogate the need for allogeneic platelet transfusion support in autologous transplantation (see, e.g., Bertolini et al, *Blood.* 89:2679-2688, 1997).

As noted above, transfusion of ex vivo expanded megakaryocyte progenitor cells may also be used to shorten the time of platelet recovery in the thrombocytopenia induced by radiotherapy or chemotherapy. In this regard, it has been shown that transfusion of CD34+ cells expanded with TPO+IL-11+heparin (to increase the number of megakaryocyte progenitor cells) into irradiated nonobese diabetic/severe combined immunodeficient mice significantly accelerated platelet recovery (see, e.g., Feng, et al., *Experimental Hematology.* 33:1537-1543, 2005). In certain embodiments, hematopoietic stem cells (or other biological samples having cells that are capable of differentiating along the hematopoietic lineage) may be expanded ex vivo in the presence of PEGylated YRS polypeptides, to increase the formation of megakaryocyte progenitors, and then administered to a subject prior to, during, or after radiotherapy or chemotherapy, to increase platelet recovery in the subject. In certain embodiments, PEGylated YRS polypeptides may be administered directly to such subjects, either separately or in combination with ex vivo treatments.

Accordingly, whether ex vivo or in vitro, PEGylated YRS polypeptides may be used in the treatment of cancer. For instance, as noted above, PEGylated YRS polypeptide-based treatments may be used in combination with chemotherapy, radiotherapy, autologous peripheral blood progenitor cell transplant, bone marrow transplants, or other cancer therapies that impact platelet formation. "Cancer" relates generally to a class of diseases or conditions in which a group of cells display one or more of uncontrolled growth (i.e., division beyond normal limits), invasion (i.e., intrusion on and destruction of adjacent tissues), and metastasis (i.e., spread to other locations in the body via lymph or blood). These malignant properties of cancers differentiate them from benign cancers, which are self-limited, and typically do not invade or metastasize. Also included are myelodysplastic syndromes.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. Examples of cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma. Also included are "cancer stem cells," a small population of tumor cells that behave like stem cells (i.e., potential for indefinite self renewal), which are often refractory to therapeutic agents due to their dormancy, and which may contribute to the recurrence of cancer. Specific examples of cancer stem cells include "blast cells," the circulating precursor cells leading to leukemia (AML). In certain embodiments, PEGylated YRS polypeptides modulate the growth or differentiation of these and other circulating cells, including circulating immune or hematopoietic cells such as hematopoietic stem cells.

As noted above, PEGylated YRS polypeptides and/or PEGylated YRS polypeptide-expanded megakaryocyte progenitor cells may be administered in combination with chemotherapeutic agents, for instance, to increase platelet recovery. In certain embodiments, the chemotherapy is high-dose chemotherapy, which is often used in conjunction with CD34+ stem cell transplants (or other hematopoietic progenitor cell transplants). Merely by way of illustration, ex vivo expansion of megakaryocyte progenitor cells may provide a complementary transplant product able to enhance platelet production in patients with neuroblastoma (or other cancer) who undergo transplantation with CD34(+) cells following high-dose chemotherapy. Otherwise, these patients show prolonged delays in platelet recovery. Administration protocols for increasing platelet recovering in chemotherapy can be optimized according to techniques in the art.

Examples of general classes of chemotherapeutic or cytotoxic agents included, without limitation, alkylating agents, anti-metabolites, anthracyclines, anti-tumor antiobiotics, platinums, type I topoisomerase inhibitors, type II topoisomerase inhibitors, vinca alkaloids, and taxanes. Examples of particular chemotherapeutic or cytotoxic agents include, without limitation, chlorambucil, cyclophosphamide, lomustine (CCNU), melphalan, procarbazine, thiotepa, carmustine (BCNU), busulfan, daunorubicin, doxorubicin, idarubicin, epirubicin, mitoxantrone, bleomycin, cisplatin, carboplatin, oxaliplatin, camptothecins, irinotecan, topotecan, amsacrine, etoposide, etoposide phosphate, teniposide, vincristine, vinblastine, vinorelbine, vindesine, paclitaxel, and others described herein and known in the art.

PEGylated YRS polypeptides and ex vivo expanded megakaryocyte progenitor cells may also be used in other tissue transplant therapies associated with reduced platelet levels. For instance, reduced platelets are common after liver transplantation due to platelet sequestration secondary to hypersplenism, and increasing platelet levels may improve post-transplant recovery. Liver transplants may be used to treat chronic active hepatitis and cirrhosis (from alcoholism, unknown cause, or biliary), biliary atresia, which is an incomplete development of the bile duct, and end-stage liver disease, among other liver-related diseases. Since liver transplantation is often a successful treatment for patients with liver related diseases, PEGylated YRS polypeptides or ex vivo expanded megakaryocyte progenitor cells produced therefrom (or both) can be used in combination with liver transplants for treating these and other liver diseases. The treatment of other types of liver damage is also contemplated, whether by transplant or by direct treatment with PEGylated YRS polypeptides, including liver damage related to hepatitis virus infection (e.g., HCV).

As noted above, certain embodiments relate to the use of PEGylated YRS polypeptides to reduce the number of megakaryocytes, megakaryocyte progenitors, or platelets, whether in a subject in vivo or in tissue culture in vitro or ex vivo. These and related embodiments may be used to treat conditions associated with increased numbers of any one or more of megakaryocytes, megakaryocyte progenitors, or platelets, such as by reducing thrombopoiesis. Specific embodiments include the use of PEGylated YRS polypeptide variants of YRS (Y341A) to reduce thrombopoiesis or megakaryopoiesis, particularly those that have been converted from having a thrombopoietic-stimulatory activity to having a thrombopoiesis-reducing activity.

Included are conditions associated with thrombocythemia or thrombocytosis, myeloproliferative conditions in which excess platelets are produced, often due to an increased number of megakaryocytes, leading to abnormal blood clotting or bleeding. In essential thrombocythemia, the platelet count is usually 2 to 4 or more times higher than normal. Thrombocythemia is typically characterized as either primary, for which the cause is not known, or secondary, for which the cause is known. Occasionally, primary thrombocythemia changes into a more serious disorder, such as polycythemia vera or certain types of leukemia. Secondary thrombocythemia may associate with bleeding, removal of the spleen, infections, rheumatoid arthritis, certain cancers, premature destruction of red blood cells (hemolysis), iron deficiency, and sarcoidosis, among other conditions known in the art.

As noted above, also included are direct in vivo methods of modulating hematopoiesis. These direct in vivo methods may be used alone or in combination with other treatments, including in combination with the ex vivo treatments described above. For in vivo treatment of human and non-human subjects, the subject is usually administered a pharmaceutical formulation comprising a PEGylated YRS polypeptide of the present invention. When used for in vivo therapy, the polypeptides of the subject invention are administered to the patient in therapeutically effective amounts (e.g., amounts that modulate hematopoiesis). The polypeptides may be administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The polypeptides may be administered parenterally, when possible, at the target cell site, or intravenously. Intravenous or subcutaneous administration of the polypeptide is preferred in certain embodiments.

For parenteral administration, the polypeptides or related agents may be formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The polypeptides will typically be formulated in such vehicles at concentrations of about 0.01 mg/ml to about 1 mg/ml to about 10 mg/ml, or more.

Generally, a therapeutically effective amount of polypeptide is administered to a subject or patient. In particular embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

Pharmaceutical Formulations, Administration, and Kits

Embodiments of the present invention include compositions comprising PEGylated YRS polypeptides formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain embodiments, the PEGylated YRS polypeptide have a solubility that is desirable for the particular mode of administration, such intravenous administration. Examples of desirable solubilities include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, subcutaneously, intravenously, intramuscularly, intra-arterially, intrathecally, intraparenchymally, intracisternally, intraventricularlly, intraurethrally, intrasternally, intracranially, intrasynovially, or even intraperitoneally as described, for example, in U.S. Pat. No. 5,543,158; U.S. Pat. No. 5,641, 515 and U.S. Pat. No. 5,399,363 (each specifically incorporated herein by reference in its entirety). Suitable devices for parenteral administration include needle (including microneedle) injectors, needle-free injectors, and infusion techniques.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinyl-alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises Atrigel™ (QLT, Inc., Vancouver, B.C.). The Atrigel® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regime. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In particular embodiments, the amount of a composition or agent administered will generally range from a dosage of from about 0.1 to about 100 mg/kg/day, and typically from about 0.1 to 10 mg/kg where administered orally or intravenously. In particular embodiments, a dosage is 5 mg/kg or 7.5 mg/kg. In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In certain embodiments, a composition or agent is administered in a single dosage of 0.1 to 10 mg/kg or 0.5 to 5 mg/kg. In other embodiments, a composition or agent is administered in a dosage of 0.1 to 50 mg/kg/day, 0.5 to 20 mg/kg/day, or 5 to 20 mg/kg/day.

In certain embodiments, a composition or agent is administered orally or intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 µg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 ng/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain polypeptide-based embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to, anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Production of YRS Polypeptides

Introduction

Codon optimized DNA sequences encoding the YRS polypeptides YRS(1-353) containing the mutations C67S, C250S and A4C, ("YRS(1-353)A4C"), or containing the mutations C67S, C250S and A351C ("YRS(1-353) A351C"), were generated by deleting the C-terminal portion of the full length bacterial codon optimized version of the TyrRS synthetase also containing the Y341A mutation (SEQ ID NO:36) to yield a codon optimized N-terminal YRS fragment encoding amino acids 1-353 of the full length YRS. This construct was optimized for site specific PEGylation by mutating two internal cysteines to serine residues (C67S and C250S) and through the introduction of a new surface exposed cysteine residue which was introduced near either the N-terminus or C-terminus (A4C, near the N-terminus or A351C, near the C-terminus). Polyethylene glycol was then coupled to either end of the protein through a maleimide-thiol reaction. PEGylated YRS(1-353)A4C and YRS(1-353)A351C surprisingly displayed higher biological activity compared to the non PEGylated proteins, and showed improved PK properties when injected into Sprague Dawley rats compared to the non PEGylated parent molecules.

Preparation of YRS Polypeptide DNA Constructs

Codon optimized DNA encoding the full length TyrRS synthetase containing the Y341A mutation (SEQ ID NO:36) was synthesized by GeneArt/Invitrogen, Carlsbad. The gene was then amplified by PCR with AccuPrime Pfx SuperMix (Invitrogen 12344) using the following primers (Integrated DNA Technologies):

```
                                       (SEQ ID NO: 37)
CTTTAAGAAGGAGATATACATATGGGTGATGCACCGTCACCG
```
and
```
                                       (SEQ ID NO: 38)
GTGGTGGTGGTGGTGCTCGAGTTAGCTAATATTGCCACCTTTCAG.
```

The resulting amplicon and the recipient pET24 expression vector (Novagen 69750-3) (1:1 w/w) were digested with NdeI and Xho I (New England Biolabs R0146S and R0111S) at 37° C. overnight and then purified with QIAquick PCR Purification Kit (Qiagen 28104). The amplicon was then ligated into the pET24 vector with T4 DNA ligase (Invitrogen 15224) at room temperature for 5 hours. A Novablue cell line (Novagen 71251-4) was transformed by ligation and spread on a kanamycin plate (Teknova L1097) at 37° C. overnight. The colonies were picked and grown overnight at 37° C. The plasmids from different colonies were purified by the QIAprep Spin Miniprep Kit (Qiagen 27106). Plasmid clones were verified by sequencing.

The His-tag sequence after the stop codon in the pET24 vector was deleted by mutagenesis using the primers

```
                                       (SEQ ID NO: 39)
GAAAGGTGGCAATATTAGCTAATGAGATCCGGCTGCTAACAAAGC
```
and
```
                                       (SEQ ID NO: 40)
GCTTTGTTAGCAGCCGGATCTCATTAGCTAATATTGCCACCTTTC.
```

The mutagenesis was done with the QuikChange Lightning Site-Directed mutagenesis kit (Agilent 210518) following manufacturer's protocol. After eighteen thermal cycles (95° C. for 20 sec, 50° C. for 20 sec and 68° C. for 3 min 30 sec), Dpn I enzyme was added and the sample was incubated at 37° C. for 2 hours. XL10 gold competent cells (Agilent 200314) were transformed with the sample and spread onto a kanamycin plate. The colonies were picked, cultured overnight at 37° C. and the plasmids were purified by mini-prep. Plasmid clones were verified by sequencing.

The T7 promoter of the vector was replaced with a Tac promoter (underlined region as shown below) with the following primers using the QuikChange Lightning Site-Directed Mutagenesis Kit:

```
                                       (SEQ ID NO: 41)
ATCGAGATCTCGATCCCGCGAAATGAGCTGTTGACAATTAATCATC

GGCTCGTATAATGTGTGGAATTGTGAGCGGATAACAATTC
```
and
```
                                       (SEQ ID NO: 42)
GAATTGTTATCCGCTCACAATTCCACACATTATACGAGCCGATGAT

TAATTGTCAACAGCTCATTTCGCGGGATCGAGATCTCGAT.
```

The alanine at position 341 was replaced with native tyrosine with the following primers using the QuikChange Lightning Site-Directed Mutagenesis Kit:

```
                                       (SEQ ID NO: 43)
CACTGAAAAAACTGGCAAGCGCAGCATATCCGGATCCGAGCAAAC

AGAAACCG
```
and
```
                                       (SEQ ID NO: 44)
CGGTTTCTGTTTGCTCGGATCCGGATATGCTGCGCTTGCCAGTTTTT

TCAGTG.
```

Deletion of amino acids 354 to 528 and replacement of two cysteines at position 67 and 250 by serines residues were performed in a single mutagenesis step with the following primers using the QuikChange Lightning Multi Site-Directed Mutagenesis Kit (Agilent, 210513):

```
                                       (SEQ ID NO: 45)
GGGCTTTGTTAGCAGCCGGATCTCATTAACCTTTTGCCATCGGTTTC

TG, (SEQ ID NO: 46)
GCAGATCAGCAAACAGAATGGTAACTTCGCTACCGGCTTTCAGAAA

ATCGGCAATTTTGC
```
and
```
                                       (SEQ ID NO: 47)
ATTATTTTCCACATTACCCGGTTCGCTAAAGGCTTTTTTCAGTTTTTT

TT

TCACATCTTC.
```

Next, the alanines at position 4 or position 351 were replaced by cysteine residues using the following primers using the QuikChange Lightning Site-Directed Mutagenesis Kit:

```
                                       (SEQ ID NO: 48)
GGAGATATACATATGGGTGATTGCCCGTCACCGGAAGAAAAACTG, (SEQ ID NO: 49)
CAGTTTTTCTTCCGGTGACGGGCAATCACCCATATGTATATCTCC, (SEQ ID NO: 50)
CCGAGCAAACAGAAACCGATGTGCAAAGGTTAATGAGATCCGGCT
```
and
```
                                       (SEQ ID NO: 51)
AGCCGGATCTCATTAACCTTTGCACATCGGTTTCTGTTTGCTCGG.
```

In addition to the non-tagged A4C and A351C YRS fragments, C-terminal 6×His-tagged versions were also cloned to enable affinity purification. The polynucleotide encoding a polyhistidine tag was inserted immediately before the stop codon with the following primers using the QuikChange Lightning Site-Directed Mutagenesis Kit:

```
                                       (SEQ ID NO: 52)
CCGAGCAAACAGAAACCGATGGCAAAAGGTCATCATCATCATCAT

CATTAATGAGATCCGGCTGCTAACAAAGCCCGA, (SEQ ID NO: 53)
TCGGGCTTTGTTAGCAGCCGGATCTCATTAATGATGATGATGATGA

TGACCTTTTGCCATCGGTTTCTGTTTGCTCGG,
```

-continued (SEQ ID NO: 54)
CCGAGCAAACAGAAACCGATGTGCAAAGGTCATCATCATCATCATC

ATTAATGAGATCCGGCTGCTAACAAAGCCCGA and (SEQ ID NO: 55)
TCGGGCTTTGTTAGCAGCCGGATCTCATTAATGATGATGATGATGA

TGACCTTTGCACATCGGTTTCTGTTTGCTCGG

The final non-tagged and HIS-tagged YRS(1-353)A4C and YRS(1-353)A351C vector constructs (both also containing C67S and C250S mutations) were verified by sequencing. The polynucleotide sequence of non-tagged YRS(1-353)A4C is set forth in SEQ ID NO:56 and the corresponding polypeptide sequence is set forth in SEQ ID NO:57. The polynucleotide sequence of HIS-tagged YRS (1-353)A4C is set forth in SEQ ID NO:58 and the corresponding polypeptide sequence is set forth in SEQ ID NO:59.

The polynucleotide sequence of non-tagged YRS(1-353) A351C is set forth in SEQ ID NO: 60 and the corresponding polypeptide sequence is set forth in SEQ ID NO:61. The polynucleotide sequence of HIS-tagged YRS(1-353)A351C is set forth in SEQ ID NO:62 and the corresponding polypeptide sequence is set forth in SEQ ID NO:63.

Expression Strain

The BL21 *E. coli* B F-ompT hsdS(rB- mB-) gal dcm (Novagen 69449-4) was transformed with the YRS polypeptide expression constructs. Briefly, the plasmid (1 µl) was added to 50 µl of competent cells. The reaction was mixed and incubated on ice for 30 minutes. The reaction was heat-shocked at 42° C. for 30 seconds followed by a cold-shock on ice for 2 minutes. SOC medium (500 µl) was added and the tube was incubated at 37° C., 250 rpm for 1 hour. Finally, an aliquot of the culture (50 µl) was spread on a kanamycin plate (Teknova S9641) and incubated at 37° C. overnight. A single colony was picked and used for expression scale-up as described below.

Medium

The M9YE medium was prepared by mixing 200 ml sterile M9 minimal salt 5× (BD248510), 778 ml 30 g/L yeast extract in sterile purified water (BD212750), 20 ml sterilized 20% glucose (Sigma G7021) and 2 ml sterile 1.0 M MgSO4 (Sigma M7506). The feeding solution contains 5% yeast extract, 50% glucose, trace elements and 2 g/L magnesium sulfate. Kanamycin sulfate (Invitrogen 15160) was added to a final concentration of 100 µg/ml in both M9YE and feeding solution.

Fed-Batch Fermentation

A 0.5 L fermentor (Infors-HT) with Iris software was used for the fed-batch fermentation. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 0.5 L/min with an oil-free diaphragm air compressor (Cole-Parmer). The air was passed through a 0.2 µm Midisart 2000 filter (Sartorius 17805). The pure oxygen (West Air) was supplied automatically to control the dissolved oxygen level at higher cell density. The temperature was controlled at 30° C. with a Neslab RTE7 circulator (Thermo Scientific). The foaming was controlled by addition of the antifoam 204 (Sigma A8311). The initial volume of M9YE medium in the fermentor was 0.3 L. The fermentor was inoculated with 15 ml of the seed culture grown overnight at 30° C. and 250 rpm. When the glucose was depleted in the vessel, the concentrated feeding solution was introduced into the vessel by a peristaltic pump set at 0.12 ml/min. When the optical density of the cells at 600 nm reached above 40, the culture was induced with 0.5 mM IPTG (Fisher Scientific BP1755). The culture was run overnight (20-hour fed-batch phase) and harvested by centrifugation at 6,000 g for 30 min. The cell pellet was stored at −20° C. until purification.

Typically, based on the band intensity on the SDS-PAGE, the expression level in the soluble fraction was about 0.4-1.2 mg/L.

Purification

Frozen cell pellets were resuspended in 20 mM sodium phosphate buffer, 500 mM NaCl, 10 mM imidazole at pH 6.5 and then subjected to microfluidization at 14,000 psi (Microfluidics, Microfluidizer M110L). Insoluble debris were removed by centrifugation at 10,000 g for 30 minutes. The supernatant was passed through 0.45 µm cellulose acetate membrane (Corning 430516). The protein was bound to Ni-NTA superflow (Qiagen 30430) packed in a chromatography column, washed with 200 column volumes of 20 mM sodium phosphate, 500 mM sodium chloride, 10 mM imidazole and 0.1% Triton X-100 followed by 200 column volumes of the same buffer without Triton X-100. The protein was eluted with 4 column volumes of the elution buffer containing 20 mM phosphate, 500 mM NaCl and 500 mM imidazole at pH 6.5. Lower pH increased the solubility and recovery. FIG. 1 shows the percentage of protein recovery dialyzing against different buffers. The NaCl concentration and pH value are shown in the legend. All buffers contain 10 mM sodium phosphate. The data surprisingly demonstrates that protein recovery is significantly enhanced when the proteins are stored under slightly acidic conditions, e.g. within the range of about pH 5.5 to about pH 7.0, or more preferably about pH 6.0 to about pH 6.5.

Western Blot

Proteins separated by SDS-PAGE under reducing conditions were transferred to nitrocellulose membrane (Invitrogen, IB3010-02) using iBlot Gel Transfer Device (Invitrogen, IB1001) for 7 minutes. The membranes containing transferred proteins were blocked with TTBS plus milk (10 mM Tris, 150 mM NaCl, pH 7.5 and 5% non-fat dry milk) for 1 hour at room temperature. After blocking, the nitrocellulose membrane was treated with a 1:1000-dilution of rabbit polyclonal anti YRS (1-364aa) antibody (Lampire, anti-aTyr010/4913) for 1.5 hour at room temperature. The membrane was washed three times with the 50 ml TTBS buffer and then incubated with 1:5000-dilution of goat anti-rabbit polyclonal antibodies conjugated with alkaline phosphatase (Pierce, 31340) for 1 hour at room temperature. The membrane was washed three times with the TTBS buffer. The blot was developed using BCIP/NBT (Sigma B6404). The bands for YRS(1-353)A4C and YRS(1-353) A351C showed up at approximately 40 kDa. (Data not shown)

Mass Spectrometry

Purified protein (YRS(1-353)A4C or YRS(1-353)A351C) at 1 mg/mL was diluted 1:10 into 0.1% formic acid and 6 µl of the sample was injected into a C4 capillary column on the Dionex Ultimate3000 HPLC system. The ThermoFisher LTQ ion trap mass spectrometer was coupled to the downstream of the HPLC. The protein was eluted from the column by a 35-minute gradient of 5-70% acetonitrile in 0.1% formic acid at a flow rate of 0.9 µL/min. The LTQ was operated on a full MS scan mode (300-2,000 m/z) with a spray voltage of 2.5 kV. The major peaks on the chromatograph were analyzed with ThermoFisher deconvoluting algorithm ProMass to obtain the molecular weights. The resulting molecular weights confirmed the identities of the YRS(1-353)A4C and YRS(1-353)A351C. (Data not shown)

N-Terminal Sequencing

The purified, unPEGylated YRS(1-353)A4C and YRS(1-353)A351C samples (10 ul at 1 mg/ml) were sent to Alphalyse (Palo Alto, Calif.) for N-terminal sequencing. The analysis was performed on an ABI Procise 494 sequencer. It was found that 31% of the methionine was cleaved in the case of YRS(1-353)A4C and 66% of the methionine was cleaved in the case of YRS(1-353)A351C.

Example 2

Preparation of Linear Pegylated YRS Polypeptides

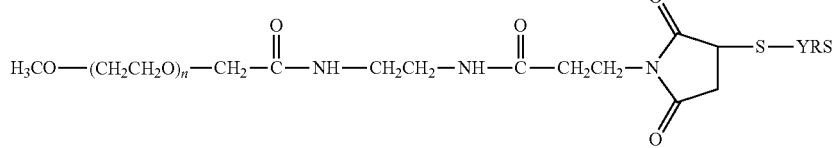

wherein n=about 200 to 800;

YRS is YRS(1-353)A4C or (1-353)A351C, and wherein the PEG moiety is attached via either Cys4 or Cys351.

Pre-activated linear 20 kDa, 40 kDa and 60 kDa PEG-maleimide reagents were purchased from Jenkem, (M-MAL-20K, M-MAL-40K, and M-MAL-60K), and used to create 20 kDa, 40 kDa, and 60 kDa PEGylated versions of both YRS(1-353)A4C and YRS(1-353)A351C. (Jenkem-YRS(1-353)A4C-20K, Jenkem-YRS(1-353)A4C-40K, Jenkem-YRS(1-353)A4C-60K; and Jenkem-YRS(1-353)A351C-20K, Jenkem-YRS(1-353)A351C-40K, Jenkem-YRS(1-353)A351C-60K respectively)

Purified YRS polypeptides YRS(1-353)A4C or YRS(1-353)A351C (1.5-2 mg/ml) (Example 1) were incubated with 1 mM dithiothreitol (Fluka 43819) overnight at 4° C. or with >8 mM effective concentration of immobilized TCEP (tris (2-carboxyethyl)phosphine)agarose (Pierce, 77712) at room temperature for 2 hours to reduce any disulfide bond formation. The samples were buffer exchanged to 1×PBS (Invitrogen, 10010-049) pH adjusted to 6.0, using HiTrap desalting columns (General Electric 17-1408-01). The samples were then passed through an HiTrap Q HP column (General Electric 17-1153-01) as a polishing step and to remove endotoxins.

The Methoxy PEG Maleimide PEGylation reagents from the manufacturer were resuspended in 1×PBS and adjusted to pH 6.0 to make a final concentration of 50-100 mg/ml. The YRS polypeptides YRS(1-353)A4C or YRS(1-353) A351C were mixed with the activated PEG reagent at molar ratio of either 1:1 or 1:5. The reactions were run for either 2 hours at room temperature or overnight at 4° C. on a shaker. Completion of the reaction was checked using SDS-PAGE to confirm the molecular weight shift due to PEGylation (Example 5).

Example 3

Preparation of Additional Linear Pegylated YRS Polypeptides

Using similar reaction conditions as described in Example 2, and using the following reagents in place of the Jenkem reagents, the following PEGylated YRS polypeptides of MW 10 KDa to 60 KDa may be readily prepared.

Use of PEG2-0007 from Nanocs, yields:

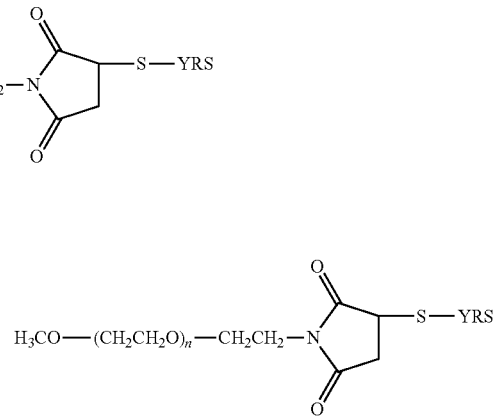

wherein n=about 400 to 600;

YRS is YRS(1-353)A4C or (1-353)A351C, and wherein the PEG moiety is attached via either Cys4 or Cys351.

The resulting PEGylated YRS polypeptides ((Nanocs-YRS(1-353)A4C-40K, and Nanocs-YRS(1-353)A351C-40K) were analyzed by SDS-PAGE as described in Example 5.

Use of SUNBRIGHT ME-200MA, ME400MA, or ME600MA from NOF yields:

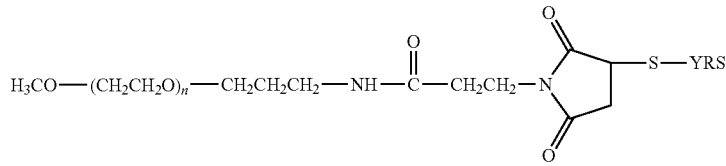

wherein n=about 200 to 600;

YRS is YRS(1-353)A4C or (1-353)A351C, and wherein the PEG moiety is attached via either Cys4 or Cys351.

The resulting PEGylated YRS polypeptides ((SUNBRIGHT-YRS(1-353)A4C-20K, SUNBRIGHT-YRS(1-353)A4C-40K, SUNBRIGHT-YRS(1-353)A4C-60K; and SUNBRIGHT-YRS(1-353)A351C-20K, SUNBRIGHT-YRS(1-353)A351C-40K, and SUNBRIGHT-YRS(1-353) A351C-60K respectively) were analyzed by SDS-PAGE as described in Example 5.

Use of JENKEM M-VS-20K yields:

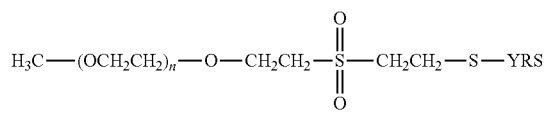

wherein n=about 200 to 600;
YRS is YRS(1-353)A4C or (1-353)A351C, and
wherein the PEG moiety is attached via either Cys4 or Cys351.

Use of NANOCS PEG2-0014 yields:

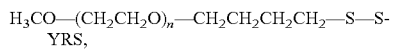

wherein n=about 100 to 600;
YRS is YRS(1-353)A4C or (1-353)A351C, and
wherein the PEG moiety is attached via either Cys4 or Cys351.

Example 4

Preparation of Exemplary Branched Pegylated YRS Polypeptides

Using similar reaction conditions as described in Example 2, and using the following reagents in place of the Jenkem reagents, the following PEGylated YRS polypeptides with branched chain PEG moieties of MW 10 KDa to 60 KDa may be readily prepared.

Use of SUNBRIGHT LY-400MA from NOF yields:

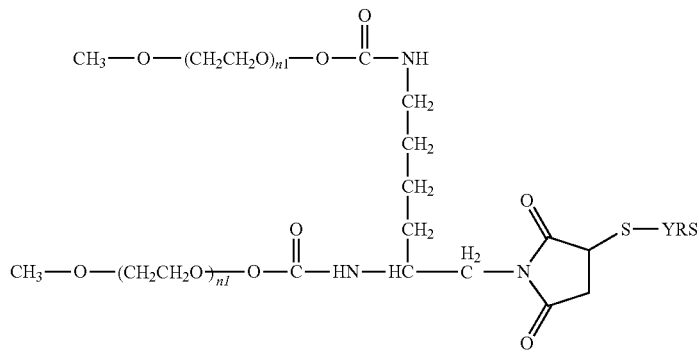

wherein $n_1$=about 200 to 600;
YRS is YRS(1-353)A4C or (1-353)A351C, and
wherein the PEG moiety is attached via either Cys4 or Cys351.

Use of A0002-1 Y-MAL-40K from JENKEM yields:

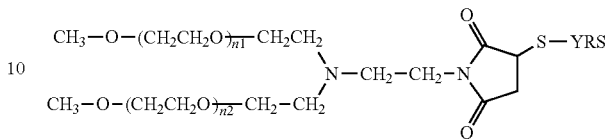

wherein n1=about 200 to 600;
YRS is YRS(1-353)A4C or (1-353)A351C, and
wherein the PEG moiety is attached via either Cys4 or Cys351.

Use of SUNBRIGHT GL2-200GS, GL2-400GS or GL2-600GS from NOF yields:

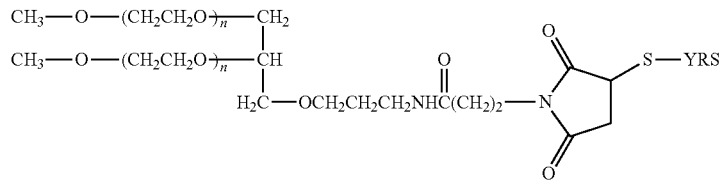

wherein n=about 200 to 600;
YRS is YRS(1-353)A4C or (1-353)A351C, and
wherein the PEG moiety is attached via either Cys4 or Cys351.

Example 5

SDS-Page Analysis of Pegylated YRS Polypeptides

Protein samples (15 μl) mixed with 4×LDS sample buffer (5 μl) (Invitrogen, NP0007) plus β-mercaptoethanol (Fisher Scientific, O3446I-100) of selected 40K PEGylated YRS proteins from Example 2 (Jenkem-YRS(1-353)A4C-40K Nanocs-YRS(1-353)A4C-40K, Nanocs-YRS(1-353)A351C-40K; SUNBRIGHT-NOF-YRS(1-353)A4C-40K, SUNBRIGHT-NOF-YRS(1-353)A351C-40K) were analyzed by sodium dodecyl sulfate polyacrylamide gel electrophoresis using 4-12% NuPAGE Bis-Tris gel (Invitrogen, NP0335) and MOPS running buffer (Invitrogen, NP000102). Electrophoresis was carried out at 150 volts until the dye front reached the bottom of the gel. The gel was stained with Coomassie-based reagent, Instant Blue (Novexin) and destained with water. The bands for unPEGylated YRS(1-353)A4C and YRS(1-353)A351C migrated with an apparent molecular weight of approximately 40 kDa. The bands for PEGylated YRS(1-353)A4C and YRS(1-353)A351C which were PEGylated with any of the 40 kDa PEGs migrated with an apparent molecular weight of approximately >80 kDa.

Figure 2A:
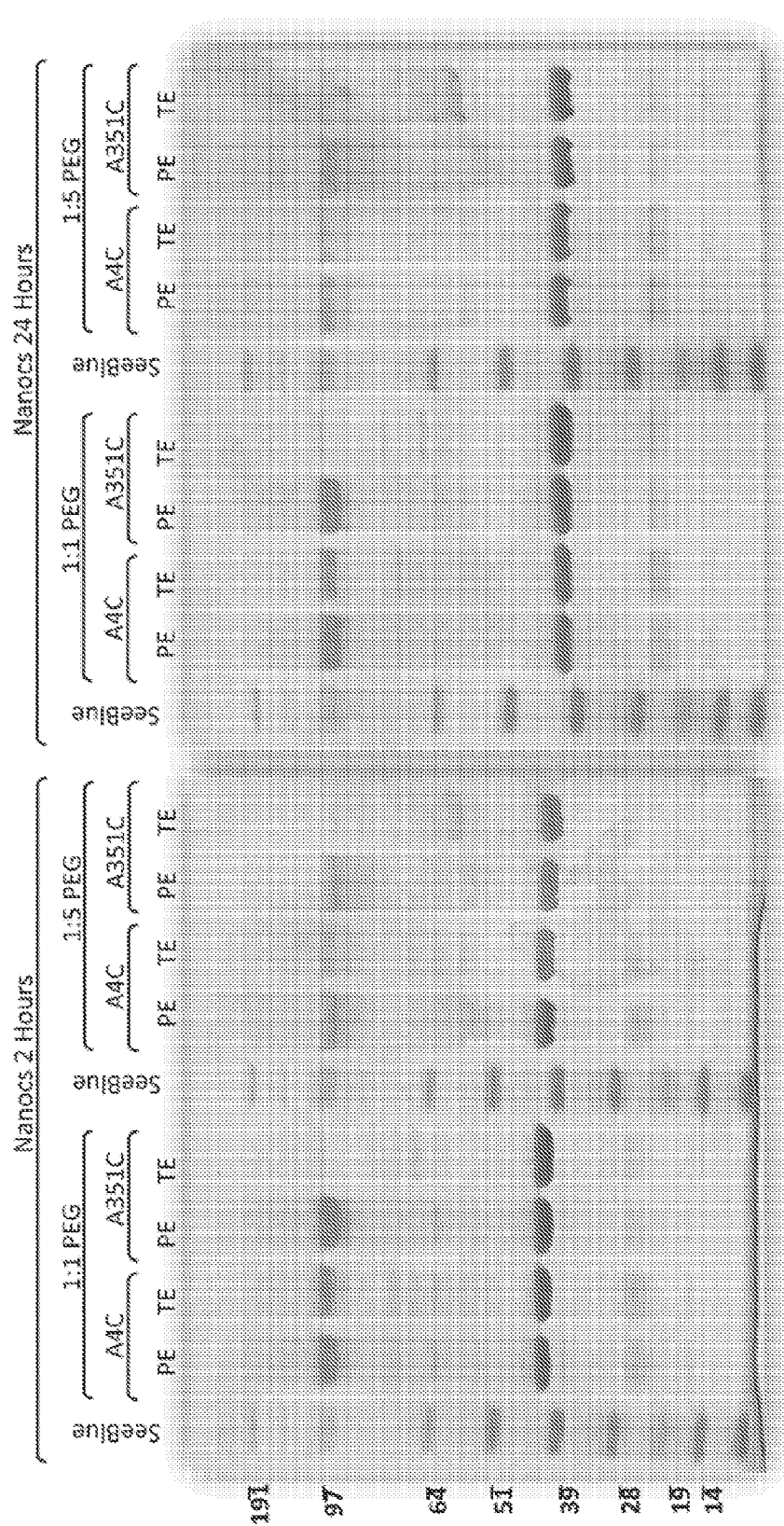
FIG. 2 shows the screening results for optimizing the PEGylation conditions screening for the YRS(1-353)A4C and YRS(1-353)A351C proteins using different commercially available PEGylation reagents from Nanocs and Jen-Kem.
Figure 2B:
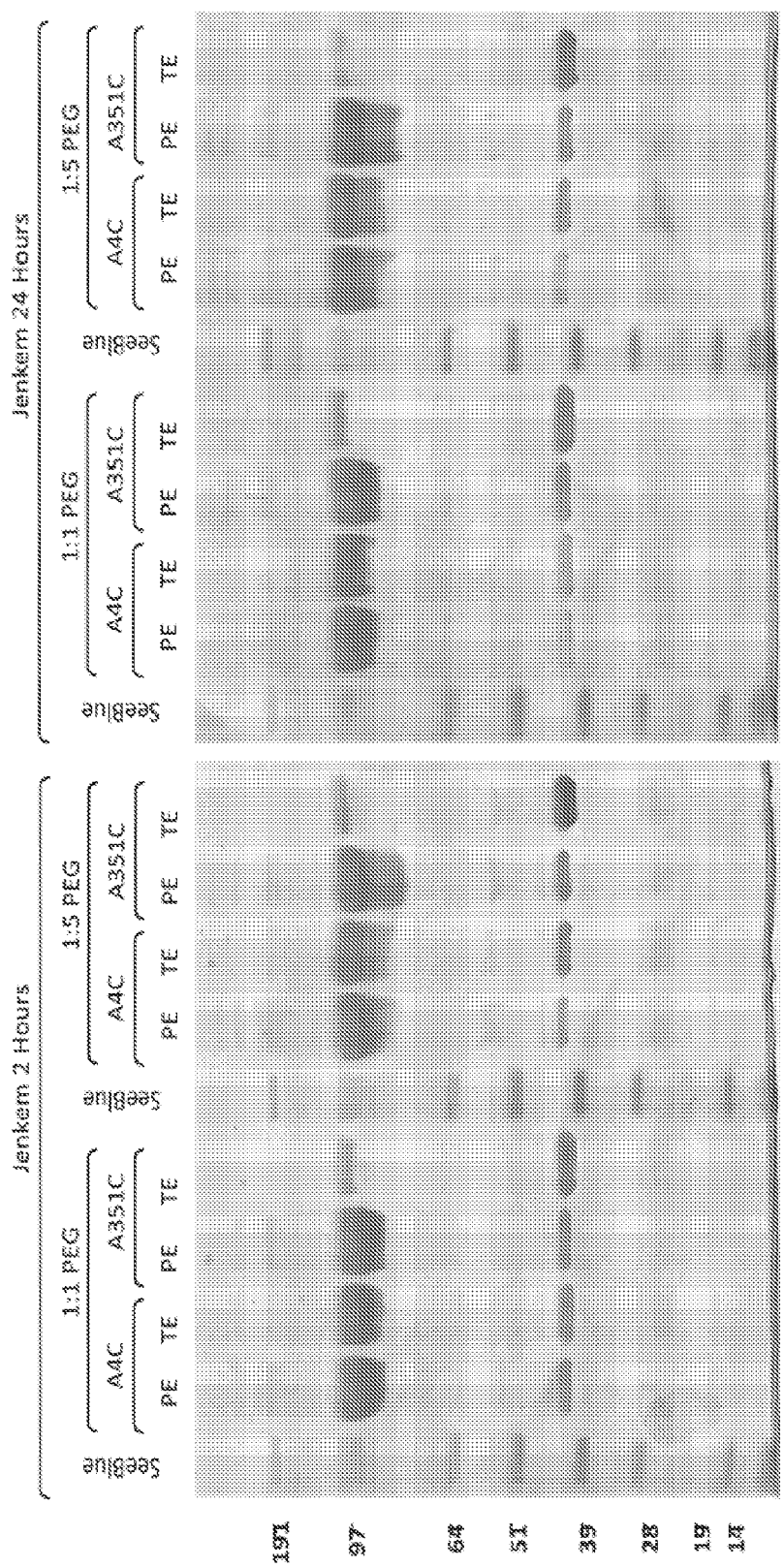
Figure 3A:
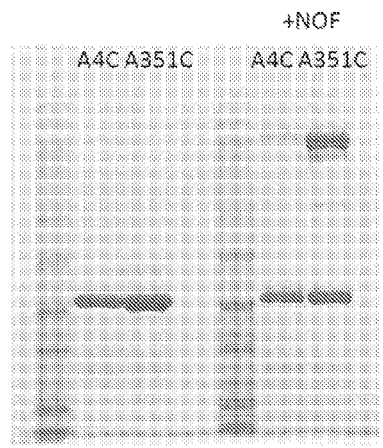
FIG. 3 shows an SDS-PAGE analysis of the unPEGylated and PEGylated versions of the YRS(1-353)A4C and YRS(1-353)A351C proteins, after labeling with PEGylation reagents from NOF (FIG. 3A), and in reducing and non reducing conditions (FIG. 3B).
Figure 3B:
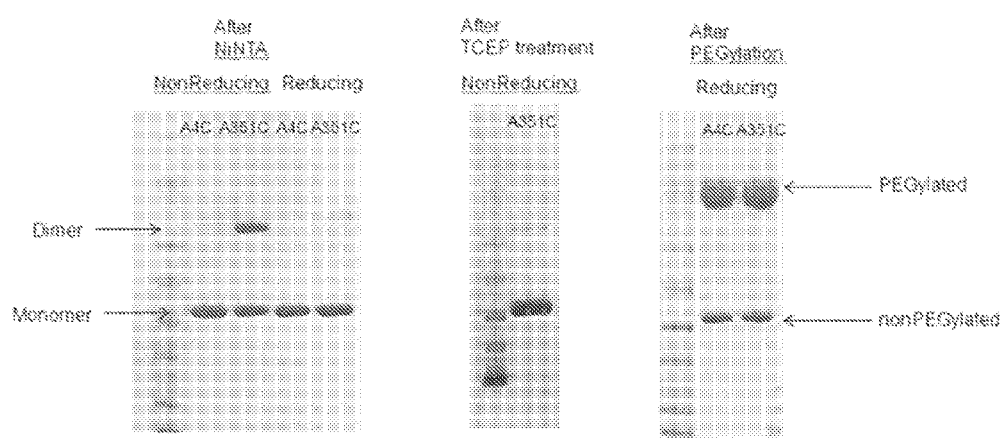

The comparison demonstrated that Jenkem's M-MAL-40K PEG showed the highest coupling efficiency among three different PEG reagents tested. Incubation for 2 hours at room temperature or overnight at 4° C. with a 1:1 protein to PEG ratio was sufficient to reach at least 80~90% coupling efficiency. After PEGylation, the proteins were stored in aliquots at −80° C. FIGS. 2 and 3A shows the results for PEGylation condition screening, and FIG. 3B shows the SDS-PAGE analysis of YRS(1-353)A4C (A4C in the Figure) and YRS(1-353)A351C (A351C in the Figure) in both reducing and non reducing conditions, and after PEGylation with Jenkem's M-MAL-40K PEG.

Additional characterization studies were also conducted with 3 different sizes of linear MPEG-maleimide (40 kDa, 30 kDa, and 20 kDa) from JenKem Technology and NOF Corporation, without prior reduction by reducing agents. The protein in these coupling reactions was 1-3 mg/ml; and the molar ratio of MPEG-maleimide to protein was 1-1.5. The reactions were carried out either at room temperature for 2 hours or at 4° C. for 15-20 hours with gentle mixing. All PEG reagents had similar PEGylation efficiency as determined by SDS-PAG (data not shown).

Figure 4:
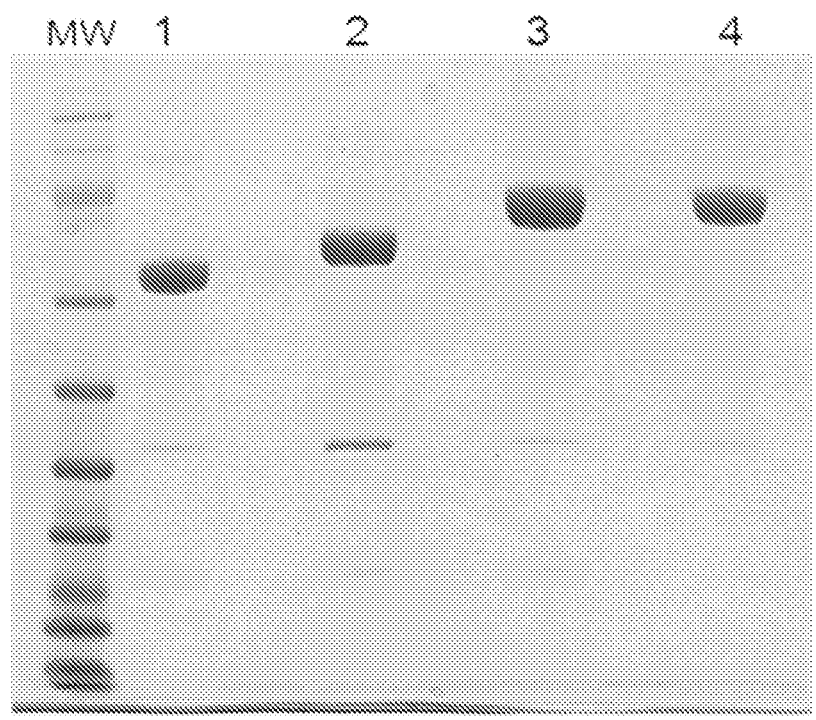
FIG. 4 shows an SDS-PAGE analysis of purified PEGylated YRS proteins of various molecular weights. Lane 1 showing YRS(1-353)A4C after PEGylation with a 20 kDa PEG; lane 2 showing YRS(1-353)A4C after PEGylation with a 30 kDa PEG; lane 3 showing YRS(1-353)A4C after PEGylation with a 40 kDa PEG and lane 4 showing YRS(1-353)A351C after PEGylation with a 40 kDa PEG.
Figure 5A:
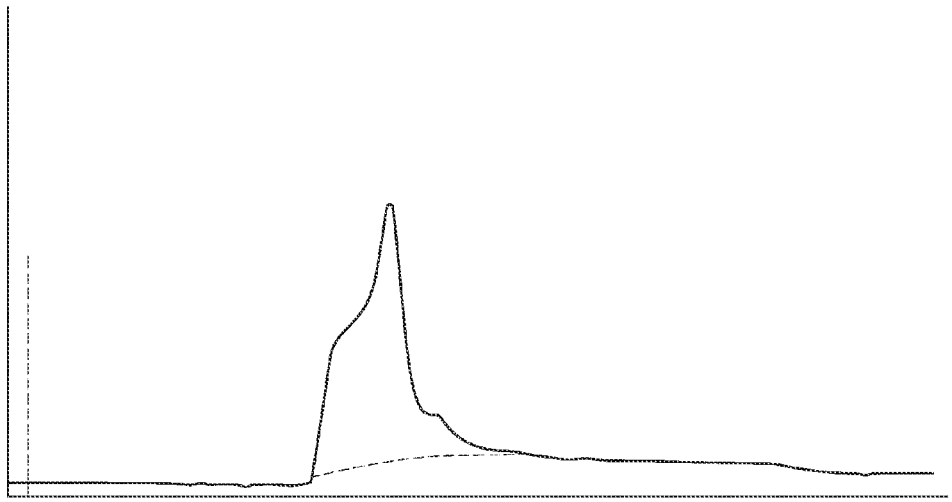
FIGS. 5A-5D show the results of size exclusion chromatography of PEGylated polypeptides.
Figure 5B:
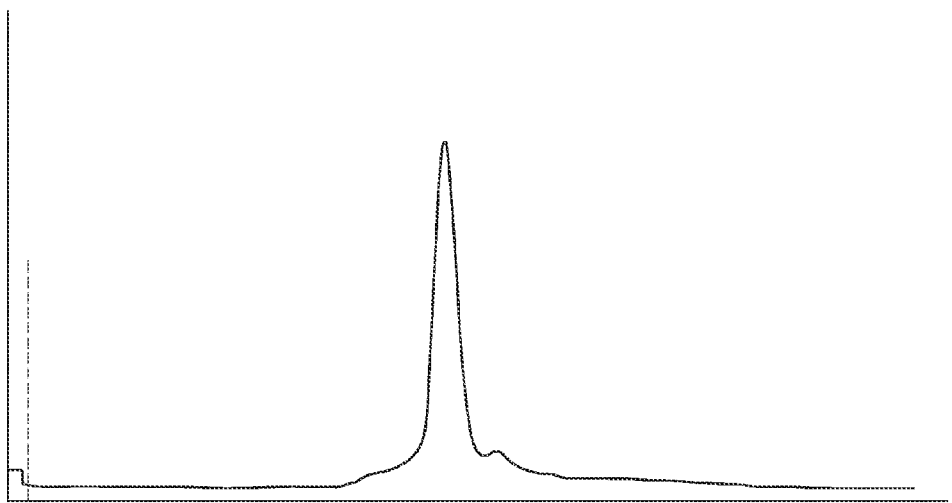
Figure 5C:
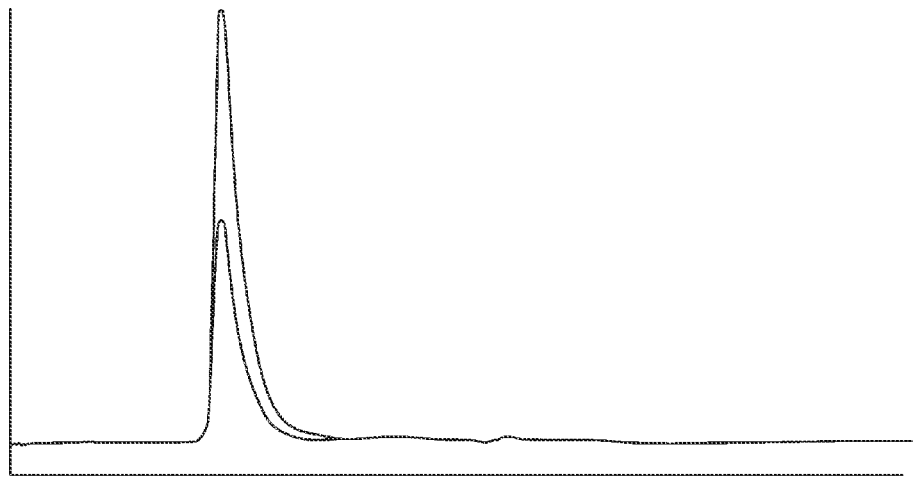
Figure 5D:
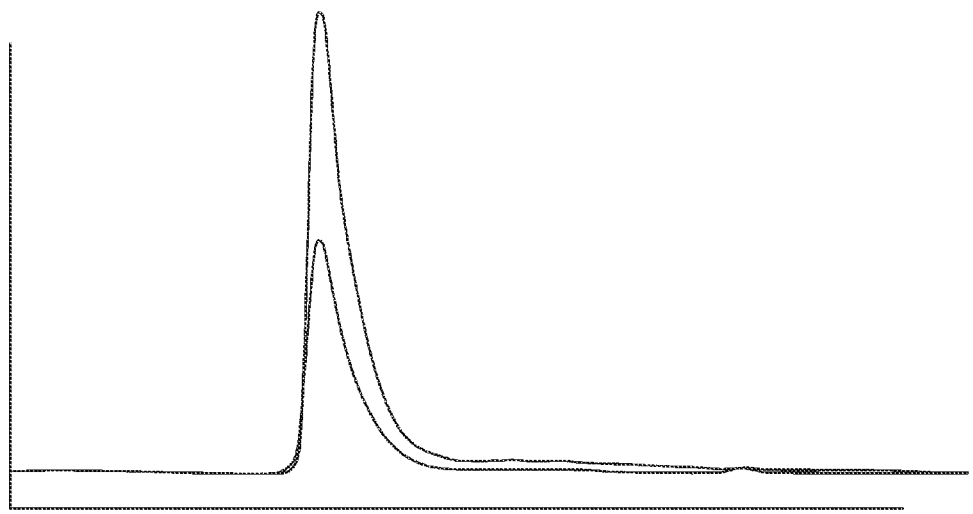

Purification and SDS-PAGE Analysis of PEGylated YRS A4C (1-353) and PEGylated A351C (1-353) Polypeptides The PEGylation reaction mixtures were diluted with 1 volume of Buffer A (20 mM sodium phosphate, pH 6.0) and 1 volume of water, and loaded onto a SP Sepharose HP column, pre-equilibrated with Buffer A. The YRS(1-353)A4C and YRS(1-353)A351C polypeptides were eluted off the column over a gradient of 0 to 0.8 M NaCl in buffer A, and were separated from excess MPEG-maleimide and unconjugated protein. This methodology is also applicable for purifying the PEGylated polypeptides with different length of MPEG attached, including 20 kDa, 30 kDa, and 40 kDa of linear MPEGs. FIG. 4 shows the SDS-PAGE analysis of purified YRS(1-353)A4C and YRS(1-353)A351C PEGylated polypeptides of varying molecular weights. This data demonstrates that these YRS polypeptides can be reliably and reproducibly PEGylated with PEG reagents with a wide range of molecular weights, and result in soluble PEGylated proteins in high yield.

Example 6

Biophysical Characterization of the Pegylated YRS Polypeptides

Size Exclusion Chromatography

The protein samples (100 µL) including YRS(1-353)A4C and YRS(1-353)A351C before and after PEGylation with Jenkem's M-MAL-40K PEG were loaded onto the sample loop on a GE Healthcare AKTA FPLC. A Superdex 200 10/300 GL size exclusion column (GE Healthcare, cat. no. 17-5175-01) was used for separation. The column was first equilibrated with 1.5 column volume (CV) of 1×PBS buffer, followed by sample injection. The column was run with 1×PBS isocratic flow and the absorbance at 280 nm was monitored. The whole process was controlled with the Unicorn software. The elution volume was used to estimate the molecular weight based on comparison with gel filtration calibration kits (GE Healthcare, cat. no. 28-4038-41 and 28-4038-42). The chromatograms showed that the majority of A4C and A351C (without PEGylation) formed dimers. After PEGylation with Jenkem's M-MAL-40K PEG, the elution volumes were significantly reduced due to the large hydrodynamic radius of the PEG. The apparent MW of PEGylated A4C/A351C is 8 fold larger than the theoretical MW due to large hydrodynamic radius of the PEG. FIG. 5 shows the result of the size exclusion chromatography.

Analytical Ultracentrifugation

Figure 6A:
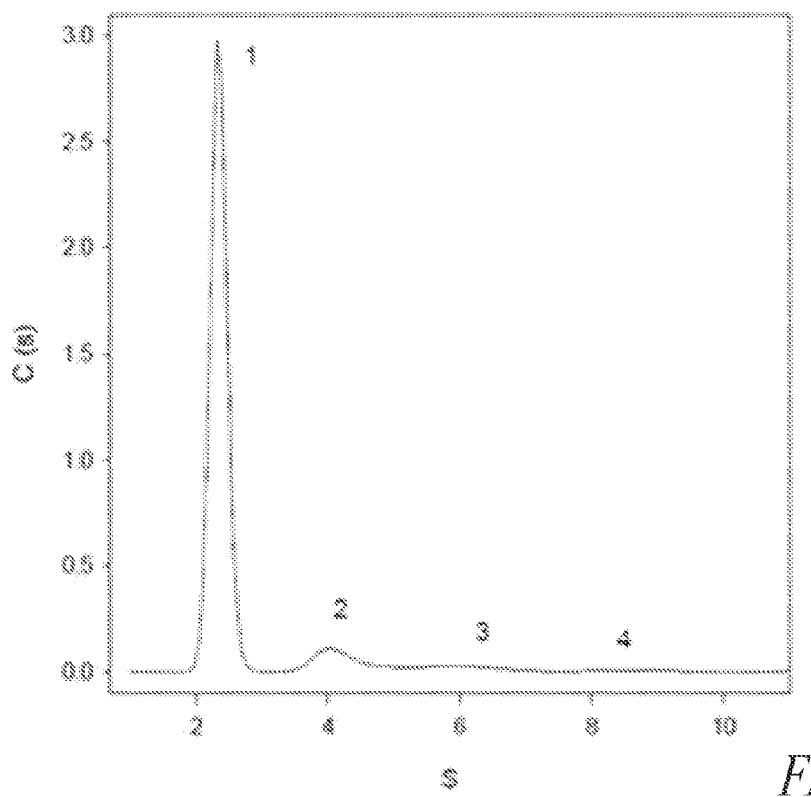
FIG. 6A shows the sedimentation velocity characteristics of PEGylated YRS (1-353) A4C determined by analytical ultracentrifugation.
Figure 6B:
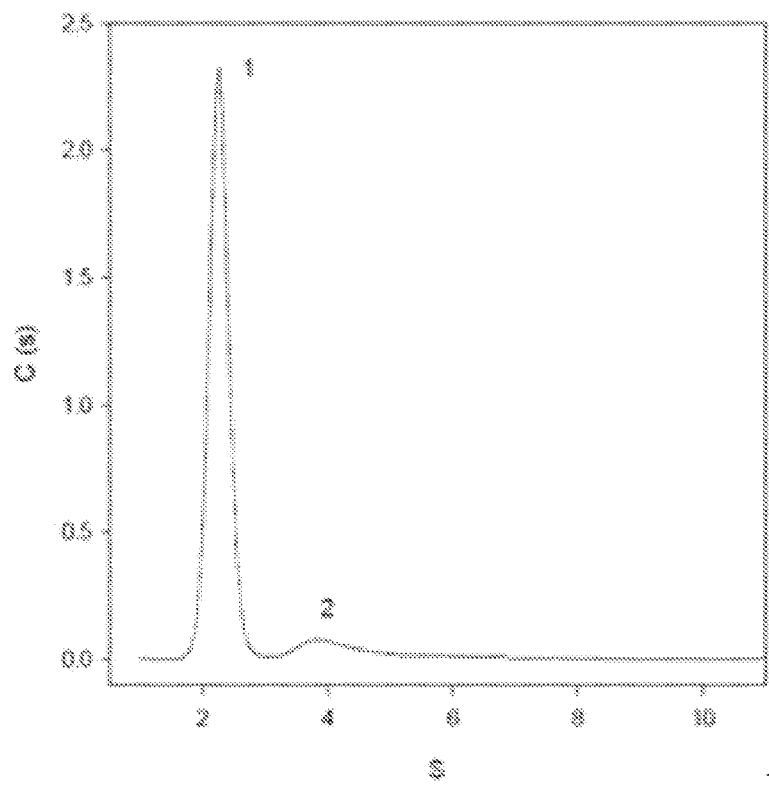
FIG. 6B shows the sedimentation velocity characteristics of PEGylated YRS(1-353)A351C determined by analytical ultracentrifugation.

Sedimentation velocity experiments were performed using a Proteome Lab XL-I (Beckman Coulter) analytical ultracentrifuge. Protein samples of PEGylated YRS (Jenkem-YRS(1-353)A4C-40K and Jenkem YRS(1-353)A351C-40K) in PBS (pH 6.0) were loaded at a concentration of 0.8 mg/ml in 2-channel cells and centrifuged in An-50 Ti 8-place rotor at 30,000 rpm, 25° C. for 14 hours. Data were analyzed using SEDFIT software (sedfitsedphat.nibib.nih.gov/software/default.aspx). The results demonstrated that in both cases, the majority of the PEGylated proteins formed a dimer of approximately 160 kDa (FIG. 6).

Circular Dichroism

Figure 7A:
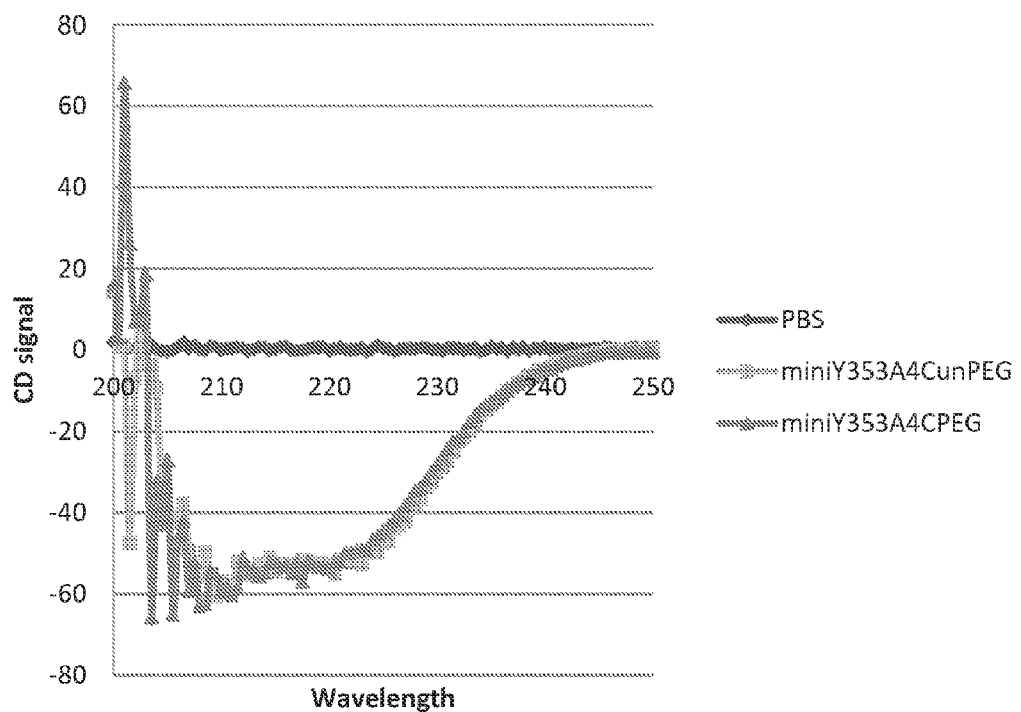
FIG. 7A shows a comparison between PEGylated and unPEGylated YRS(1-353)A4C.
Figure 7B:
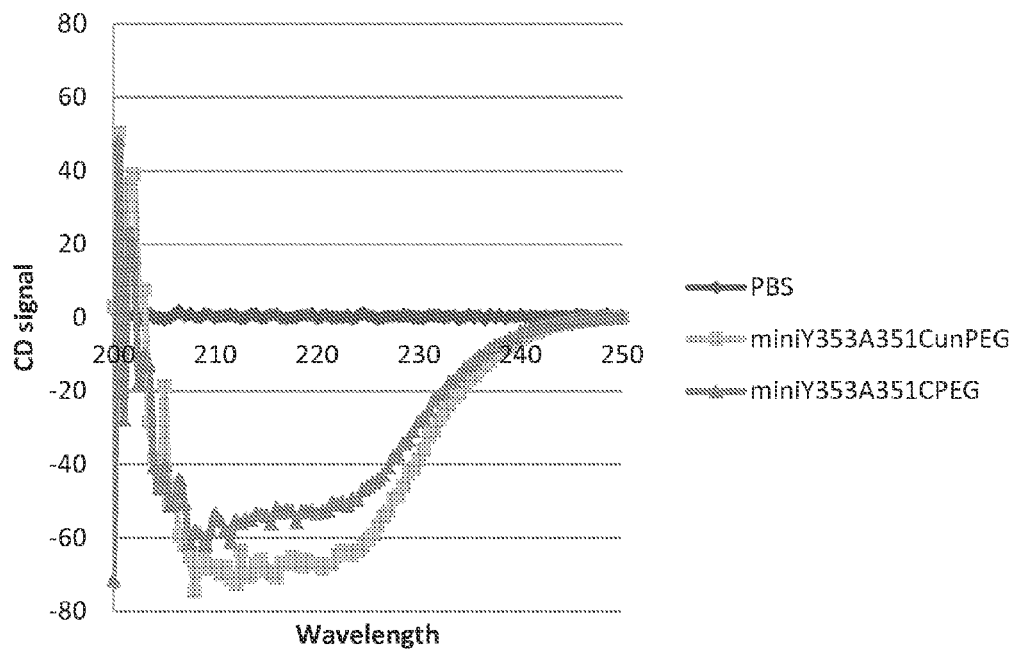
FIG. 7B shows a comparison between PEGylated and unPEGylated YRS(1-353)A351C.

The secondary structure of YRS(1-353)A4C and YRS(1-353)A351C before and after PEGylation was determined by AVIV model 400 circular dichroism and compared to the wild-type tyrosyl t-RNA synthetase YRS polypeptide YRS (1-364). The sample (350 ul) was loaded into a rectangular quartz cuvette with 1 mm path length (Hellma 110-QS) and inserted into the cell holder. The data acquisition software was opened and the scanning wavelength was set to be from 190 nm to 250 nm with frequency of 1 nm. The temperature was set to be at 25° C. The data were imported into Excel and the curves were plotted. All samples showed a profile substantially identical to that of the wild-type tyrosyl t-RNA synthetase YRS polypeptide YRS (1-364), demonstrating that there was no significant secondary structure change after mutagenesis and PEGylation. FIG. 7 shows the circular dichroism analysis of YRS(1-353)A4C and YRS(1-353)A351C before and after PEGylation with Jenkem's M-MAL-40K PEG. The difference of CD signal intensity is due to concentration differences between samples.

Example 7

Characterization of In Vitro Activity

As a surrogate measure of biological activity, a tRNA synthetase charging assay was used to assess whether the YRS(1-353)A4C and YRS(1-353)A351C proteins still retained tRNA aminoacylation activity after mutagenesis and PEGylation. The assay is based on the measurement of Tritium-labeled tyrosine coupled onto tRNA catalyzed by the YRS polypeptide. Briefly, 20 ul of the tRNA mix containing 100 mM HEPES buffer, 20 mM KCl, 2 mM ATP, 4 mM MgCl2, 2 mM DTT, 250 µM Baker's yeast tRNA and 1.25 U/mL pyrophosphatase were mixed with 10 µl 10-100 nM YRS polypeptide sample followed by addition of 10 µl of 2 µM 3H-Tyr plus 28 µM L-Tyr. An aliquot (5 µl) was taken every 3 minutes up to 15 minutes and spotted onto a filter rinsed with 125 µl wash buffer containing 5% trichloroacetic acid plus 100 µM L-tyrosine. The filter was washed with the 3×350 ml wash buffer followed by 100 ml 95% ethanol. The filter was then dried under lamp and transferred into a scintillation vial. The scintillation count for 1 minute was measured in a Beckman LS 6500 Scintillation Counter. The linear regression of the data was analyzed with Microsoft Excel to obtain the slope which is proportional to the activity of the synthetase.

Figure 8A:
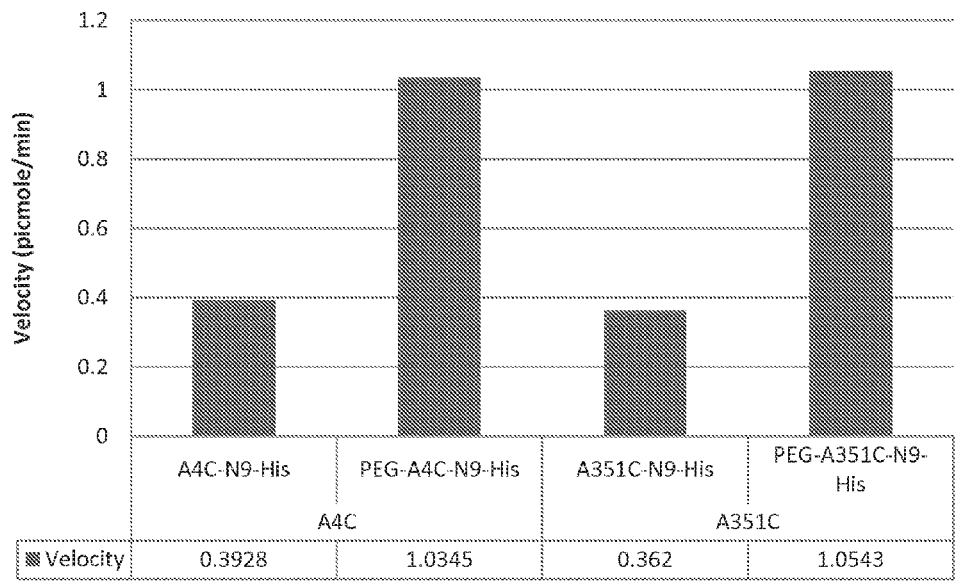
FIG. 8 shows the relative enzymatic activity for YRS A4C (1-353) and YRS A351C (1-353) before and after PEGylation in two independent repeats of the charging assay experiment shown in FIGS. 8A and 8B respectively.
Figure 8B:
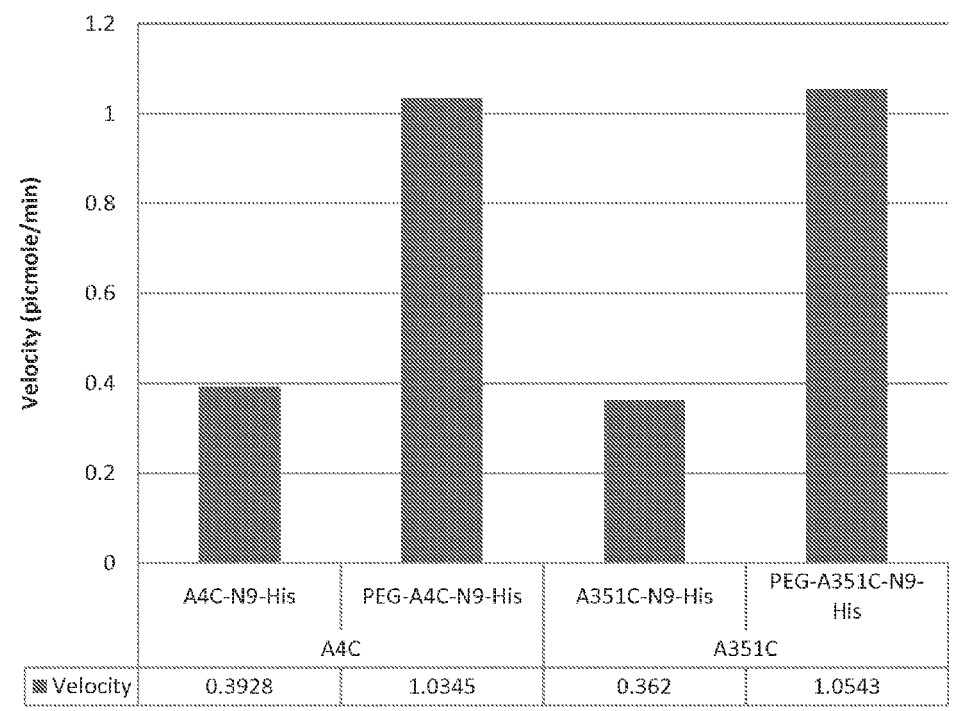

The data shows (FIG. 8) that in two independent experiments PEGylation of both YRS(1-353)A4C and YRS(1-353)A351C resulted in significant increases (2.6 to 2.2 fold and 2.9 to 5 fold) in activity compared to the unmodified YRS polypeptide when measured at 25 nM. Thus these results surprisingly demonstrate that PEGylation of the YRS polypeptides at either the N or C terminus increased the relative activity of the proteins in an in vitro assay by from about 2 to 5 fold. This increase in activity was more evident when the PEG moiety was couple to the C-terminus compared to the N-terminus.

Example 8

Pharmacokinetics of Pegylated YRS Polypeptides In Vivo

Figure 9:
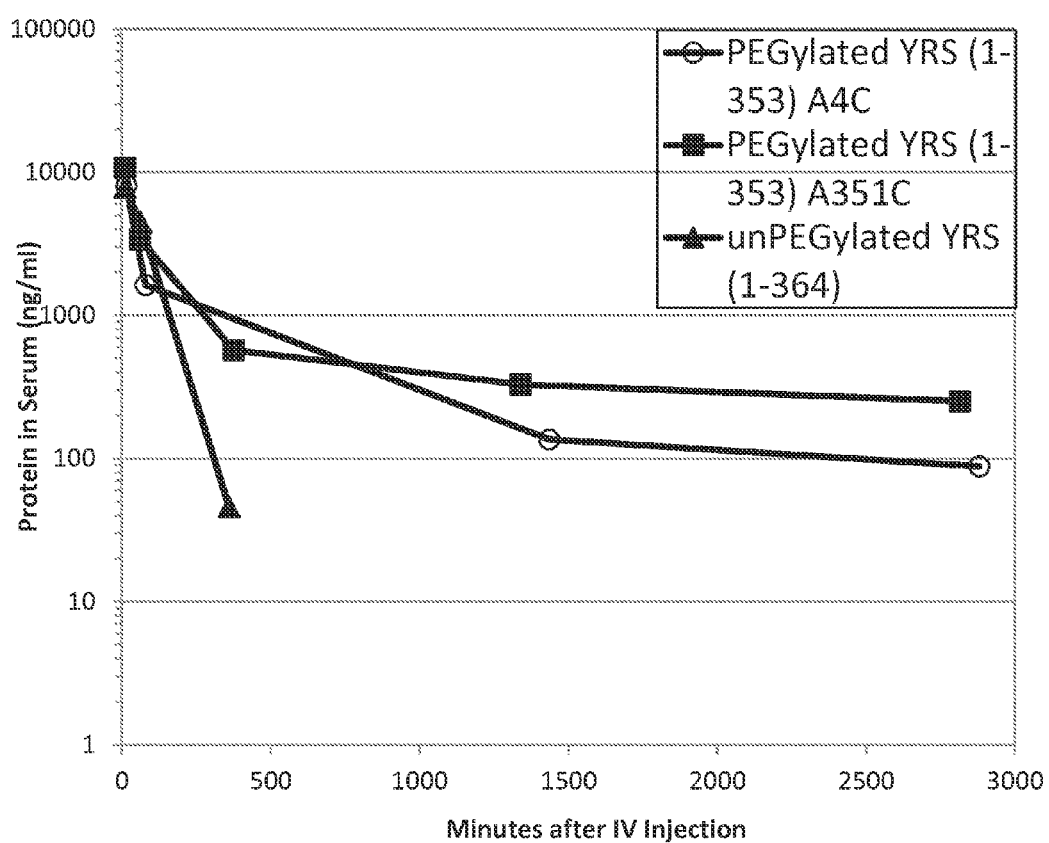
FIG. 9 shows the results of a pharmacokinetic analysis of PEGylated YRS (1-353)A4C (A4C Rat7) and PEGylated YRS (1-353)A351C (A351C Rat4) compared to the unPEGylated protein (N10 Rat 5) in an in vivo Sprague Dawley rat model.

PEGylated Jenkem YRS(1-353)A4C-40K or JenKem-YRS(1-353)A351C-40K were prepared according to Example 1, and administrated to male Sprague Dawley rats by intravenous bolus injection through jugular vein cannulae at a dose of 500 μg/kg. Blood samples (200 μl) were drawn at multiple time points after injection (10 min, 1 hr, 6 hr, 24 hr, 48 hr) and processed into serum. The level of drug in the serum was measured with an antibody sandwich, using a custom bivalent Fab (AbD Serotec, Planegg, Germany) generated against an N-terminal fragment (amino acids 1-364) of tyrosyl-tRNA synthetase as the capture antibody and an anti-PEG backbone antibody (Epitomics, Burlingame, Calif., catalog no. 3104-1) as the detection antibody. Detection was achieved using electrochemiluminescent technology (Meso Scale Discovery, Gaithersburg, Md.). Pharmacokinetic parameters were determined using non-compartmental analysis (PK Solutions, Summit Research Services, Montrose, Colo.). The elimination half-life of PEGylated YRS(1-353)A4C and PEGylated YRS(1-353) A351C was determined to be 38 and 36 hours, respectively. FIG. 9 shows the PK data of the Jenkem YRS(1-353)A4C-40K and Jenkem YRS(1-353)A353C-40K in the Sprague Dawley rat model. The data demonstrated a significant increase in PK characteristics compared to the unmodified proteins.

Example 9

Differential Scanning Calorimetry (DSC)

Figure 10A:
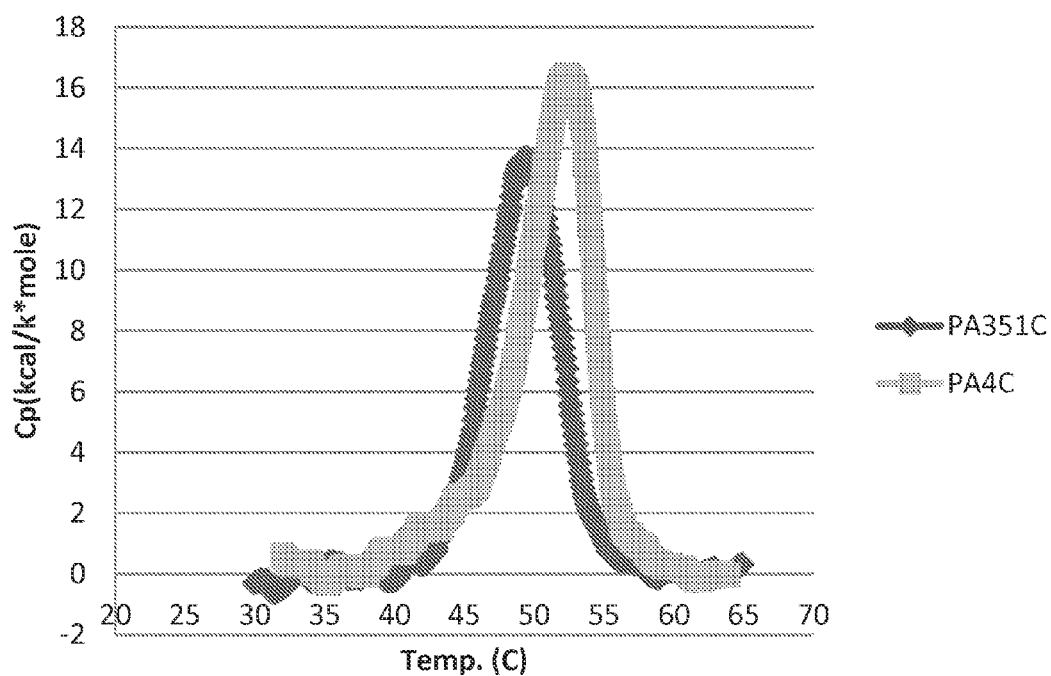
FIG. 10A shows the thermal unfolding curves of PEGylated YRS (1-353) A351C black diamonds, (PA351C) and PEGylated YRS(1-353)A4C grey squares (PA4C) determined in a differential scanning calorimetry.
Figure 10B:
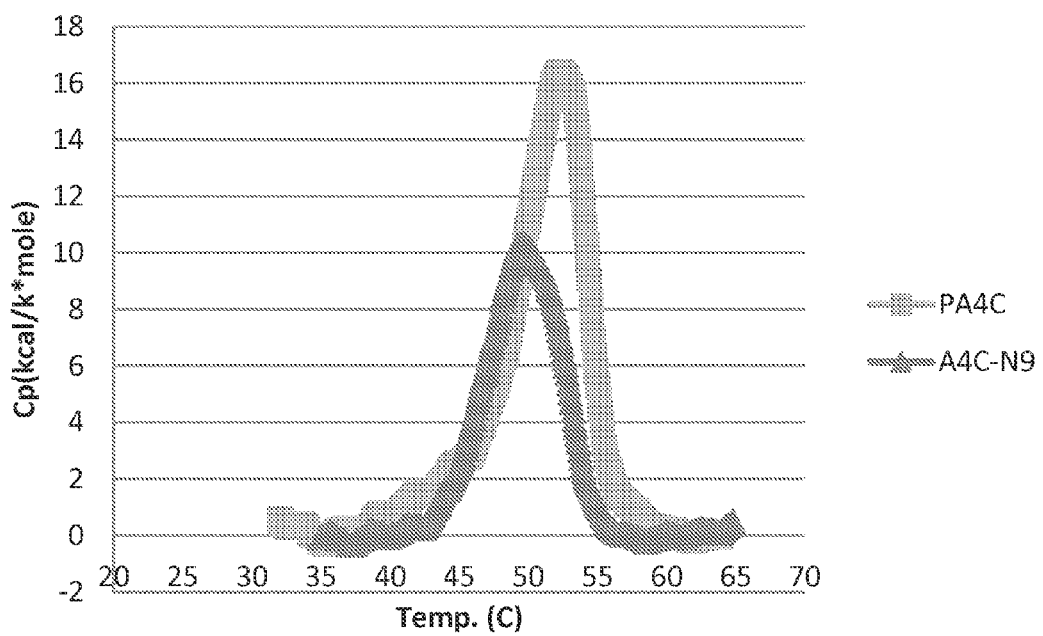
FIG. 10B shows the thermal unfolding curves of PEGylated YRS(1-353)A4C grey squares (PA4C and unPEGylated YRS(1-353) A4C black triangles (A4C-N9) as determined in a differential scanning calorimetry.

The folding stability of YRS(1-353)A4C and YRS(1-353) A351C before and after PEGylation with Jenkem's M-MAL-40K PEG was evaluated by DSC. PEGylated protein samples were dialyzed in pH6 and pH7 citrate-phosphate buffers and analyzed on a Differential Scanning calorimeter. The sample concentration was at 0.4 mg/ml with a total volume of 0.6 ml. The scan range was 20-80° C. at a rate of 1° C./min. The Tm values are summarized in Table E1. FIG. 10 shows the thermal unfolding curves.

TABLE E1

Tm values (° C.) of YRS(1-353)A4C and YRS(1-353)A351C before and after PEGylation with Jenkem's M-MAL-40K at pH 6 and 7

|  | pH 6 | pH 7 |
| --- | --- | --- |
| JenKem-YRS(1-353)A351C-40K | 49.4 | 46.7 |
| YRS(1-353)A351C | Not determined | Not determined |
| JenKem-YRS(1-353)A4C-40K | 52.3 | 47.3 |
| YRS(1-353)A4C | 49.7 | Not determined |

The results demonstrate significantly increased thermal stability of the PEGylated YRS polypeptides when stored at pH 6 compared to pH 7. A non PEGylated full length YRS variant also had better thermal stability at pH 6 than pH 7 (data not shown). Surprisingly the data also demonstrated a significant increase in thermal stability of the PEGylated proteins compared to the non PEGylated proteins. Similarly, the PEGylated YRS(1-353) polypeptides had better thermal stability compared to a non PEGylated full length YRS variant (data not shown).

Example 10

Stability of Pegylated YRS Polypeptides During Freeze Thaw and Storage

A preliminary stability evaluation was performed on JenKem-YRS(1-353)A4C-40K at 3.9 mg/ml and JenKem-YRS(1-353)A351C-40K) at 3.0 mg/ml. The PEGylated proteins were kept in a pH 6 PBS buffer and subjected to 6 times freeze-thaw, 4° C. storage of 7 days, and room temperature (~23° C.) storage of 24 hours. The protein samples at various time points were analyzed by visual inspection for visible precipitation, UV reading for recovery, SDS-PAGE for general purity/protein integrity, and SE-HPLC for aggregation. All samples appeared to be clear and colorless solutions. There was no significant change in protein recovery as measured by UV readings. SDS-PAGE did not show any change for all samples compared to the time 0 control. SE-HPLC profiles for all samples were similar but detected slight increase in high molecular weight species with more freeze-thaw and longer storage times. In general, both JenKem-YRS(1-353)A351C-40K) and JenKem-YRS(1-353)A4C-40K were stable at the above conditions in the pH 6 PBS formulation buffer (data not shown).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A PEGylated tyrosyl-tRNA synthetase (YRS) polypeptide selected from,
   (a) a YRS polypeptide consisting of a sequence that is at least 95% identical to the sequence set forth in SEQ ID NO:7 YRS(1-353), which is modified by A4C, C67S, and C250S substitutions, where a maleimide monomethoxy polyethylene glycol (mPEG) derivative of about 40,000 Daltons is covalently attached via a thio ether linkage to A4C;
   (b) a YRS polypeptide consisting of a sequence that is at least 98% identical to the sequence set forth in SEQ ID NO:7 YRS(1-353), which is modified by A4C, C67S, and C250S substitutions, where a maleimide monomethoxy polyethylene glycol (mPEG) derivative of about 40,000 Daltons is covalently attached via a thio ether linkage to A4C;
   (c) a YRS polypeptide consisting of the sequence set forth in SEQ ID NO:7 YRS(1-353), which is modified by A4C, C67S, and C250S substitutions, where a maleimide monomethoxy polyethylene glycol (mPEG) derivative of about 40,000 Daltons is covalently attached via a thio ether linkage to A4C;
   (d) a YRS polypeptide consisting of a sequence that is at least 95% identical to the sequence set forth in SEQ ID NO:7 YRS(1-353), which is modified by C67S, C250S, and A351C substitutions, where a maleimide monomethoxy polyethylene glycol (mPEG) derivative of about 40,000 Daltons is covalently attached via a thio ether linkage to A351C;
   (e) a YRS polypeptide consisting of a sequence that is at least 98% identical to the sequence set forth in SEQ ID NO:7 YRS(1-353), which is modified by C67S, C250S, and A351C substitutions, where a maleimide monomethoxy polyethylene glycol (mPEG) derivative of about 40,000 Daltons is covalently attached via a thio ether linkage to A351; and
   (f) a YRS polypeptide consisting of the sequence set forth in SEQ ID NO:7 YRS(1-353), which is modified by C67S, C250S, and A351C substitutions, where a maleimide monomethoxy polyethylene glycol (mPEG) derivative of about 40,000 Daltons is covalently attached via a thio ether linkage to A351C.

2. The PEGylated YRS polypeptide of claim 1, wherein the PEGylated product exhibits a higher specific activity in a charging assay compared to the non PEGylated protein.

3. The PEGylated YRS polypeptide of claim 1, comprising the structure:

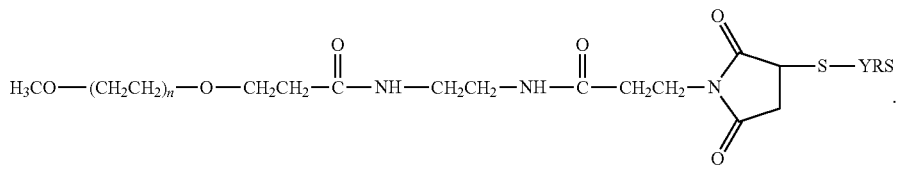

4. The PEGylated YRS polypeptide of claim 1, comprising the structure:

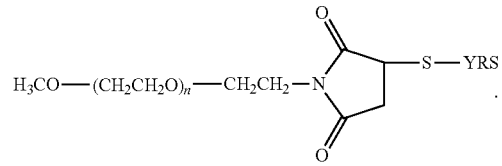

5. The PEGylated YRS polypeptide of claim 1:

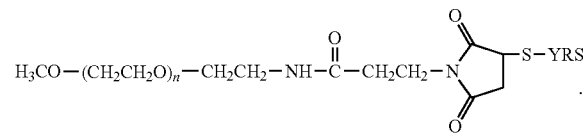

6. The PEGylated YRS polypeptide of claim 1:

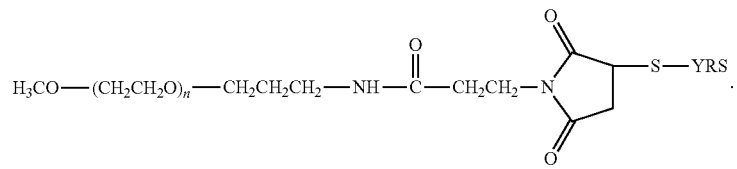

7. The PEGylated YRS polypeptide of claim 1, wherein the YRS polypeptide has substantially the same secondary structure as unmodified YRS polypeptide, as determined via UV circular dichroism analysis.

8. The PEGylated YRS polypeptide of claim 1, wherein the PEGylated YRS polypeptide has a plasma or sera pharmacokinetic AUC profile at least 5-fold greater than unmodified YRS polypeptide when administered to rats.

9. The PEGylated YRS polypeptide of claim 1, wherein the PEGylated YRS polypeptide has greater than 2 fold the activity of the unPEGylated protein in a charging assay.

10. The PEGylated YRS polypeptide of claim 1, wherein the PEGylated YRS polypeptide has greater than 3 fold the activity of the unPEGylated protein in a charging assay.

11. The PEGylated YRS polypeptide of claim 1, wherein the PEGylated YRS polypeptide has greater than 4 fold the activity of the unPEGylated protein in a charging assay.

12. A dosing regimen which maintains an average steady-state concentration of YRS polypeptide in the subjects's plasma of between about 0.3 µg/ml and about 3 µg/ml when using a dosing interval of 3 days or longer, comprising administering to the patient a therapeutic dose of PEGylated YRS polypeptide of any of claim 1.

13. A method for maintaining YRS polypeptide levels above the minimum effective therapeutic level in a subject in need thereof, comprising administering to the subject a therapeutic dose of PEGylated YRS polypeptide of claim 1.

14. A method for treating a hematopoiesis related disease in a subject in need thereof, comprising administering to the subject a therapeutic dose of PEGylated YRS polypeptide of claim 1.

15. The method of claim 14, wherein the hematopoiesis related disease is selected from thrombocytopenia, lymphocytopenia, neutropenia, basopenia, eosinopenia, anemias, polycythemia, neutrophilia, eosinophilia, or basophilia.

16. A method for treating a subject with a myelodysplastic syndrome comprising administering to the subject a therapeutic dose of PEGylated YRS polypeptide of claim 1 and a pharmaceutically acceptable carrier.

17. The method of claim 16, wherein the myelodysplastic syndrome is selected from Refractory Anemia (RA)(ICD-O code M9980/3), Refactory cytopenia with unilineage dysplasia (Refactory anemia, Refactory neutropenia, and Refractory thrombocytopenia), Refractory Anemia with Ring Sideroblasts (RARS) (ICD-O code M9982/3), Refractory Anemia with Ring Sideroblasts thrombocytosis, Refractory cytopenia with multilineage dysplasia (RCMD), Refractory Anemia with Excess Blasts (RAEB) (ICD-O code M9983/3), Refractory Anemia with Excess Blasts I or II, Refractory Anemia with Excess Blasts in Transformation (RAEB-T) (ICD-O code M9984/3), Chronic Myelomonocytic Leukemia (CMML) (ICD-O code M9945/3), 5q-syndrome, myelodysplastic-myeloproliferative overlap syndromes, Myelodysplasia unclassifiable, and refractory cytopenia of childhood.

18. A pharmaceutical composition comprising a PEGylated tyrosyl-tRNA synthetase (YRS) polypeptide of claim 1 and a pharmaceutically acceptable carrier or excipient.

19. The pharmaceutical composition of claim 18, wherein the composition is buffered to a pH of about 5.5 to about 6.5.

20. The pharmaceutical composition of claim 18, wherein the composition is buffered to a pH of about 6.0.

21. The pharmaceutical composition of claim 18, wherein the composition is buffered with a phosphate buffer at a concentration of about 10 to 20 mM.

22. The pharmaceutical composition of claim 18, wherein the composition is characterized by decreased aggregation of the PEGylated YRS polypeptides of any of claims 3 to 6 compared to a composition incubated under identical conditions but at pH 7.0 or higher.

\* \* \* \* \*